US012467925B2

(12) United States Patent
Sabeti et al.

(10) Patent No.: US 12,467,925 B2
(45) Date of Patent: Nov. 11, 2025

(54) CRISPR EFFECTOR SYSTEM BASED DIAGNOSTICS FOR HEMORRHAGIC FEVER DETECTION

(71) Applicants: THE BROAD INSTITUTE, INC., Cambridge, MA (US); PRESIDENT AND FELLOWS OF HARVARD COLLEGE, Cambridge, MA (US)

(72) Inventors: Pardis Sabeti, Cambridge, MA (US); Cameron Myhrvold, Cambridge, MA (US); Catherine Amanda Freije, Cambridge, MA (US); Anna Elizabeth Lachenauer, Cambridge, MA (US); Kayla Grace Barnes, Cambridge, MA (US)

(73) Assignees: THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 1071 days.

(21) Appl. No.: 17/282,424

(22) PCT Filed: Oct. 3, 2019

(86) PCT No.: PCT/US2019/054561

§ 371 (c)(1),
(2) Date: Apr. 2, 2021

(87) PCT Pub. No.: WO2020/072816

PCT Pub. Date: Apr. 9, 2020

(65) Prior Publication Data

US 2021/0396756 A1 Dec. 23, 2021

Related U.S. Application Data

(60) Provisional application No. 62/740,728, filed on Oct. 3, 2018.

(51) Int. Cl.
*C12Q 1/6823* (2018.01)
*C12Q 1/70* (2006.01)
*G01N 33/569* (2006.01)

(52) U.S. Cl.
CPC ..... *G01N 33/56983* (2013.01); *C12Q 1/6823* (2013.01); *C12Q 1/701* (2013.01); *G01N 2333/08* (2013.01)

(58) Field of Classification Search
CPC ......... G01N 33/56983; G01N 2333/08; C12Q 1/6823; C12Q 1/701; C12Q 1/6816
See application file for complete search history.

(56) References Cited

FOREIGN PATENT DOCUMENTS

| | | | | | |
|---|---|---|---|---|---|
| WO | WO-2014197607 | A1 * | 12/2014 | ........... | C12Q 1/6883 |
| WO | 2017/218573 | A1 | 12/2017 | | |
| WO | WO-2018170340 | A1 * | 9/2018 | ........... | C12N 15/115 |
| WO | 2020/072816 | A1 | 4/2020 | | |

OTHER PUBLICATIONS

Genbank KM821910Lassa virus strain G3283-SLE-2013 segment S glycoprotein precursor (GPC) and nucleoprotein (NP) genes, complete cds (https://www.ncbi.nlm.nih.gov/nuccore/km821910, Jan. 8, 2015).*
Smargon et al., (2017, Molecular Cell 65, 618-630).*
Kim (Current Opinion in Biomedical Engineering 2017, 4:106-115).*
Moreno-Mateos (Nature Methods (2015) vol. 12, pp. 982-988).*
Rose (Proc. Natl. Acad. Sci. USA vol. 93, pp. 14998-15000, Dec. 1996).*
"International Preliminary Report on Patentability received in PCT Application No. PCT/US2019/054561", mailed on Apr. 15, 2021, 9 pages.
"International Search Report & Written Opinion received in PCT Application No. PCT/US2019/054561", mailed on Dec. 18, 2019, 14 pages.
"Introduction to Lassa Fever Managing Infectious Hazards", World Health Organization, 2018, 22 pages.
Abudayyeh, et al., "C2C2 is a Single-Component Programmable RNA-Guided RNA-Targeting CRISPR Effector", Science, vol. 353, No. 6299, Aug. 5, 2016, 23 pages.
Ajayi, et al., "Containing a Lassa Fever Epidemic in a Resource-Limited Setting: Outbreak Description and Lessons Learned from Abakaliki, Nigeria (Jan.-Mar. 2012)", International Journal of Infectious Diseases, vol. 17, 2013, e1011-e1016.
Andersen, et al., "Clinical Sequencing Uncovers Origins and Evolution of Lassa Virus", Cell, vol. 162, No. 4, Aug. 13, 2015, 24 pages.
Bausch, et al., "Diagnosis and Clinical Virology of Lassa Fever as Evaluated by Enzyme-Linked Immunosorbent Assay, Indirect FluorescentAntibody Test, and Virus Isolation", Journal of Clinical Microbiology, vol. 38, No. 7, Jul. 2000, 2670-2677.
Bhagat, et al., "Dean Flow Fractionation (DFF) Isolation of Circulating Tumor Cells (CTCs) from Blood", 15th International Conference on Miniaturized Systems for Chemistry and Life Sciences, Oct. 2011, 524-526.
Boisen, et al., "Development of Prototype Filovirus Recombinant Antigen Immunoassays", The Journal of Infectious Diseases, vol. 212, Supplement 2, 2015, S359-S367.
Boisen, et al., "Field Validation of Recombinant Antigen Immunoassays for Diagnosis of Lassa Fever", Scientific Reports, vol. 8, 5939, 2018, 14 pages.
Brainard, et al., "Risk Factors for Transmission of Ebola or Marburg Virus Disease: a Systematic Review and Meta-Analysis", International Journal of Epidemiology, vol. 45, No. 1, 2016, 102-116.

(Continued)

*Primary Examiner* — Cynthia B Wilder
(74) *Attorney, Agent, or Firm* — Johnson, Marcou, Isaacs & Nix, LLC; F. Brent Nix, Esq.; Ming Zhang

(57) ABSTRACT

The embodiments disclosed herein utilize RNA targeting effectors to provide a robust CRISPR-based diagnostic for hemorrhagic fever virus applications. Embodiments disclosed herein can differentiate between hemorrhagic fever viruses that present with similar symptoms, as well as between strains of a hemorrhagic fever virus.

23 Claims, 17 Drawing Sheets

Specification includes a Sequence Listing.

(56) References Cited

OTHER PUBLICATIONS

Changula, et al., "Ebola and Marburg Virus Diseases in Africa: Increased Risk of Outbreaks in Previously Unaffected Areas?", Microbiology and Immunology, vol. 58, 2014, 483-491.
Chen, et al., "CRISPR-Cas12a Target Binding Unleashes Indiscriminate Single-stranded DNase Activity", Science, vol. 360, No. 6387, Apr. 27, 2018, 12 pages.
Das, et al., "Ultra-Portable, Wireless Smartphone Spectrophotometer for Rapid, Non-Destructive Testing of Fruit Ripeness", Nature Scientific Reports, vol. 6, No. 32504, Sep. 2016, 8 pages.
Demby, et al., "Early Diagnosis of Lassa Fever by Reverse Transcription-PCR", Journal of Clinical Microbiology, vol. 32, No. 12, Dec. 1994, 2898-2903.
East-Seletsky, et al., "Two Distinct RNase Activities of CRISPR-C2c2 Enable Guide-RNA Processing and RNA Detection", Nature, vol. 538, No. 7624, Oct. 13, 2016, 17 pages.
Gire, et al., "Genomic Surveillance Elucidates Ebola Virus Origin and Transmission During the 2014 Outbreak", Science, vol. 345, No. 6202, Sep. 12, 2014, 11 pages.
Goba, et al., "An Outbreak of Ebola Virus Disease in the Lassa Fever Zone", The Journal of Infectious Diseases, vol. 214, Supplement 3, 2016, S110-S121.
Gootenberg, et al., "Multiplexed and Portable Nucleic Acid Detection Platform with Cas13, Cas12a, and Csm6", Science, vol. 360, No. 6387, Apr. 27, 2018, 14 pages.
Gootenberg, et al., "Nucleic Acid Detection With CRISPR-Cas13a/C2c2", Science, vol. 356, No. 6336, Apr. 28, 2017, 12 pages.
Hale, et al., "RNA-Guided RNA Cleavage by a CRISPR RNA-Cas Protein Complex", Cell, vol. 139, No. 5, Nov. 25, 2009, 945-956.
Hale, et al., "Target RNA Capture and Cleavage by the Cmr Type III-B CRISPR-Cas Effector Complex", Genes & Development, vol. 28, No. 21, Sep. 29, 2014, 13 pages.
Hou, et al., "Direct Detection and Drug-Resistance Profiling of Bacteremias Using Inertial Microfluidics", Lab Chip, vol. 15, No. 10, May 21, 2015, 2297-2307.
Hou, et al., "Microfluidic Devices for Blood Fractionation", Micromachines, vol. 2, 2011, 319-343.
Hou, et al., "Pathogen Isolation from Whole Blood using a Microchannel Device," MIT Technology Licensing Office, printed Nov. 2, 2021.
Jia, et al., "CARD 2017: Expansion and Model-Centric Curation of the Comprehensive Antibiotic Resistance Database", Nucleic Acids Research, vol. 45, Jan. 4, 2017, D566-D573.
Li, et al., "CRISPR-Cas 12a has both cis- and trans-cleavage activities on single-stranded DNA", Cell Res. (EPub), vol. 28, No. 4, 2018, 3 pages.
Matranga, et al., "Enhanced Methods for Unbiased Deep Sequencing of Lassa and Ebola RNA Viruses from Clinical and Biological Samples", Genome Biology, vol. 15, No. 11, Nov. 18, 2014, 12 pages.
Metsky, et al., "Capturing Sequence Diversity in Metagenomes with Comprehensive and Scalable Probe Design", Nature Biotechnology, vol. 37, No. 2, Feb. 2019, 16 pages.
Myhrvold, et al., "Field-Deployable Viral Diagnostics Using CRISPR-Cas13", Science, vol. 360, Apr. 27, 2018, 444-448.
Nikisins, et al., "International External Quality Assessment Study for Molecular Detection of Lassa Virus", PLOS Neglected Tropical Diseases, vol. 9, No., 5, e0003793, May 2015, 15 pages.
Pang, et al., "Comprehensive Multiplex One-Step Real-Time TaqMan qRT-PCR Assays for Detection and Quantification of Hemorrhagic Fever Viruses", PLOS ONE, vol. 9, Issue 4, e95635, Apr. 1, 2014, 11 pages.
Pardee, et al., "Paper-Based Synthetic Gene Networks", Cell, vol. 159, No. 4, Nov. 6, 2014, 28 pages.
Pardee, et al., "Rapid, Low-Cost Detection of Zika Virus Using Programmable Biomolecular Components", Cell, vol. 165, No. 5, May 19, 2016, 24 pages.
Park, et al., "Ebola Virus Epidemiology, Transmission, and Evolution during Seven Months in Sierra Leone", Cell, vol. 161, No. 7, Jun. 18, 2015, 1516-1526.
Peng, et al., "An Archaeal CRISPR Type III-B System Exhibiting Distinctive RNA Targeting Features and Mediating Dual RNA and DNA Interference", Nucleic Acids Research, vol. 43, No. 1, Jan. 2015, 406-417.
Platt, et al., "CRISPR-Cas9 Knockin Mice for Genome Editing and Cancer Modeling", Cell, vol. 159, No. 2, Oct. 9, 2014, 31 pages.
Rasca, et al., "Viral Hemorrhagic Fever Diagnostics", Clinical Infectious Diseases, vol. 62, Jan. 15, 2016, 214-219.
Samai, et al., "Co-Transcriptional DNA and RNA Cleavage During Type III CRISPR-Cas Immunity", Cell, vol. 161, No. 6, May 21, 2015, 1164-1174.
Shaffer, et al., "A Medical Records and Data Capture and Management System for Lassa Fever in Sierra Leone: Approach, Implementation, and Challenges", PLoS One, vol. 14, No. 3, e0214284, Mar. 28, 2019, 20 pages.
Shafiee, et al., "Paper and Flexible Substrates as Materials for Biosensing Platforms to Detect Multiple Biotargets", Scientific Reports, vol. 5, No. 8719, Mar. 6, 2015, 1-9.
Shmakov, et al., "Discovery and Functional Characterization of Diverse Class 2 Crispr-Cas Systems", Molecular Cell., vol. 60, No. 3, Nov. 1, 2015, 385-397.
Shmakov, et al., "Diversity and Evolution of Class 2 CRISPR-Cas Systems", Nature Reviews Microbiology, vol. 15, No. 3, Mar. 2017, 30 pages.
Smargon, et al., "Cas 13B is a Type VI-B CRISPR-Associated RNA-Guided RNAse Differentially Regulated by Accessory Proteins Csx27 and Csx28", Molecular Cell, vol. 65, No. 4, Feb. 16, 2017, 30 pages.
St John, et al., "Existing and Emerging Technologies for Point-of-Care Testing", The Clinical Biochemist Reviews, vol. 35, No. 3, Aug. 2014, 155-167.
Trombley, et al., "Comprehensive Panel of Real-Time TaqMan™ Polymerase Chain Reaction Assays for Detection and Absolute Quantification of Filoviruses, Arenaviruses, and New World Hantaviruses", The American Society of Tropical Medicine and Hygiene, vol. 85, No. 5, 2010, 954-960.
Vashist, et al., "Commercial Smartphone-Based Devices and Smart Applications for Personalized Healthcare Monitoring and Management", Diagnostics, vol. 4, No. 3, Aug. 14, 2014, 104-128.
Wang, et al., "Flexible Substrate-Based Devices for Point-of-Care Diagnostics", Trends in Biotechnology, vol. 34, No. 11, Nov. 2016, 20 pages.
Zetsche, et al., "Cpf1 is a Single RNA-Guided Endonuclease of a Class 2 CRISPR-Cas System", Cell, vol. 163, No. 3, Oct. 22, 2015, 759-771.
Zhao, et al., "Signal Amplification of Glucosamine-6-Phosphate Based on Ribozyme GlmS", Biosensors and Bioelectronics, vol. 62, Dec. 15, 2014, 337-342.
Wu, Dongying, "Systematic identification of gene families for use as "markers" for phylogenetic and phylogeny-driven ecological studies of bacteria and archaea and their major subgroups," arXiv:1307.8690 [q-bio.GN], no date, all enclosed pages cited.

* cited by examiner

CRISPR EFFECTOR SYSTEM BASED DIAGNOSTICS FOR HEMORRHAGIC FEVER DETECTION

CROSS-REFERENCE TO RELATED APPLICATIONS

This application claims the benefit of International Application No. PCT/US2019/054561 filed Oct. 3, 2019, which claims priority to U.S. Provisional Application No. 62/740,728 filed Oct. 3, 2018. The entire contents of the above-identified applications are hereby fully incorporated herein by reference.

STATEMENT REGARDING FEDERALLY SPONSORED RESEARCH

This invention was made with government support under Grant No. All 14855 awarded by the National Institutes of Health, and Grant No. D18AC00006 awarded by the Department of Defense. The government has certain rights in the invention.

TECHNICAL FIELD

The subject matter disclosed herein is generally directed to systems and methods of rapid diagnostics of hemorrhagic fever, particularly with the use of CRISPR effector systems.

REFERENCE TO AN ELECTRONIC SEQUENCE LISTING

The content of the Electronic Sequence Listing (BROD_2545WP_ST25.txt); Size is 130,556 bytes and was created on Thursday, Oct. 3, 2019 is incorporated herein by reference in its entirety.

BACKGROUND

Hemorrhagic fevers can be spread by contact with infected animals, people, or insects. The symptoms of LF closely resemble those of other hemorrhagic fevers, such as Ebola virus disease (EVD) and Marburg virus disease (MVD) (Racsa et al., 2016). It is of great clinical and public health importance to be able to distinguish LF from these two diseases; because EVD and MVD are more commonly spread through human contact than LF, knowledge of the cause of infection for a patient presenting symptoms of hemorrhagic fever allows healthcare workers to take proper precautionary steps when treating the patient (Brainard et al., 2016). Lassa fever (LF) is a viral hemorrhagic fever (VHF) endemic to Sierra Leone, Nigeria, Guinea, and Liberia (Andersen et al., 2015). LF is caused by infection with Lassa virus (LASV), a highly virulent Biosafety Level 4 (BL-4) pathogen (Andersen et al., 2015; Paessler & Walker, 2013). LASV infection most commonly occurs through contact with the rodent *Mastomys natalensis*, the natural LASV reservoir, although human-to-human transmissions can also occur (Andersen et al., 2015; World Health Organization, 2018). LF causes thousands of deaths each year in West Africa, and case fatality rates among hospitalized patients may exceed 50%, affecting all ages and both genders (Andersen et al., 2015; Paessler & Walker, 2013). LF is difficult to diagnose because its wide range of clinical symptoms, including fever, vomiting, and hemorrhage, are similar to those seen with other tropical diseases, such as Ebola, Marburg, Malaria, Dengue, or Typhoid (Frame et al., 1970; Goba et al., 2016; Racsa et al., 2016; Shaffer et al., 2014). The recent increase in hemorrhagic fever outbreaks in Western Africa, from both LASV and other viruses, underscores the urgent need for accurate viral diagnostic methods to facilitate diagnosis and proper treatment of these viral diseases (Changula et al., 2014; World Health Organization, 2018).

Sensitive and deployable diagnostic tools are particularly vital for LASV and EBOV because early diagnosis enables timely clinical care and containment of the virus. The antiviral drug ribavirin is the current standard-of-care for treatment of LF but is most effective when given in the early stages of infection, often before specific clinical symptoms have presented (Shaffer et al., 2014). Furthermore, lack of early diagnosis can facilitate the spread of LF in regions prone to viral outbreaks, exacerbating its devastating effects (Ajayi et al., 2013; Racsa et al., 2016). An ongoing LF outbreak in Nigeria—the largest ever reported in the country-combined with reduced sensitivity of published molecular diagnostics for current LASV strains highlights the need for immediate improvement of LASV detection methods (Boisen et al., Scientific Reports, in press; World Health Organization, 2018).

LASV is a single-stranded RNA arenavirus (Andersen et al., 2015), and EBOV is a single-stranded negative-sense RNA virus. The LASV genome is comprised of two segments that encode four proteins (FIG. 1*a*). The L-segment (7.3 kb) encodes the L (polymerase) and Z (matrix), while the S-segment (3.4 kb) encodes the NP (nucleoprotein) and GPC (glycoprotein) (Bowen, 2000). The LASV genome evolves rapidly and has been shown to diverge up to 32% between strains (Andersen et al., 2015). Sequencing data has distinguished four LASV lineages located in distinct regions in Western Africa, designated I, II, III, and IV (FIG. 1*b*) (Bowen, 2000). Lineage I consists of the prototype LP strain of LASV. Lineage II (N-II) contains strains from southern central Nigeria and is the country's predominant clade. Lineage III (N-III) contains strains from northern central Nigeria. Lineage IV (SL-IV) contains all strains from Guinea, Liberia, and Sierra Leone.

As nucleic acid diagnostics become increasingly relevant for a variety of healthcare applications, detection technologies that provide high specificity and sensitivity at low cost would be of great utility in both clinical and basic research settings.

The extreme genetic diversity of the LASV genome hinders development of accurate diagnostic tools. Efforts to create a single diagnostic test that can detect all viral diversity are complicated by deeply divergent LASV clades, which contain high levels of nucleotide variation and are almost genetically distinct (Andersen et al., 2015). LASV's fast rate of viral evolution quickly renders diagnostics obsolete, so diagnostic platforms must be easily adaptable to emerging viral strains in order to maintain clinical relevance (Andersen et al., 2015).

Another great challenge to LASV and EBOV diagnosis is the remote location of some endemic regions. Many endemic districts lack access to health clinics and hospitals, rendering diagnostics that require trained laboratory staff or expensive equipment unusable. Because LASV and EBOV are RNA viruses, they are easily susceptible to degradation, which reduces the sensitivity of diagnostics that target viral sequences. Proper cold conditions, achieved via a cold chain, prevent RNA degradation, but even well-established West African hospitals may have difficulty maintaining cold chains because of inconsistent electrical power or other restricted resources (Bausch et al., 2000). Available resources in endemic regions necessitate a point-of-care diagnostic that does not require a well-equipped laboratory or a cold chain for field detection of modern viral strains.

There are a number of published LASV diagnostics, but all lack either the sensitivity or the logistic feasibility required for reliable detection of current viral strains in endemic regions. Reverse Transcription-quantitative Polymerase Chain Reaction (RT-qPCR) assays include the Nikisins RT-qPCR assay, the current "gold standard" for LASV detection and is approved by the CDC for universal field LF diagnosis developed on viral strains from 2007 or older (Nikisins et al., 2015). However, because of recent viral evolution among strains, this diagnostic results in a 5-10% false negative rate on current clinical samples (Andersen et al., 2015). The Trombley RT-qPCR assay is used by some West African hospitals, including Kenema Government Hospital (KGH) in Sierra Leone, for clinical diagnosis in addition to the Nikisins assay (Trombley et al., 2010). Laboratory technicians at KGH have observed that the Trombley assay also lacks the sensitivity required for reliable clinical diagnosis of current patient samples. An additional limitation of these methods is that RT-qPCR assays require a stable cold chain to prevent extracted RNA from deteriorating, which can result in false-negative results (Bausch et al., 2000). West African health centers may lack the staff, electrical power, or laboratory space to carry out RT-qPCR assays.

Enzyme-Linked Immunosorbent Assay (ELISA), while providing early detection and prognostic information with specificity and sensitivity comparable to the gold standard LF RT-qPCR. (Bausch et al., 2000), is inherently limited for a rapidly evolving virus like LASV; unlike assays that detect viral genome, antigen- and antibody-based tests can take months to develop, so it is not feasible to quickly develop ELISAs in response to an emerging viral outbreak or a new viral clade. Additionally, ELISAs cannot be performed on deactivated samples and thus require BL4-capable facilities, which limits their accessibility in remote areas. The ReLASV® RDT is an antigen detection test that targets the LASV NP, and while developed by Corgenix, Inc. for rapid and remote diagnosis of LASV, since RDTs target protein antigens rather than viral genome sequences, they can take months to years to redesign against evolved viral strains. Antigen tests are clinically less sensitive than PCR, and the current RDT has shown limited efficacy in detecting Nigerian strains of the virus (Boisen, 2015; Bowen et al., 2000).

Accordingly, rapid testing capable of reliable detection of current viral strains that can be used with the limited resources of endemic regions would be a great improvement.

SUMMARY

In one aspect, the invention provides a system for detecting the presence of one or more hemorrhagic fever viruses in a sample comprising one or more CRISPR systems and a masking construct. The one or more CRISPR systems each comprise an effector protein and one or more guide molecules designed to bind to one or more corresponding target molecules of one or more hemorrhagic fever viruses. In some embodiments, the one or more guide molecules are guide RNAs selected from the group consisting of SEQ ID NOs: 80, 87-92, 109-126, 139-156, 159-172, 207-228, 249-281, 329-366, and 393-416. In some embodiments, the one or more guide RNAs are designed to bind to one or more target molecules that are diagnostic for a disease state, for example, a hemorrhagic fever virus.

In some embodiments, the system further comprises nucleic acid amplification reagents. The nucleic acid amplification reagents comprise recombinase polymerase amplification (RPA) reagents, nucleic acid sequence-based amplification (NASBA) reagents, loop-mediated isothermal amplification (LAMP) reagents, strand displacement amplification (SDA) reagents, helicase-dependent amplification (HDA) reagents, nicking enzyme amplification reaction (NEAR) reagents, RT-PCR reagents, multiple displacement amplification (MDA) reagents, rolling circle amplification (RCA) reagents, ligase chain reaction (LCR) reagents, ramification amplification method (RAM) reagents, transposase based amplification reagents; or Programmable CRISPR Nicking Amplification (PCNA) reagents. In some embodiments, the RPA reagents comprise one or more primer pairs selected from the group consisting of SEQ ID NOs: 78, 79, 81-86, 93-108, 127-138, 173-206, 233-248, 285-328, 370-392. In other embodiments, the nucleic acid amplification reagents include transposase-based amplification reagents such as the transposase of prokaryotic transposon Tn5.

In some aspects, the system further comprises an enrichment CRISPR system, wherein the enrichment CRISPR system is designed to bind the corresponding target molecules prior to detection by the detection CRISPR system. The enrichment CRISPR system, in some embodiments, is designed to bind the corresponding target molecules prior to detection by the detection CRISPR system. The enrichment CRISPR system in a specific embodiment comprises a catalytically inactive CRISPR effector protein, which, in some instances is a catalytically inactive C2c2. The enrichment CRISPR effector protein can, in some embodiments, further comprise a tag, wherein the tag is used to pull down the enrichment CRISPR effector system, or to bind the enrichment CRISPR system to a solid substrate.

In further embodiments, the CRISPR system effector protein is an RNA-targeting effector protein. In one aspect, the RNA-targeting effector protein comprises one or more Higher Eukaryotes and Prokaryotes Nucleotide-binding (HEPN) domains, which can, in some embodiments comprise a RxxxxH motif sequence. In an embodiment, the RxxxH motif comprises a R{N/H/K]X1X2X3H sequence (SEQ ID NO:1). In some embodiments, the R{N/H/K] X1X2X3H sequence is defined wherein X1 is R, S, D, E, Q, N, G, or Y, and X2 is independently I, S, T, V, or L, and X3 is independently L, F, N, Y, V, I, S, D, E, or A.

Example RNA-targeting effector proteins include Cas13b and C2c2 (now known as Cas13a). It will be understood that the term "C2c2" herein is used interchangeably with "Cas13a". In another example embodiment, the RNA-targeting effector protein is C2c2, which in some embodiments is within 20 kb of a Cas1 gene. In some embodiments, the C2c2 effector protein is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira.*

In some embodiments, the C2c2 or Cas13b effector protein is from an organism selected from the group consisting of: *Leptotrichia shahii; Leptotrichia wadei* (Lw2); *Listeria seeligeri; Lachnospiraceae bacterium* MA2020*; Lachnospiraceae bacterium* NK4A179*;* [*Clostridium*]*aminophilum* DSM 10710*; Carnobacterium gallinarum* DSM 4847*; Carnobacterium gallinarum* DSM 4847 (second CRISPR Loci); *Paludibacter propionicigenes* WB4*; Listeria weihenstepha-*

*nensis* FSL R9-0317*; Listeriaceae bacterium* FSL M6-0635*; Leptotrichia wadei* F0279*; Rhodobacter capsulatus* SB 1003*; Rhodobacter capsulatus* R121*; Rhodobacter capsulatus* DE442*; Leptotrichia buccalis* C-1013-b; *Herbinix hemicellulosilytica;* [*Eubacterium*] *rectale; Eubacteriaceae bacterium* CHKCI004*; Blautia* sp. Marseille-P2398*; Leptotrichia* sp. oral taxon 879 str. F0557*; Lachnospiraceae bacterium* NK4A144*; Chloroflexus aggregans; Demequina aurantiaca; Thalassospira* sp. TSL5-1*; Pseudobutyrivibrio* sp. OR37*; Butyrivibrio* sp. YAB3001*; Blautia* sp. Marseille-P2398*; Leptotrichia* sp. Marseille-P3007*; Bacteroides ihuae; Porphyromonadaceae bacterium* KH3CP3RA; *Listeria riparia*; and *Insolitispirillum peregrinum*. In one embodiment, the C2c2 effector protein is a *L. wadei* F0279 or *L. wadei* F0279 (Lw2) C2C2 effector protein.

The RNA-based masking construct of the system can, in some embodiments, suppress generation of a detectable positive signal. In some embodiments, the RNA-based masking construct suppresses generation of a detectable positive signal by masking the detectable positive signal, or generating a detectable negative signal instead; the RNA-based masking construct comprises a silencing RNA that suppresses generation of a gene product encoded by a reporting construct, wherein the gene product generates the detectable positive signal when expressed; and/or the RNA-based masking construct is a ribozyme that generates the negative detectable signal, and wherein the positive detectable signal is generated when the ribozyme is deactivated. In one embodiment, the detectable ligand is a fluorophore and the masking component is a quencher molecule. In one embodiment when the RNA-based masking construct is a ribozyme, the ribozyme converts a substrate to a first color and wherein the substrate converts to a second color when the ribozyme is deactivated.

In an embodiment, the RNA-based masking agent is an RNA aptamer and/or comprises an RNA-tethered inhibitor, which is some instances, sequesters an enzyme, wherein the enzyme generates a detectable signal upon release from the aptamer or RNA tethered inhibitor by acting upon a substrate. In some embodiments, the aptamer is an inhibitory aptamer that inhibits an enzyme and prevents the enzyme from catalyzing generation of a detectable signal from a substrate or wherein the RNA-tethered inhibitor inhibits an enzyme and prevents the enzyme from catalyzing generation of a detectable signal from a substrate. In some instances, when the RNA-tethered inhibits an enzyme, the enzyme is thrombin, protein C, neutrophil elastase, subtilisin, horseradish peroxidase, beta-galactosidase, or calf alkaline phosphatase; in some embodiments, the enzyme is thrombin and the substrate is para-nitroanilide covalently linked to a peptide substrate for thrombin, or 7-amino-4-methylcoumarin covalently linked to a peptide substrate for thrombin. In an aspect, the aptamer sequesters a pair of agents that when released from the aptamers combine to generate a detectable signal.

The RNA-based masking construct can comprise, in some embodiments, an RNA oligonucleotide to which a detectable ligand and a masking component are attached. In some embodiments the RNA-based masking construct comprises a nanoparticle held in aggregate by bridge molecules, wherein at least a portion of the bridge molecules comprises RNA, and wherein the solution undergoes a color shift when the nanoparticle is disbursed in solution. In some instances, the nanoparticle is a colloidal metal, which is, in some instances, colloidal gold. In further embodiments, the RNA-based masking construct comprising a quantum dot linked to one or more quencher molecules by a linking molecule, wherein at least a portion of the linking molecule comprises RNA. In other embodiments, the RNA-based masking construct comprises RNA in complex with an intercalating agent, wherein the intercalating agent changes absorbance upon cleavage of the RNA. In specific embodiments, the intercalating agent is pyronine-Y or methylene blue.

In some embodiments, the system comprises two or more CRISPR systems, and RNA-based masking constructs. Each CRISPR system comprises an effector protein and one or more guide molecules designed to bind to one or more corresponding target molecules of one or more hemorrhagic fever viruses. In an embodiment, each RNA-based masking construct comprises a cutting motif sequence that is preferentially cut by one of the CRISPR effector proteins after the CRISPR effector protein is activated.

Methods of using the detection system are also provided herein. The system can be used in methods for detecting viral nucleic acid in one or more samples, comprising: contacting one or more samples with a nucleic acid detection system as disclosed herein. In some embodiments, the methods comprise applying contacted one or more samples to a lateral flow immunochromatographic assay. In some embodiments, the methods comprise detecting viral nucleic acid in a sample comprising amplifying the sample nucleic acid using one or more of the probes according to SEQ ID NO: X-X; combining the sample with an effector protein, one or more guide RNAs according to SEQ ID NO: X-X, and an RNA-based masking construct. In some embodiments, the one or more guide RNAs are designed to bind to corresponding virus specific target molecules. In the methods, the RNA effector protein is activated via binding of the one or more guide RNAs to the one or more virus-specific target molecules, wherein activating the RNA effector protein results in modification of the RNA-based masking construct such that a detectable positive signal is produced. In some embodiments, the method includes detecting the signal, and detection of the signal indicates the presence of a hemorrhagic fever virus. The method does not, in some embodiments, include the step of extracting RNA from the sample.

The methods in some embodiments include the step of amplifying the sample nucleic acid comprising nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), RT-PCR, multiple displacement amplification (MDA), rolling circle amplification (RCA), ligase chain reaction (LCR), ramification amplification method (RAM), transposase based amplification; or Programmable CRISPR Nicking Amplification (PCNA). In some embodiments, the step of amplifying the sample nucleic acid comprises contacting the sample with one or more of the probes according to SEQ ID NO: SEQ ID NOs: 78, 79, 81-86, 93-108, 127-138, 173-206, 233-248, 285-328, 370-392.

In some embodiments, the sample is a biological sample comprising blood, plasma, serum, urine, or saliva.

In some embodiments, the methods include the step of applying the sample to one or more lateral flow strips. In some embodiments, the lateral flow strip of the methods and systems comprises an upstream first antibody directed against a first molecule, and a downstream second antibody directed against a second molecule, and wherein uncleaved RNA-based masking construct is bound by said first antibody if the target nucleic acid is not present in said sample, and wherein cleaved RNA-based masking construct is bound both by said first antibody and said second antibody if the target nucleic acid is present in said sample. The masking construct, in some instances comprises an RNA oligonucleotide designed to bind a G-quadruplex forming sequence, wherein a G-quadruplex structure is formed by the G-quadruplex forming sequence upon cleavage of the masking construct, and wherein the G-quadruplex structure generates a detectable positive signal.

The methods disclosed herein can further include the step of comparing a detectable positive signal with a (synthetic) standard signal.

In some embodiments, the system is capable of distinguishing between two or more hemorrhagic fever viruses and/or strains of a particular hemorrhagic fever virus. In some embodiments, the hemorrhagic fever virus is Lassa virus, Hantavirus, Crimean-Congo hemorrhagic fever virus, Lujo virus, Ebola virus, Marburg virus, or Rift Valley fever virus. The hemorrhagic fever virus in some instances is Lassa virus, Ebola virus, or Marburg virus. The systems and methods can be used to distinguish between strains of Lassa virus SL-IV, N-II, or N-III. In some embodiments, the systems and methods disclosed herein are used to detect one or more hemorrhagic fever viruses or strains, or distinguish between hemorrhagic fever viruses or strains. In some instances, when the hemorrhagic fever virus of interest is Lassa virus, the one or more guide molecules are guide RNAs selected from the group consisting of SEQ ID NO: 87-92, 109-126, 139-156, 207-228, 249-281, 329-36; when the hemorrhagic fever virus of interest is Ebola virus, the one or more guide molecules are guide RNAs selected from the group consisting of SEQ ID NO:80, 159-172; and when the hemorrhagic fever virus of interest is Marburg virus, one or more guide molecules are guide RNAs selected from the group consisting of SEQ ID NO:393-416.

Kits for detecting viral nucleic acids in a sample are also disclosed herein, comprising nucleic acid amplification reagents; one or more of the probes according to SEQ ID NO: 80, 87-92, 109-126, 139-156, 159-172, 207-228, 249-281, 329-366, 393-416; a CRISPR system comprising an effector protein and/or one or more of the guide RNAs according to SEQ ID NO: 78, 79, 81-86, 93-108, 127-138, 173-206, 233-248, 285-328, 370-392, wherein the guide RNAs are designed to bind to corresponding target molecules; an RNA-based masking construct; and one or more lateral flow strips.

A diagnostic device is also disclosed herein, and in some embodiments, comprises one or more individual discrete volumes, each individual discrete volume comprising one or more CRISPR systems. In some instances, each individual discrete volume further comprises one or more detection aptamers comprising a masked RNA polymerase promoter binding site or a masked primer binding site. In an embodiment, each individual discrete volume further comprises nucleic acid amplification reagents. In some instances, the target molecule is a target DNA and the individual discrete volumes further comprise a primer that binds the target DNA and comprises an RNA polymerase promoter. In other instances, the target molecule is RNA. In some instances, the individual discrete volumes are droplets. In some embodiments, the individual discrete volumes are defined on a solid substrate, in some specific embodiments, the individual discrete volumes are microwells, in some instances, the individual discrete volumes are spots defined on a substrate. In some instances, the substrate is a flexible materials substrate, which can be, in some instances, a paper substrate or a flexible polymer-based substrate.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 3A is an alignment of the Broad RT-qPCR assay (SEQ ID NO:2-22) and FIG. 3B is an alignment of the Nikisins RT-qPCR assay (SEQ ID NO:23-43). The Broad assay was designed using novel computational methods (Siddle, Metsky et al., in submission) to target conserved regions of the LASV genome, because degeneracy in primer- or probe-binding regions reduces the sensitivity of RT-qPCR assays. Degeneracy between strains can be visualized by the mean pairwise identity graphs at the top of each alignment. Bars show the percentage of sequences with the consensus residue at a given position, with a taller bar indicating a larger percentage of sequences sharing the consensus residue.

FIG. 4A shows reactions with probe concentration of 100 nm were more efficient those with concentrations of 200 nm. Fluorescence is quantified in Relative Fluorescence Units (RFUs). FIG. 4B charts RT-qPCR standard curve, showing linearity over a range of 4 orders of magnitude. The slope of the standard curve is −4.32 and the R2 value is 0.98.

FIG. 6A charts how the Broad assay positively detected a similar number of sequencing-positive SL-IV patient samples and significantly more sequencing-positive N-II patient samples compared to the Nikisins assay. FIG. 6B shows the two RT-qPCR assays had comparable Ct scores when detecting samples from the SL-IV clade (upper), but the Broad assay had lower Ct scores, which indicates higher assay efficiency, than the Nikisins assay for samples from the N-II clade (lower). Ct scores for all samples positively detected by both RT-qPCR assays are shown. Error bars represent one standard deviation based on three technical replicates.

FIG. 14A includes results of Cas13a-based detection reaction performed on assay-specific GBlock templates at a concentration of $10^9$. No amplification method was used for this reaction. FIG. 14B charts SHERLOCK detection of assay-specific GBlock at a concentration of $10^4$. GBlock templates were amplified using field-adapted RT-PCR methods described in section 2.3.2 and detected via a SHERLOCK detection step. FIG. 14C includes results of detection of EBOV patient samples using an EBOV SHERLOCK assay developed. The grey dashed line indicates the positive sample cutoff at 3 SD above the NTC. For panels A, B, and C, SHERLOCK reactions measured using the LightCycler 96 System's endpoint fluorescence measurements in relative fluorescence units (RFUs). All reactions were run in triplicate. Error bars indicate 1 SD.

FIG. 15A includes results of each SHERLOCK assay on a serial dilution of crRNA-specific GBlocks with concentrations from $10^5$ down to $10^1$. FIG. 15B provides results tested for each assay on a 1:20 dilution of one clade-specific clinical sample.

Figure 1A:
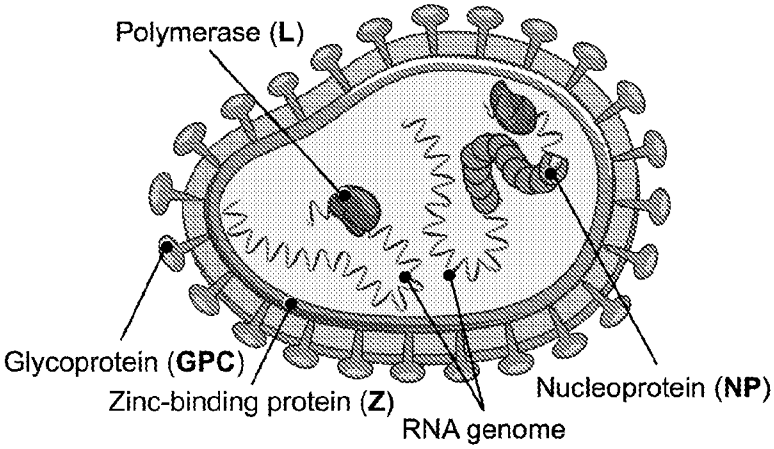
FIG. 1A is a Schematic of Lassa virus (LASV) virions.
Figure 1B:
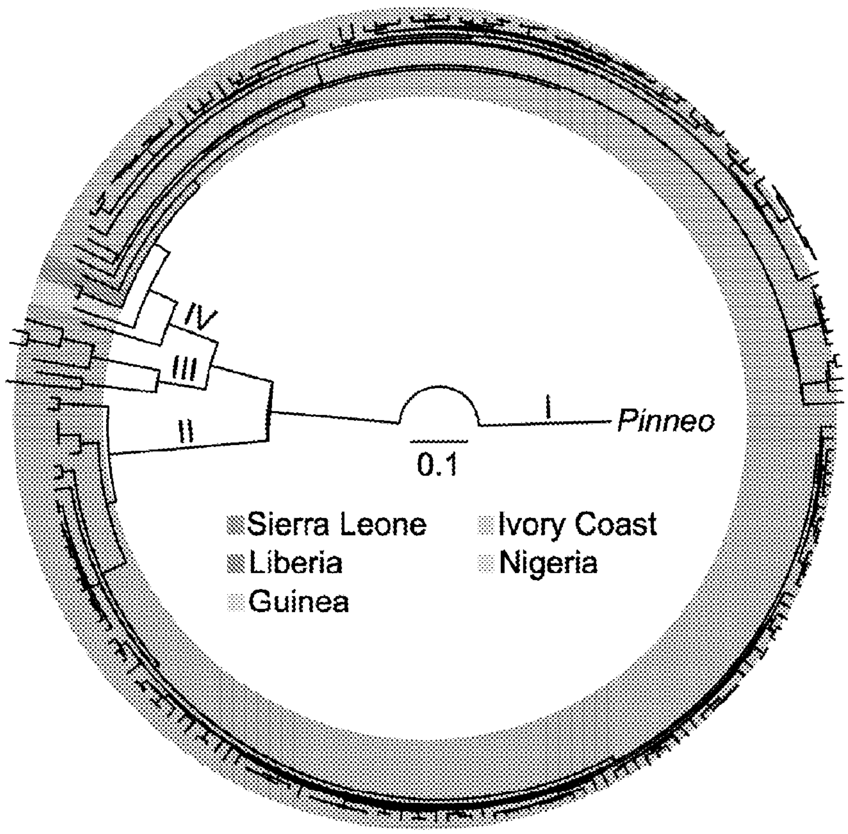
FIG. 1B is a phylogenetic tree of LASV S-segments showing four known viral lineages and their distinct geographic locations. Lineages N-II and SL-IV encompass a majority of LASV genetic diversity in Nigeria and Sierra Leone, respectively. Figures adapted from Andersen et al., 2015.
Figure 2:
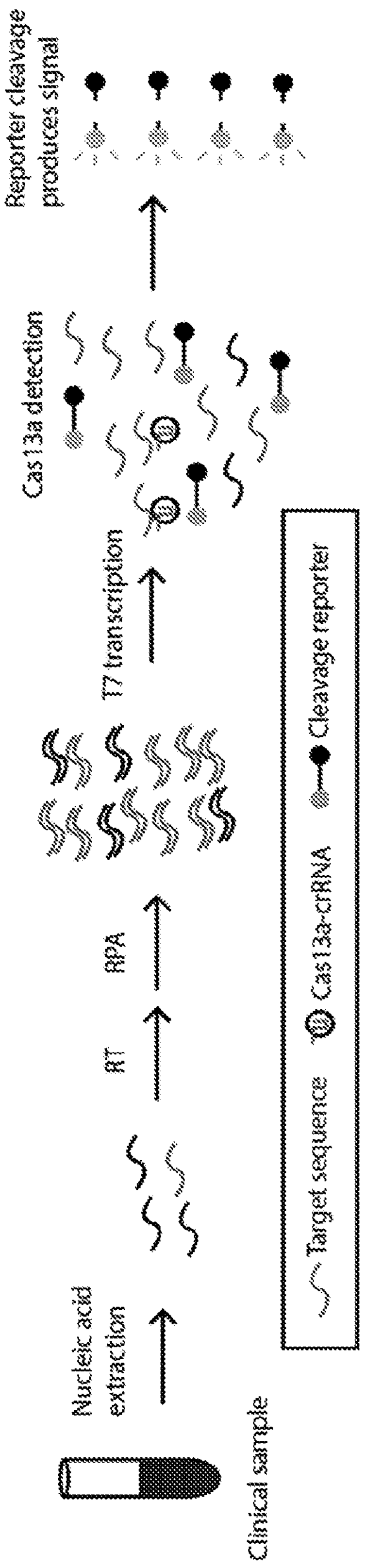
FIG. 2 depicts an exemplary method of clinical sample of hemorrhagic fever diagnosis using the Specific High-Sensitivity Enzymatic Reporter unlocking (SHERLOCK) detection pipeline. Nucleic acid is extracted from a clinical sample. RPA reactions amplify the target sequence via isothermal amplification. T7 RNA Polymerase reverse transcribes the amplified cDNA RPA product to RNA. Cas13a identifies and cleaves the target RNA sequence, initiating a collateral cleavage effect. Collateral cleavage of a RNA reporter results in fluorescence signal. Figure adapted from Myhrvold et al., Science, in press.
Figure 3A:
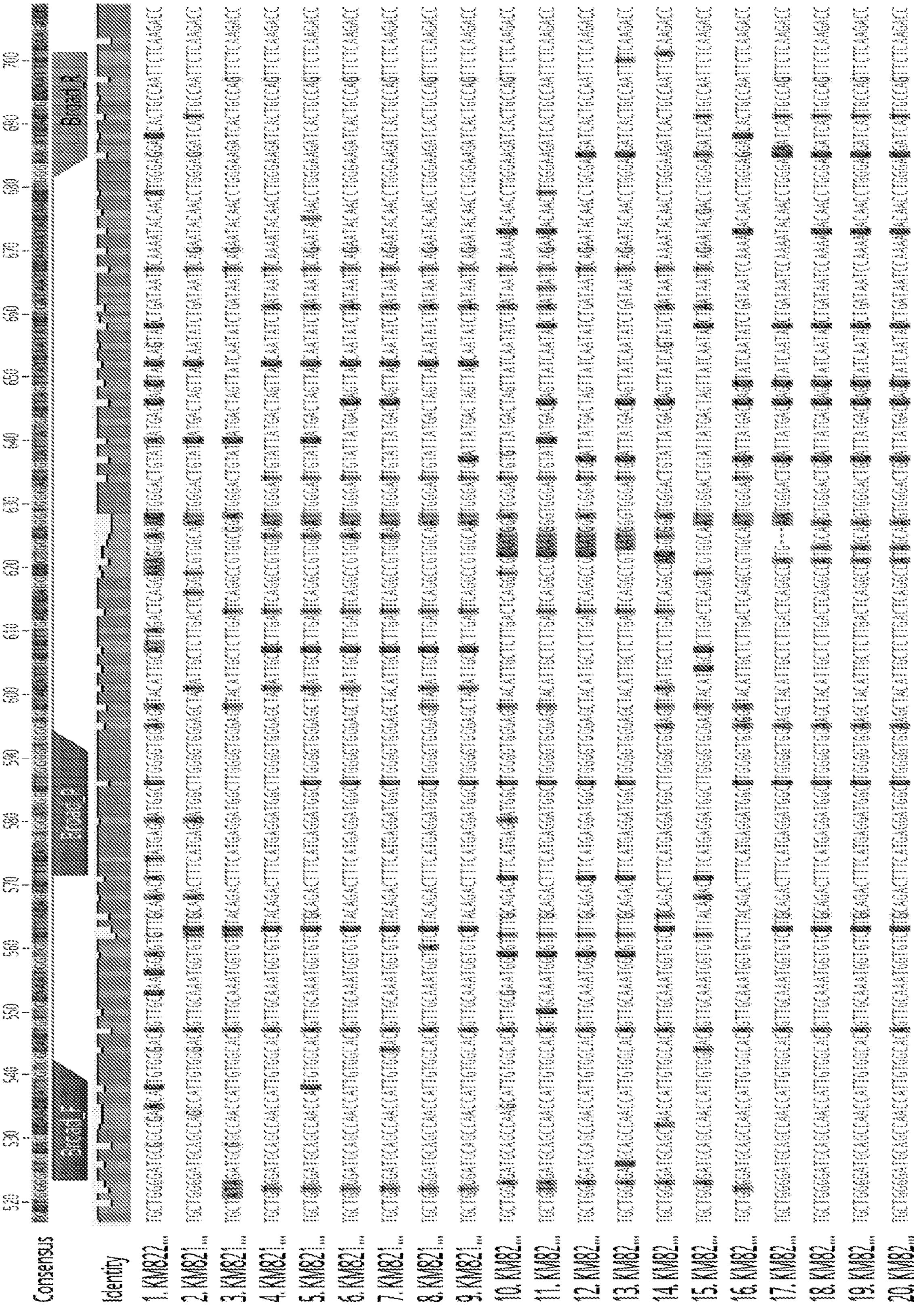
FIG. 3A-3B shows alignments to published Lassa virus (LASV) sequences of the SL-IV clade.
Figure 3B:
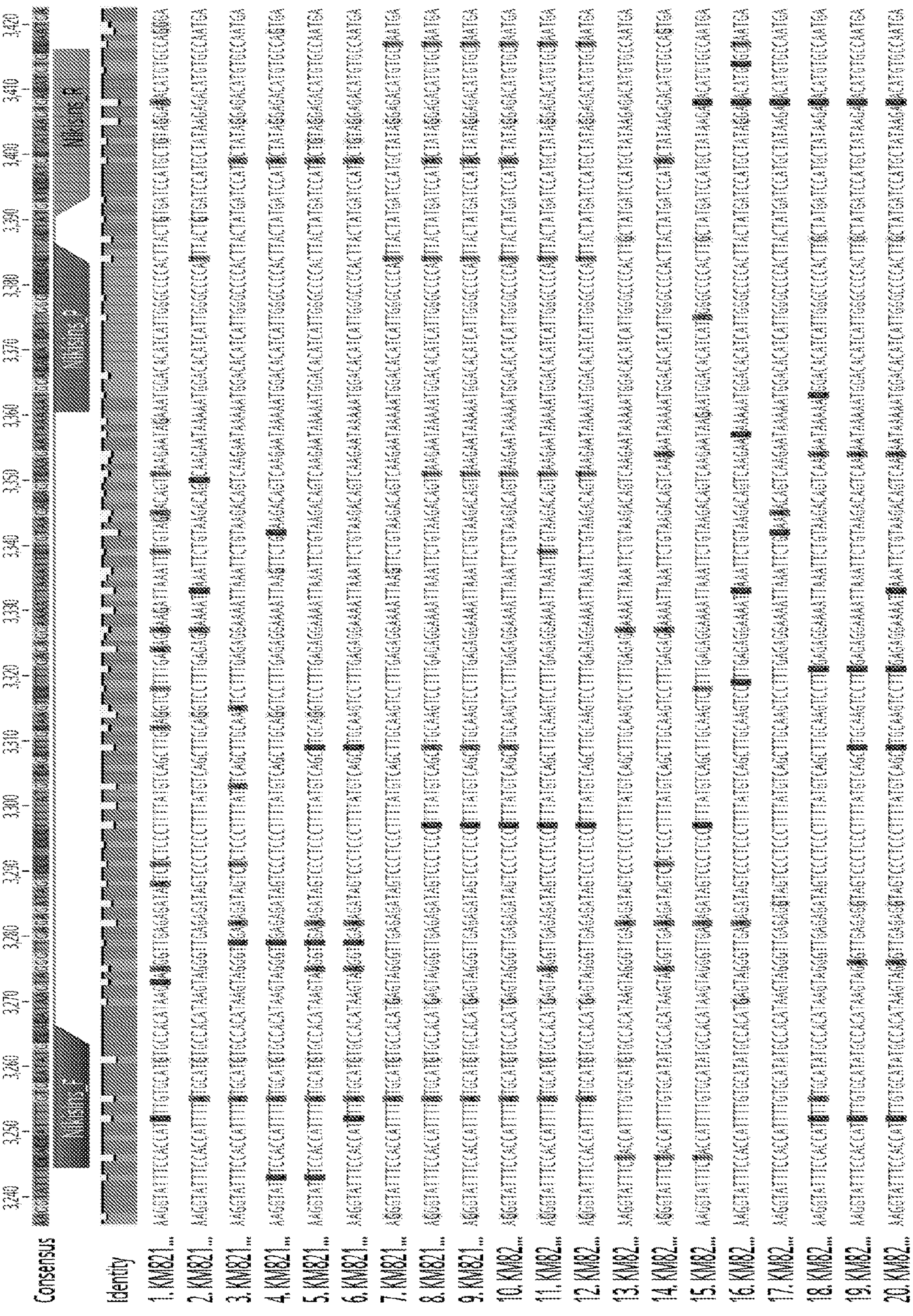
Figure 4A:
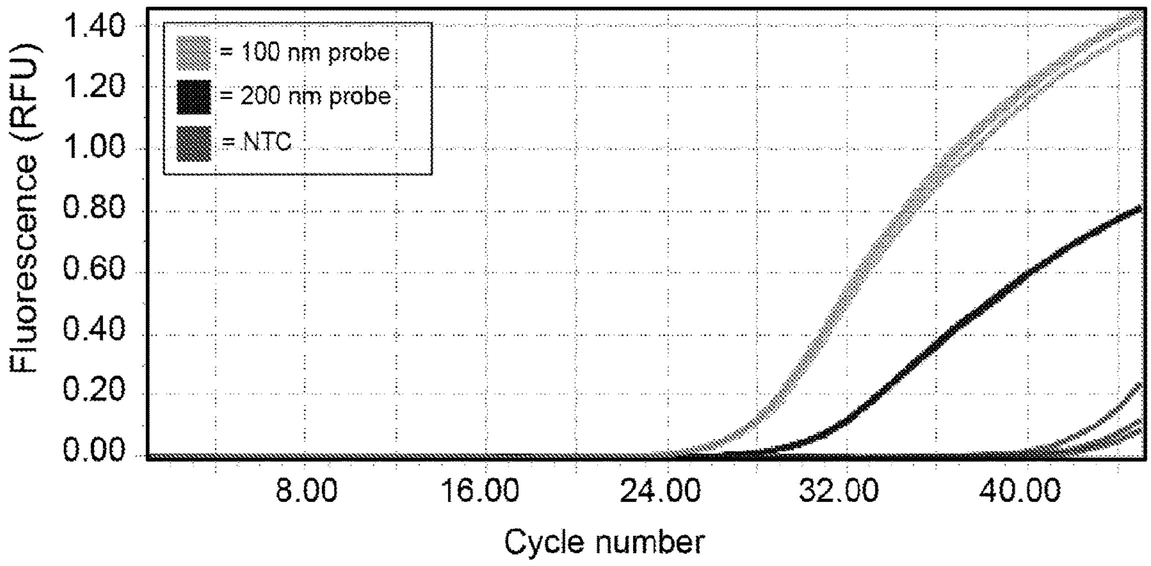
FIG. 4A-4B graphs studies of optimization of Broad RT-qPCR.
Figure 4B:
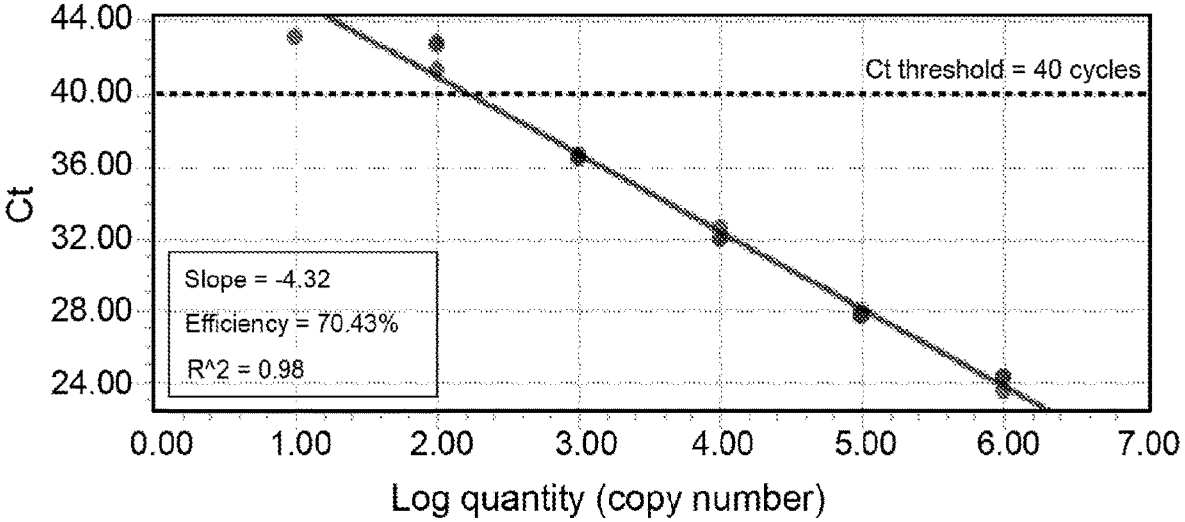

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook);

Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

"C2c2" is now referred to as "Cas13a", and the terms are used interchangeably herein unless indicated otherwise.

All publications, published patent documents, and patent applications cited herein are hereby incorporated by reference to the same extent as though each individual publication, published patent document, or patent application was specifically and individually indicated as being incorporated by reference.

Overview

Microbial Clustered Regularly Interspaced Short Palindromic Repeats (CRISPR) and CRISPR-associated (CRISPR-Cas) adaptive immune systems contain programmable endonucleases, such as Cas9 and Cpf1 (Shmakov et al., 2017; Zetsche et al., 2015). Single effector RNA-guided RNases have been recently discovered (Shmakov et al., 2015) and characterized (Abudayyeh et al., 2016; Smargon et al., 2017), including C2c2, providing a platform for specific RNA sensing. RNA-guided RNases can be easily and conveniently reprogrammed using CRISPR RNA (crRNAs) to cleave target RNAs. Unlike the DNA endonucleases Cas9 and Cpf1, which cleave only its DNA target, RNA-guided RNases, like C2c2, remains active after cleaving its RNA target, leading to "collateral" cleavage of non-targeted RNAs in proximity (Abudayyeh et al., 2016).

The presently disclosed embodiments utilize RNA targeting effectors to provide a robust CRISPR-based diagnostic for hemorrhagic fever viruses with attomolar sensitivity. Embodiments disclosed herein can detect both DNA and RNA with comparable levels of sensitivity and can differentiate targets from non-targets based on single base pair differences. Moreover, the embodiments disclosed herein can be prepared in freeze-dried format for convenient distribution and point-of-care (POC) applications. Such embodiments are useful in hemorrhagic viral detection, and detection of disease-associated cell free DNA. The embodiments disclosed herein may also be referred to as SHERLOCK (Specific High-sensitivity Enzymatic Reporter unLOCKing). In some embodiments, the SHERLOCK CRISPR-based diagnostic platform is utilized to provide an alternative method for LASV, EBOV or other hemorrhagic fever virus detection. Advantageously, the methods disclosed herein can be utilized in regions lacking PCR capacity. SHERLOCK is easily field-deployable and allows for rapid diagnosis, making it an ideal candidate for a point-of-care diagnostic. The SHERLOCK platform circumvents numerous logistic constraints that normally limit the feasibility of diagnostic assays in endemic regions. SHERLOCK reagents can be lyophilized and rehydrated, thus circumventing the need for a cold chain. SHERLOCK detection can be carried out on glass fiber paper, which drastically reduces the cost of reactions and eliminates the need for expensive laboratory equipment (Gootenberg et al., 2017). The methods disclosed herein can also be utilized with readily available lab equipment including a light cycler.

In one aspect, the embodiments disclosed herein are directed to a system for detecting the presence of hemorrhagic fever viruses in a sample comprising a CRISPR system comprising an effector protein and one or more guide molecules corresponding to one or more target molecules of one or more hemorrhagic fever viruses, and an RNA masking construct, and optional amplification reagents to amplify target nucleic acid molecules in a sample. In certain example embodiments, the system may further comprise one or more detection aptamers. The one or more detection aptamers may comprise an RNA polymerase site or primer binding site. The one or more detection aptamers can specifically bind one or more target polypeptides and can be configured such that the RNA polymerase site or primer binding site is exposed only upon binding of the detection aptamer to a target peptide. Exposure of the RNA polymerase site facilitates generation of a trigger RNA oligonucleotide using the aptamer sequence as a template. Accordingly, in such embodiments the one or more guide RNAs are configured to bind to a trigger RNA.

In one aspect, the one or more guide molecules are guide RNAs. In some embodiments, the guide RNAs are selected from the group consisting of SEQ ID NO: 80, 87-92, 109-126, 139-156, 159-172, 207-228, 249-281, 329-366, and 393-416. In one aspect, the guide RNAs correspond to target molecules of a hemorrhagic fever virus of interest selected from Lassa virus, Hantavirus, Crimean-Congo hemorrhagic fever virus, Lujo virus, Ebola virus, Marburg virus, or Rift Valley fever virus. In one embodiment, the hemorrhagic fever virus is Lassa virus or Ebola virus. In some instances, the Lass virus is SL-IV, N-II, or N-III. In some embodiments, when the hemorrhagic fever virus is Lassa virus, the one or more guide molecules are guide RNAs selected from the group consisting of SEQ ID NO: 87-92, 109-126, 139-156, 207-228, 249-281, 329-36; when the hemorrhagic fever virus is Ebola virus, the one or more guide molecules are guide RNAs selected from the group consisting of SEQ ID NO: 80, 159-172; or when the hemorrhagic fever virus is Marburg virus, one or more guide molecules are guide RNAs selected from the group consisting of SEQ ID NO: 393-416.

Guide Sequences

As used herein, the term "guide sequence," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence and to direct sequence-specific binding of a RNA-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Guide Modifications

In certain embodiments, guides of the invention comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine (Ψ), $N^1$-methylpseudouridine ($me^1Ψ$), 5-methoxyuridine(5 moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl(cEt), or 2'-O-methyl-3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015; Ragdarm et al., 0215, *PNAS, E*7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI: 10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl(cEt), or 2'-O-methyl-3'-thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS, E*7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife*, 2017, 6:e25312, DOI:10.7554).

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, use is made of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target RNA may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromouridine, pseudouridine (Ψ), $N^1$-methylpseudouridine ($me^1\Psi$), 5-methoxyuridine(5 moU), inosine, 7-methylguanosine, 2'-O-methyl-3'-phosphorothioate (MS), S-constrained ethyl(cEt), phosphorothioate (PS), or 2'-O-methyl-3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., *Nature Biomedical Engineering,* 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

A guide sequence, and hence a nucleic acid-targeting guide RNA may be selected to target any target nucleic acid sequence. In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nuclear RNA (snoRNA), double stranded RNA (dsRNA), non coding RNA (ncRNA), long non-coding RNA (lncRNA), and small cytoplasmic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In certain embodiments, the spacer length of the guide RNA is less than 28 nucleotides. In certain embodiments, the spacer length of the guide RNA is at least 18 nucleotides and less than 28 nucleotides. In certain embodiments, the spacer length of the guide RNA is between 19 and 28 nucleotides. In certain embodiments, the spacer length of the guide RNA is between 19 and 25 nucleotides. In certain embodiments, the spacer length of the guide RNA is 20 nucleotides. In certain embodiments, the spacer length of the guide RNA is 23 nucleotides. In certain embodiments, the spacer length of the guide RNA is 25 nucleotides.

In certain embodiments, modulations of cleavage efficiency can be exploited by introduction of mismatches, e.g. 1 or more mismatches, such as 1 or 2 mismatches between spacer sequence and target sequence, including the position of the mismatch along the spacer/target. The more central (i.e. not 3' or 5') for instance a double mismatch is, the more cleavage efficiency is affected. Accordingly, by choosing mismatch position along the spacer, cleavage efficiency can be modulated. By means of example, if less than 100% cleavage of targets is desired (e.g. in a cell population), 1 or more, such as preferably 2 mismatches between spacer and target sequence may be introduced in the spacer sequences. The more central along the spacer of the mismatch position, the lower the cleavage percentage.

In certain example embodiments, the cleavage efficiency may be exploited to design single guides that can distinguish two or more targets that vary by a single nucleotide, such as a single nucleotide polymorphism (SNP), variation, or (point) mutation. The CRISPR effector may have reduced sensitivity to SNPs (or other single nucleotide variations) and continue to cleave SNP targets with a certain level of efficiency. Thus, for two targets, or a set of targets, a guide RNA may be designed with a nucleotide sequence that is complementary to one of the targets i.e. the on-target SNP. The guide RNA is further designed to have a synthetic mismatch. As used herein a "synthetic mismatch" refers to a non-naturally occurring mismatch that is introduced upstream or downstream of the naturally occurring SNP, such as at most 5 nucleotides upstream or downstream, for instance 4, 3, 2, or 1 nucleotide upstream or downstream, preferably at most 3 nucleotides upstream or downstream, more preferably at most 2 nucleotides upstream or downstream, most preferably 1 nucleotide upstream or downstream (i.e. adjacent the SNP). When the CRISPR effector binds to the on-target SNP, only a single mismatch will be formed with the synthetic mismatch and the CRISPR effector will continue to be activated and a detectable signal produced. When the guide RNA hybridizes to an off-target SNP, two mismatches will be formed, the mismatch from the SNP and the synthetic mismatch, and no detectable signal generated. Thus, the systems disclosed herein may be designed to distinguish SNPs within a population. For, example the systems may be used to distinguish pathogenic strains that differ by a single SNP or detect certain disease specific SNPs, such as but not limited to, disease associated SNPs, such as without limitation cancer associated SNPs.

In certain embodiments, the guide RNA is designed such that the SNP is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the SNP is located on position 1, 2, 3, 4, 5, 6, 7, 8, or 9 of the spacer sequence (starting at the 5' end). In certain embodiments, the guide RNA is designed such that the SNP is located on position 2, 3, 4, 5, 6, or 7 of the spacer sequence (starting at the 5' end). In certain embodiments, the guide RNA is designed such that the SNP is located on position 3, 4, 5, or 6 of the spacer sequence (starting at the 5' end). In certain embodiments, the guide RNA is designed such that the SNP is located on position 3 of the spacer sequence (starting at the 5' end).

In certain embodiments, the guide RNA is designed such that the mismatch (e.g. the synthetic mismatch, i.e. an additional mutation besides a SNP) is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the mismatch is located on position 1, 2, 3, 4, 5, 6, 7, 8, or 9 of the spacer sequence (starting at the 5' end). In certain embodiments, the guide RNA is designed such that the mismatch is located on position 4, 5, 6, or 7 of the spacer sequence (starting at the 5' end). In certain embodiments, the guide RNA is designed such that the mismatch is located on position 5 of the spacer sequence (starting at the 5' end).

In certain embodiments, the guide RNA is designed such that the mismatch is located 2 nucleotides upstream of the SNP (i.e. one intervening nucleotide).

In certain embodiments, the guide RNA is designed such that the mismatch is located 2 nucleotides downstream of the SNP (i.e. one intervening nucleotide).

In certain embodiments, the guide RNA is designed such that the mismatch is located on position 5 of the spacer sequence (starting at the 5' end) and the SNP is located on position 3 of the spacer sequence (starting at the 5' end).

The embodiments described herein comprehend inducing one or more nucleotide modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s). The mutations can include the introduction, deletion, or substitution of 1-75 nucleotides at each target sequence of said cell(s) via the guide(s) RNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 40, 45, 50, 75, 100, 200, 300, 400 or 500 nucleotides at each target sequence of said cell(s) via the guide(s) RNA(s).

Typically, in the context of an endogenous CRISPR system, formation of a CRISPR complex (comprising a guide sequence hybridized to a target sequence and complexed with one or more Cas proteins) results in cleavage in or near (e.g. within 1, 2, 3, 4, 5, 6, 7, 8, 9, 10, 20, 50, or more base pairs from) the target sequence, but may depend on for instance secondary structure, in particular in the case of RNA targets.

In one aspect, the embodiments disclosed herein are directed to a nucleic acid detection system comprising two or more CRISPR systems one or more guide RNAs designed to bind to corresponding target molecules, a masking construct, and optional amplification reagents to amplify target nucleic acid molecules in a sample. In certain example embodiments, the system may further comprise one or more detection aptamers. The one or more detection aptamers may comprise a RNA polymerase site or primer binding site. The one or more detection aptamers specifically bind one or more target polypeptides and are configured such that the RNA polymerase site or primer binding site is exposed only upon binding of the detection aptamer to a target peptide. Exposure of the RNA polymerase site facilitates generation of a trigger RNA oligonucleotide using the aptamer sequence as a template. Accordingly, in such embodiments the one or more guide RNAs are configured to bind to a trigger RNA.

In another aspect, the embodiments disclosed herein are directed to a diagnostic device comprising a plurality of individual discrete volumes. Each individual discrete volume comprises a CRISPR effector protein, one or more guide RNAs designed to bind to a corresponding target molecule, and a masking construct. In certain example embodiments, RNA amplification reagents may be pre-loaded into the individual discrete volumes or be added to the individual discrete volumes concurrently with or subsequent to addition of a sample to each individual discrete volume. The device may be a microfluidic based device, a wearable device, or device comprising a flexible material substrate on which the individual discrete volumes are defined.

In another aspect, the embodiments disclosed herein are directed to a method for detecting target nucleic acids in a sample comprising distributing a sample or set of samples into a set of individual discrete volumes, each individual discrete volume comprising a CRISPR effector protein, one or more guide RNAs designed to bind to one target oligonucleotides, and a masking construct. The set of samples are then maintained under conditions sufficient to allow binding of the one or more guide RNAs to one or more target molecules. Binding of the one or more guide RNAs to a target nucleic acid in turn activates the CRISPR effector protein. Once activated, the CRISPR effector protein then deactivates the masking construct, for example, by cleaving the masking construct such that a detectable positive signal is unmasked, released, or generated. Detection of the positive detectable signal in an individual discrete volume indicates the presence of the target molecules.

In yet another aspect, the embodiments disclosed herein are directed to a method for detecting polypeptides. The method for detecting polypeptides is similar to the method for detecting target nucleic acids described above. However, a peptide detection aptamer is also included. The peptide detection aptamers function as described above and facilitate generation of a trigger oligonucleotide upon binding to a target polypeptide. The guide RNAs are designed to recognize the trigger oligonucleotides thereby activating the CRISPR effector protein. Deactivation of the masking construct by the activated CRISPR effector protein leads to unmasking, release, or generation of a detectable positive signal.

RNA-Based Masking Constructs

As used herein, a "masking construct" refers to a molecule that can be cleaved or otherwise deactivated by an activated CRISPR system effector protein described herein. The term "masking construct" may also be referred to in the alternative as a "detection construct." In certain example embodiments, the masking construct is a RNA-based masking construct. The RNA-based masking construct comprises a RNA element that is cleavable by a CRISPR effector protein. Cleavage of the RNA element releases agents or produces conformational changes that allow a detectable signal to be produced. Example constructs demonstrating how the RNA element may be used to prevent or mask generation of detectable signal are described below and embodiments of the invention comprise variants of the same. Prior to cleavage, or when the masking construct is in an 'active' state, the masking construct blocks the generation or detection of a positive detectable signal. It will be understood that in certain example embodiments a minimal background signal may be produced in the presence of an active RNA masking construct. A positive detectable signal may be any signal that can be detected using optical, fluorescent, chemiluminescent, electrochemical or other detection methods known in the art. The term "positive detectable signal" is used to differentiate from other detectable signals that may be detectable in the presence of the masking construct. For example, in certain embodiments a first signal may be detected when the masking agent is present (i.e. a negative detectable signal), which then converts to a second signal (e.g. the positive detectable signal) upon detection of the target molecules and cleavage or deactivation of the masking agent by the activated CRISPR effector protein.

In certain example embodiments, the masking construct may suppress generation of a gene product. The gene product may be encoded by a reporter construct that is added to the sample. The masking construct may be an interfering RNA involved in a RNA interference pathway, such as a short hairpin RNA (shRNA) or small interfering RNA (siRNA). The masking construct may also comprise microRNA (miRNA). While present, the masking construct suppresses expression of the gene product. The gene product may be a fluorescent protein or other RNA transcript or proteins that would otherwise be detectable by a labeled probe, aptamer, or antibody but for the presence of the masking construct. Upon activation of the effector protein the masking construct is cleaved or otherwise silenced allowing for expression and detection of the gene product as the positive detectable signal.

In certain example embodiments, the masking construct may sequester one or more reagents needed to generate a detectable positive signal such that release of the one or more reagents from the masking construct results in generation of the detectable positive signal. The one or more reagents may combine to produce a colorimetric signal, a chemiluminescent signal, a fluorescent signal, or any other detectable signal and may comprise any reagents known to be suitable for such purposes. In certain example embodiments, the one or more reagents are sequestered by RNA aptamers that bind the one or more reagents. The one or more reagents are released when the effector protein is activated upon detection of a target molecule and the RNA aptamers are degraded.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a RNA-based aptamer that can be cleaved by the activated effector protein upon detection of a target molecule.

In certain other example embodiments, the masking construct binds to an immobilized reagent in solution thereby blocking the ability of the reagent to bind to a separate labeled binding partner that is free in solution. Thus, upon application of a washing step to a sample, the labeled binding partner can be washed out of the sample in the absence of a target molecule. However, if the effector protein is activated, the masking construct is cleaved to a degree sufficient to interfere with the ability of the masking construct to bind the reagent thereby allowing the labeled binding partner to bind to the immobilized reagent. Thus, the labeled binding partner remains after the wash step indicating the presence of the target molecule in the sample. In certain aspects, the masking construct that binds the immobilized reagent is an RNA aptamer. The immobilized reagent may be a protein and the labeled minding partner may be a labeled antibody. Alternatively, the immobilized reagent may be streptavidin and the labeled binding partner may be labeled biotin. The label on the binding partner used in the above embodiments may be any detectable label known in the art. In addition, other known binding partners may be used in accordance with the overall design described herein.

In certain example embodiments, the masking construct may comprise a ribozyme. Ribozymes are RNA molecules having catalytic properties. Ribozymes, both naturally and engineered, comprise or consist of RNA that may be targeted by the effector proteins disclosed herein. The ribozyme may be selected or engineered to catalyze a reaction that either generates a negative detectable signal or prevents generation of a positive control signal. Upon deactivation of the ribozyme by the activated effector protein the reaction generating a negative control signal, or preventing generation of a positive detectable signal, is removed thereby allowing a positive detectable signal to be generated. In one example embodiment, the ribozyme may catalyze a colorimetric reaction causing a solution to appear as a first color. When the ribozyme is deactivated the solution then turns to a second color, the second color being the detectable positive signal. An example of how ribozymes can be used to catalyze a colorimetric reaction are described in Zhao et al. "Signal amplification of glucosamine-6-phosphate based on ribozyme glmS," Biosens Bioelectron. 2014; 16:337-42, and provide an example of how such a system could be modified to work in the context of the embodiments disclosed herein. Alternatively, ribozymes, when present can generate cleavage products of, for example, RNA transcripts. Thus, detection of a positive detectable signal may comprise detection of non-cleaved RNA transcripts that are only generated in the absence of the ribozyme.

In certain example embodiments, the one or more reagents is a protein, such as an enzyme, capable of facilitating generation of a detectable signal, such as a colorimetric, chemiluminescent, or fluorescent signal, that is inhibited or sequestered such that the protein cannot generate the detectable signal by the binding of one or more RNA aptamers to the protein. Upon activation of the effector proteins disclosed herein, the RNA aptamers are cleaved or degraded to an extent that they no longer inhibit the protein's ability to generate the detectable signal. In certain example embodiments, the aptamer is a thrombin inhibitor aptamer. In certain example embodiments the thrombin inhibitor aptamer has a sequence of GGGAACAAAGCUGAAGUA-CUUACCC (SEQ ID NO: 44). When this aptamer is cleaved, thrombin will become active and will cleave a peptide colorimetric or fluorescent substrate. In certain example embodiments, the colorimetric substrate is para-nitroanilide (pNA) covalently linked to the peptide substrate for thrombin. Upon cleavage by thrombin, pNA is released and becomes yellow in color and easily visible to the eye. In certain example embodiments, the fluorescent substrate is 7-amino-4-methylcoumarin a blue fluorophore that can be detected using a fluorescence detector. Inhibitory aptamers may also be used for horseradish peroxidase (HRP), beta-galactosidase, or calf alkaline phosphatase (CAP) and within the general principals laid out above.

In certain embodiments, RNAse activity is detected colorimetrically via cleavage of enzyme-inhibiting aptamers. One potential mode of converting RNAse activity into a colorimetric signal is to couple the cleavage of an RNA aptamer with the re-activation of an enzyme that is capable of producing a colorimetric output. In the absence of RNA cleavage, the intact aptamer will bind to the enzyme target and inhibit its activity. The advantage of this readout system is that the enzyme provides an additional amplification step: once liberated from an aptamervia collateral activity (e.g. Cas13a collateral activity), the colorimetric enzyme will continue to produce colorimetric product, leading to a multiplication of signal.

In certain embodiments, an existing aptamer that inhibits an enzyme with a colorimetric readout is used. Several aptamer/enzyme pairs with colorimetric readouts exist, such as thrombin, protein C, neutrophil elastase, and subtilisin. These proteases have colorimetric substrates based upon pNA and are commercially available. In certain embodiments, a novel aptamer targeting a common colorimetric enzyme is used. Common and robust enzymes, such as beta-galactosidase, horseradish peroxidase, or calf intestinal alkaline phosphatase, could be targeted by engineered aptamers designed by selection strategies such as SELEX. Such strategies allow for quick selection of aptamers with nanomolar binding efficiencies and could be used for the development of additional enzyme/aptamer pairs for colorimetric readout.

In certain embodiments, RNAse activity is detected colorimetrically via cleavage of RNA-tethered inhibitors. Many common colorimetric enzymes have competitive, reversible inhibitors: for example, beta-galactosidase can be inhibited by galactose. Many of these inhibitors are weak, but their effect can be increased by increases in local concentration. By linking local concentration of inhibitors to RNAse activity, colorimetric enzyme and inhibitor pairs can be engineered into RNAse sensors. The colorimetric RNAse sensor based upon small-molecule inhibitors involves three components: the colorimetric enzyme, the inhibitor, and a bridging RNA that is covalently linked to both the inhibitor and enzyme, tethering the inhibitor to the enzyme. In the uncleaved configuration, the enzyme is inhibited by the increased local concentration of the small molecule; when the RNA is cleaved (e.g. by Cas13a collateral cleavage), the inhibitor will be released and the colorimetric enzyme will be activated.

In certain embodiments, RNAse activity is detected colorimetrically via formation and/or activation of G-quadruplexes. G quadraplexes in DNA can complex with heme (iron (III)-protoporphyrin IX) to form a DNAzyme with peroxidase activity. When supplied with a peroxidase substrate (e.g. ABTS: (2,2'-Azinobis [3-ethylbenzothiazoline-6-sulfonic acid]-diammonium salt)), the G-quadraplex-heme complex in the presence of hydrogen peroxide causes oxidation of the substrate, which then forms a green color in solution. An example G-quadraplex forming DNA sequence is: GGGTAGGGCGGGTTGGGA (SEQ ID NO:45). By hybridizing an RNA sequence to this DNA aptamer, formation of the G-quadraplex structure will be limited. Upon RNAse collateral activation (e.g. C2c2-complex collateral activation), the RNA staple will be cleaved allowing the G quadraplex to form and heme to bind. This strategy is particularly appealing because color formation is enzymatic, meaning there is additional amplification beyond RNAse activation.

In certain example embodiments, the masking construct may be immobilized on a solid substrate in an individual discrete volume (defined further below) and sequesters a single reagent. For example, the reagent may be a bead comprising a dye. When sequestered by the immobilized reagent, the individual beads are too diffuse to generate a detectable signal, but upon release from the masking construct are able to generate a detectable signal, for example by aggregation or simple increase in solution concentration. In certain example embodiments, the immobilized masking agent is a RNA-based aptamer that can be cleaved by the activated effector protein upon detection of a target molecule.

In one example embodiment, the masking construct comprises a detection agent that changes color depending on whether the detection agent is aggregated or dispersed in solution. For example, certain nanoparticles, such as colloidal gold, undergo a visible purple to red color shift as they move from aggregates to dispersed particles. Accordingly, in certain example embodiments, such detection agents may be held in aggregate by one or more bridge molecules. See e.g. FIG. 43. At least a portion of the bridge molecule comprises RNA. Upon activation of the effector proteins disclosed herein, the RNA portion of the bridge molecule is cleaved allowing the detection agent to disperse and resulting in the corresponding change in color. See e.g. FIG. 46. In certain example embodiments the, bridge molecule is a RNA molecule. In certain example embodiments, the detection agent is a colloidal metal. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

When the RNA bridge is cut by the activated CRISPR effector, the beforementioned color shift is observed. In certain example embodiments the particles are colloidal metals. In certain other example embodiments, the colloidal metal is a colloidal gold. In certain example embodiments, the colloidal nanoparticles are 15 nm gold nanoparticles (AuNPs). Due to the unique surface properties of colloidal gold nanoparticles, maximal absorbance is observed at 520 nm when fully dispersed in solution and appear red in color to the naked eye. Upon aggregation of AuNPs, they exhibit a red-shift in maximal absorbance and appear darker in color, eventually precipitating from solution as a dark purple aggregate. In certain example embodiments the nanoparticles are modified to include DNA linkers extending from the surface of the nanoparticle. Individual particles are linked together by single-stranded RNA (ssRNA) bridges that hybridize on each end of the RNA to at least a portion of the DNA linkers. Thus, the nanoparticles will form a web of linked particles and aggregate, appearing as a dark precipitate. Upon activation of the CRISPR effectors disclosed herein, the ssRNA bridge will be cleaved, releasing the AU NPS from the linked mesh and producing a visible red color. Example DNA linkers and RNA bridge sequences are listed below. Thiol linkers on the end of the DNA linkers may be used for surface conjugation to the AuNPS. Other forms of conjugation may be used. In certain example embodiments, two populations of AuNPs may be generated, one for each DNA linker. This will help facilitate proper binding of the ssRNA bridge with proper orientation. In certain example embodiments, a first DNA linker is conjugated by the 3' end while a second DNA linker is conjugated by the 5' end.

TABLE 1A

| | |
|---|---|
| C2c2 colorimetric DNA1 | TTATAACTATTCCTAAAAAAAAAAA/3ThioMC3-D/ (SEQ. I.D. No. 46) |
| C2c2 colorimetric DNA2 | /5ThioMC6-D/AAAAAAAAAACTCCCCTAATAACAAT (SEQ. I.D. No. 47) |
| C2c2 colorimetric bridge | GGGUAGGAAUAGUUAUAAUUUCCCUUUCCCAUUGUUAUUAGGGAG (SEQ. I.D. No. 48) |

In certain other example embodiments, the masking construct may comprise an RNA oligonucleotide to which are attached a detectable label and a masking agent of that detectable label. An example of such a detectable label/masking agent pair is a fluorophore and a quencher of the fluorophore. Quenching of the fluorophore can occur as a result of the formation of a non-fluorescent complex between the fluorophore and another fluorophore or non-fluorescent molecule. This mechanism is known as ground-state complex formation, static quenching, or contact quenching. Accordingly, the RNA oligonucleotide may be designed so that the fluorophore and quencher are in sufficient proximity for contact quenching to occur. Fluorophores and their cognate quenchers are known in the art and can be selected for this purpose by one having ordinary skill in the art. The particular fluorophore/quencher pair is not critical in the context of this invention, only that selection of the fluorophore/quencher pairs ensures masking of the fluorophore. Upon activation of the effector proteins disclosed herein, the RNA oligonucleotide is cleaved thereby severing the proximity between the fluorophore and quencher needed to maintain the contact quenching effect. Accordingly, detection of the fluorophore may be used to determine the presence of a target molecule in a sample.

In certain other example embodiments, the masking construct may comprise one or more RNA oligonucleotides to which are attached one or more metal nanoparticles, such as gold nanoparticles. In some embodiments, the masking construct comprises a plurality of metal nanoparticles crosslinked by a plurality of RNA oligonucleotides forming a closed loop. In one embodiment, the masking construct comprises three gold nanoparticles crosslinked by three RNA oligonucleotides forming a closed loop. In some embodiments, the cleavage of the RNA oligonucleotides by the CRISPR effector protein leads to a detectable signal produced by the metal nanoparticles.

In certain other example embodiments, the masking construct may comprise one or more RNA oligonucleotides to which are attached one or more quantum dots. In some embodiments, the cleavage of the RNA oligonucleotides by the CRISPR effector protein leads to a detectable signal produced by the quantum dots.

In one example embodiment, the masking construct may comprise a quantum dot. The quantum dot may have multiple linker molecules attached to the surface. At least a portion of the linker molecule comprises RNA. The linker molecule is attached to the quantum dot at one end and to one or more quenchers along the length or at terminal ends of the linker such that the quenchers are maintained in sufficient proximity for quenching of the quantum dot to occur. The linker may be branched. As above, the quantum dot/quencher pair is not critical, only that selection of the quantum dot/quencher pair ensures masking of the fluorophore. Quantum dots and their cognate quenchers are known in the art and can be selected for this purpose by one having ordinary skill in the art Upon activation of the effector proteins disclosed herein, the RNA portion of the linker molecule is cleaved thereby eliminating the proximity between the quantum dot and one or more quenchers needed to maintain the quenching effect. In certain example embodiments the quantum dot is streptavidin conjugated. RNA are attached via biotin linkers and recruit quenching molecules with the sequences/5Bfiosg/UCUCGUACGUUC/3IAbRQSp/(SEQ ID NO. 49) or /5Biosg/UCUCGUACGUUCUCUCGUACGUUC/3IAbRQSp/(SEQ ID NO. 50), where /5Biosg/is a biotin tag and/31AbRQSp/is an Iowa black quencher. Upon cleavage, by the activated effectors disclosed herein the quantum dot will fluoresce visibly.

In a similar fashion, fluorescence energy transfer (FRET) may be used to generate a detectable positive signal. FRET is a non-radiative process by which a photon from an energetically excited fluorophore (i.e. "donor fluorophore") raises the energy state of an electron in another molecule (i.e. "the acceptor") to higher vibrational levels of the excited singlet state. The donor fluorophore returns to the ground state without emitting a fluoresce characteristic of that fluorophore. The acceptor can be another fluorophore or non-fluorescent molecule. If the acceptor is a fluorophore, the transferred energy is emitted as fluorescence characteristic of that fluorophore. If the acceptor is a non-fluorescent molecule the absorbed energy is loss as heat. Thus, in the context of the embodiments disclosed herein, the fluorophore/quencher pair is replaced with a donor fluorophore/acceptor pair attached to the oligonucleotide molecule. When intact, the masking construct generates a first signal (negative detectable signal) as detected by the fluorescence or heat emitted from the acceptor. Upon activation of the effector proteins disclosed herein the RNA oligonucleotide is cleaved and FRET is disrupted such that fluorescence of the donor fluorophore is now detected (positive detectable signal).

In certain example embodiments, the masking construct comprises the use of intercalating dyes which change their absorbance in response to cleavage of long RNAs to short nucleotides. Several such dyes exist. For example, pyronine-Y will complex with RNA and form a complex that has an absorbance at 572 nm. Cleavage of the RNA results in loss of absorbance and a color change. Methylene blue may be used in a similar fashion, with changes in absorbance at 688 nm upon RNA cleavage. Accordingly, in certain example embodiments the masking construct comprises a RNA and intercalating dye complex that changes absorbance upon the cleavage of RNA by the effector proteins disclosed herein.

In certain example embodiments, the masking construct may comprise an initiator for an HCR reaction. See e.g. Dirks and Pierce. PNAS 101, 15275-15728 (2004). HCR reactions utilize the potential energy in two hairpin species. When a single-stranded initiator having a portion of complementary to a corresponding region on one of the hairpins is released into the previously stable mixture, it opens a hairpin of one speces. This process, in turn, exposes a single-stranded region that opens a hairpin of the other species. This process, in turn, exposes a single stranded region identical to the original initiator. The resulting chain reaction may lead to the formation of a nicked double helix that grows until the hairpin supply is exhausted. Detection of the resulting products may be done on a gel or colorimetrically. Example colorimetric detection methods include, for example, those disclosed in Lu et al. "Ultra-sensitive colorimetric assay system based on the hybridization chain reaction-triggered enzyme cascade amplification ACS Appl Mater Interfaces, 2017, 9(1):167-175, Wang et al. "An enzyme-free colorimetric assay using hybridization chain reaction amplification and split aptamers" Analyst 2015, 150, 7657-7662, and Song et al. "Non covalent fluorescent labeling of hairpin DNA probe coupled with hybridization chain reaction for sensitive DNA detection." Applied Spectroscopy, 70(4): 686-694 (2016).

In certain example embodiments, the masking construct may comprise a HCR initiator sequence and a cleavable structural element, such as a loop or hairpin, that prevents the initiator from initiating the HCR reaction. Upon cleavage of the structure element by an activated CRISPR effector protein, the initiator is then released to trigger the HCR reaction, detection thereof indicating the presence of one or more targets in the sample. In certain example embodiments, the masking construct comprises a hairpin with a RNA loop. When an activated CRISPR effector protein cuts the RNA loop, the initiator can be released to trigger the HCR reaction.

Crispr Effector Proteins

In general, a CRISPR-Cas or CRISPR system as used herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference. CRISPR effector proteins described in International Application No. PCT/US2017/065477, Tables 1-6, pages 40-52, can be used in the presently disclosed methods, systems and devices, and are specifically incorporated herein by reference.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U. In certain embodiments, the effector protein may be *Leptotrichia shahii* C2c2p, more preferably *Leptotrichia shahii* DSM 19757 C2c2, and the 3' PAM is a 5' H.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

The nucleic acid molecule encoding a CRISPR effector protein, in particular C2c2, is advantageously codon optimized CRISPR effector protein. An example of a codon optimized sequence, is in this instance a sequence optimized for expression in eukaryotes, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell, in particular a C2c2 transgenic cell, in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well-established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter U6.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprises one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in PCT/US2017/038154 entitled "Novel Type VI CRISPR Orthologs and Systems," at, for example, pages 256-264 and 285-336, U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application 62/484,786 entitled "Novel Type VI CRISPR Orthologs and Systems," filed on Apr. 12, 2017.

In an embodiment of the invention, a HEPN domain comprises at least one RxxxxH motif comprising the sequence of R{N/H/K}X1X2X3H (SEQ ID NO:1). In an embodiment of the invention, a HEPN domain comprises a RxxxxH motif comprising the sequence of R{N/H}X1X2X3H (SEQ ID NO:51). In an embodiment of the invention, a HEPN domain comprises the sequence of R{N/K}X1X2X3H (SEQ ID NO:52). In certain embodiments, X1 is R, S, D, E, Q, N, G, Y, or H. In certain embodiments, X2 is I, S, T, V, or L. In certain embodiments, X3 is L, F, N, Y, V, I, S, D, E, or A.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

In particular embodiments, the Type VI RNA-targeting Cas enzyme is C2c2. In other example embodiments, the Type VI RNA-targeting Cas enzyme is Cas 13b. In particular embodiments, the homologue or orthologue of a Type VI protein such as C2c2 as referred to herein has a sequence homology or identity of at least 30%, or at least 40%, or at least 50%, or at least 60%, or at least 70%, or at least 80%, more preferably at least 85%, even more preferably at least 90%, such as for instance at least 95% with a Type VI protein such as C2c2 (e.g., based on the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2). In further embodiments, the homologue or orthologue of a Type VI protein such as C2c2 as referred to herein has a sequence identity of at least 30%, or at least 40%, or at least 50%, or at least 60%, or at least 70%, or at least 80%, more preferably at least 85%, even more preferably at least 90%, such as for instance at least 95% with the wild type C2c2 (e.g., based on the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM10710) C2c2, *Carnobacterium gallinarum* (DSM4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2).

In certain other example embodiments, the CRISPR system the effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016. . Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

RNase function in CRISPR systems is known, for example mRNA targeting has been reported for certain type III CRISPR-Cas systems (Hale et al., 2014, *Genes Dev*, vol. 28, 2432-2443; Hale et al., 2009, *Cell*, vol. 139, 945-956; Peng et al., 2015, *Nucleic acids research*, vol. 43, 406-417) and provides significant advantages. In the *Staphylococcus epidermis* type III-A system, transcription across targets results in cleavage of the target DNA and its transcripts, mediated by independent active sites within the Cas10-Csm ribonucleoprotein effector protein complex (see, Samai et al., 2015, Cell, vol. 151, 1164-1174). A CRISPR-Cas system, composition or method targeting RNA via the present effector proteins is thus provided.

In an embodiment, the Cas protein may be a C2c2 ortholog of an organism of a genus which includes but is not limited to *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*. Species of organism of such a genus can be as otherwise herein discussed.

In certain example embodiments, the C2c2 effector proteins of the invention include, without limitation, the following 21 ortholog species (including multiple CRISPR loci): *Leptotrichia shahii; Leptotrichia wadei* (Lw2); *Listeria seeligeri; Lachnospiraceae bacterium* MA2020; *Lachnospiraceae bacterium* NK4A179; [*Clostridium*]*aminophilum* DSM 10710; *Carnobacterium gallinarum* DSM 4847; *Carnobacterium gallinarum* DSM 4847 (second CRISPR Loci); *Paludibacter propionicigenes* WB4; *Listeria weihenstephanensis* FSL R9-0317; *Listeriaceae bacterium* FSL M6-0635; *Leptotrichia wadei* F0279; *Rhodobacter capsulatus* SB 1003; *Rhodobacter capsulatus* R121; *Rhodobacter capsulatus* DE442; *Leptotrichia buccalis* C-1013-b; *Herbinix hemicellulosilytica;* [*Eubacterium*] *rectale; Eubacteriaceae bacterium* CHKCI004; *Blautia* sp. Marseille-P2398; and *Leptotrichia* sp. oral taxon 879 str. F0557. Twelve (12) further non-limiting examples are: *Lachnospiraceae bacterium* NK4A144; *Chloroflexus aggregans; Demequina aurantiaca; Thalassospira* sp. TSL5-1; *Pseudobutyrivibrio* sp. OR37; *Butyrivibrio* sp. YAB3001; *Blautia* sp. Marseille-P2398; *Leptotrichia* sp. Marseille-P3007; *Bacteroides ihuae; Porphyromonadaceae bacterium* KH3CP3RA; *Listeria riparia*; and *Insolitispirillum peregrinum.*

Some methods of identifying orthologues of CRISPR-Cas system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. A chimeric enzyme can comprise a first fragment and a second fragment, and the fragments can be of CRISPR enzyme orthologs of organisms of genera herein mentioned or of species herein mentioned; advantageously the fragments are from CRISPR enzyme orthologs of different species.

In embodiments, the C2c2 protein as referred to herein also encompasses a functional variant of C2c2 or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be man-made. Advantageous embodiments can involve engineered or non-naturally occurring Type VI RNA-targeting effector protein.

In an embodiment, nucleic acid molecule(s) encoding the C2c2 or an ortholog or homolog thereof, may be codon-optimized for expression in a eukaryotic cell. A eukaryote can be as herein discussed. Nucleic acid molecule(s) can be engineered or non-naturally occurring.

In an embodiment, the C2c2 or an ortholog or homolog thereof, may comprise one or more mutations and hence nucleic acid molecule(s) coding for same may have mutation(s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

In an embodiment, the C2c2 or an ortholog or homolog thereof, may comprise one or more mutations. The mutations may be artificially introduced mutations and may include but are not limited to one or more mutations in a catalytic domain. Examples of catalytic domains with reference to a Cas enzyme may include but are not limited to HEPN domains.

In an embodiment, the C2c2 or an ortholog or homolog thereof, may be used as a generic nucleic acid binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In certain example embodiments, the C2c2 effector protein may be from an organism selected from the group consisting of; *Leptotrichia, Listeria*, Corynebacter, Sutterella, *Legionella, Treponema, Filifactor, Eubacterium, Streptococcus, Lactobacillus, Mycoplasma, Bacteroides, Flaviivola, Flavobacterium*, Sphaerochaeta, Azospirillum, *Gluconacetobacter, Neisseria, Roseburia, Parvibaculum, Staphylococcus, Nitratifractor, Mycoplasma*, and *Campylobacter.*

In certain embodiments, the effector protein may be a *Listeria* sp. C2c2p, preferably *Listeria* seeligeri C2c2p, more preferably *Listeria* seeligeri serovar 1/2b str. SLCC3954 C2c2p and the crRNA sequence may be 44 to 47 nucleotides in length, with a 5' 29-nt direct repeat (DR) and a 15-nt to 18-nt spacer.

In certain embodiments, the effector protein may be a *Leptotrichia* sp. C2c2p, preferably *Leptotrichia shahii* C2c2p, more preferably *Leptotrichia shahii* DSM 19757 C2c2p and the crRNA sequence may be 42 to 58 nucleotides in length, with a 5' direct repeat of at least 24 nt, such as a 5' 24-28-nt direct repeat (DR) and a spacer of at least 14 nt, such as a 14-nt to 28-nt spacer, or a spacer of at least 18 nt, such as 19, 20, 21, 22, or more nt, such as 18-28, 19-28, 20-28, 21-28, or 22-28 nt.

In certain example embodiments, the effector protein may be a *Leptotrichia* sp., *Leptotrichia wadei* F0279, or a *Listeria* sp., preferably *Listeria* newyorkensis FSL M6-0635.

In certain example embodiments, the C2c2 effector proteins of the invention include, without limitation, the following 21 ortholog species (including multiple CRISPR loci): *Leptotrichia shahii; Leptotrichia wadei* (Lw2); *Listeria seeligeri; Lachnospiraceae bacterium* MA2020*; Lachnospiraceae bacterium* NK4A179*;* [*Clostridium*]*aminophilum* DSM 10710*; Carnobacterium gallinarum* DSM 4847*; Carnobacterium gallinarum* DSM 4847 (second CRISPR Loci); *Paludibacter propionicigenes* WB4*; Listeria* weihenstephanensis FSL R9-0317*; Listeriaceae bacterium* FSL M6-0635*; Leptotrichia wadei* F0279*; Rhodobacter capsulatus* SB 1003*; Rhodobacter capsulatus* R121*; Rhodobacter capsulatus* DE442*; Leptotrichia buccalis* C-1013-b; *Herbinix hemicellulosilytica;* [*Eubacterium*] *rectale; Eubacteriaceae bacterium* CHKCI004*; Blautia* sp. Marseille-P2398; and *Leptotrichia* sp. oral taxon 879 str. F0557. Twelve (12) further non-limiting examples are: *Lachnospiraceae bacterium* NK4A144*; Chloroflexus aggregans; Demequina aurantiaca; Thalassospira* sp. TSL5-1*; Pseudobutyrivibrio* sp. OR37*; Butyrivibrio* sp. YAB3001*; Blautia* sp. Marseille-P2398*; Leptotrichia* sp. Marseille-P3007*; Bacteroides ihuae; Porphyromonadaceae bacterium* KH3CP3RA; *Listeria riparia*; and *Insolitispirillum peregrinum.*

In certain embodiments, the C2c2 protein according to the invention is or is derived from one of the orthologues or is a chimeric protein of two or more of the orthologues as described in this application, or is a mutant or variant of one of the orthologues (or a chimeric mutant or variant), including dead C2c2, split C2c2, destabilized C2c2, etc. as defined herein elsewhere, with or without fusion with a heterologous/functional domain.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017.

Amplification of Target

In certain example embodiments, target RNAs and/or DNAs may be amplified prior to activating the CRISPR effector protein. Any suitable RNA or DNA amplification technique may be used. In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

In certain example embodiments, the RNA or DNA amplification is NASBA, which is initiated with reverse transcription of target RNA by a sequence-specific reverse primer to create a RNA/DNA duplex. RNase H is then used to degrade the RNA template, allowing a forward primer containing a promoter, such as the T7 promoter, to bind and initiate elongation of the complementary strand, generating a double-stranded DNA product. The RNA polymerase promoter-mediated transcription of the DNA template then creates copies of the target RNA sequence. Importantly, each of the new target RNAs can be detected by the guide RNAs thus further enhancing the sensitivity of the assay. Binding of the target RNAs by the guide RNAs then leads to activation of the CRISPR effector protein and the methods proceed as outlined above. The NASBA reaction has the additional advantage of being able to proceed under moderate isothermal conditions, for example at approximately 41° C., making it suitable for systems and devices deployed for early and direct detection in the field and far from clinical laboratories.

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, a RNA polymerase promoter, such as a T7 promoter, is added to one of the primers. This results in an amplified double-stranded DNA product comprising the target sequence and a RNA polymerase promoter. After, or during, the RPA reaction, a RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above. In some embodiments, the RPA reagents comprise one or more primer pairs selected from the group consisting of SEQ. ID NO: XX-XX.

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride ($MgCl_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate $[(NH_4)_2SO_4]$, or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In some instances, the nucleic acid amplification reagents comprise recombinase polymerase amplification (RPA) reagents, nucleic acid sequence-based amplification (NASBA) reagents, loop-mediated isothermal amplification (LAMP) reagents, strand displacement amplification (SDA) reagents, helicase-dependent amplification (HDA) reagents, nicking enzyme amplification reaction (NEAR) reagents, RT-PCR reagents, multiple displacement amplification (MDA) reagents, rolling circle amplification (RCA) reagents, ligase chain reaction (LCR) reagents, ramification amplification method (RAM) reagents, transposase based amplification reagents; or Programmable CRISPR Nicking Amplification (PCNA) reagents.

In certain embodiments, detection of DNA with the methods or systems of the invention requires transcription of the (amplified) DNA into RNA prior to detection.

It will be evident that detection methods of the invention can involve nucleic acid amplification and detection procedures in various combinations. The nucleic acid to be detected can be any naturally occurring or synthetic nucleic acid, including but not limited to DNA and RNA, which may be amplified by any suitable method to provide an intermediate product that can be detected. Detection of the intermediate product can be by any suitable method including but not limited to binding and activation of a CRISPR protein which produces a detectable signal moiety by direct or collateral activity.

Hemorrhagic Fever Viruses

The systems, methods and devices disclosed herein can be used to detect RNA viruses that are able to cause hemorrhagic fevers. In some embodiments, the virus is selected from a virus from the family *Arenaviridae, Bunyaviridae, Filoviridae, Flaviviridae, Paramyxoviridae*, or *Rhabdoviridae*, including viruses from the genus *Hantavirus, Nairovirus, Phlebovirus, Henipavirus*. In some instances, the virus is selected from Lassa virus, Lujo virus, Junin virus, Machupo virus, Sabia virus, Chapare virus, Guanarito virus, hemorrhagic fever with renal syndrome (HFRS), Alkhurma Hemorrhagic Fever virus, the Crimean-Congo hemorrhagic fever (CCHF) virus, lymphocytic choriomeningitis virus, Garissa virus, Ilesha virus, Rift Valley fever virus, Ebola virus, Marburg virus, dengue, yellow fever, Omsk hemorrhagic fever virus, Kyasanur Forest disease virus, or a rhabdovirus.

METHODS

In another aspect, the embodiments disclosed herein are directed to a method for detecting target nucleic acids of a hemorrhagic fever virus in a sample comprising distributing a sample or set of samples into a set of individual discrete volumes, each individual discrete volume comprising a CRISPR effector protein, one or more guide RNAs designed to bind to one target oligonucleotides, and a masking construct. The set of samples are then maintained under conditions sufficient to allow binding of the one or more guide RNAs to one or more target molecules. Binding of the one or more guide RNAs to a target nucleic acid in turn activates the CRISPR effector protein. Once activated, the CRISPR effector protein then deactivates the masking construct, for example, by cleaving the masking construct such that a detectable positive signal is unmasked, released, or generated. Detection of the positive detectable signal in an individual discrete volume indicates the presence of the target molecules.

Target RNA/DNA Enrichment

In certain example embodiments, target RNA or DNA may first be enriched prior to detection or amplification of the target RNA or DNA. In certain example embodiments, this enrichment may be achieved by binding of the target nucleic acids by a CRISPR effector system.

Current target-specific enrichment protocols require single-stranded nucleic acid prior to hybridization with probes. Among various advantages, the present embodiments can skip this step and enable direct targeting to double-stranded DNA (either partly or completely double-stranded). In addition, the embodiments disclosed herein are enzyme-driven targeting methods that offer faster kinetics and easier workflow allowing for isothermal enrichment. In certain example embodiments enrichment may take place at temperatures as low as 20-37° C. In certain example embodiments, a set of guide RNAs to different target nucleic acids are used in a single assay, allowing for detection of multiple targets and/or multiple variants of a single target.

In certain example embodiments, a dead CRISPR effector protein may bind the target nucleic acid in solution and then subsequently be isolated from said solution. For example, the dead CRISPR effector protein bound to the target nucleic acid, may be isolated from the solution using an antibody or other molecule, such as an aptamer, that specifically binds the dead CRISPR effector protein.

In other example embodiments, the dead CRISPR effector protein may bound to a solid substrate. A fixed substrate may refer to any material that is appropriate for or can be modified to be appropriate for the attachment of a polypeptide or a polynucleotide. Possible substrates include, but are not limited to, glass and modified functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, the solid support comprises a patterned surface suitable for immobilization of molecules in an ordered pattern. In certain embodiments a patterned surface refers to an arrangement of different regions in or on an exposed layer of a solid support. In some embodiments, the solid support comprises an array of wells or depressions in a surface. The composition and geometry of the solid support can vary with its use. In some embodiments, the solids support is a planar structure such as a slide, chip, microchip and/or array. As such, the surface of the substrate can be in the form of a planar layer. In some embodiments, the solid support comprises one or more surfaces of a flowcell. The term "flowcell" as used herein refers to a chamber comprising a solid surface across which one or more fluid reagents can be flowed. Example flowcells and related fluidic systems and detection platforms that can be readily used in the methods of the present disclosure are described, for example, in Bentley et al. Nature 456:53-59 (2008), WO 04/0918497, U.S. Pat. No. 7,057,026; WO 91/06678; WO 07/123744; U.S. Pat. Nos. 7,329,492; 7,211,414; 7,315,019; 7,405,281, and US 2008/0108082. In some embodiments, the solid support or its surface is non-planar, such as the inner or outer surface of a tube or vessel. In some embodiments, the solid support comprise microspheres or beads. "Microspheres," "bead," "particles," are intended to mean within the context of a solid substrate to mean small discrete particles made of various material including, but not limited to, plastics, ceramics, glass, and polystyrene. In certain embodiments, the microspheres are magnetic microspheres or beads. Alternatively or additionally, the beads may be porous. The bead sizes range from nanometers, e.g. 100 nm, to millimeters, e.g. 1 mm.

A sample containing, or suspected of containing, the target nucleic acids may then be exposed to the substrate to allow binding of the target nucleic acids to the bound dead CRISPR effector protein. Non-target molecules may then be washed away. In certain example embodiments, the target nucleic acids may then be released from the CRISPR effector protein/guide RNA complex for further detection using the methods disclosed herein. In certain example embodiments, the target nucleic acids may first be amplified as described herein.

In certain example embodiments, the CRISPR effector may be labeled with a binding tag. In certain example embodiments the CRISPR effector may be chemically tagged. For example, the CRISPR effector may be chemically biotinylated. In another example embodiment, a fusion may be created by adding additional sequence encoding a fusion to the CRISPR effector. One example of such a fusion is an AviTag™, which employs a highly targeted enzymatic conjugation of a single biotin on a unique 15 amino acid peptide tag. In certain embodiments, the CRISPR effector may be labeled with a capture tag such as, but not limited to, GST, Myc, hemagglutinin (HA), green fluorescent protein (GFP), flag, His tag, TAP tag, and Fc tag. The binding tag, whether a fusion, chemical tag, or capture tag, may be used to either pull down the CRISPR effector system once it has bound a target nucleic acid or to fix the CRISPR effector system on the solid substrate.

In certain example embodiments, the guide RNA may be labeled with a binding tag. In certain example embodiments, the entire guide RNA may be labeled using in vitro transcription (IVT) incorporating one or more biotinylated nucleotides, such as, biotinylated uracil. In some embodiments, biotin can be chemically or enzymatically added to the guide RNA, such as, the addition of one or more biotin groups to the 3' end of the guide RNA. The binding tag may be used to pull down the guide RNA/target nucleic acid complex after binding has occurred, for example, by exposing the guide RNA/target nucleic acid to a streptavidin coated solid substrate.

Accordingly, in certain example embodiments, an engineered or non-naturally-occurring CRISPR effector may be used for enrichment purposes. In an embodiment, the modification may comprise mutation of one or more amino acid residues of the effector protein. The one or more mutations may be in one or more catalytically active domains of the effector protein. The effector protein may have reduced or abolished nuclease activity compared with an effector protein lacking said one or more mutations. The effector protein may not direct cleavage of the RNA strand at the target locus of interest. In a preferred embodiment, the one or more mutations may comprise two mutations. In a preferred embodiment the one or more amino acid residues are modified in a C2c2 effector protein, e.g., an engineered or non-naturally-occurring effector protein or C2c2. In particular embodiments, the one or more modified of mutated amino acid residues are one or more of those in C2c2 corresponding to R597, H602, R1278 and H1283 (referenced to Lsh C2c2 amino acids), such as mutations R597A, H602A, R1278A and H1283A, or the corresponding amino acid residues in Lsh C2c2 orthologues.

In particular embodiments, the one or more modified of mutated amino acid residues are one or more of those in C2c2 corresponding to K2, K39, V40, E479, L514, V518, N524, G534, K535, E580, L597, V602, D630, F676, L709, 1713, R717 (HEPN), N718, H722 (HEPN), E773, P823, V828, 1879, Y880, F884, Y997, L1001, F1009, L1013, Y1093, L1099, L1111, Y1114, L1203, D1222, Y1244, L1250, L1253, K1261, 11334, L1355, L1359, R1362, Y1366, E1371, R1372, D1373, R1509 (HEPN), H1514 (HEPN), Y1543, D1544, K1546, K1548, V1551, 11558, according to C2c2 consensus numbering. In certain embodiments, the one or more modified of mutated amino acid residues are one or more of those in C2c2 corresponding to R717 and R1509. In certain embodiments, the one or more modified of mutated amino acid residues are one or more of those in C2c2 corresponding to K2, K39, K535, K1261, R1362, R1372, K1546 and K1548. In certain embodiments, said mutations result in a protein having an altered or modified activity. In certain embodiments, said mutations result in a protein having a reduced activity, such as reduced specificity. In certain embodiments, said mutations result in a protein having no catalytic activity (i.e. "dead" C2c2). In an embodiment, said amino acid residues correspond to Lsh C2c2 amino acid residues, or the corresponding amino acid residues of a C2c2 protein from a different species. Devices that can facilitate these steps. In some embodiments, to reduce the size of a fusion protein of the Cas13b effector and the one or more functional domains, the C-terminus of the Cas13b effector can be truncated while still maintaining its RNA binding function. For example, at least 20 amino acids, at least 50 amino acids, at least 80 amino acids, or at least 100 amino acids, or at least 150 amino acids, or at least 200 amino acids, or at least 250 amino acids, or at least 300 amino acids, or at least 350 amino acids, or up to 120 amino acids, or up to 140 amino acids, or up to 160 amino acids, or up to 180 amino acids, or up to 200 amino acids, or up to 250 amino acids, or up to 300 amino acids, or up to 350 amino acids, or up to 400 amino acids, may be truncated at the C-terminus of the Cas13b effector. Specific examples of Cas13b truncations include C-terminal Δ984-1090, C-terminal Δ1026-1090, and C-terminal Δ1053-1090, C-terminal Δ934-1090, C-terminal Δ884-1090, C-terminal Δ834-1090, C-terminal Δ784-1090, and C-terminal Δ734-1090, wherein amino acid positions correspond to amino acid positions of *Prevotella* sp. P5-125 Cas13b protein.

The above enrichment systems may also be used to deplete a sample of certain nucleic acids. For example, guide RNAs may be designed to bind non-target RNAs to remove the non-target RNAs from the sample. In one example embodiment, the guide RNAs may be designed to bind nucleic acids that do carry a particular nucleic acid variation. For example, in a given sample a higher copy number of non-variant nucleic acids may be expected. Accordingly, the embodiments disclosed herein may be used to remove the non-variant nucleic acids from a sample, to increase the efficiency with which the detection CRISPR effector system can detect the target variant sequences in a given sample.

Amplification and/or Enhancement of Detectable Positive Signal

In certain example embodiments, further modification may be introduced that further amplify the detectable positive signal. For example, activated CRISPR effector protein collateral activation may be use to generate a secondary target or additional guide sequence, or both. In one example embodiment, the reaction solution would contain a secondary target that is spiked in at high concentration. The secondary target may be distinct from the primary target (i.e. the target for which the assay is designed to detect) and in certain instances may be common across all reaction volumes. A secondary guide sequence for the secondary target may be protected, e.g. by a secondary structural feature such as a hairpin with a RNA loop, and unable to bind the second target or the CRISPR effector protein. Cleavage of the protecting group by an activated CRISPR effector protein (i.e. after activation by formation of complex with the primary target(s) in solution) and formation of a complex with free CRISPR effector protein in solution and activation from the spiked in secondary target. In certain other example embodiments, a similar concept is used with a second guide sequence to a secondary target sequence. The secondary target sequence may be protected a structural feature or protecting group on the secondary target. Cleavage of a protecting group off the secondary target then allows additional CRISPR effector protein/second guide sequence/secondary target complex to form. In yet another example embodiment, activation of CRISPR effector protein by the primary target(s) may be used to cleave a protected or circularized primer, which is then released to perform an isothermal amplification reaction, such as those disclosed herein, on a template that encodes a secondary guide sequence, secondary target sequence, or both. Subsequent transcription of this amplified template would produce more secondary guide sequence and/or secondary target sequence, followed by additional CRISPR effector protein collateral activation.

Detection of Proteins

The systems, devices, and methods disclosed herein may also be adapted for detection of polypeptides (or other molecules) in addition to detection of nucleic acids, via incorporation of a specifically configured polypeptide detection aptamer. The polypeptide detection aptamers are distinct from the masking construct aptamers discussed above. First, the aptamers are designed to specifically bind to one or more target molecules. In one example embodiment, the target molecule is a target polypeptide. In another example embodiment, the target molecule is a target chemical compound, such as a target therapeutic molecule. Methods for designing and selecting aptamers with specificity for a given target, such as SELEX, are known in the art. In addition to specificity to a given target the aptamers are further designed to incorporate a RNA polymerase promoter binding site. In certain example embodiments, the RNA polymerase promoter is a T7 promoter. Prior to binding the aptamer binding to a target, the RNA polymerase site is not accessible or otherwise recognizable to a RNA polymerase. However, the aptamer is configured so that upon binding of a target the structure of the aptamer undergoes a conformational change such that the RNA polymerase promoter is then exposed. An aptamer sequence downstream of the RNA polymerase promoter acts as a template for generation of a trigger RNA oligonucleotide by a RNA polymerase. Thus, the template portion of the aptamer may further incorporate a barcode or other identifying sequence that identifies a given aptamer and its target. Guide RNAs as described above may then be designed to recognize these specific trigger oligonucleotide sequences. Binding of the guide RNAs to the trigger oligonucleotides activates the CRISPR effector proteins which proceeds to deactivate the masking constructs and generate a positive detectable signal as described previously.

Accordingly, in certain example embodiments, the methods disclosed herein comprise the additional step of distributing a sample or set of sample into a set of individual discrete volumes, each individual discrete volume comprising peptide detection aptamers, a CRISPR effector protein, one or more guide RNAs, a masking construct, and incubating the sample or set of samples under conditions sufficient to allow binding of the detection aptamers to the one or more target molecules, wherein binding of the aptamer to a corresponding target results in exposure of the RNA polymerase promoter binding site such that synthesis of a trigger RNA is initiated by the binding of a RNA polymerase to the RNA polymerase promoter binding site.

In another example embodiment, binding of the aptamer may expose a primer binding site upon binding of the aptamer to a target polypeptide. For example, the aptamer may expose a RPA primer binding site. Thus, the addition or inclusion of the primer will then feed into an amplification reaction, such as the RPA reaction outlined above.

In certain example embodiments, the aptamer may be a conformation-switching aptamer, which upon binding to the target of interest may change secondary structure and expose new regions of single-stranded DNA. In certain example embodiments, these new-regions of single-stranded DNA may be used as substrates for ligation, extending the aptamers and creating longer ssDNA molecules which can be specifically detected using the embodiments disclosed herein. The aptamer design could be further combined with ternary complexes for detection of low-epitope targets, such as glucose (Yang et al. 2015: DOI: 10.1021/ acs.analchem.5b01634). Example conformation shifting aptamers and corresponding guide RNAs (crRNAs) are shown below.

TABLE 1B

| | |
|---|---|
| Thrombin aptamer | (SEQ ID NO: 53) |
| Thrombin ligation probe | (SEQ ID NO: 54) |
| Thrombin RPA forward 1 primer | (SEQ ID NO: 55) |
| Thrombin RPA forward 2 primer | (SEQ ID NO: 56) |
| Thrombin RPA reverse 1 primer | (SEQ ID NO: 57) |
| Thrombin crRNA 1 | (SEQ ID NO: 58) |
| Thrombin crRNA 2 | (SEQ ID NO: 59) |
| Thrombin crRNA 3 | (SEQ ID NO: 60) |
| PTK7 full length amplicon control | (SEQ ID NO: 61) |
| PTK7 aptamer | (SEQ ID NO: 62) |
| PTK7 ligation probe | (SEQ ID NO: 63) |
| PTK7 RPA forward 1 primer | (SEQ ID NO: 64) |
| PTK7 RPA reverse 1 primer | (SEQ ID NO: 65) |
| PTK7 crRNA 1 | (SEQ ID NO: 66) |
| PTK7 crRNA 2 | (SEQ ID NO: 67) |
| PTK7 crRNA 3 | (SEQ ID NO: 68) |

Example Methods and Assays

The low cost and adaptability of the assay platform lends itself to a number of applications including (i) hemorrhagic fever viral RNA/DNA/protein quantitation, (ii) rapid, multiplexed RNA/DNA and protein expression detection of hemorrhagic fever viruses of interest, and (iii) sensitive detection of target nucleic acids, peptides, and proteins in both clinical and environmental samples. Additionally, the systems disclosed herein may be adapted for detection of transcripts within biological settings, such as cells. Given the highly specific nature of the CRISPR effectors described herein, it may possible to track allelic specific expression of transcripts or hemorrhagic fever disease-associated mutations in live cells.

In certain example embodiments, a single guide sequence specific to a single target is placed in separate volumes. Each volume may then receive a different sample or aliquot of the same sample. In certain example embodiments, multiple guide sequences each to separate target may be placed in a single well such that multiple targets may be screened in a different well. In order to detect multiple guide RNAs in a single volume, in certain example embodiments, multiple effector proteins with different specificities may be used. For example, different orthologs with different sequence specificities may be used. For example, one orthologue may preferentially cut A, while others preferentially cut C, G, U/T. Accordingly, masking constructs completely comprising, or comprised of a substantial portion, of a single nucleotide may be generated, each with a different fluorophore that can be detected at differing wavelengths. In this way up to four different targets may be screened in a single individual discrete volume. In certain example embodiments, different orthologues from a same class of CRISPR effector protein may be used, such as two Cas13a orthologues, two Cas13b orthologues, or two Cas13c orthologues, which is described in International Application No. PCT/US2017/065477, Tables 1-6, pages 40-52, and incorporated herein by reference. On certain other example embodiments, different orthologues with different nucleotide editing preferences may be used such as a Cas13a and Cas13b orthologs, or a Cas13a and a Cas13c orthologs, or a Cas13b orthologs and a Cas13c orthologs etc. In certain example embodiments, a Cas13 protein with a polyU preference and a Cas13 protein with a polyA preference are used. In certain example embodiments, the Cas13 protein with a polyU preference is a *Prevotella intermedia* Cas13b. and the Cas13 protein with a polyA preference is a *Prevotella* sp. MA2106 Cas13b protein (PsmCas13b). In certain example embodiments, the Cas13 protein with a polyU preference is a *Leptotrichia wadei* Cas13a (LwaCas13a) protein and the Cas13 protein with a poly A preference is a *Prevotella* sp. MA2106 Cas13b protein. In certain example embodiments, the Cas13 protein with a polyU preference is Capnocytophaga canimorsus Cas13b protein (CcaCas13b).

In addition to single base editing preferences. Additional detection constructs can be designed based on other motif cutting preferences of Cas13 and Cas12 orthologs. For example, Cas13 or Cas12 orthologs may preferentially cut a dinucleotide sequence, a trinucleotide sequence or more complex motifs comprising 4, 5, 6, 7, 8, 9, or 10 nucleotide motifs. Thus the upper bound for multiplex assays using the embodiments disclosed herein is primarily limited by the number of distinguishable detectable labels and the detection channels needed to detect them. In certain example embodiments, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different targets are detected. Example methods for identifying such motifs are further disclosed in the Working Examples below.

CRISPR effector systems are capable of detecting down to attomolar concentrations of target molecules, and due to the sensitivity of said systems, a number of applications that require rapid and sensitive detection may benefit from the embodiments disclosed herein, and are contemplated to be within the scope of the invention. Example assays and applications are described in further detail below.

Microbial Applications

In certain example embodiments, the systems, devices, and methods, disclosed herein are directed to detecting the presence of one or more microbial agents in a sample, such as a biological sample obtained from a subject. In certain example embodiments, the microbe may be a bacterium, a fungus, a yeast, a protozoa, a parasite, or a virus. Accordingly, the methods disclosed herein can be adapted for use in other methods (or in combination) with other methods that require quick identification of microbe species, monitoring the presence of microbial proteins (antigens), antibodies, antibody genes, detection of certain phenotypes (e.g. bacterial resistance), monitoring of disease progression and/or outbreak, and antibiotic/antiviral screening. Because of the rapid and sensitive diagnostic capabilities of the embodiments disclosed here, detection of microbe species type, down to a single nucleotide difference, and the ability to be deployed as a POC device, the embodiments disclosed herein may be used guide therapeutic regimens, such as selection of the appropriate antibiotic or antiviral. The embodiments disclosed herein may also be used to screen environmental samples (air, water, surfaces, food etc.) for the presence of microbial contamination.

Disclosed is a method to identify microbial species, in particular hemorrhagic fever viruses, or the like. Particular embodiments disclosed herein describe methods and systems that will identify and distinguish microbial species within a single sample, or across multiple samples, allowing for recognition of many different microbes. The present methods allow the detection of pathogens and distinguishing between two or more species of one or more organisms, e.g., bacteria, viruses, yeast, protozoa, and fungi or a combination thereof, in a biological or environmental sample, by detecting the presence of a target nucleic acid sequence in the sample. A positive signal obtained from the sample indicates the presence of the microbe. Multiple microbes can be identified simultaneously using the methods and systems of the invention, by employing the use of more than one effector protein, wherein each effector protein targets a specific microbial target sequence. In this way, a multi-level analysis can be performed for a particular subject in which any number of microbes can be detected at once. In some embodiments, simultaneous detection of multiple microbes may be performed using a set of probes that can identify one or more microbial species.

Multiplex analysis of samples enables large-scale detection of samples, reducing the time and cost of analyses. However, multiplex analyses are often limited by the availability of a biological sample. In accordance with the invention, however, alternatives to multiplex analysis may be performed such that multiple effector proteins can be added to a single sample and each masking construct may be combined with a separate quencher dye. In this case, positive signals may be obtained from each quencher dye separately for multiple detection in a single sample.

Disclosed herein are methods for distinguishing between two or more species of one or more organisms in a sample. The methods are also amenable to detecting one or more species of one or more organisms in a sample.

Microbe Detection

In some embodiments, a method for detecting microbes in samples is provided comprising distributing a sample or set of samples into one or more individual discrete volumes, the individual discrete volumes comprising a CRISPR system as described herein; incubating the sample or set of samples under conditions sufficient to allow binding of the one or more guide RNAs to one or more microbe-specific targets; activating the CRISPR effector protein via binding of the one or more guide RNAs to the one or more target molecules, wherein activating the CRISPR effector protein results in modification of the RNA-based masking construct such that a detectable positive signal is generated; and detecting the detectable positive signal, wherein detection of the detectable positive signal indicates a presence of one or more target molecules in the sample. The one or more target molecules may be mRNA, gDNA (coding or non-coding), tRNA, or rRNA comprising a target nucleotide tide sequence that may be used to distinguish two or more microbial species/strains from one another. The guide RNAs may be designed to detect target sequences. The embodiments disclosed herein may also utilize certain steps to improve hybridization between guide RNA and target RNA sequences. Methods for enhancing ribonucleic acid hybridization are disclosed in WO 2015/085194, entitled "Enhanced Methods of Ribonucleic Acid Hybridization" which is incorporated herein by reference. The microbe-specific target may be RNA or DNA or a protein. If DNA method may further comprise the use of DNA primers that introduce a RNA polymerase promoter as described herein. If the target is a protein than the method will utilized aptamers and steps specific to protein detection described herein.

Detection of Single Nucleotide Variants

In some embodiments, one or more identified target sequences may be detected using guide RNAs that are specific for and bind to the target sequence as described herein. The systems and methods of the present invention can distinguish even between single nucleotide polymorphisms present among different microbial species and therefore, use of multiple guide RNAs in accordance with the invention may further expand on or improve the number of target sequences that may be used to distinguish between species. For example, in some embodiments, the one or more guide RNAs may distinguish between microbes at the species, genus, family, order, class, phylum, kingdom, or phenotype, or a combination thereof.

Detection Based on rRNA Sequences

In certain example embodiments, the devices, systems, and methods disclosed herein may be used to distinguish multiple microbial species in a sample. In certain example embodiments, identification may be based on ribosomal RNA sequences, including the 16S, 23S, and 5S subunits. Methods for identifying relevant rRNA sequences are disclosed in U.S. Patent Application Publication No. 2017/0029872. In certain example embodiments, a set of guide RNA may designed to distinguish each species by a variable region that is unique to each species or strain. Guide RNAs may also be designed to target RNA genes that distinguish microbes at the genus, family, order, class, phylum, kingdom levels, or a combination thereof. In certain example embodiments where amplification is used, a set of amplification primers may be designed to flanking constant regions of the ribosomal RNA sequence and a guide RNA designed to distinguish each species by a variable internal region. In certain example embodiments, the primers and guide RNAs may be designed to conserved and variable regions in the 16S subunit respectfully. Other genes or genomic regions that uniquely variable across species or a subset of species such as the RecA gene family, RNA polymerase R subunit, may be used as well. Other suitable phylogenetic markers, and methods for identifying the same, are discussed for example in Wu et al. arXiv:1307.8690 [q-bio.GN].

In certain example embodiments, a method or diagnostic is designed to screen microbes across multiple phylogenetic and/or phenotypic levels at the same time. For example, the method or diagnostic may comprise the use of multiple CRISPR systems with different guide RNAs. A first set of guide RNAs may distinguish, for example, between mycobacteria, gram positive, and gram negative bacteria. These general classes can be even further subdivided. For example, guide RNAs could be designed and used in the method or diagnostic that distinguish enteric and non-enteric within gram negative bacteria. A second set of guide RNA can be designed to distinguish microbes at the genus or species level. Thus a matrix may be produced identifying all mycobacteria, gram positive, gram negative (further divided into enteric and non-enteric) with each genus of species of bacteria identified in a given sample that fall within one of those classes. The foregoing is for example purposes only. Other means for classifying other microbe types are also contemplated and would follow the general structure described above.

Screening for Drug Resistance

In certain example embodiments, the devices, systems and methods disclosed herein may be used to screen for microbial genes of interest, for example antibiotic and/or antiviral resistance genes. Guide RNAs may be designed to distinguish between known genes of interest. Samples, including clinical samples, may then be screened using the embodiments disclosed herein for detection of such genes. The ability to screen for drug resistance at POC would have tremendous benefit in selecting an appropriate treatment regime. In certain example embodiments, the antibiotic resistance genes are carbapenemases including KPC, NDM1, CTX-M15, OXA-48. Other antibiotic resistance genes are known and may be found for example in the Comprehensive Antibiotic Resistance Database (Jia et al. "CARD 2017: expansion and model-centric curation of the Comprehensive Antibiotic Resistance Database." Nucleic Acids Research, 45, D566-573).

Ribavirin is an effective antiviral that hits a number of RNA viruses. Several clinically important viruses have evolved ribavirin resistance including Foot and Mouth Disease Virus doi:10.1128/JVI.03594-13; polio virus (Pfeifer and Kirkegaard. PNAS, 100(12):7289-7294, 2003); and hepatitis C virus (Pfeiffer and Kirkegaard, J. Virol. 79(4): 2346-2355, 2005). A number of other persistent RNA viruses, such as hepatitis and HIV, have evolved resistance to existing antiviral drugs: hepatitis B virus (lamivudine, tenofovir, entecavir) doi:10/1002/hep22900; hepatitis C virus (telaprevir, BILN2061, ITMN-191, SCh6, boceprevir, AG-021541, ACH-806) doi:10.1002/hep.22549; and HIV (many drug resistance mutations) hivdb.standford.edu. The embodiments disclosed herein may be used to detect such variants among others.

Aside from drug resistance, there are a number of clinically relevant mutations that could be detected with the embodiments disclosed herein, such as persistent versus acute infection and increased infectivity of Ebola.

As described herein elsewhere, closely related microbial species (e.g. having only a single nucleotide difference in a given target sequence) may be distinguished by introduction of a synthetic mismatch in the gRNA.

Set Cover Approaches

In particular embodiments, a set of guide RNAs is designed that can identify, for example, all microbial species within a defined set of microbes. In certain example embodiments, the methods for generating guide RNAs as described herein may be compared to methods disclosed in WO 2017/040316, incorporated herein by reference. As described in WO 2017040316, a set cover solution may identify the minimal number of target sequences probes or guide RNAs needed to cover an entire target sequence or set of target sequences, e.g. a set of genomic sequences. Set cover approaches have been used previously to identify primers and/or microarray probes, typically in the 20 to 50 base pair range. See, e.g. Pearson et al., cs.virginia.edu/-robins/papers/primers_dam11_final.pdf., Jabado et al. Nucleic Acids Res. 2006 34(22):6605-11, Jabado et al. Nucleic Acids Res. 2008, 36(1):e3 doi10.1093/nar/gkm1106, Duitama et al. Nucleic Acids Res. 2009, 37(8): 2483-2492, Phillippy et al. BMC Bioinformatics. 2009, 10:293 doi:10.1186/1471-2105-10-293. However, such approaches generally involved treating each primer/probe as k-mers and searching for exact matches or allowing for inexact matches using suffix arrays. In addition, the methods generally take a binary approach to detecting hybridization by selecting primers or probes such that each input sequence only needs to be bound by one primer or probe and the position of this binding along the sequence is irrelevant. Alternative methods may divide a target genome into predefined windows and effectively treat each window as a separate input sequence under the binary approach—i.e. they determine whether a given probe or guide RNA binds within each window and require that all of the windows be bound by the state of some probe or guide RNA. Effectively, these approaches treat each element of the "universe" in the set cover problem as being either an entire input sequence or a pre-defined window of an input sequence, and each element is considered "covered" if the start of a probe or guide RNA binds within the element. These approaches limit the fluidity to which different probe or guide RNA designs are allowed to cover a given target sequence.

In contrast, the embodiments disclosed herein are directed to detecting longer probe or guide RNA lengths, for example, in the range of 70 bp to 200 bp that are suitable for hybrid selection sequencing. In addition, the methods disclosed WO 2017/040316 herein may be applied to take a pan-target sequence approach capable of defining a probe or guide RNA sets that can identify and facilitate the detection sequencing of all species and/or strains sequences in a large and/or variable target sequence set. For example, the methods disclosed herein may be used to identify all variants of a given virus, or multiple different viruses in a single assay. Further, the method disclosed herein treat each element of the "universe" in the set cover problem as being a nucleotide of a target sequence, and each element is considered "covered" as long as a probe or guide RNA binds to some segment of a target genome that includes the element. These type of set cover methods may be used instead of the binary approach of previous methods, the methods disclosed in herein better model how a probe or guide RNA may hybridize to a target sequence. Rather than only asking if a given guide RNA sequence does or does not bind to a given window, such approaches may be used to detect a hybridization pattern—i.e. where a given probe or guide RNA binds to a target sequence or target sequences—and then determines from those hybridization patterns the minimum number of probes or guide RNAs needed to cover the set of target sequences to a degree sufficient to enable both enrichment from a sample and sequencing of any and all target sequences. These hybridization patterns may be determined by defining certain parameters that minimize a loss function, thereby enabling identification of minimal probe or guide RNA sets in a way that allows parameters to vary for each species, e.g. to reflect the diversity of each species, as well as in a computationally efficient manner that cannot be achieved using a straightforward application of a set cover solution, such as those previously applied in the probe or guide RNA design context.

The ability to detect multiple transcript abundances may allow for the generation of unique microbial signatures indicative of a particular phenotype. Various machine learning techniques may be used to derive the gene signatures. Accordingly, the guide RNAs of the CRISPR systems may be used to identify and/or quantitate relative levels of biomarkers defined by the gene signature in order to detect certain phenotypes. In certain example embodiments, the gene signature indicates susceptibility to an antibiotic, resistance to an antibiotic, or a combination thereof.

In one aspect of the invention, a method comprises detecting one or more pathogens. In this manner, differentiation between infection of a subject by individual microbes may be obtained. In some embodiments, such differentiation may enable detection or diagnosis by a clinician of specific diseases, for example, different variants of a disease. Preferably the pathogen sequence is a genome of the pathogen or a fragment thereof. The method further may comprise determining the evolution of the pathogen. Determining the evolution of the pathogen may comprise identification of pathogen mutations, e.g. nucleotide deletion, nucleotide insertion, nucleotide substitution. Amongst the latter, there are non-synonymous, synonymous, and noncoding substitutions. Mutations are more frequently non-synonymous during an outbreak. The method may further comprise determining the substitution rate between two pathogen sequences analyzed as described above. Whether the mutations are deleterious or even adaptive would require functional analysis, however, the rate of non-synonymous mutations suggests that continued progression of this epidemic could afford an opportunity for pathogen adaptation, underscoring the need for rapid containment. Thus, the method may further comprise assessing the risk of viral adaptation, wherein the number non-synonymous mutations is determined. (Gire, et al., *Science* 345, 1369, 2014).

Monitoring Microbe Outbreaks

In some embodiments, a CRISPR system or methods of use thereof as described herein may be used to determine the evolution of a pathogen outbreak. The method may comprise detecting one or more target sequences from a plurality of samples from one or more subjects, wherein the target sequence is a sequence from a microbe causing the outbreaks. Such a method may further comprise determining a pattern of pathogen transmission, or a mechanism involved in a disease outbreak caused by a pathogen.

The pattern of pathogen transmission may comprise continued new transmissions from the natural reservoir of the pathogen or subject-to-subject transmissions (e.g. human-to-human transmission) following a single transmission from the natural reservoir or a mixture of both. In one embodiment, the pathogen transmission may be bacterial or viral transmission, in such case, the target sequence is preferably a microbial genome or fragments thereof. In one embodiment, the pattern of the pathogen transmission is the early pattern of the pathogen transmission, i.e. at the beginning of the pathogen outbreak. Determining the pattern of the pathogen transmission at the beginning of the outbreak increases likelihood of stopping the outbreak at the earliest possible time thereby reducing the possibility of local and international dissemination.

Determining the pattern of the pathogen transmission may comprise detecting a pathogen sequence according to the methods described herein. Determining the pattern of the pathogen transmission may further comprise detecting shared intra-host variations of the pathogen sequence between the subjects and determining whether the shared intra-host variations show temporal patterns. Patterns in observed intrahost and interhost variation provide important insight about transmission and epidemiology (Gire, et al., 2014).

Detection of shared intra-host variations between the subjects that show temporal patterns is an indication of transmission links between subject (in particular between humans) because it can be explained by subject infection from multiple sources (superinfection), sample contamination recurring mutations (with or without balancing selection to reinforce mutations), or co-transmission of slightly divergent viruses that arose by mutation earlier in the transmission chain (Park, et al., *Cell* 161(7):1516-1526, 2015). Detection of shared intra-host variations between subjects may comprise detection of intra-host variants located at common single nucleotide polymorphism (SNP) positions. Positive detection of intra-host variants located at common (SNP) positions is indicative of superinfection and contamination as primary explanations for the intra-host variants. Superinfection and contamination can be parted on the basis of SNP frequency appearing as inter-host variants (Park, et al., 2015). Otherwise superinfection and contamination can be ruled out. In this latter case, detection of shared intra-host variations between subjects may further comprise assessing the frequencies of synonymous and nonsynonymous variants and comparing the frequency of synonymous and nonsynonymous variants to one another. A nonsynonymous mutation is a mutation that alters the amino acid of the protein, likely resulting in a biological change in the microbe that is subject to natural selection. Synonymous substitution does not alter an amino acid sequence. Equal frequency of synonymous and nonsynonymous variants is indicative of the intra-host variants evolving neutrally. If frequencies of synonymous and nonsynonymous variants are divergent, the intra-host variants are likely to be maintained by balancing selection. If frequencies of synonymous and nonsynonymous variants are low, this is indicative of recurrent mutation. If frequencies of synonymous and nonsynonymous variants are high, this is indicative of co-transmission (Park, et al., 2015).

Like Ebola virus, Lassa virus (LASV) can cause hemorrhagic fever with high case fatality rates. Andersen et al. generated a genomic catalog of almost 200 LASV sequences from clinical and rodent reservoir samples (Andersen, et al., Cell Volume 162, Issue 4, p 738-750, 13 Aug. 2015). Andersen et al. show that whereas the 2013-2015 EVD epidemic is fueled by human-to-human transmissions, LASV infections mainly result from reservoir-to-human infections. Andersen et al. elucidated the spread of LASV across West Africa and show that this migration was accompanied by changes in LASV genome abundance, fatality rates, codon adaptation, and translational efficiency. The method may further comprise phylogenetically comparing a first pathogen sequence to a second pathogen sequence, and determining whether there is a phylogenetic link between the first and second pathogen sequences. The second pathogen sequence may be an earlier reference sequence. If there is a phylogenetic link, the method may further comprise rooting the phylogeny of the first pathogen sequence to the second pathogen sequence. Thus, it is possible to construct the lineage of the first pathogen sequence. (Park, et al., 2015).

The method may further comprise determining whether the mutations are deleterious or adaptive. Deleterious mutations are indicative of transmission-impaired viruses and dead-end infections, thus normally only present in an individual subject. Mutations unique to one individual subject are those that occur on the external branches of the phylogenetic tree, whereas internal branch mutations are those present in multiple samples (i.e. in multiple subjects). Higher rate of nonsynonymous substitution is a characteristic of external branches of the phylogenetic tree (Park, et al., 2015).

In internal branches of the phylogenetic tree, selection has had more opportunity to filter out deleterious mutants. Internal branches, by definition, have produced multiple descendent lineages and are thus less likely to include mutations with fitness costs. Thus, lower rate of nonsynonymous substitution is indicative of internal branches (Park, et al., 2015).

Synonymous mutations, which likely have less impact on fitness, occurred at more comparable frequencies on internal and external branches (Park, et al., 2015).

By analyzing the sequenced target sequence, such as viral genomes, it is possible to discover the mechanisms responsible for the severity of the epidemic episode such as during the 2014 Ebola outbreak. For example, Gire et al. made a phylogenetic comparison of the genomes of the 2014 outbreak to all 20 genomes from earlier outbreaks suggests that the 2014 West African virus likely spread from central Africa within the past decade. Rooting the phylogeny using divergence from other ebolavirus genomes was problematic (6, 13). However, rooting the tree on the oldest outbreak revealed a strong correlation between sample date and root-to-tip distance, with a substitution rate of $8\times10^{-4}$ per site per year (13). This suggests that the lineages of the three most recent outbreaks all diverged from a common ancestor at roughly the same time, around 2004, which supports the hypothesis that each outbreak represents an independent zoonotic event from the same genetically diverse viral population in its natural reservoir. They also found out that the 2014 EBOV outbreak might be caused by a single transmission from the natural reservoir, followed by human-to-human transmission during the outbreak. Their results also suggested that the epidemic episode in Sierra Leone might stem from the introduction of two genetically distinct viruses from Guinea around the same time (Gire, et al., 2014).

It has been also possible to determine how the Lassa virus spread out from its origin point, in particular thanks to human-to-human transmission and even retrace the history of this spread 400 years back (Andersen, et al., *Cell* 162(4): 738-50, 2015).

In relation to the work needed during the 2013-2015 EBOV outbreak and the difficulties encountered by the medical staff at the site of the outbreak, and more generally, the method of the invention makes it possible to carry out sequencing using fewer selected probes such that sequencing can be accelerated, thus shortening the time needed from sample taking to results procurement. Further, kits and systems can be designed to be usable on the field so that diagnostics of a patient can be readily performed without need to send or ship samples to another part of the country or the world.

In any method described above, sequencing the target sequence or fragment thereof may be used any of the sequencing processes described above. Further, sequencing the target sequence or fragment thereof may be a near-real-time sequencing. Sequencing the target sequence or fragment thereof may be carried out according to previously described methods (Experimental Procedures: Matranga et al., 2014; and Gire, et al., 2014). Sequencing the target sequence or fragment thereof may comprise parallel sequencing of a plurality of target sequences. Sequencing the target sequence or fragment thereof may comprise Illumina sequencing.

Analyzing the target sequence or fragment thereof that hybridizes to one or more of the selected probes may be an identifying analysis, wherein hybridization of a selected probe to the target sequence or a fragment thereof indicates the presence of the target sequence within the sample.

Currently, primary diagnostics are based on the symptoms a patient has. However, various diseases may share identical symptoms so that diagnostics rely much on statistics. For example, malaria triggers flu-like symptoms: headache, fever, shivering, joint pain, vomiting, hemolytic anemia, jaundice, hemoglobin in the urine, retinal damage, and convulsions. These symptoms are also common for septicemia, gastroenteritis, and viral diseases. Amongst the latter, Ebola hemorrhagic fever has the following symptoms fever, sore throat, muscular pain, headaches, vomiting, diarrhea, rash, decreased function of the liver and kidneys, internal and external hemorrhage.

When a patient is presented to a medical unit, for example in tropical Africa, basic diagnostics will conclude to malaria because statistically, malaria is the most probable disease within that region of Africa. The patient is consequently treated for malaria although the patient might not actually have contracted the disease and the patient ends up not being correctly treated. This lack of correct treatment can be life-threatening especially when the disease the patient contracted presents a rapid evolution. It might be too late before the medical staff realizes that the treatment given to the patient is ineffective and comes to the correct diagnostics and administers the adequate treatment to the patient.

The method of the invention provides a solution to this situation. Indeed, because the number of guide RNAs can be dramatically reduced, this makes it possible to provide on a single chip selected probes divided into groups, each group being specific to one disease, such that a plurality of diseases, e.g. viral infection, can be diagnosed at the same time. Thanks to the invention, more than 3 diseases can be diagnosed on a single chip, preferably more than 4, 5, 6, 7, 8, 9, 10, 11, 12, 13, 14, 15, 16, 17, 18, 19, 20 diseases at the same time, preferably the diseases that most commonly occur within the population of a given geographical area. Since each group of selected probes is specific to one of the diagnosed diseases, a more accurate diagnosis can be performed, thus diminishing the risk of administering the wrong treatment to the patient.

In other cases, a disease such as a viral infection may occur without any symptoms, or had caused symptoms but they faded out before the patient is presented to the medical staff. In such cases, either the patient does not seek any medical assistance or the diagnostics is complicated due to the absence of symptoms on the day of the presentation.

The present invention may also be used in concert with other methods of diagnosing disease, identifying pathogens and optimizing treatment based upon detection of nucleic acids, such as mRNA in crude, non-purified samples.

The method of the invention also provides a powerful tool to address this situation. Indeed, since a plurality of groups of selected guide RNAs, each group being specific to one of the most common diseases that occur within the population of the given area, are comprised within a single diagnostic, the medical staff only need to contact a biological sample taken from the patient with the chip. Reading the chip reveals the diseases the patient has contracted.

In some cases, the patient is presented to the medical staff for diagnostics of particular symptoms. The method of the invention makes it possible not only to identify which disease causes these symptoms but at the same time determine whether the patient suffers from another disease he was not aware of.

This information might be of utmost importance when searching for the mechanisms of an outbreak. Indeed, groups of patients with identical viruses also show temporal patterns suggesting a subject-to-subject transmission links.

Screening Microbial Genetic Perturbations

In certain example embodiments, the CRISPR systems disclosed herein may be used to screen microbial genetic perturbations. Such methods may be useful, for example to map out microbial pathways and functional networks. Microbial cells may be genetically modified and then screened under different experimental conditions. As described above, the embodiments disclosed herein can screen for multiple target molecules in a single sample, or a single target in a single individual discrete volume in a multiplex fashion. Genetically modified microbes may be modified to include a nucleic acid barcode sequence that identifies the particular genetic modification carried by a particular microbial cell or population of microbial cells. A barcode is s short sequence of nucleotides (for example, DNA, RNA, or combinations thereof) that is used as an identifier. A nucleic acid barcode may have a length of 4-100 nucleotides and be either single or double-stranded. Methods for identifying cells with barcodes are known in the art. Accordingly, guide RNAs of the CRISPR effector systems described herein may be used to detect the barcode. Detection of the positive detectable signal indicates the presence of a particular genetic modification in the sample. The methods disclosed herein may be combined with other methods for detecting complimentary genotype or phenotypic readouts indicating the effect of the genetic modification under the experimental conditions tested. Genetic modifications to be screened may include, but are not limited to a gene knock-in, a gene knock-out, inversions, translocations, transpositions, or one or more nucleotide insertions, deletions, substitutions, mutations, or addition of nucleic acids encoding an epitope with a functional consequence such as altering protein stability or detection. In a similar fashion, the methods described herein may be used in synthetic biology application to screen the functionality of specific arrangements of gene regulatory elements and gene expression modules.

In certain example embodiments, the methods may be used to screen hypomorphs. Generation of hypomorphs and their use in identifying key bacterial functional genes and identification of new antibiotic therapeutics as disclosed in PCT/US2016/060730 entitled "Multiplex High-Resolution Detection of Micro-organism Strains, Related Kits, Diagnostic Methods and Screening Assays" filed Nov. 4, 2016, which is incorporated herein by reference.

The different experimental conditions may comprise exposure of the microbial cells to different chemical agents, combinations of chemical agents, different concentrations of chemical agents or combinations of chemical agents, different durations of exposure to chemical agents or combinations of chemical agents, different physical parameters, or both. In certain example embodiments the chemical agent is an antibiotic or antiviral. Different physical parameters to be screened may include different temperatures, atmospheric pressures, different atmospheric and non-atmospheric gas concentrations, different pH levels, different culture media compositions, or a combination thereof.

Screening Environmental Samples

The methods disclosed herein may also be used to screen environmental samples for contaminants by detecting the presence of target nucleic acid or polypeptides. For example, in some embodiments, the invention provides a method of detecting microbes, comprising: exposing a CRISPR system as described herein to a sample; activating an RNA effector protein via binding of one or more guide RNAs to one or more microbe-specific target RNAs or one or more trigger RNAs such that a detectable positive signal is produced. The positive signal can be detected and is indicative of the presence of one or more microbes in the sample. In some embodiments, the CRISPR system may be on a substrate as described herein, and the substrate may be exposed to the sample. In other embodiments, the same CRISPR system, and/or a different CRISPR system may be applied to multiple discrete locations on the substrate. In further embodiments, the different CRISPR system may detect a different microbe at each location. As described in further detail above, a substrate may be a flexible materials substrate, for example, including, but not limited to, a paper substrate, a fabric substrate, or a flexible polymer-based substrate.

In accordance with the invention, the substrate may be exposed to the sample passively, by temporarily immersing the substrate in a fluid to be sampled, by applying a fluid to be tested to the substrate, or by contacting a surface to be tested with the substrate. Any means of introducing the sample to the substrate may be used as appropriate.

As described herein, a sample for use with the invention may be a biological or environmental sample, such as a food sample (fresh fruits or vegetables, meats), a beverage sample, a paper surface, a fabric surface, a metal surface, a wood surface, a plastic surface, a soil sample, a freshwater sample, a wastewater sample, a saline water sample, exposure to atmospheric air or other gas sample, or a combination thereof. For example, household/commercial/industrial surfaces made of any materials including, but not limited to, metal, wood, plastic, rubber, or the like, may be swabbed and tested for contaminants. Soil samples may be tested for the presence of pathogenic bacteria or parasites, or other microbes, both for environmental purposes and/or for human, animal, or plant disease testing. Water samples such as freshwater samples, wastewater samples, or saline water samples can be evaluated for cleanliness and safety, and/or potability, to detect the presence of, for example, *Cryptosporidium parvum, Giardia lamblia*, or other microbial contamination. In further embodiments, a biological sample may be obtained from a source including, but not limited to, a tissue sample, saliva, blood, plasma, sera, stool, urine, sputum, mucous, lymph, synovial fluid, cerebrospinal fluid, ascites, pleural effusion, seroma, pus, or swab of skin or a mucosal membrane surface. In some particular embodiments, an environmental sample or biological samples may be crude samples and/or the one or more target molecules may not be purified or amplified from the sample prior to application of the method. Identification of microbes may be useful and/or needed for any number of applications, and thus any type of sample from any source deemed appropriate by one of skill in the art may be used in accordance with the invention.

In some embodiments, checking for food contamination by a virus that can be spread, in restaurants or other food providers; food surfaces; also checking food quality for manufacturers and regulators to determine the purity of meat sources; or identifying air or water contamination with pathogens.

A microbe in accordance with the invention may be a pathogenic microbe or a microbe that results in food or consumable product spoilage. A pathogenic microbe may be pathogenic or otherwise undesirable to humans, animals, or plants. For human or animal purposes, a microbe may cause a disease or result in illness. Animal or veterinary applications of the present invention may identify animals infected with a microbe. For example, the methods and systems of the invention may identify companion or farm animals with pathogens. In certain example embodiments, the virus may be any viral species that causes hemorrhagic fever, or other microbe causing similar symptoms.

Sample Types

Appropriate samples for use in the methods disclosed herein include any conventional biological sample obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as an infection with a pathogenic microorganism, such as a pathogenic bacteria or virus). For example, a biological sample can be a biological fluid obtained from, for example, blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis), or a swab of skin or mucosal membrane surface.

A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will be appreciated that any method of obtaining tissue from a subject can be utilized, and that the selection of the method used will depend upon various factors such as the type of tissue, age of the subject, or procedures available to the practitioner. Standard techniques for acquisition of such samples are available in the art. See, for example Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

In other embodiments, a sample may be an environmental sample, such as water, soil, or a surface such as industrial or medical surface. In some embodiments, methods such as disclosed in US patent publication No. 2013/0190196 may be applied for detection of nucleic acid signatures, specifically RNA levels, directly from crude cellular samples with a high degree of sensitivity and specificity. Sequences specific to each pathogen of interest may be identified or selected by comparing the coding sequences from the pathogen of interest to all coding sequences in other organisms by BLAST software.

Several embodiments of the present disclosure involve the use of procedures and approaches known in the art to successfully fractionate clinical blood samples. See, e.g. the procedure described in Han Wei Hour et al., Microfluidic Devices for Blood Fractionation, Micromachines 2011, 2, 319-343; Ali Asgar S. Bhagat et al., *Dean Flow Fractionation (DFF) Isolation of Circulating Tumor Cells (CTCs) from Blood,* 15$^{th}$ International Conference on Miniaturized Systems for Chemistry and Life Sciences, Oct. 2-6, 2011, Seattle, WA; and International Patent Publication No. WO2011109762, the disclosures of which are herein incorporated by reference in their entirety. Blood samples are commonly expanded in culture to increase sample size for testing purposes. In some embodiments of the present invention, blood or other biological samples may be used in methods as described herein without the need for expansion in culture.

Further, several embodiments of the present disclosure involve the use of procedures and approaches known in the art to successfully isolate pathogens from whole blood using spiral microchannel, as described in Han Wei Hour et al., Pathogen Isolation from Whole Blood Using Spiral Microchannel, Case No. 15995JR, Massachusetts Institute of Technology, manuscript in preparation, the disclosure of which is herein incorporated by reference in its entirety.

Owing to the increased sensitivity of the embodiments disclosed herein, in certain example embodiments, the assays and methods may be run on crude samples or samples where the target molecules to be detected are not further fractionated or purified from the sample.

Devices

In another aspect, the embodiments disclosed herein are directed to a diagnostic device comprising a plurality of individual discrete volumes. Each individual discrete volume comprises a CRISPR effector protein, one or more guide RNAs designed to bind to a corresponding target molecule, and a masking construct. In certain example embodiments, RNA amplification reagents may be pre-loaded into the individual discrete volumes or be added to the individual discrete volumes concurrently with or subsequent to addition of a sample to each individual discrete volume. The device may be a microfluidic based device, a wearable device, or device comprising a flexible material substrate on which the individual discrete volumes are defined.

The systems described herein can be embodied on diagnostic devices. A number of substrates and configurations may be used. The devices may be capable of defining multiple individual discrete volumes within the device. As used herein an "individual discrete volume" refers to a discrete space, such as a container, receptacle, or other defined volume or space that can be defined by properties that prevent and/or inhibit migration of target molecules, for example a volume or space defined by physical properties such as walls, for example the walls of a well, tube, or a surface of a droplet, which may be impermeable or semi-permeable, or as defined by other means such as chemical, diffusion rate limited, electro-magnetic, or light illumination, or any combination thereof that can contain a sample within a defined space. Individual discrete volumes may be identified by molecular tags, such as nucleic acid barcodes. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the use of non-walled, or semipermeable discrete volumes is that some reagents, such as buffers, chemical activators, or other agents may be passed through the discrete volume, while other materials, such as target molecules, may be maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain embodiments, the compartment is an aqueous droplet in a water-in-oil emulsion. In specific embodiments, any of the applications, methods, or systems described herein requiring exact or uniform volumes may employ the use of an acoustic liquid dispenser.

In certain example embodiments, the device comprises a flexible material substrate on which a number of spots may be defined. Flexible substrate materials suitable for use in diagnostics and biosensing are known within the art. The flexible substrate materials may be made of plant derived fibers, such as cellulosic fibers, or may be made from flexible polymers such as flexible polyester films and other polymer types. Within each defined spot, reagents of the system described herein are applied to the individual spots. Each spot may contain the same reagents except for a different guide RNA or set of guide RNAs, or where applicable, a different detection aptamer to screen for multiple targets at once. Thus, the systems and devices herein may be able to screen samples from multiple sources (e.g. multiple clinical samples from different individuals) for the presence of the same target, or a limited number of targets, or aliquots of a single sample (or multiple samples from the same source) for the presence of multiple different targets in the sample. In certain example embodiments, the elements of the systems described herein are freeze dried onto the paper or cloth substrate. Example flexible material based substrates that may be used in certain example devices are disclosed in Pardee et al. *Cell.* 2016, 165(5):1255-66 and Pardee et al. *Cell.* 2014, 159(4):950-54. Suitable flexible material-based substrates for use with biological fluids, including blood are disclosed in International Patent Application Publication No. WO/2013/071301 entitled “Paper based diagnostic test” to Shevkoplyas et al. U.S. Patent Application Publication No. 2011/0111517 entitled “Paper-based microfluidic systems” to Siegel et al. and Shafiee et al. “Paper and Flexible Substrates as Materials for Biosensing Platforms to Detect Multiple Biotargets” Scientific Reports 5:8719 (2015). Further flexible based materials, including those suitable for use in wearable diagnostic devices are disclosed in Wang et al. “Flexible Substrate-Based Devices for Point-of-Care Diagnostics” Cell 34(11):909-21 (2016). Further flexible based materials may include nitrocellulose, polycarbonate, methylethyl cellulose, polyvinylidene fluoride (PVDF), polystyrene, or glass (see e.g., US20120238008). In certain embodiments, discrete volumes are separated by a hydrophobic surface, such as but not limited to wax, photoresist, or solid ink.

In some embodiments, a dosimeter or badge may be provided that serves as a sensor or indicator such that the wearer is notified of exposure to certain microbes or other agents. For example, the systems described herein may be used to detect a particular pathogen. Likewise, aptamer based embodiments disclosed above may be used to detect both polypeptide as well as other agents, such as chemical agents, to which a specific aptamer may bind. Such a device may be useful for surveillance of soldiers or other military personnel, as well as clinicians, researchers, hospital staff, and the like, in order to provide information relating to exposure to potentially dangerous agents as quickly as possible, for example for biological or chemical warfare agent detection. In other embodiments, such a surveillance badge may be used for preventing exposure to dangerous microbes or pathogens in immunocompromised patients, burn patients, patients undergoing chemotherapy, children, or elderly individuals.

Samples sources that may be analyzed using the systems and devices described herein include biological samples of a subject or environmental samples. Environmental samples may include surfaces or fluids. The biological samples may include, but are not limited to, saliva, blood, plasma, sera, stool, urine, sputum, mucous, lymph, synovial fluid, spinal fluid, cerebrospinal fluid, a swab from skin or a mucosal membrane, or combination thereof. In an example embodiment, the environmental sample is taken from a solid surface, such as a surface used in the preparation of food or other sensitive compositions and materials.

In other example embodiments, the elements of the systems described herein may be place on a single use substrate, such as swab or cloth that is used to swab a surface or sample fluid. For example, the system could be used to test for the presence of a pathogen on a food by swabbing the surface of a food product, such as a fruit or vegetable. Similarly, the single use substrate may be used to swab other surfaces for detection of certain microbes or agents, such as for use in security screening. Single use substrates may also have applications in forensics, where the CRISPR systems are designed to detect, for example identifying DNA SNPs that may be used to identify a suspect, or certain tissue or cell markers to determine the type of biological matter present in a sample. Likewise, the single use substrate could be used to collect a sample from a patient—such as a saliva sample from the mouth—or a swab of the skin. In other embodiments, a sample or swab may be taken of a meat product on order to detect the presence of absence of contaminants on or within the meat product.

Near-real-time microbial diagnostics are needed for food, clinical, industrial, and other environmental settings (see e.g., Lu T K, Bowers J, and Koeris M S., Trends Biotechnol. 2013 June; 31(6):325-7). In certain embodiments, the present invention is used for rapid detection of foodborne pathogens using guide RNAs specific to a pathogen (e.g., *Campylobacter jejuni, Clostridium perfringens, Salmonella* spp., *Escherichia coli, Bacillus cereus, Listeria monocytogenes, Shigella* spp., *Staphylococcus aureus, Staphylococcal enteritis, Streptococcus, Vibrio cholerae, Vibrio parahaemolyticus, Vibrio vulruficus, Yersinia enterocolitica* and *Yersinia pseudotuberculosis, Brucella* spp., *Corynebacterium ulcerans, Coxiella burnetii*, or *Plesiomonas shigelloides*).

In certain embodiments, the device is or comprises a flow strip. For instance, a lateral flow strip allows for RNAse (e.g. C2c2) detection by color. The RNA reporter is modified to have a first molecule (such as for instance FITC) attached to the 5' end and a second molecule (such as for instance biotin) attached to the 3' end (or vice versa). The lateral flow strip is designed to have two capture lines with anti-first molecule (e.g. anti-FITC) antibodies hybridized at the first line and anti-second molecule (e.g. anti-biotin) antibodies at the second downstream line. As the reaction flows down the strip, uncleaved reporter will bind to anti-first molecule antibodies at the first capture line, while cleaved reporters will liberate the second molecule and allow second molecule binding at the second capture line. Second molecule sandwich antibodies, for instance conjugated to nanoparticles, such as gold nanoparticles, will bind any second molecule at the first or second line and result in a strong readout/signal (e.g. color). As more reporter is cleaved, more signal will accumulate at the second capture line and less signal will appear at the first line. In certain aspects, the invention relates to the use of a follow strip as described herein for detecting nucleic acids or polypeptides. In certain aspects, the invention relates to a method for detecting nucleic acids or polypeptides with a flow strip as defined herein, e.g. (lateral) flow tests or (lateral) flow immunochromatographic assays.

In certain example embodiments, the device is a microfluidic device that generates and/or merges different droplets (i.e. individual discrete volumes). For example, a first set of droplets may be formed containing samples to be screened and a second set of droplets formed containing the elements of the systems described herein. The first and second set of droplets are then merged and then diagnostic methods as described herein are carried out on the merged droplet set. Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly(dimethylsiloxane) (PDMS), and poly(methyl methacrylate) (PMMA). In one embodiment, soft lithography in PDMS may be used to prepare the microfluidic devices. For example, a mold may be made using photolithography which defines the location of flow channels, valves, and filters within a substrate. The substrate material is poured into a mold and allowed to set to create a stamp. The stamp is then sealed to a solid support, such as but not limited to, glass. Due to the hydrophobic nature of some polymers, such as PDMS, which absorbs some proteins and may inhibit certain biological processes, a passivating agent may be necessary (Schoffner et al. *Nucleic Acids Research,* 1996, 24:375-379). Suitable passivating agents are known in the art and include, but are not limited to, silanes, parylene, n-Dodecyl-b-D-maltoside (DDM), pluronic, Tween-20, other similar surfactants, polyethylene glycol (PEG), albumin, collagen, and other similar proteins and peptides.

In certain example embodiments, the system and/or device may be adapted for conversion to a flow-cytometry readout in or allow to all of sensitive and quantitative measurements of millions of cells in a single experiment and improve upon existing flow-based methods, such as the PrimeFlow assay. In certain example embodiments, cells may be cast in droplets containing unpolymerized gel monomer, which can then be cast into single-cell droplets suitable for analysis by flow cytometry. A detection construct comprising a fluorescent detectable label may be cast into the droplet comprising unpolymerized gel monomer. Upon polymerization of the gel monomer to form a bead within a droplet. Because gel polymerization is through free-radical formation, the fluorescent reporter becomes covalently bound to the gel. The detection construct may be further modified to comprise a linker, such as an amine. A quencher may be added post-gel formation and will bind via the linker to the reporter construct. Thus, the quencher is not bound to the gel and is free to diffuse away when the reporter is cleaved by the CRISPR effector protein. Amplification of signal in droplet may be achieved by coupling the detection construct to a hybridization chain reaction (HCR initiator) amplification. DNA/RNA hybrid hairpins may be incorporated into the gel which may comprise a hairpin loop that has a RNase sensitive domain. By protecting a strand displacement toehold within a hairpin loop that has a RNase sensitive domain, HCR initiators may be selectively deprotected following cleavage of the hairpin loop by the CRISPR effector protein. Following deprotection of HCR initiators via toehold mediated strand displacement, fluorescent HCR monomers may be washed into the gel to enable signal amplification where the initiators are deprotected.

An example of microfluidic device that may be used in the context of the invention is described in Hour et al. "Direct Detection and drug-resistance profiling of bacteremias using inertial microfluidics" Lap Chip. 15(10):2297-2307 (2016).

In systems described herein, may further be incorporated into wearable medical devices that assess biological samples, such as biological fluids, of a subject outside the clinic setting and report the outcome of the assay remotely to a central server accessible by a medical care professional. The device may include the ability to self-sample blood, such as the devices disclosed in U.S. Patent Application Publication No. 2015/0342509 entitled "Needle-free Blood Draw to Peeters et al., U.S. Patent Application Publication No. 2015/0065821 entitled "Nanoparticle Phoresis" to Andrew Conrad.

In certain example embodiments, the device may comprise individual wells, such as microplate wells. The size of the microplate wells may be the size of standard 6, 24, 96, 384, 1536, 3456, or 9600 sized wells. In certain example embodiments, the elements of the systems described herein may be freeze dried and applied to the surface of the well prior to distribution and use.

The devices disclosed herein may further comprise inlet and outlet ports, or openings, which in turn may be connected to valves, tubes, channels, chambers, and syringes and/or pumps for the introduction and extraction of fluids into and from the device. The devices may be connected to fluid flow actuators that allow directional movement of fluids within the microfluidic device. Example actuators include, but are not limited to, syringe pumps, mechanically actuated recirculating pumps, electroosmotic pumps, bulbs, bellows, diaphragms, or bubbles intended to force movement of fluids. In certain example embodiments, the devices are connected to controllers with programmable valves that work together to move fluids through the device. In certain example embodiments, the devices are connected to the controllers discussed in further detail below. The devices may be connected to flow actuators, controllers, and sample loading devices by tubing that terminates in metal pins for insertion into inlet ports on the device.

As shown herein the elements of the system are stable when freeze dried, therefore embodiments that do not require a supporting device are also contemplated, i.e. the system may be applied to any surface or fluid that will support the reactions disclosed herein and allow for detection of a positive detectable signal from that surface or solution. In addition to freeze-drying, the systems may also be stably stored and utilized in a pelletized form. Polymers useful in forming suitable pelletized forms are known in the art.

In certain embodiments, the CRISPR effector protein is bound to each discrete volume in the device. Each discrete volume may comprise a different guide RNA specific for a different target molecule. In certain embodiments, a sample is exposed to a solid substrate comprising more than one discrete volume each comprising a guide RNA specific for a target molecule. Not being bound by a theory, each guide RNA will capture its target molecule from the sample and the sample does not need to be divided into separate assays. Thus, a valuable sample may be preserved. The effector protein may be a fusion protein comprising an affinity tag. Affinity tags are well known in the art (e.g., HA tag, Myc tag, Flag tag, His tag, biotin). The effector protein may be linked to a biotin molecule and the discrete volumes may comprise streptavidin. In other embodiments, the CRISPR effector protein is bound by an antibody specific for the effector protein. Methods of binding a CRISPR enzyme has been described previously (see, e.g., US20140356867A1).

The devices disclosed herein may also include elements of point of care (POC) devices known in the art for analyzing samples by other methods. See, for example St John and Price, "Existing and Emerging Technologies for Point-of-Care Testing" (Clin Biochem Rev. 2014 August; 35(3): 155-167).

The present invention may be used with a wireless lab-on-chip (LOC) diagnostic sensor system (see e.g., U.S. Pat. No. 9,470,699 "Diagnostic radio frequency identification sensors and applications thereof"). In certain embodiments, the present invention is performed in a LOC controlled by a wireless device (e.g., a cell phone, a personal digital assistant (PDA), a tablet) and results are reported to said device.

Radio frequency identification (RFID) tag systems include an RFID tag that transmits data for reception by an RFID reader (also referred to as an interrogator). In a typical RFID system, individual objects (e.g., store merchandise) are equipped with a relatively small tag that contains a transponder. The transponder has a memory chip that is given a unique electronic product code. The RFID reader emits a signal activating the transponder within the tag through the use of a communication protocol. Accordingly, the RFID reader is capable of reading and writing data to the tag. Additionally, the RFID tag reader processes the data according to the RFID tag system application. Currently, there are passive and active type RFID tags. The passive type RFID tag does not contain an internal power source, but is powered by radio frequency signals received from the RFID reader. Alternatively, the active type RFID tag contains an internal power source that enables the active type RFID tag to possess greater transmission ranges and memory capacity. The use of a passive versus an active tag is dependent upon the particular application.

Lab-on-the chip technology is well described in the scientific literature and consists of multiple microfluidic channels, input or chemical wells. Reactions in wells can be measured using radio frequency identification (RFID) tag technology since conductive leads from RFID electronic chip can be linked directly to each of the test wells. An antenna can be printed or mounted in another layer of the electronic chip or directly on the back of the device. Furthermore, the leads, the antenna and the electronic chip can be embedded into the LOC chip, thereby preventing shorting of the electrodes or electronics. Since LOC allows complex sample separation and analyses, this technology allows LOC tests to be done independently of a complex or expensive reader. Rather a simple wireless device such as a cell phone or a PDA can be used. In one embodiment, the wireless device also controls the separation and control of the microfluidics channels for more complex LOC analyses. In one embodiment, a LED and other electronic measuring or sensing devices are included in the LOC-RFID chip. Not being bound by a theory, this technology is disposable and allows complex tests that require separation and mixing to be performed outside of a laboratory.

In preferred embodiments, the LOC may be a microfluidic device. The LOC may be a passive chip, wherein the chip is powered and controlled through a wireless device. In certain embodiments, the LOC includes a microfluidic channel for holding reagents and a channel for introducing a sample. In certain embodiments, a signal from the wireless device delivers power to the LOC and activates mixing of the sample and assay reagents. Specifically, in the case of the present invention, the system may include a masking agent, CRISPR effector protein, and guide RNAs specific for a target molecule. Upon activation of the LOC, the microfluidic device may mix the sample and assay reagents. Upon mixing, a sensor detects a signal and transmits the results to the wireless device. In certain embodiments, the unmasking agent is a conductive RNA molecule. The conductive RNA molecule may be attached to the conductive material. Conductive molecules can be conductive nanoparticles, conductive proteins, metal particles that are attached to the protein or latex or other beads that are conductive. In certain embodiments, if DNA or RNA is used then the conductive molecules can be attached directly to the matching DNA or RNA strands. The release of the conductive molecules may be detected across a sensor. The assay may be a one step process.

Since the electrical conductivity of the surface area can be measured precisely quantitative results are possible on the disposable wireless RFID electro-assays. Furthermore, the test area can be very small allowing for more tests to be done in a given area and therefore resulting in cost savings. In certain embodiments, separate sensors each associated with a different CRISPR effector protein and guide RNA immobilized to a sensor are used to detect multiple target molecules. Not being bound by a theory, activation of different sensors may be distinguished by the wireless device.

In addition to the conductive methods described herein, other methods may be used that rely on RFID or Bluetooth as the basic low-cost communication and power platform for a disposable RFID assay. For example, optical means may be used to assess the presence and level of a given target molecule. In certain embodiments, an optical sensor detects unmasking of a fluorescent masking agent.

In certain embodiments, the device of the present invention may include handheld portable devices for diagnostic reading of an assay (see e.g., Vashist et al., Commercial Smartphone-Based Devices and Smart Applications for Personalized Healthcare Monitoring and Management, *Diagnostics* 2014, 4 (3), 104-128; mReader from Mobile Assay; and Holomic Rapid Diagnostic Test Reader).

As noted herein, certain embodiments allow detection via colorimetric change which has certain attendant benefits when embodiments are utilized in POC situations and/or in resource poor environments where access to more complex detection equipment to readout the signal may be limited. However, portable embodiments disclosed herein may also be coupled with hand-held spectrophotometers that enable detection of signals outside the visible range. An example of a hand-held spectrophotometer device that may be used in combination with the present invention is described in Das et al. "Ultra-portable, wireless smartphone spectrophotometer for rapid, non-destructive testing of fruit ripeness." Nature Scientific Reports. 2016, 6:32504, DOI: 10.1038/srep32504. Finally, in certain embodiments utilizing quantum dot-based masking constructs, use of a hand held UV light, or other suitable device, may be successfully used to detect a signal owing to the near complete quantum yield provided by quantum dots.

Viruses

In certain example embodiments, the systems, devices, and methods, disclosed herein are directed to detecting viruses in a sample. The embodiments disclosed herein may be used to detect viral infection (e.g. of a subject or plant), or determination of a viral strain, including viral strains that differ by a single nucleotide polymorphism. The virus may be a DNA virus, an RNA virus, or a retrovirus. Non-limiting example of viruses useful with the present invention include, but are not limited to a virus from the family *Arenaviridae, Bunyaviridae, Filoviridae, Flaviviridae, Paramyxoviridae*, or *Rhabdoviridae*, including viruses from the genus *Hantavirus, Nairovirus, Phlebovirus*, and/or *Henipavirus*. In some instances, the virus is selected from Lassa virus, Lujo virus, Junin virus, Machupo virus, Sabia virus, Chapare virus, Guanarito virus, hemorrhagic fever with renal syndrome (HFRS), Alkhurma Hemorrhagic Fever virus, the Crimean-Congo hemorrhagic fever (CCHF) virus, lymphocytic choriomeningitis virus, Garissa virus, Ilesha virus, Rift Valley fever virus, Ebola virus, Marburg virus, dengue, yellow fever, Omsk hemorrhagic fever virus, Kyasanur Forest disease virus, or a rhabdovirus. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is one or a combination of Lassa virus, Lujo virus, Junin virus, Machupo virus, Sabia virus, Chapare virus, Guanarito virus, hemorrhagic fever with renal syndrome (HFRS), Alkhurma Hemorrhagic Fever virus, the Crimean-Congo hemorrhagic fever (CCHF) virus, lymphocytic choriomeningitis virus, Garissa virus, Ilesha virus, Rift Valley fever virus, Ebola virus, Marburg virus, dengue, yellow fever, Omsk hemorrhagic fever virus, Kyasanur Forest disease virus, or a rhabdovirus.

In certain example embodiments, the devices, systems, and methods disclosed herein may be used to distinguish viral species or clades in a sample. In certain example embodiments, a set of guide RNAs may be designed to distinguish each species by a variable region that is unique to each species or strain. Guide RNAs may also be designed to target RNA genes that distinguish microbes at the genus, family, order, class, phylum, kingdom levels, or a combination thereof. In certain example embodiments where amplification is used, a set of amplification primers may be designed to flanking constant regions of the RNA sequence and a guide RNA designed to distinguish each species by a variable internal region. In certain example embodiments, other genes or genomic regions that uniquely variable across species or a subset of species may be used as well. Other suitable phylogenetic markers, and methods for identifying the same, are discussed for example in Wu et al. arXiv: 1307.8690 [q-bio.GN].

In certain example embodiments, species identification can be performed based on genes that are present in multiple copies in the genome, such as mitochondrial genes like CYTB. In certain example embodiments, species identification can be performed based on highly expressed and/or highly conserved genes such as GAPDH, Histone H2B, enolase, or LDH.

In certain example embodiments, a method or diagnostic is designed to screen viruses across multiple phylogenetic and/or phenotypic levels at the same time. For example, the method or diagnostic may comprise the use of multiple CRISPR systems with different guide RNAs. A first set of guide RNAs may distinguish, for example, between Lassa virus N-II or Lassa virus N-III other clades, or other hemorrhagic fever viruses. The guide RNAs could be designed and used in the method or diagnostic that distinguishes drug-resistant strains, in general or with respect to a specific drug or combination of drugs. A second set of guide RNA can be designed to distinguish microbes at the species level. The foregoing is for example purposes only. Other means for classifying other types of hemorrhagic fever viruses are also contemplated and would follow the general structure described above.

In certain example embodiments, the devices, systems and methods disclosed herein may be used to screen for hemorrhagic viral genes of interest, for example drug resistance genes. Guide RNAs may be designed to distinguish between known genes of interest. Samples, including clinical samples, may then be screened using the embodiments disclosed herein for detection of one or more such genes. The ability to screen for drug resistance at POC would have tremendous benefit in selecting an appropriate treatment regime. In certain example embodiments, the drug resistance genes are genes encoding proteins such as transporter proteins.

In some embodiments, a CRISPR system, detection system or methods of use thereof as described herein may be used to determine the evolution of a viral outbreak. The method may comprise detecting one or more target sequences from a plurality of samples from one or more subjects, wherein the target sequence is a sequence from an animal spreading or causing the outbreaks. Such a method may further comprise determining a pattern of viral transmission, or a mechanism involved in a disease outbreak caused by a hemorrhagic fever virus source. The samples may be derived from one or more humans, and/or be derived from one or more animals.

Biomarker Detection

In certain example embodiments, the systems, devices, and methods disclosed herein may be used for biomarker detection. For example, the systems, devices and method disclosed herein may be used for SNP detection and/or genotyping. The systems, devices and methods disclosed herein may be also used for the detection of any disease state or disorder characterized by aberrant gene expression. Aberrant gene expression includes aberration in the gene expressed, location of expression and level of expression. The embodiments disclosed herein may be used for screening panels of different SNPs associated with hemorrhagic viruses. As described herein elsewhere, closely related genotypes/alleles or biomarkers (e.g. having only a single nucleotide difference in a given target sequence) may be distinguished by introduction of a synthetic mismatch in the gRNA.

In an aspect, the invention relates to a method for detecting target nucleic acids in samples for detection of one or more hemorrhagic virus, comprising:

a. distributing a sample or set of samples into one or more individual discrete volumes, the individual discrete volumes comprising a CRISPR system according to the invention as described herein;
b. incubating the sample or set of samples under conditions sufficient to allow binding of the one or more guide RNAs to one or more target molecules;
c. activating the CRISPR effector protein via binding of the one or more guide RNAs to the one or more target molecules, wherein activating the CRISPR effector protein results in modification of the RNA-based masking construct such that a detectable positive signal is generated; and d. detecting the detectable positive signal, wherein detection of the detectable positive signal indicates a presence of one or more target molecules in the sample.

Sample Types

The sensitivity of the assays described herein are well suited for detection of target nucleic acids in a wide variety of biological sample types, including sample types in which the target nucleic acid is dilute or for which sample material is limited. Biomarker screening may be carried out on a number of sample types including, but not limited to, saliva, urine, blood, feces, sputum, and cerebrospinal fluid. The embodiments disclosed herein may also be used to detect up- and/or down-regulation of genes. For example, a sample may be serially diluted such that only over-expressed genes remain above the detection limit threshold of the assay.

In certain embodiments, the present invention provides steps of obtaining a sample of biological fluid (e.g., urine, blood plasma or serum, sputum, cerebral spinal fluid), and extracting the nucleic acid. The nucleotide sequence to be detected, may be a fraction of a larger molecule or can be present initially as a discrete molecule.

In certain embodiments, blood samples are collected and plasma immediately separated from the blood cells by centrifugation. Serum may be filtered and stored frozen until nucleic acid extraction.

In certain example embodiments, target nucleic acids are detected directly from a crude or unprocessed sample, such as blood, serum, saliva, cerebrospinal fluid, sputum, or urine. In certain example embodiments, the target nucleic acid is cell free DNA.

The invention is further described in the following examples, which do not limit the scope of the invention described in the claims.

WORKING EXAMPLES

Example 1—Lassa Virus RT-PCR

An updated RT-qPCR assay using recently-sequenced LASV strains from the SL-IV and N-II clades was optimized. The goal of designing a RT-qPCR with new target sequences was to provide more sensitive detection of current LASV strains than the Nikisins RT-qPCR assay, currently considered the gold standard. Because this assay was developed using a more diverse set of recent viral strains compared to published RT-qPCR assays, its sensitivity to current strains is improved and can detect strains from a wider geographic range.

Broad RT-qPCR Assay Validation on Recent LASV Patient Samples

Figure 6A:
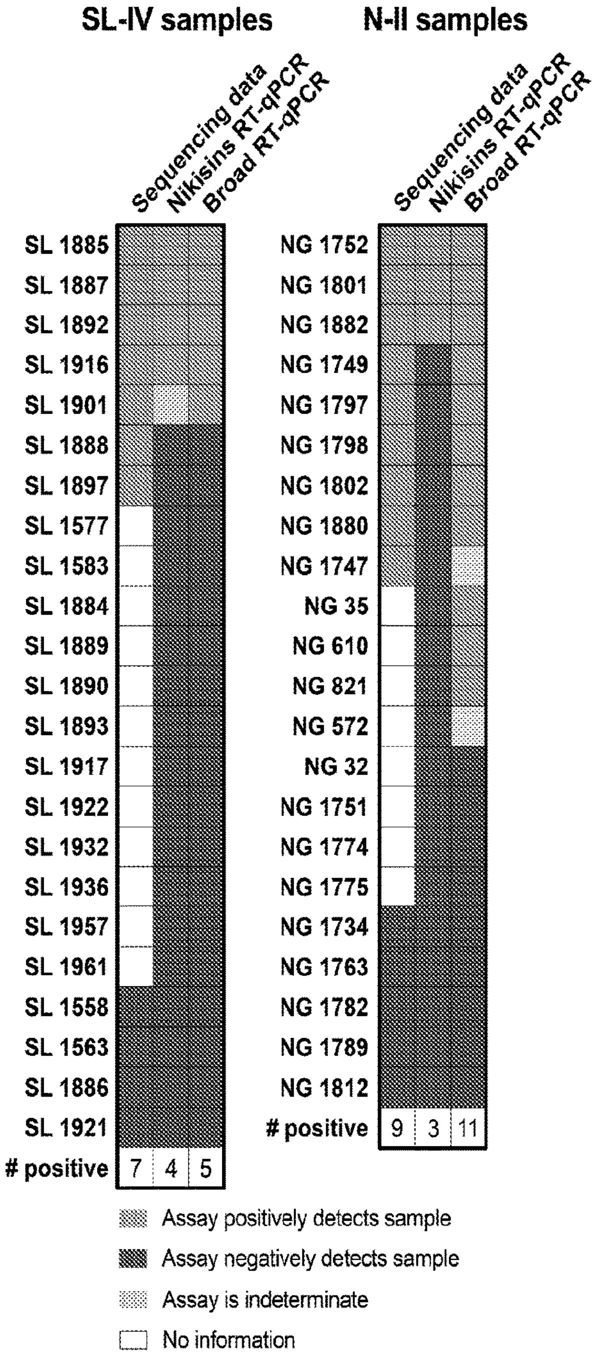
FIG. 6A-6B provides comparison of diagnostic results of the Broad RT-qPCR assay and the Nikisins RT-qPCR assay tested in parallel on 45 blinded LASV patient samples.
Figure 6B:
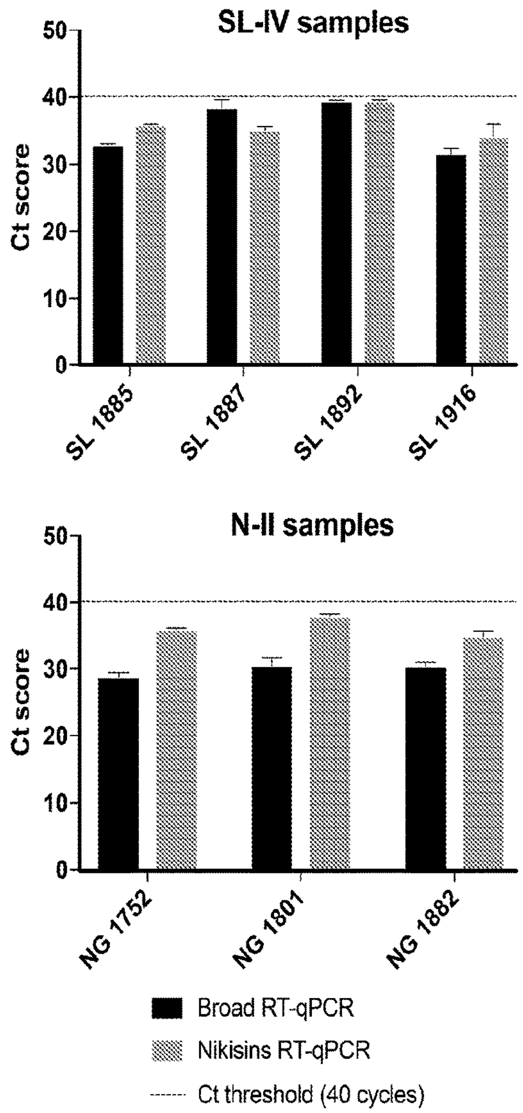

The Broad RT-qPCR assay was tested in parallel with the Nikisins RT-qPCR assay on a blinded panel of 45 LASV patient samples from clades SL-IV (n=23) and N-II (n=22). Applicant also compared the results to sequencing data performed, which is a more definitive measure of the presence of absence of LASV than RT-qPCR (FIG. 6*a*). The Broad and Nikisins assays detected similar numbers of sequencing-positive SL-IV samples (Broad=5/7; Nikisins=4/7), while the Broad assay detected a notably larger number of sequencing-positive N-II patient samples than did the Nikisins assay (Broad=8/9; Nikisins=3/9) (Table 1). Ct scores indicate RT-qPCR assay efficiency, with lower Ct scores indicating a more efficient assay. The two assays had similar efficiencies when detecting SL-IV samples, but the Broad assay was more efficient than the Nikisins assay in detecting N-II samples (FIG. 6*b*). The percentage of clade-specific samples detected by each RT-qPCR assay is displayed for the SL-IV clade, the N-II clade, and both clades combined.

TABLE 2A

Table 1: The Broad RT-qPCR assay detects a higher percentage of sequencing-positive LASV patient samples than the Nikisins RT-qPCR assay for the SL-IV and N-II clades.

| | SL-IV samples | N-II samples | All samples |
|---|---|---|---|
| Nikisins RT-qPCR | 4/7 (57.1%) | 3/9 (33.3%) | 7/16 (43.8%) |
| Broad RT-qPCR | 5/7 (71.4%) | 8/9 (88.9%) | 13/16 (81.3%) |

The Broad assay has similar detection rates compared to the Nikisins assay for LASV sequencing-positive samples from the SL-IV clade and stronger detection rates than the Nikisins assay for LASV sequencing-positive samples from the N-II clade. Previous work by Andersen et al. demonstrates that the SL-IV and N-II clades show high levels of genetic divergence and that N-II LASV strains are much older and more genetically diverse than SL-IV strains (Andersen et al., 2015).

Although a Ct cutoff of 40 is used by other published LASV RT-qPCR assays (Demby et al., 1994; Pang et al., 2014), this threshold is imperfect and did not accurately diagnose all tested samples. Some sequencing-positive samples had Ct scores of over 40 cycles and thus were considered RT-qPCR negative. Difficulty in determining an accurate Ct threshold highlights the need for alternative diagnostic methods, especially for low-titer samples in this grey area with Ct scores around the RT-qPCR limit of detection.

The Broad RT-qPCR assay efficiency of 70.43% could contribute to a lack of detection some sequencing-positive samples with low viral loads such as sample NG 1747 (FIG. 6*a*). Reduced assay efficiency is caused in part by primer degeneracy; due to the large amount of LASV genetic variation, the Broad_F and Broad_R primers have 7 and 10 degenerate base pairs, respectively, which may reduce primers' *affini* ty for their target sequence and also enable primers to bind to and amplify off-target sequences. Off-target PCR amplification including primer dimer can interfere with quantification in assays that use non-specific dsDNA binding dye because the dye will also be bound by the off-target amplification products. Because the Broad assay quantifies fluorescence via a sequence-specific probe rather than non-specific dye, quantification of off-target PCR products was not a concern. However, amplification of off-target templates can further reduce the efficiency of probe-based assays such as the Broad assay by competing for PCR enzymes.

Broad RT-qPCR Assay Validation in the Field

The Broad assay was also validated in the field by running the assay on a blinded panel of 52 recent LASV patient samples from clade SL-IV at Kenema Government Hospital (KGH). RNA quality was not held constant between all diagnostic methods; due to its remote location, KGH has frequent power outages that cause freezer failures, thawing of reagents, and subsequent degradation of RNA samples. On many samples Applicant carried out the Broad assay several months to years after other diagnostic tests had been completed, so sample RNA may have significantly degraded during this time due to repeated freeze-thaws. If viral quantity in the samples was low at the point of patient blood draw, then degradation may be more profound. Because the Broad assay targets viral RNA, poor RNA quality could result in false negatives.

Figure 7:
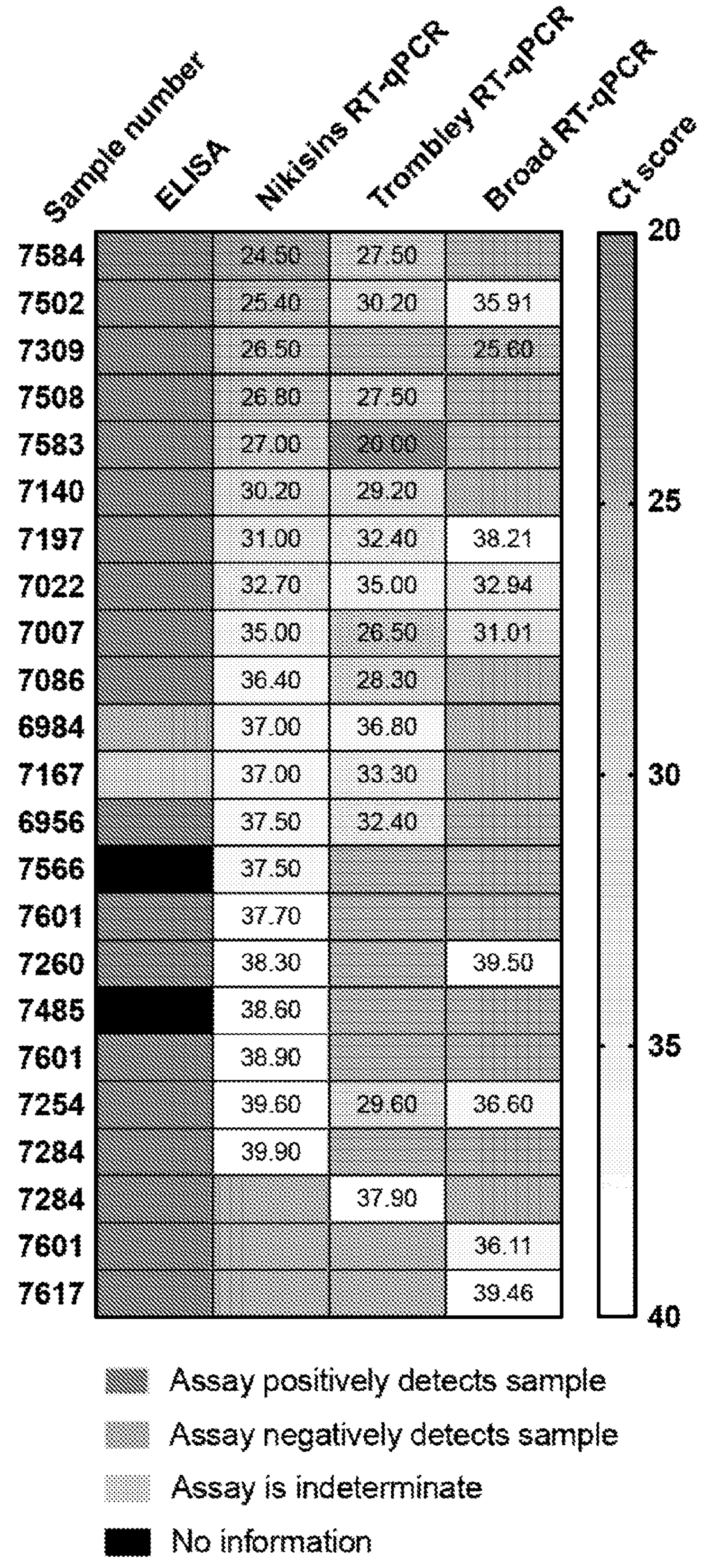
FIG. 7 compares diagnostic results of the Broad RT-qPCR assay and two published RT-qPCR assays tested on 52 LASV patient samples at Kenema Government Hospital (KGH). These experiments confirm that the Broad RT-qPCR assay can detect LASV samples from clade SL-IV in the field. Ct scores for all samples that were positively detected by at least one RT-qPCR assay are shown. Data from LASV antigen-based ELISA tests run on the same samples is included identify positive samples. RNA quality was not held constant between assays, so comparisons of assay performance could not be made.

The Broad assay detected 9 LASV samples (FIG. 7). ELISA, Nikisins RT-qPCR, and Trombley RT-qPCR results for the same samples are shown to identify positive samples but are not used to draw comparisons with the Broad RT-qPCR results because the RNA quality was not constant between all diagnostic methods. All samples detected by the Broad assay were also positive by both ELISA and RDT, indicating that they were true positives even after possible sample degradation. These results show that the Broad assay is working in the field and can capture samples confirmed positive by other diagnostic methods. Interestingly, the Broad assay detected two samples that were not picked up by the Nikisins or Trombley assays (SL 7601 and SL 7617). The ability of the Broad assay to detect samples not detected by other RT-qPCR assays indicates that this assay is a valuable addition to current LASV diagnostic methods at KGH because it expands the viral genetic diversity captured by RT-qPCR assays.

TABLE 2B

Broad RT-qPCR assay

| Primer name | Primer sequence |
|---|---|
| Broad_F | 5' - GATGCRGCYRAYCAYTGTG - 3' (SEQ ID NO: 69) |
| Broad_R | 5' - GAR AAC TGG CAG TGA TCT TCC - 3' (SEQ ID NO: 70) |
| Broad_P | FAM-TTYATGAGG/ZEN/ATGGCTTGGGGTGG-3IABkFQ (SEQ ID NO: 71) |

TABLE 2C

Trombley RT-qPCR assay

| Primer name | Primer sequence |
|---|---|
| F548 | 5'-GGAATGAGTGGTGGTAATCAAGG-3' (SEQ ID NO: 72) |
| R617 | 5'-TTTTCACATCCCAAACTCTCACC-3' (SEQ ID NO: 73) |
| p594A | FAM-ACTCCATCTCTCCCAGCCCGAGC-TAMRA (SEQ ID NO: 74) |

TABLE 2D

Nikisins RT-qPCR assay (SEQ ID NO: 75-77)

| Primer name | Primer sequence |
|---|---|
| Nikisins_F | 5' - CCACCATYTTRTGCATRTGCCA - 3' (SEQ ID NO: 75) |
| Nikisins_R | 5' - GCACATGTNTCHTAYAGYATGGAYCA -3' (SEQ ID NO: 76) |
| Nikisins_P | FAM-AARTGGGGYCCDATGATGTGYCCWTT-BBQ (SEQ ID NO:: 77) |

Example 2—SHERLOCK Assay for Lassa Virus

The SHERLOCK pipeline was utilized to develop a CRISPR-based diagnostic panel that targets three clades of the virus: N-II, N-III, and SL-IV. A SHERLOCK diagnostic was developed to a) encompass current viral diversity and b) provide a field-deployable kit for use in remote endemic regions. Here, Applicant describes three independent SHERLOCK assays developed, each of which targets one of the three clades.

Methods

Sherlock Detection Strategy and Assay Design

The genetic diversity found in current LASV patient samples received at the Sabeti Lab's collaborator institutions and hospitals in West Africa, including KGH, the Irrua Specialist Teaching Hospital, and Redeemer's University were examined. Patient samples fell within three viral clades: all samples collected in Sierra Leone fell within SL-IV, a majority of samples from Nigeria fell within N-II, and a minority of samples from Nigeria fell within the newly emerging N-III. Because the three clades are genetically distinct, separate SHERLOCK assays were designed to independently detect each clade. The SHERLOCK assays developed for SL-IV will be referred to as "SL-IV assays"; N-II as "N-II assays"; and N-III as "N-III assays."

Assays for the three clades were designed using reference sequence alignments provided by Dr. Baniecki and Dr. Siddle. N-II and SL-IV alignments from Dr. Baniecki referenced in section 2.1.2 were used to design assays for N-II and SL-IV, respectively. Dr. Siddle provided an alignment of sequences from a recent outbreak in Nigeria of the N-III clade. Dr. Siddle sequenced these samples in the fall of 2017 through the spring of 2018. These sequences are not yet published.

Using these alignments, RPA primers and crRNAs were designed for the three clades using CATCH (Compact Aggregation of Targets for Comprehensive Hybridization), a probe design software developed by Mr. Metsky (Siddle, Metsky et al., in submission). CATCH designs a set of oligo probes that target a user-specified group of viral sequences based on several user-defined parameters: "guide_length," which determines the length of the oligo; "mismatches," which defines the threshold number of tolerated mismatches between the oligo and the target sequence; "window_size," which indicates the length of the window in which oligos are designed and corresponds to the length of the amplicon; and "cover_frac," which indicates the fraction of sequences that are captured by the oligo. Table 3 displays the parameters inputted into CATCH for crRNA and RPA primer design. Parameters were determined based on published SHERLOCK and RPA methods (Gootenberg et al., 2017; Piepenburg et al., 2006). "guide_length" defines the length of the designed oligo probe; "mismatches" defines the threshold number of tolerated mismatches between the oligo probe and the target sequence; "window_size" corresponds to the length of the amplicon; and "cover_frac" indicates the fraction of sequences within the viral alignment that are captured by the oligo probe. Oligo probe lengths and amplicon sizes were chosen based on published methods (Gootenberg et al., 2017; Piepenburg et al., 2006). CATCH outputs a list of all oligo probes that fit input criteria and assigns each a score from 0-1. This score correlates with the number of genomes the oligo covers, with a higher score indicating that the oligo covers more genomes.

TABLE 3

| crRNA and RPA primer parameters inputted into CATCH. | | | | |
|---|---|---|---|---|
| | guidelength | mismatches | window_size | cover_frac |
| crRNA | 28 | 10 | 200 | .9 |
| RPA primer | 30 | 10 | 200 | .9 |

LASV contains few highly-conserved regions. Binding of crRNAs were prioritized to the most highly-conserved genome regions in the assay design. crRNAs minimally tolerate base pair mismatches with their target sequences, while RPA reactions are more tolerant of these mismatches because RPA achieves amplification via strand displacement rather than primer annealing (Abudayyeh et al., 2016; Gootenberg et al., 2017; Piepenburg et al., 2006).

crRNA parameters were first inputted into CATCH, with the 4 crRNAs with the highest scores for the SL-IV assay chosen. Because the N-II and N-III assays were created after the SL-IV assay, a larger number of crRNAs for these assays (n=9) after observing significant variation between the cutting efficiencies of SL-IV crRNAs were chosen. The chosen crRNA sequences outputted by CATCH were aligned to their respective sequence alignments using the primer testing feature of Geneious 10.3.1 (Kearse et al., 2012). RPA primer parameters were then subsequently inputted into CATCH with oligo sequences outputted by CATCH chosen that were located within 200 basepairs of chosen crRNA sequences. The highest-ranked 3 primer pairs that amplified the binding region of each crRNA were chosen. Some primer pairs amplified the binding region of more than one crRNA. Primer sequences were chosen and aligned to their respective clade-specific sequence alignments using the primer testing feature of Geneious 10.3.1 (Kearse et al., 2012). Using the mean pairwise identity feature of Geneious 10.3.1 (Kearse et al., 2012), Degenerate base pairs at the ends of all designed crRNAs and primers were searched, if the end of a crRNA or primer contained a base pair that had a mean pairwise identity of less than 70%, meaning that fewer than 70% of aligned sequences contained the crRNA or primer's base pair at this position, the designed sequence was shortened by up to 3 nucleotides to eliminate the degenerate base pair. Although altering primer or crRNA length may reduce assay efficiency, eliminating degenerate base pairs increases the likelihood that designed crRNAs and primers will bind to their target sequences.

4 crRNAs and 12 RPA primers using CATCH for the SL-IV assay; 9 crRNAs and 16 RPA primers for the N-II assay; and 9 crRNAs and 12 RPA primers for the N-III assay were designed. As RPA creates DNA products and Cas13a cleaves RNA, a T7 promoter sequence was added to the 5' end of all forward primers to enable downstream transcription from the DNA product to RNA. All RPA primer pairs were ordered at 99% degeneracy (Integrated DNA Technologies). crRNAs were ordered as DNA and included the LwaCas13 direct repeat sequence and the T7 promoter sequence so that RNA products could be reverse transcribed. crRNAs were ordered at either 95%, 90%, or 85% degeneracy, depending on the number of degenerate base pairs within the sequence (Integrated DNA Technologies). Of note, because crRNAs are ordered as DNA, the DNA sequence corresponds to the reverse-complement of both the direct repeat and spacer so that transcription into RNA produces a crRNA complementary to the target sequence. All designed RPA primer and crRNA sequences are included in the tables herein.

GBlock fragments (Integrated DNA Technologies) for each RPA amplicon were designed using the annotation feature of Geneious 10.3.1 (Kearse et al., 2012) based off of the consensus sequence of the clade-specific alignment. GBlocks were ordered without degenerate bases. In order to guarantee RPA primer binding, GBlocks contained bases upstream and downstream of the targeted amplicon.

Sherlock Pipeline Protocol and Data Analysis

GBlock fragments (Integrated DNA Technologies) for each RPA amplicon were designed using the annotation feature of Geneious 10.3.1 (Kearse et al., 2012) based off of the consensus sequence of the clade-specific alignment. GBlocks were ordered without degenerate bases. In order to guarantee RPA primer binding, GBlocks contained bases upstream and downstream of the targeted amplicon. The SHERLOCK pipeline is comprised of two reactions: (1) an isothermal amplification step (RPA) and (2) a Cas13-based detection step.

RPA reactions were carried out using the TwistDx™ RT-RPA kit at a volume of 10 μL/well, according to the manufacturer's instructions. The following reagents were added to the RPA reaction mix: Rehydration buffer (TwistDx™); RPA pellets containing contain reverse transcriptase, recombinases, single-stranded DNA binding (SSB) protein, and polymerase (TwistDx™); 10 μM primer mix; nuclease-free water; and magnesium acetate. For RPA reactions with RNA input, Murine RNase inhibitor (NEB M3014L) was added to the reaction mix at a concentration of 2 units/μL to prevent RNase activity. RPA reactions were performed both alone and as a precursor to SHERLOCK detection. For those RPA reactions performed alone during RPA optimization experiments, SYTO™ 9 dye (Thermofisher) was added to the reaction mix, which specifically stains double stranded DNA. Applicant ran these reactions on the Lightcycler 96 System (Roche), which measured double-stranded amplification products via the fluorescent dye. Reactions were run for 20 minutes at 41° C. on the SYBR Green dye detection channel with the following filter set conditions: excitation at 470 nm and emission at 514 nm. Unlike the RT-qPCR assays, RPAs are not quantitative, meaning that the number of viral particles cannot be quantified using a Ct score and can often have high background. For those RPA reactions performed as precursors to the SHERLOCK detection step, Applicant did not add SYTO™ 9 dye and ran the reactions on a thermocycler for 20 minutes at 41° C.

Cas13a-based detection reactions were performed according to published methods using RNase Alert v2 (ThermoFisher Scientific) as the reporter (Gootenberg et al., 2017; Myhrvold et al., Science, in press). The following reagents were added to the SHERLOCK reaction mix: nuclease-free water; rNTPs at a concentration of 25 nM (New England Biolabs); RNase Inhibitor, Murine (New England Biolabs); background RNA at a concentration of 500 ng/μL (RNA purified from cultured HEK293FT cells using a Qiagen blood and cell culture RNA extraction kit); MgCl2 at a concentration of 1 M (New England Biolabs); RNase Alert v2 (ThermoFisher Scientific); Cas13a protein (Genscript); and T7 RNA polymerase (New England Biolabs). Applicant ran all reactions with three technical replicates on Biotek microplate readers. Dr. Myhrvold, Dr. Barnes and Applicant ran the SL-IV crRNA optimization reactions on a Synergy H4 plate reader (Biotek). Applicant ran all other SHERLOCK reactions on a Cytation 5 plate reader (Biotek). Sabeti Lab members noted concordance between these two machines and use them interchangeably (Myhrvold et al., Science, in press). Fluorescence kinetics were measured via a monochromator with excitation at 485 nm and emission at 520 nm. Reactions were run at 37° C. for 3 hours, with a reading every 5 minutes.

To analyze all SHERLOCK reactions, Applicant performed background correction by subtracting fluorescence values after 10 minutes when minimum fluorescence was observed from the final fluorescence values at 3 hours. For SHERLOCK reactions cross-comparing multiple crRNAs, target-specific fluorescence was calculated to normalize each target reaction to its NTC control.

Target-specific fluorescence accounts for the varying background activity caused by spurious crRNA cleavage, which can differ depending on the crRNA used. Target-specific fluorescence is calculated by subtracting the average background-corrected fluorescence of three NTC reactions for a given crRNA at 3 hours from the average background-corrected fluorescence of three template target reactions of the same crRNA at 3 hours. Applicant calculated standard deviation (SD) for each template-specific fluorescence value using the following equation:

$$\text{Template-specific fluorescence SD}=\sqrt{\text{SDoftemplatereaction}^2+\text{SDofNTC}^2}$$

Optimization of SHERLOCK Assays crRNA Optimization for the Cas13a-Based Detection Step All designed crRNAs were prepared based on published methods (Gootenberg et al., 2017; Myhrvold et al., Science, in press). The crRNA DNA templates were annealaed to a primer matching the T7 promoter sequence (final concentration of 10 uM). In-vitro transcription of the crRNAs using the HiScribe T7 High Yield RNA Synthesis Kit (NEB) according to the manufacturer's instructions and incubated the reactions overnight at 37° C. Applicant purified the crRNAs using RNAClean XP beads (Beckman Coulter) at a 2× ratio of beads to reaction volume with an additional supplementation of 1.8× isopropanol.

crRNAs were optimized for the SL-IV assay, and the crRNAs for the N-II and N-III assays independently. The Cas13a detection step of SHERLOCK was performed as described herein, using all designed crRNAs. Each crRNA was tested against a GBlock template (10 #copies/μL) and a NTC. Applicant defined the most efficient crRNAs for each clade as having the highest target-specific fluorescence, which is the difference in fluorescence between the substrate and NTC reactions, with the three most efficient crRNAs for each clade selected for further assay optimization.

RPA Primer Optimization for the Isothermal Amplification Step

RPA primers were prepared according to manufacturer's instructions by diluting them to a concentration of 10 μm using nuclease-free water (Integrated DNA Technologies). GBlock templates were prepared according to manufacturer's instructions (Integrated DNA Technologies). Applicant diluted each GBlock to a working concentration of 10 copies/μL using nuclease-free water.

The SL-IV assay primer optimization experiments were carried out for the N-II and N-III assays independently. To determine which RPA primers resulted in the greatest amplification, all possible primer pair combinations were tested both on primer-specific GBlock templates at a concentration of 10; copies/μL (Integrated DNA Technologies) and on a NTC containing nuclease-free water. n=9 combinations for the SL-IV assay; n=13 combinations for the N-II assay and n=14 for the N-III assay were tested.

Primer pairs were evaluated based on 2 criteria: 1) better primer pairs had higher total fluorescence and 2) better primer pairs had a larger difference in fluorescence between the template reaction and the NTC. Because total fluorescence correlates to amount of DNA amplification that occurs during the reaction, greater fluorescence results in more sensitive detection as more of the template is available for the detection step of SHERLOCK. However, RPA experiments have demonstrated that RPA reactions do not solely amplify the target; nonspecific background amplification of other nucleic acid material also occurs. NTC reactions are therefore an informative control for the amount of off-target amplification of a given primer pair. Primer pairs with high background, as visualized by high fluorescence values for NTC reactions, are less desirable for SHERLOCK as they have the potential to lead to off-target crRNA activity.

Several primer pairs were designed for each crRNA. Based on the results of the RPA reactions, Applicant ranked the best primer pairs associated with each crRNA identified in the crRNA optimization experiments.

Creation of Full SHERLOCK Assays

After determining the three best crRNAs in each clade and the strongest RPA primer pairs, Applicant identified combinations of crRNAs and primer pairs that created full SHERLOCK assays, and paired each of the top crRNAs, identified in the crRNA optimization section, with the highest-ranking RPA primer set that amplified a template containing the crRNA binding region. A total of nine SHERLOCK assays were used going forward: three assays targeting the SL-IV clade; three targeting the N-II clade; and three targeting the N-III clade. A series of validation experiments in the following sections, including limit of detection, cross-reactivity, and testing on patient samples, were conducted to ultimately determine the single strongest SHERLOCK assay for each clade.

SHERLOCK Limit of Detection

To assess the sensitivity of the SHERLOCK assays, limit of detection (LOD) reactions were carried out on the nine optimized assays (three per clade) with each experiment conducted independently. For each assay, SHERLOCK reactions were ran as described in the methods on a series of ten-fold serial dilutions of assay-specific GBlock templates (concentrations ranged from $10^0$-$10^\$$ copies/μL). Applicant also tested each assay on an NTC containing nuclease-free water. Background-subtracted fluorescence values were calculated for all tested concentrations of GBlock template as described in the methods. Assuming a normal distribution of sample fluorescence, the lowest analyte concentration that can be reliably distinguished from NTCs with a confidence interval of >99% must have a mean background-subtracted fluorescence value that is 3 standard deviations (SD) above that of the NTC reactions. All GBlock concentrations with background-subtracted fluorescence levels above this cutoff were determined to be above the LOD (Armbruster et al., 2008).

SHERLOCK Cross-Reactivity with Other VHF-Inducing Viruses

Cross-reactivity experiments were conducted to determine if the SHERLOCK assays would positively detect two other viruses that cause symptoms hemorrhagic fever: Ebola virus (EBOV) and Marburg virus (MARV). Applicant tested the cross-reactivity of the nine optimized assays using the SHERLOCK detection platform protocol outlined herein. Applicant tested four templates on all assays: EBOV Macona seed stock (EBOV_IRF0189), Marburg Angola seed stock (Marburg_IRF0169), assay-specific GBlock ($10^4$ copies/μL) as a positive control, and nuclease-free water as a negative control. An assay was defined as cross-reactive if it outputted a background-subtracted fluorescence measurement for either the MARV or the EBOV seed stock that was greater than 3 SD above the nuclease-free water negative control.

SHERLOCK Validation on Recent LASV Patient Samples

SHERLOCK assays were tested on a panel of clade-specific extracted RNA patient samples available in-house at the Broad Institute. For the SL-IV and N-II SHERLOCK assays, Applicant tested the same blinded panel of patient samples used for RT-qPCR validation. This sample continuity allowed comparison of results of the SHERLOCK assays to results of the Broad and Nikisins RT-qPCR assays on a sample-by-sample basis. At the time of validation testing, only seven sequencing-positive N-III LASV samples from the 2018 outbreak in Nigeria were available in-house. All patient samples were diluted 1:20 in nuclease-free water, which is the same dilution factor that was used in RT-qPCR validation reactions. All samples were tested using the SHERLOCK pipeline described in the methods, and a NTC reaction using nuclease-free water was also performed for each assay. For each sample, template-specific fluorescence calculated as described herein.

Determining Positive Sample Fluorescence Cutoffs for Designed SHERLOCK Assays

Because SHERLOCK diagnostics are a newly-developed technology, there is no standard or published standard methods for determining a fluorescence cutoff value to define if a sample is positive or negative. For each developed assay, Applicant established a baseline fluorescence value for negative samples by averaging the background-subtracted fluorescence values of 5 NTC reactions. Applicant compared the average NTC background-subtracted fluorescence values to the background-subtracted fluorescence values of six confirmed sequencing-negative patient samples tested on the SL-IV and N-II assays in section 2.2.6. Applicant did not compare N-III patient samples because sequencing-negative samples on the N-III assays were not tested. The fluorescence values of the six sequencing-negative patient samples were within one SD of the NTC reactions for all SL-IV and N-II assays, so Applicant concluded that averaging NTC fluorescence values was a reasonable representation of a LASV negative sample.

The results of SHERLOCK data was calibrated to SL-IV and N-II sequencing results to establish a positive fluorescence cutoff that maximized the number of true positives reported by SHERLOCK while minimizing the number of false positives and false negatives. A high cutoff is preferred because it reduces the likelihood of false positives, but the cutoff should not be too high as to also avoid reporting false negatives. Despite no standard thresholding method, one previously-used approach defined positive samples as being three SDs outside of their assay-specific negative threshold value (Myhrvold et al., Science, in press). Samples were evaluated using a positive sample fluorescence cutoff of 3 SD above the average NTC background-subtracted fluorescence value. Under these stringent cutoffs, several sequencing-positive samples in each clade were designated as negative by SHERLOCK. Under a positive sample fluorescence cutoff of 2 SD above the average NTC background-subtracted fluorescence value, 2 more sequencing-positive samples were detected as positive by SHERLOCK than when using a cutoff of 3 SD and no additional false negatives were reported. When samples were evaluated using a positive sample fluorescence cutoff of 1 SD, 4 samples that were negative by Broad and Nikisins RT-qPCR but did not have available sequencing data were reported as SHERLOCK positive. Optimal positive sample fluorescence cutoff was 2 SD above the average NTC background-subtracted fluorescence value; under this cutoff a greater number of sequencing- and RT-qPCR-positive LASV samples were categorized as positive by SHERLOCK compared to a cutoff of 3 SD, but no additional false positives were reported.

Samples tested were evaluated as either Lassa positive or Lassa negative using the positive fluorescence cutoff of 2 SD above the average NTC background-subtracted fluorescence. Applicant compared these SHERLOCK results to RT-qPCR and sequencing results to evaluate the sensitivity of SHERLOCK assays in comparison to other detection methods. Applicant determined the strongest SHERLOCK assay for each clade, defined as the assay that detected the largest number of sequencing-positive patient samples.

Adapting SHERLOCK Technologies to Field-Applicable Protocols

Developing Afield-Adapted SHERLOCK Protocol

During the summer of 2017, Applicant travelled to KGH to assess the feasibility of conducting SHERLOCK reactions in West Africa. SHERLOCK assays were adapted to available resources at KGH and to simplify the SHERLOCK protocol to reduce necessary laboratory staff training. Two components of the protocol presented herein were adjusted: (1) the RPA reaction was replaced with a RT-PCR amplification step and a SPRI clean-up, and (2) the LightCycler 96 System (Roche) was used to measure reaction fluorescence rather than the Cytation 5 plate reader (Biotek). In the following section, the SHERLOCK pipeline with these two alterations is referred to as field-adapted SHERLOCK protocol.

Although published methods use RPA reactions are used for template amplification rather than RT-PCR reactions due to increased reaction speed (Gootenberg et al, 2017; Myhrvold et al., Science, in press), both types of reactions can amplify the target sequence for input into the detection reaction. RT-PCR reactions are preferable at KGH because the KGH laboratory staff is already trained in RT-PCR reactions and have the necessary RT-PCR reagents available in-house.

Applicant adapted the amplification step of SHERLOCK to a RT-PCR reaction using reagents and machines available at KGH. A RT-PCR reaction was developed using the TaqMan® RNA-to-$C_T$™ 1-Step Kit (Applied Biosystems) based on manufacturer's protocol. For each reaction, Applicant added 2× master mix containing AmpliTaq Gold® Polymerase UP and dNTPs (Applied Biosystems); nuclease-free water; assay-specific primer mix; and 40× RT enzyme mix (Applied Biosystems) containing ArrayScript™ UP Reverse Transcriptase and RNase Inhibitor. RT-PCR reactions were incubated for 2 hours. The following temperature conditions were used: 45° C. for 30 minutes (1 cycle); 95° C. for 10 minutes (1 cycle); 94° C. for 15 seconds and 60° C. for 30 seconds (45 cycles).

Because RPA primers are longer than traditional PCR primers, it was unclear whether RT-PCR amplification with designed primers would be as efficient as RPA amplification. A SPRI clean-up using the Agencourt RNAClean XP kit (Beckman Coulter) according to the manufacturer's protocol was performed and removed off-target products and concentrated cDNA amplification products, thereby improving chances of target detection by SHERLOCK.

The most significant limitation to conducting SHERLOCKs at KGH is the hospital's limited laboratory machinery. The laboratory at KGH does not possess a plate reader that measures fluorescence, as required by the SHERLOCK detection protocol, so the SHERLOCK detection protocol was adapted to the LightCycler 96 System (Roche) available in Sierra Leone. This machine is available at many of sites in West Africa, including sites that do not possess plate readers, so adapting SHERLOCK detection reactions to this machine would facilitate the technology's use in numerous remote clinical settings.

The feasibility of using the LightCycler 96 Systems (Roche) to detect SHERLOCK fluorescent output was evaluated. Applicant performed a Cas13a-based detection step as described herein using the SHERLOCK assay SL-IVb on an assay-specific GBlock at a concentration of 109 copies/μL and on a no-input control. A high concentration of GBlock was directly inputted into the detection reaction rather than first performing an amplification step on a lower concentration of GBlock to eliminate the possibility of reduced fluorescent detection due to poor template amplification. All reactions were performed in triplicate. Detection was performed on the SYBR Green I detection channel with excitation at 470 nm and emission at 514 nm. Reactions ran for 3 hours at 37° C. Endpoint fluorescence measurements of all samples were evaluated, which quantify the relative fluorescence of each sample at the end of the 3-hour reaction.

After confirming the LightCycler 96 System's ability to quantify sample fluorescence, full field-adapted SHERLOCK reactions were ran using assays SL-IVa, SL-IVb, and SL-IVc on assay-specific GBlock templates at concentrations of 104 copies/μL. RT-PCR reactions were performed on the GBlock template and a SPRI cleanup step conducted on the amplified product, as described above. Applicant used the SPRI product as input into a SHERLOCK detection reaction. The endpoint fluorescence measurements of each GBlock reaction and no-template control were evaluated to determine if significant template-specific fluorescence was observed.

Using the field-adapted SHERLOCK protocol, n=5 EBOV samples were tested using an EBOV SHERLOCK assay developed summer of 2017, and discussed in further detail in Example 3. Primer and crRNA sequences for the EBOV SHERLOCK assay are included in the Table below. Applicant tested all samples and a NTC in triplicate. The EBOV assay was tested rather than a LASV assay because at the time of this experiment, optimization of the LASV SHERLOCKs was not complete.

EBOV SHERLOCK assay (SEQ ID NO: 78-80)

| Primer name | Primer Sequence |
|---|---|
| EBOV P2_F | 5' - GACAGACTGAGGAARATAACATTGCAAAG - 3' (SEQ ID NO: 78) |
| EBOV P2_R | 5' - CAATCATACATGGRAGTGTGGCTCCAATAA - 3' (SEQ ID NO: 79) |
| **crRNA name** | **crRNA sequence** |
| EBOV G2 | TTTAACCCAAATAACTTGCACAGTTGAT (SEQ ID NO: 80) |

Because SHERLOCK is not a quantitative assay, Applicant could not use standards to quantify the amount of target in the patient samples akin to the Broad RT-qPCR analysis. Instead, SHERLOCK outcomes were determined based on the LightCycler 96 System's endpoint fluorescence measurements of each sample. The average endpoint fluorescence and SD for each sample and for the no-input control was calculated, with positive samples defined as having endpoint fluorescence values that were greater than 3 SD above the no-input control.

Adapting SHERLOCK Assays to Lateral Flow Readouts

Figure 5:
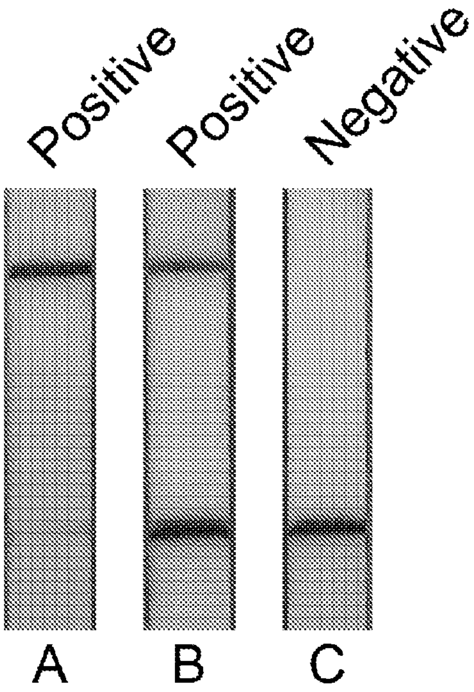
FIG. 5 provides results of Visual detection of template using lateral flow strips after 3 hours of Cas13a detection. Samples positive for the tested template display a top fluorescent band (A), while samples negative for the template display a bottom fluorescent band (C). A faint top fluorescent band accompanied by a bottom band (B) is caused by lower target concentration within the tested sample but is still considered positive for the template.

Lateral flow detection reaction was prepared according to published methods (Gootenberg et al., 2018), using the same reagents with the exception of the choice of reporter. Rather than V2 substrate, custom designed probe oligonucleotide was added at a concentration of 100 μM (Myhrvold et al., Science, in press). The SHERLOCK reaction mix was incubated for 3 hours at 37° C. on the Mastercycler® pro PCR machine (Eppendorf). After incubation, 80 μL of Hybridetect Assay Buffer (Milenia Hybridetect 1, TwistDx™) was added to each detection reaction to dilute them five-fold. One paper detection strip (Milenia Hybridetect 1, TwistDx™) was then placed into each detection reaction and incubated for 5 minutes at room temperature. After incubation, lateral flow strips were photographed using a smartphone. Applicant analyzed all tested samples based on the number of fluorescent bands present on the paper strip after incubation (FIG. 5). Lateral flow reactions that are positive for the template show a top fluorescent band on the paper strip after incubation. Lateral flow reactions that are negative for the template only show a bottom band. Lateral flow reactions are not quantitative and only display whether a template was present in a given sample, not how much template was present.

One SHERLOCK assay per clade was adapted to the lateral flow format. For each of the three clades, Applicant adapted the assay that detected the highest percentage of LASV patient samples. To evaluate each assay's limit of detection in the lateral flow format, Applicant performed lateral flow detection reactions as described above on a serial dilution of GBlocks specific to the crRNAs and on a nuclease-free water control. GBlock concentrations ranged from 105 down to 102 copies/μL for the SL-IV and N-III assays and from 105 down to 101 copies/μL for the N-II assay due to its greater sensitivity. To establish the feasibility of using the lateral flow format to detect patient samples, lateral flow reactions were performed for each assay on one clade-specific patient sample, diluted 1:20. For each clade, the patient sample with the highest target-specific fluorescence measurement from the results of the SHERLOCK detection tests was chosen.

Results

Designing Clade-Specific SHERLOCK Assays

Large variation in RT-qPCR results between geographical regions and low RT-qPCR sensitivity more broadly demonstrates a need for an alternative molecular viral diagnostic. In addition, RT-qPCR diagnostics are only feasible at hospitals with robust laboratory capabilities which is uncommon in many lower-income counties. Applicant chose to develop SHERLOCK assays in addition to the RT-qPCR assay because of their demonstrated sensitivity (Gootenberg et al., 2017) and because this novel approach has the potential to be used with minimal laboratory infrastructure.

SHERLOCK is a primer- and crRNA-based system. Given the large amount of genetic divergence between LASV strains, it is impossible to find a region of the genome long enough to bind a crRNA that is perfectly conserved across all strains. crRNAs require high specificity to bind to and cut their target sequence and do not tolerate high numbers of base-pair mismatches in their target sequences (Abudayyeh et al., 2016; Gootenberg et al., 2017). Instead of developing a single universal LASV SHERLOCK, Applicant developed three SHERLOCK assays that each targeted a distinct clade. The use of a clade-specific assay reduces target diversity and subsequently causes fewer mismatches between crRNAs and their target sequences, resulting in a more sensitive diagnostic tool.

The use of multiple assays rather than one universal assay is also a more effective means of diagnosing a rapidly-evolving pathogen like Lassa, because this approach allows for fast design and re-design of clade-specific assays as new sequencing information becomes available. While developing SHERLOCK assays for clades SL-IV and N-II, a LF outbreak emerged in Nigeria (World Health Organization, 2018). Sequencing revealed that the outbreak corresponded with new LASV genetic diversity emerging within the N-III clade, prompting development of a separate SHERLOCK assay for this clade, and showcasing the ability for nimble re-design using SHERLOCK. Redesigning a single assay that targeted both the N-III clade and previously-known clades would have taken a longer amount of time given the complications of additional genetic diversity and would have been less specific than the use of separate assays. As new clades emerge in the future, additional SHERLOCK assays can be designed and added to the assays developed to create a panel of assays that encompasses LASV diversity.

Optimization of SHERLOCK Assays crRNA Optimization

Figure 8:
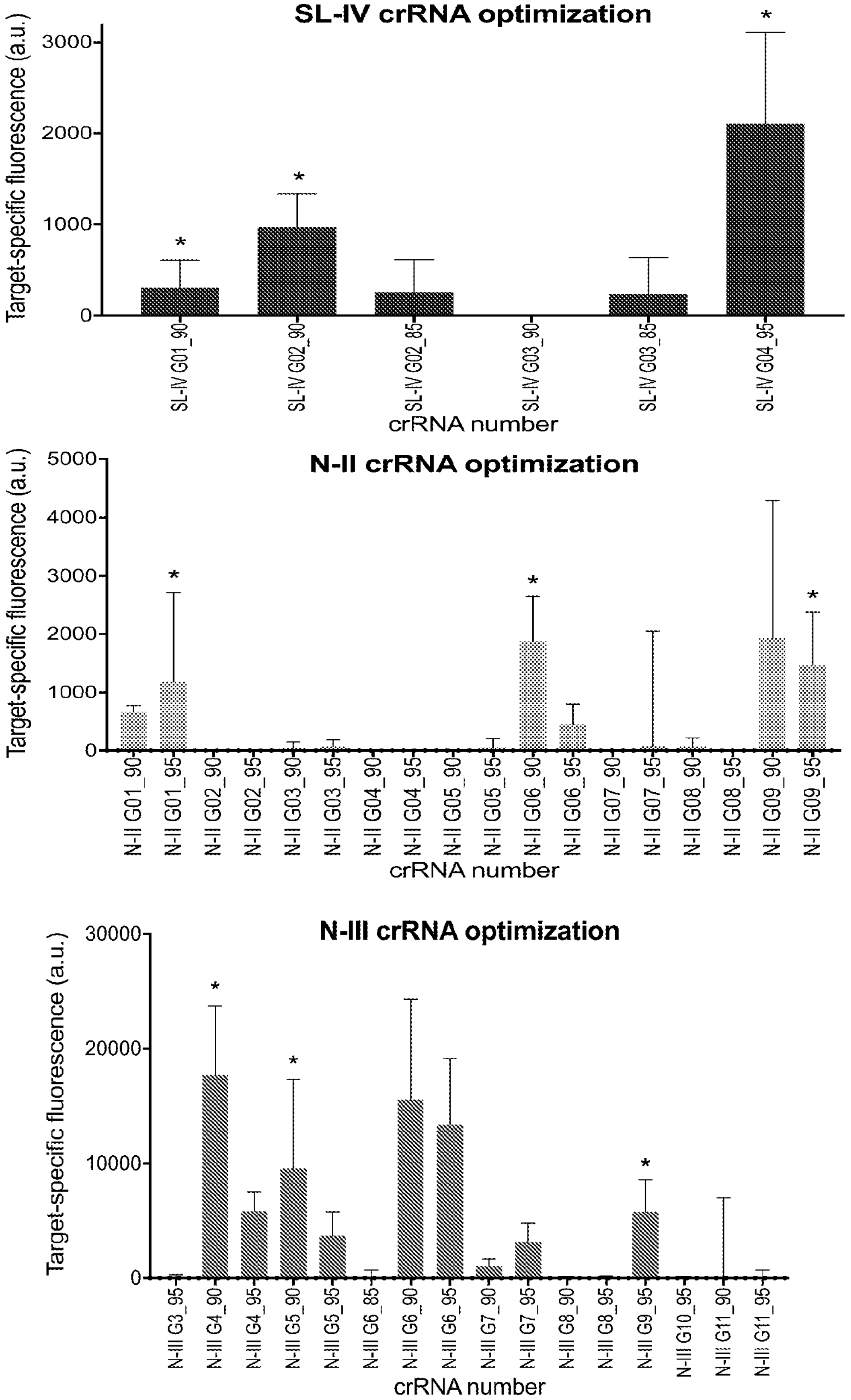
FIG. 8 provides graphs of target-specific fluorescence values of all designed crRNAs for the SL-IV, N-II, and N-III assays. Two detection reactions were performed for each crRNA, one using a GBlock template and one using nuclease-free water. All reactions were performed in triplicate. Target-specific fluorescence was calculated for each crRNA by subtracting the average fluorescence of the nuclease-free water reactions for a given crRNA from the average fluorescence of the GBlock target reaction. crRNAs were ranked by their target-specific fluorescence values, and the top three crRNAs for each assay, which are indicated by asterisks, were selected for further optimization. Error bars represent 1 SD based on three technical replicates.

After optimizing the crRNAs, as described herein, SHERLOCK detection reactions were run in triplicate on each crRNA using two different templates: a crRNA-specific GBlock at a concentration of 109 copies/μL and a NTC containing nuclease-free water (FIG. 8). Target-specific fluorescence for each crRNA was calculated by subtracting the average fluorescence of the NTC reactions for a given crRNA from the average fluorescence of the GBlock target reactions of the same crRNA.

The three crRNAs in each clade showing the highest level of target-specific fluorescence for further assay optimization were chosen, with one crRNA selected per sequence; if both the 90% and 95% degeneracy crRNAs of the same sequence showed high fluorescence, the crRNA with higher target-specific fluorescence or lower SD was chosen. Selected crRNAs are indicated by asterisks in FIG. 8 and their sequences are bolded in the tables below.

RPA Primer Optimization

Figure 9:
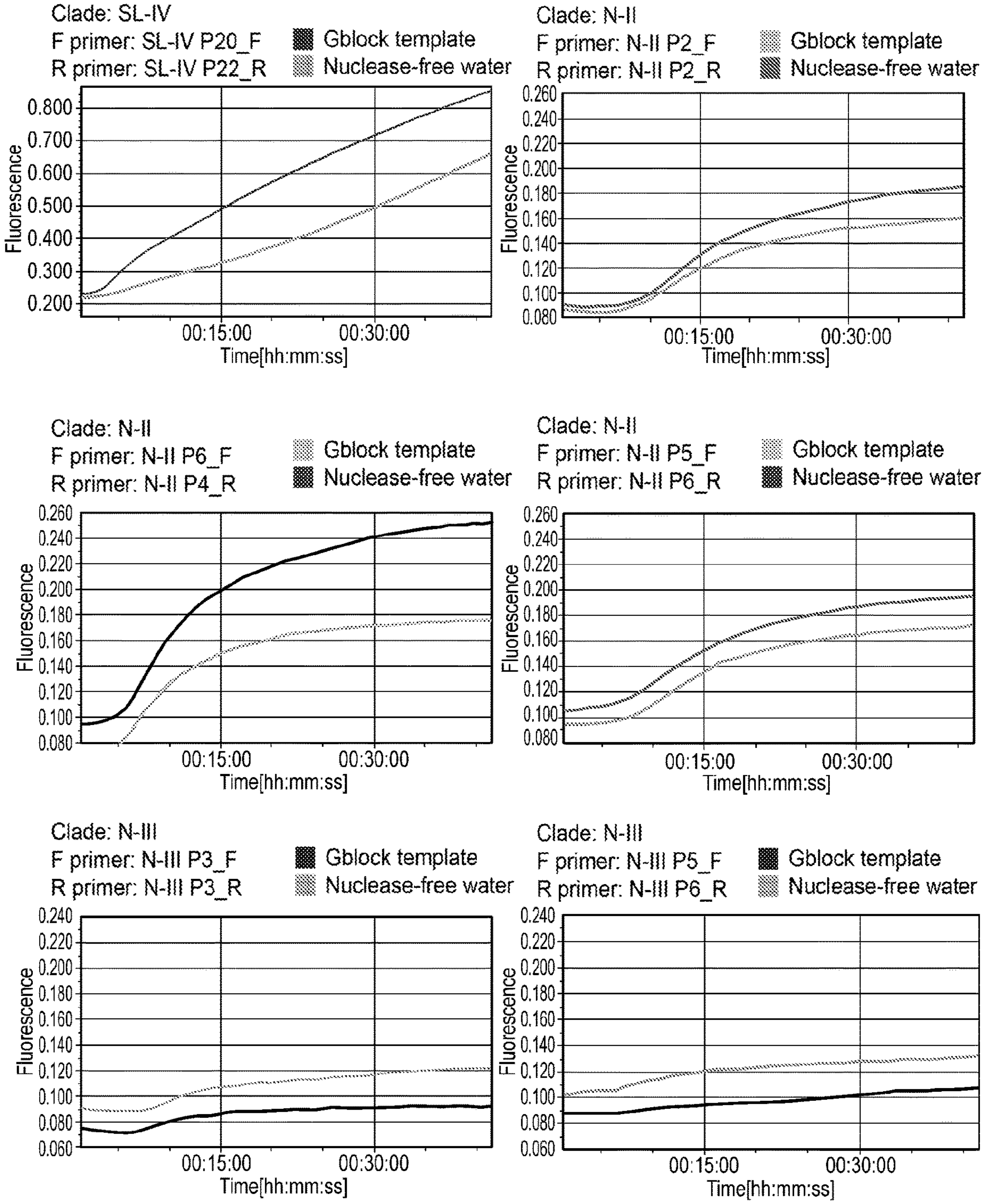
FIG. 9 includes RPA amplification curves of primer pairs chosen for further assay optimization. Each RPA primer pair was tested on two separate inputs: (1) a GBlock template at a concentration of 10 copies/μL and (2) nuclease-free water. Both amplification curves are shown for each primer pair. Better primer pairs were defined as having higher total fluorescence and a larger difference in fluorescence between the GBlock template reaction and the nuclease-free water control. Axis scales remain constant within clades but differ between clades to ensure amplification curve visibility.

Applicant optimized RPA primers as described herein. For each primer pair, Applicant ran RPA reactions using 2 inputs: a GBlock template with a concentration of $10^4$ copies/μL and a nuclease-free water control. Primer pairs were ranked based on both their total fluorescence and the difference in fluorescence between the GBlock template reaction and the nuclease-free water reaction. For each crRNA chosen in the crRNA optimization section, the primer pair that best amplified a template to which that crRNA binds was selected (FIG. 9). Chosen primer sequences are bolded below

TABLE 4

| SL-IV SHERLOCK assays (SEQ ID NO: 81-92) | |
|---|---|
| Primer Name | Primer Sequence |
| SL-IV P20_F | 5' - **CATYGMATCYTTGAGRGTCAT** - 3' SEQ ID NO: 81 |
| SL-IV P21_F | 5' - ARYTGRGARTADGTNARYCC - 3' SEQ ID NO: 82 |
| SL-IV P22_F | 5' - CATCYTTGAGRGTCATNAGCTGAGAATA - 3'. SEQ ID NO: 83 |
| SL-IV P20_R | 5' - AAYATMCTYTAYAARATHTG - 3'. SEQ ID NO: 84 |
| SL-IV P21_R | 5' - CCYGGYGARMGRAAYCCHTAYGA - 3'. SEQ ID NO: 85 |
| SL-IV P22_R | 5' - **AGGAATCCTTATGARAACATACTCTAYAA** - 3'. SEQ ID NO: 86 |
| crRNA name | crRNA sequence |
| SL-IV G1_90 | **GTGTTTTCCCARGCCCTTCCTGTTATTGA**. SEQ ID NO: 87 |
| SL-IV G2_90 | **CTTCCTGTTATTGARGTYCTTGATGCAAT**. SEQ ID NO: 88 |
| SL-IV G2_85 | CTTCCTGTTATTGARGTTCTTGATGCAAT. SEQ ID NO: 89 |
| SL-IV G3_95 | CCTGTTATTGARGTYCTTGATGCAATRT. SEQ ID NO: 90 |
| SL-IV G3_90 | CCTGTTATTGARGTTCTTGATGCAATRT. SEQ ID NO: 91 |
| SL-IV G4_95 | **TTGARGTYCTTGATGCAATRTAYG**. SEQ ID NO: 92 |

TABLE 5

| N-II SHERLOCK assays (SEQ ID NO: 93-126) | |
|---|---|
| Primer name | Primer sequence |
| N-II 01_F | 5' - CARTAYGARGCVATGAGYTGYGAYTTYAATG - 3' SEQ ID NO: 93 |
| N-II 02_F | 5' - **TTYAAYCARTAYGARGCVATGAGYTGYGA** - 3' SEQ ID NO: 94 |
| N-II 03_F | 5' - CTYTAYRAYCAYDCBYTVATGAGYATYATYTC - 3' SEQ ID NO: 95 |
| N-II 04_F | 5' - CTHAAYATGACNATGCCYYTRTCHTGYAC - 3' SEQ ID NO: 96 |
| N-II 05_F | 5' - **TGYCCYAARCCNCAYAGRMTHAAYCAHATGGG** - 3' SEQ ID NO: 97 |
| N-II 06_F | 5' - **AAYCTYTCYGAYGCVCAYARRARGRAYCT** - 3' SEQ ID NO: 98 |
| N-II 07_F | 5' - AACCACATGGGCATATGCTCATGTGGTCT - 3' SEQ ID NO: 99 |
| N-II 00_R | 5' - AGGTTGTACTGAACACTTATCTTCCC - 3' SEQ ID NO: 100 |

TABLE 5-continued

| N-II SHERLOCK assays (SEQ ID NO: 93-126) | |
|---|---|
| N-II 01_R | 5' - TGGGAAGATCACTGCCAGTTTTCTCGCCC - 3' SEQ ID NO: 101 |
| N-II 02_R | 5' - **TATTGGTAGGAAGTCATTATACAATCCCA** - 3' SEQ ID NO: 102 |
| N-II 03_R | 5' - GCTATGTAACTGCCACCCCAAGCCATCCTCAT - 3' SEQ ID NO: 103 |
| N-II 04_R | 5' - **CCACCCCAAGCCATCCTCATAAAAGTCTG** - 3' SEQ ID NO: 104 |
| N-II 05_R | 5' - TTTGAAAATGCTGTTTGGGATCAGTGCAA - 3' SEQ ID NO: 105 |
| N-II 06_R | 5' - **TAATGGACTGCATAATGTATGATGCAGC** - 3' SEQ ID NO: 106 |
| N-II 07_R | 5' - AGGAGATTTGAAAATGCTGTTTGGGATCA - 3' SEQ ID NO: 107 |
| N-II 08_R | 5' - ATGTATGATGCAGCTGTGTCAGGAGG - 3' SEQ ID NO: 108 |
| crRNA name | crRNA sequence |
| N-II G01_95 | **ATGGCYTGGGGTGGCAGYTAYATAGCAC** SEQ ID NO: 109 |
| N-II G01_90 | ATGGCYTGGGGTGGCAGYTAYATAGCAC SEQ ID NO: 110 |
| N-II G02_95 | ACYTTYATGAGRATGGCYTGGGGTGGCA SEQ ID NO: 111 |
| N-II G02_90 | ACTTTYATGAGRATGGCYTGGGGTGGCA SEQ ID NO: 112 |
| N-II G03_95 | AATCARTATGARGCRATGAGYTGTGAYT SEQ ID NO: 113 |
| N-II G03_90 | AATCAGTATGARGCAATGAGYTGTGAYT SEQ ID NO: 114 |
| N-II G04_95 | CARACYTTYATGAGRATGGCYTGGGGTG SEQ ID NO: 115 |
| N-II G04_90 | CARACTTTYATGAGRATGGCYTGGGGTG SEQ ID NO: 116 |
| N-II G05_95 | CARACYTTYATGAGRATGGCYTGGGGTG SEQ ID NO: 117 |
| N-II G05_90 | CARACTTTYATGAGRATGGCYTGGGGTG SEQ ID NO: 118 |
| N-II G06_95 | AYTTYAATCARTATGARGCRATGAGYTG SEQ ID NO: 119 |
| N-II G06_90 | **AYTTYAATCAGTATGARGCAATGAGYTG** SEQ ID NO: 120 |
| N-II G07_95 | TATGARGCRATGAGYTGTGAYTTYAATG SEQ ID NO: 121 |
| N-II G07_90 | TATGARGCAATGAGYTGTGAYTTCAATG SEQ ID NO: 122 |
| N-II G08_95 | ATGAGYTGTGAYTTYAATGGRGGRAARA SEQ ID NO: 123 |
| N-II G08_90 | ATGAGYTGTGAYTTCAATGGRGGRAAGA SEQ ID NO: 124 |
| N-II G09_95 | **TTACAGGACGACYTTGGGRCTTGADGTTCT** SEQ ID NO: 125 |
| N-II G09_90 | TTACAGGACGACYTTGGGRCTTGAKGTTCT SEQ ID NO: 126 |

Tables 6A-6B: N-III SHERLOCK assays (SEQ ID NO: 127-156)

TABLE 6A

| NIII Primers | |
|---|---|
| Primer name | Primer sequence |
| N-III P1_F | 5' - AGRTGGATGYTRATTGARGCYGARYTRAA - 3' SEQ ID NO: 127 |
| N-III P2_F | 5' - ATTGARGCYGARYTRAARTGTTTYGGRAA - 3' SEQ ID NO: 128 |
| **N-III P3-F** | **5' - CARGTRGAYYTGAATGAHGCTGTYCARGC - 3'** SEQ ID NO: 129 |
| N-III P4_F | **5'** - TRAACATGATTGAYACCAARAAGAGYTC - **3'** SEQ ID NO: 130 |
| N-III P5-**F** | 5' - **GCYTGYATGCTWGAYGGHGGYAAYATG** - 3' SEQ ID NO: 131 |
| N-III P6_F | 5' - GTYTCACCYCAAWCYATRGATGGSATYTT - 3' SEQ ID NO: 132 |

TABLE 6A-continued

| NIII Primers | |
|---|---|
| Primer name | Primer sequence |
| N-III P1_R | 5' - TGRTTYTTCATDATMAGYTGRTCRTTWAT - 3' SEQ ID NO: 133 |
| N-III P2_R | 5' - TARTTRCARTATGGTATDCCCATRATRTC - 3' SEQ ID NO: 134 |
| **N-III P3-R** | **5' - CATRTTRCCDCCRTCWAGCATRCARGCHCC - 3' V** SEQ ID NO: 135 |
| N-III P4_R | 5' - TATRTTYTCATAWGGRTTYCTYTCACCTG - 3' SEQ ID NO: 136 |
| N-III P5_R | 5' - GAYGCAATGTAAGGCCAYCCRTCTCCTGA - 3' SEQ ID NO: 137 |
| N-III P6_R | 5' - **ACYACAGTRTTTTCCCARGCYCTNCCM** - 3' SEQ ID NO: 138 |

TABLE 6B

| NIII crRNA | |
|---|---|
| crRNA name | crRNA sequence |
| N-III G3_95 | CTNTTTGAYTTYAAYAARCARGCYATW SEQ ID NO: 139 |
| N-III G3_90 | CTNTTTGAYTTYAAYAARCAAGCYATW SEQ ID NO: 140 |
| N-III G4_95 | TRAAYATGATTGAYACYAARAARAGYTC SEQ ID NO: 141 |
| **N-III G4-90** | **TRAACATGATTGAYACCAARAAGAGYTC** SEQ ID NO: 142 |
| N-III G5_95 | TBAAYRTHTCTGGYTACAAYTTYAGY SEQ ID NO: 143 |
| **N-III G5-90** | **TYAACATHTCTGGYTACAAYTTYAGY** SEQ ID NO: 144 |
| N-III G6_95 | TTBACDGCRGCWCCYARRCTRAARTTGTA SEQ ID NO: 145 |
| N-III G6_90 | TTBACWGCRGCWCCYARRCTRAARTTGTA SEQ ID NO: 146 |
| N-III G7_95 | GGDGCYTGYATGCTWGAYGGHGGYAAYATG SEQ ID NO: 147 |
| N-III G7_90 | GGRGCYTGYATGCTWGAYGGHGGYAAYATG SEQ ID NO: 148 |
| N-III G8_95 | ATSCCATCYATRGWYTGRGGTGARACY SEQ ID NO: 149 |
| N-III G8_90 | ATSCCATCYATRGWTTGRGGTGARACY SEQ ID NO: 150 |
| **N-III G9-95** | **GTYTCACCYCARWCYATRGATGGSATYTT** SEQ ID NO: 151 |
| N-III G9_90 | GTYTCACCYCAAWCYATRGATGGSATYTT SEQ ID NO: 152 |
| N-III G10_95 | CCAGGTGARAGRAAYCCWTATGARAAYAT SEQ ID NO: 153 |
| N-III G10_90 | CCAGGTGARAGRAAYCCWTATGARAAYAT SEQ ID NO: 154 |
| N-III G11_95 | TCAGGRGAYGGRTGGCCYTACRTTGCRT SEQ ID NO: 155 |
| N-III G11_90 | TCAGGAGAYGGRTGGCCTTACATTGCRT SEQ ID NO: 156 |

TABLE 7

| SHERLOCK sequences (SEQ ID NO: 157-158) | |
|---|---|
| T7promoter_25nt: | gaaatTAATACGACTCACTATAggg. SEQ ID NO: 157 |
| direct repeat: | GATTTAGACTACCCCAAAAACGAAG GGGACTAAAAC SEQ ID NO: 158 |

In several cases, the nuclease-free water control showed higher amplification than the reaction with GBlock input. Background amplification is often seen in RPA reactions due to off-target amplification, which is a notable limitation of RPA reactions. The high level of NTC amplification in FIG. 9 underscores the importance of pairing RPA amplification with a highly specific detection step like Cas13a cleavage to ensure target-specific detection.

Combining Chosen crRNAs and Primer Sets to Create Full SHERLOCK Assays

Each identified crRNA was paired with the best crRNA-specific primer set for the creation of a full SHERLOCK assay (Table 8), with combinations of crRNAs and their primer sets referenced using listed assay names for simplicity. crRNA efficiency was quantified by calculating template-specific fluorescence and selected the three most efficient crRNAs for each clade. RPA primer pairs were ranked based on absolute fluorescence and the difference in fluorescence between a GBlock template and a no input control. Each crRNA was paired with the highest-ranking RPA primer pair that amplified an amplicon containing the crRNA's binding region. Assay names for each crRNA/primer set combination will be used going forward for simplicity. Applicant developed more than one assay per clade to help combat LASV's rapid evolution and sequence divergence. Each clades' assays target different regions within the genome. If evolution occurred within the LASV genome such that the primer or crRNA-targeting region of one assay became degenerate, the other two assays could still detect samples within the clade.

Marburg virus disease (MVD) (Racsa et al., 2016). It is of great clinical and public health importance to be able to distinguish LF from these two diseases; because EVD and MVD are more commonly spread through human contact than LF, knowledge of the cause of infection for a patient presenting symptoms of hemorrhagic fever allows healthcare workers to take proper precautionary steps when treating the patient (Brainard et al., 2016). Methods described herein, including multiplexing SHERLOCK assays can be used for this purpose.

LASV SHERLOCK assays were tested on EBOV and MARV seed stocks to assess their cross-reactivity. For each assay, Applicant carried out full SHERLOCK reactions using inputs of EBOV seed stock, MARV seed stock,

TABLE 8

Table 8: 9 SHERLOCK assays created by combining chosen RPA primer pairs and crRNAs.

| Assay | SL-IV assays | | | N-II assays | | | N-III assays | | |
|---|---|---|---|---|---|---|---|---|---|
| name | SL-IVa | SL-IVb | SL-IVc | N-IIa | N-IIb | N-IIc | N-IIIa | N-IIIb | N-IIIc |
| crRNA | SL-IV G01_90 | SL-IV G02_90 | SL-IV G04_95 | N-II G01_95 | N-II G06_90 | N-II G09_95 | N-III G04_90 | N-III G05_90 | N-III G09_95 |
| Forward primer | SL-IV P20_F | SL-IV P20_F | SL-IV P20_F | N-II P2_F | N-II P6_F | N-II P5_F | N-III P3_F | N-III P3_F | NIII P5_F |
| Reverse primer | SL-IV P22_R | SL-IV P22_R | SL-IV P22_R | N-II P2_R | N-II P4_R | N-II P6_R | N-III P3_R | N-III P3_R | N-III P6_R |

Limit of Detection (LOD) of SHERLOCK Assays

Full SHERLOCK reactions were performed in triplicate as described herein on assay-specific GBlock serial dilutions ranging from $10^5$ to $10^0$ copies/μL, as well as a nuclease-free water control. The LOD was defined as the lowest GBlock concentration with a mean background-subtracted fluorescence value at least 3 SD above that of the assay-specific NTC reactions, as reactions were considered significantly distinguishable from the NTC above this threshold (Armbruster et al., 2008).

Figure 10:
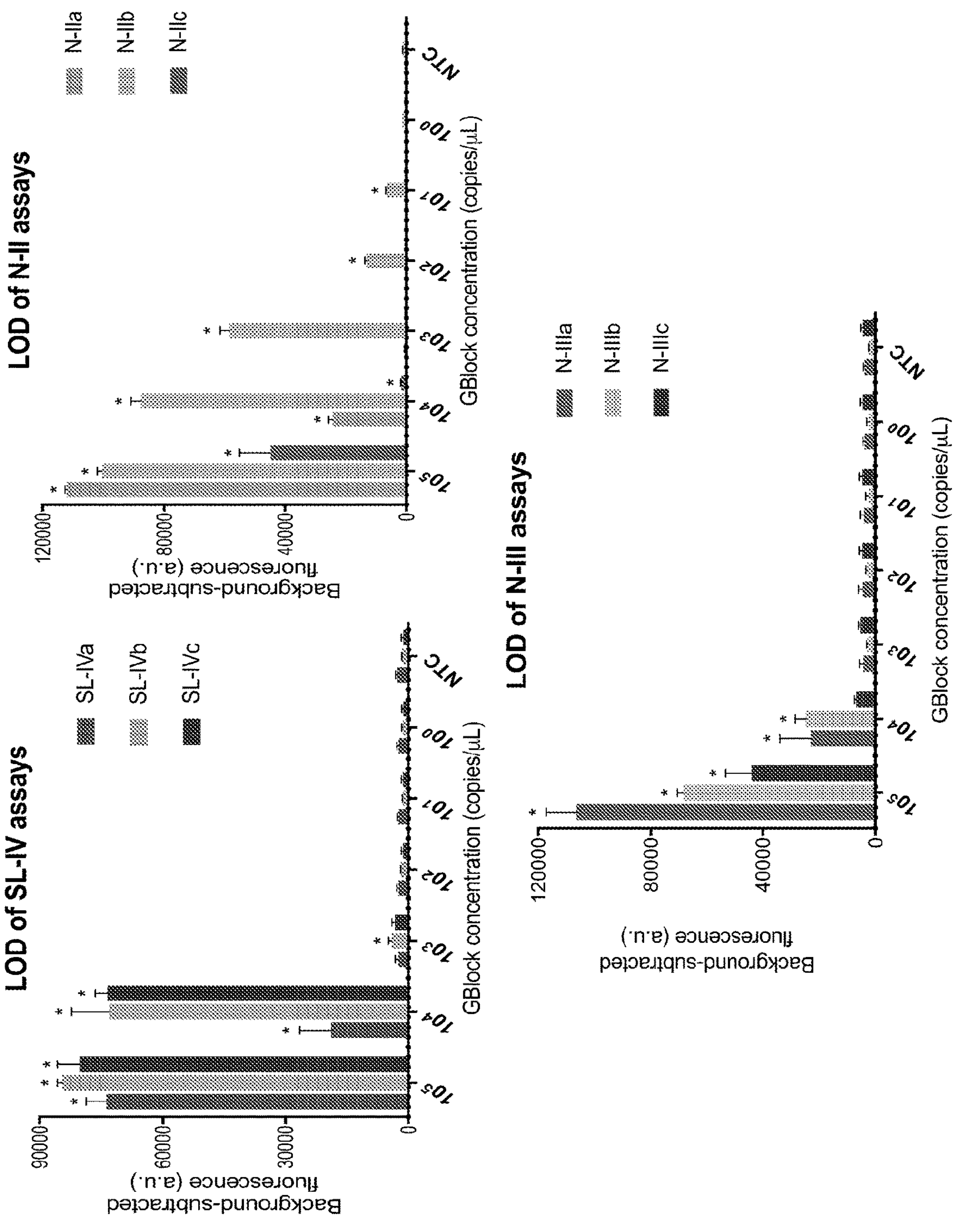
FIG. 10 includes graphs of SHERLOCK assays have varying LODs. SHERLOCK reactions were performed on a serial dilution of GBlock templates with concentrations ranging from $10^5$ to $10^0$ copies/μL as well as a nuclease-free water control and calculated background-subtracted fluorescence values for all reactions. All GBlock dilutions above the assay-specific Limit of detection (LOD) are indicated by asterisks. SHERLOCK assays are distinguished by bar color. All reactions were run in triplicate. For all panels, error bars indicate 1 S.D. based on three technical replicates.

LOD varied substantially by assay (FIG. 10). N-IIb had the lowest LOD and positively detected GBlock concentrations down to $10^1$ copies/μL, while N-IIIc had the highest LOD and only detected GBlock concentrations of $10^5$ copies/μL and above. LOD is affected by both an assay's RPA primers, which determine the extent to which a template is amplified, and its crRNA, which can have varying cutting efficiency depending on its sequence.

Viral concentration of LASV patient samples varies greatly between patients as well as over the course of infection. As patients amount an IgM response, the viral titer will decrease as antibodies target viral particles. Although there is no precise viral load that characterizes a standard LASV infection, a recent examination of 184 Lassa-suspected patients in Liberia determined that mean RNA concentration of collected patient samples was $8.13\times10^4$ viral copies/mL (Panning et al., 2010). Thus, SHERLOCK assays having a limit of detection of as low or lower than this value is targeted. Although RPA primer and crRNA optimization experiments were carried out, additional optimization could be conducted in the future to improve the sensitivity of assays, for example, oligo lengths and concentrations for both RPA primers and crRNAs could be optimized on an assay-by-assay basis.

Cross-Reactivity of SHERLOCK Assays with Other VHF-Inducing Viruses

The symptoms of LF closely resemble those of other hemorrhagic fevers, such as Ebola virus disease (EVD) and GBlock positive control at a concentration of $10^4$ copies/μL, and nuclease-free water negative control, as described in the methods. Assays were considered cross-reactive if either of the two seed stocks had background-subtracted fluorescence measurements higher than 3 SD above the NTC.

Figure 11:
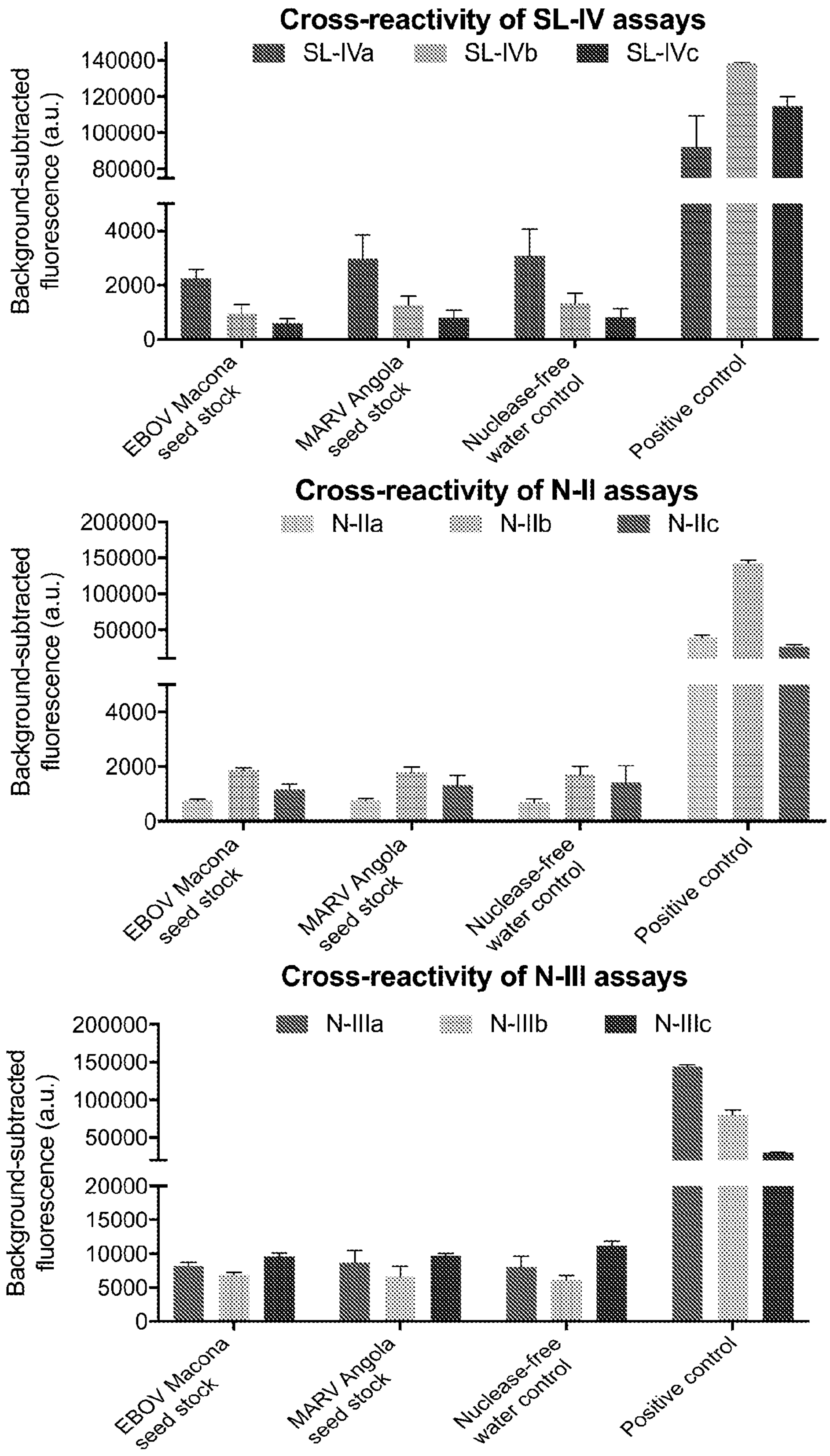
FIG. 11 charts cross-reactivity of SL-IV, N-II and N-III assays, demonstrating SHERLOCK is not cross-reactive with MARV and EBOV seed stocks. The cross-reactivity threshold was defined as 3 SD above the crRNA-specific nuclease-free water control. For all SHERLOCK assays, MARV and EBOV seed stocks were not cross-reactive. A positive control of crRNA-specific GBlock at a concentration of $10^4$ and negative control of nuclease-free water are shown for reference. SHERLOCK assays are distinguished by bar color. In all panels, error bars indicate 1 S.D. based on three technical replicates.

All SHERLOCK assays produced negative results for tested EBOV and MARV seed stocks (FIG. 11). These experiments indicate that none of the designed SHERLOCK assays positively detect EBOV or MARV; thus, these tests are an effective means of determining if a patient presenting symptoms of a hemorrhagic fever has LASV rather than EBOV or MARV.

Validation of SHERLOCK Assays on Clade-Specific LASV Patient Samples

Each SHERLOCK assay was tested on a clade-specific, blinded panel of LASV samples and results compared to generated sequencing data to assess the SHERLOCK assays' ability to accurately detect LASV patient samples. Furthermore, Applicant compared diagnostic results of the SHERLOCK assays to those of the Nikisins and Broad RT-qPCR assays to determine if the SHERLOCK assays were more sensitive in detecting LASV patient samples Each of the SL-IV SHERLOCK assays detected more sequencing-positive samples from clade SL-IV than the Nikisins RT-qPCR or the Broad RT-qPCR. Assays SL-IVb and SL-IVc detected all tested sequencing-positive samples (n=7/7) and one additional sample that had not been sequenced. The Nikisins RT-qPCR assay detected only 57.1% (n=4/7) of sequencing-positive samples. These results establish SHERLOCK assays SL-IVb and SL-IVc as more sensitive tools for diagnosis of the SL-IV clade than the Nikisins assay.

Similarly, SHERLOCK assays N-IIa and N-IIb detected more sequencing-positive samples from clade N-II than did the Nikisins assay (N-IIa SHERLOCK=4/9; N-IIb SHERLOCK=5/9; Nikisins RT-qPCR=3/9). The N-IIa and N-JIb assays detected different subsets of patient samples (FIG. 12), thus combining the results of these two SHERLOCKs produces more sensitive detection of the N-II clade than running only one assay. Together, these two assays detected 77.8% (n=7/9) of sequencing-positive samples compared to the Nikisins assay's 33% (n=3/9). Interestingly, the Broad RT-qPCR assay, which detected 88.9% (n=8/9) of samples from clade N-II, outperformed all SHERLOCK assays and the Nikisins assay for detection of this clade.

SHERLOCK N-IIIa and N-IIIb assays detected only 14.3% of sequencing-positive samples (n=1/7), while N-IIIc detected 28.6% (n=2/7). All three assays detected more samples than the Nikisins assay, which did not detect any, although none of the N-III assays detected a majority of N-III genetic diversity and would be more likely to report false negatives than true positives.

Figure 13:
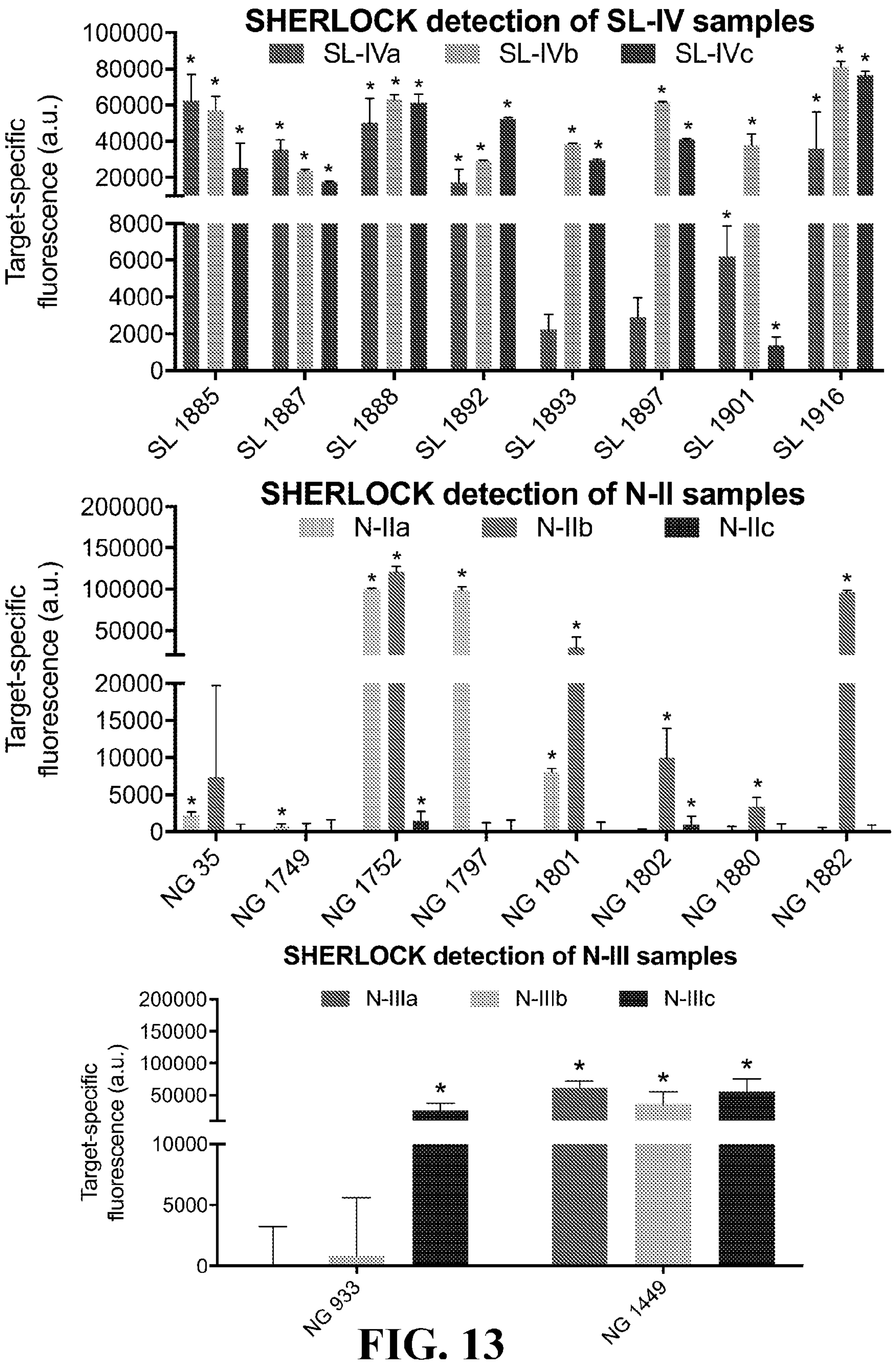
FIG. 13 includes charts of SHERLOCK detection of SL-IV, N-II and N-III samples. The SHERLOCK assays detect varying numbers of clade-specific patient samples. SL-IVb and SL-IVc both detected all sequencing-positive samples, but SL-IVb produced higher target-specific fluorescence for 7 out of the 8 samples. The N-IIb and N-IIIc assays detected the highest number of sequencing-positive N-II and N-III patient samples, respectively. Sample fluorescence values were normalized to target-specific fluorescence to facilitate cross-crRNA comparisons. All patient samples positive by at least one clade-specific SHERLOCK assay are shown, and samples positive by SHERLOCK assays are indicated by asterisks. SHERLOCK assays are distinguished by bar color. In all panels, error bars indicate 1 S.D. based on three technical replicates.

Identification of the Strongest SHERLOCK Assay(s) for Detection of Each LASV Clade In addition to comparing the outcomes of SHERLOCK assays to other types of diagnostic tests, Applicant compared the validation results of each clade's three SHERLOCK assays to each other (FIG. 13). The comparison allowed the strongest SHERLOCK assay in each clade to be identified, defined as the assay detecting the largest number of sequencing-positive patient samples. If two assays within the same clade detected the same number of positive samples, the assay with higher target-specific fluorescence values was chosen. To facilitate cross-assay comparison, template-specific fluorescence was calculated for all samples by normalizing each target reaction to its NTC control, thereby accounting for varying crRNA background activity between assays.

The SL-IVb assay was the strongest assay of all SL-IV SHERLOCKs. Both the SL-IVb and SL-IVc assays detected all 7 sequencing-positive samples from clade SL-IV as well as one sample that had not been sequenced. Detection using the SL-IVb assay resulted in higher target-specific fluorescence compared to the SL-IVc assay for 7 of the 8 positive samples (FIG. 13*a*).

Figure 12:
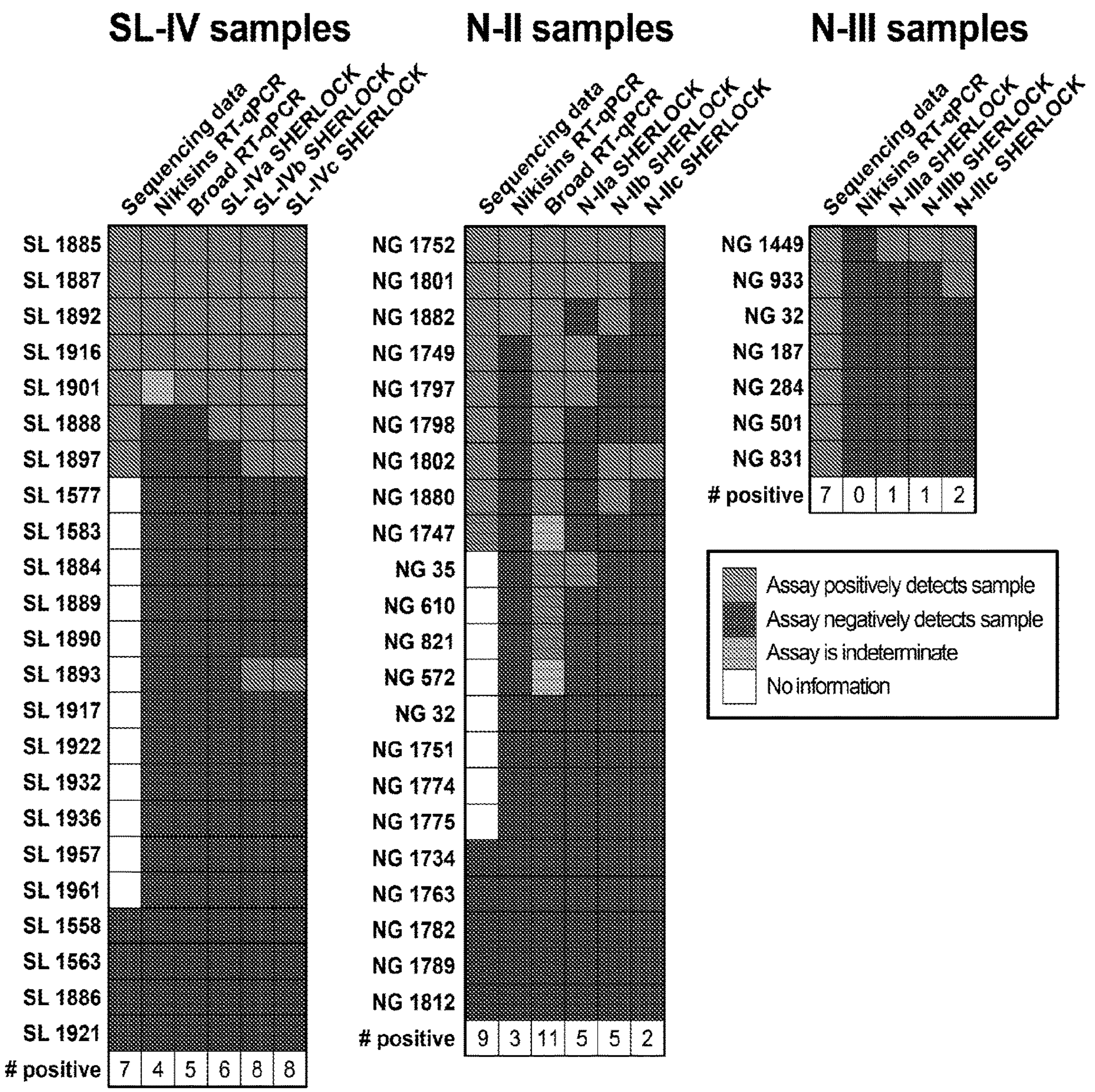
FIG. 12 provides a comparison of diagnostic outcomes for three panels of clade-specific LASV patient samples. Designed SHERLOCK assays were tested in parallel with the Nikisins RT-qPCR and the Broad RT-qPCR on clade-specific panels of patient samples that included both positive and negative samples. Sequencing information generated by other Sabeti Lab members is displayed for reference.

The N-IIb assay detected the largest number of N-II sequencing-positive samples (n=5) out of all N-II SHERLOCKs. The N-IIa assay detected 4 sequencing-positive samples as well as one sample that had not been sequenced, but the N-IIa assay showed reduced fluorescence compared to the N-IIb assay for all samples detected by both assays (FIG. 13*b*). However, the assays detected different subsets of tested samples; each assay detected three sequencing-positive samples that the other assay did not (FIG. 12). Using the N-IIa and N-IIb assays in parallel provides a significantly more sensitive diagnostic than the use of either assay alone.

The N-IIIc assay was the strongest assay of all N-III SHERLOCKs. The N-IIIc assay detected two sequencing-positive N-III samples, while all other N-III assays only detected one sample. Further validation should be done as more N-III samples become available, as the small sample size used in this study may skew results. Unlike other clades, each of the N-III assays emitted comparable target-specific fluorescence for positive samples (FIG. 13*c*).

Ultimately, these experiments established the 4 strongest SHERLOCK assays: the SL-IVb SHERLOCK assay for detection of clade SL-IV; the N-IIa and N-IIb SHERLOCK assays used together for detection of clade N-II; and the N-IIIc SHERLOCK assay for detection of clade N-III. For all LASV clades, the selected SHERLOCK assay (or assays, in the case of the N-II clade) detected a larger percentage of clade-specific patient samples than the Nikisins assay (Table 9). As shown in Table 9, selected SHERLOCK assays are the SL-IVb assay for clade SL-IV, the N-IIa and N-IIb assays used together for clade N-II, and the N-IIIc assay for clade N-III, with the percentage of clade-specific samples detected by the Nikisins RT-qPCR assay or the chosen clade-specific SHERLOCK assay(s) displayed.

TABLE 9

Table 9: All selected SHERLOCK assays detect a higher percentage of clade-specific sequencing-positive LASV patient samples than does the Nikisins RT-qPCR assay.

| | SL-IV samples | N-II samples | N-III samples | All samples |
|---|---|---|---|---|
| Nikisins RT-qPCR | 4/7 (57.1%) | 3/9 (33.3%) | 0/7 (0%) | 7/23 (30.4%) |
| Clade-specific SHERLOCK assay(s) | 7/7 (100%) | 7/9 (77.8%) | 2/7 (28.6%) | 16/23 (69.6%) |

Adapting SHERLOCK Technologies to Field-Applicable Protocols

SHERLOCK assays were used for detection of Lassa cases at KGH in Kenema, Sierra Leone, establishing the feasibility and practicality of the novel diagnostic technology in a resource-limited clinical context. Specifically, SHERLOCK assays were adapted to available resources at KGH and the SHERLOCK protocol simplified to reduce necessary laboratory staff training.

Developing Afield-Adapted SHERLOCK Protocol at KGH

Figure 14A:
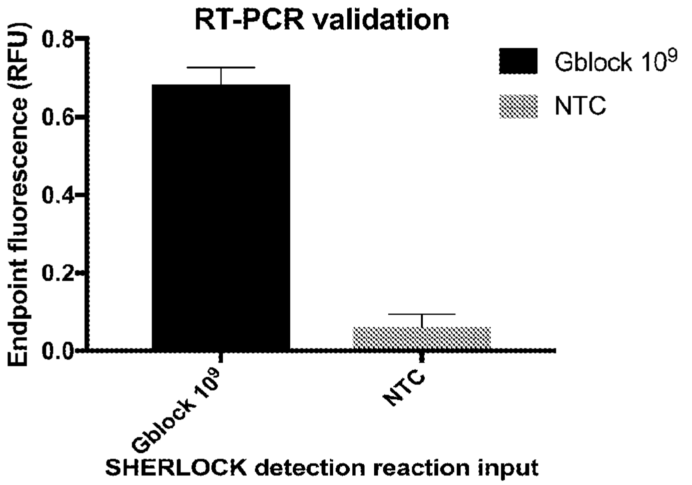
FIG. 14A-14C provides results of field-adapted SHERLOCK detection reactions conducted at KGH.

Due to the lack of a plate reader at KGH, Applicant established the feasibility of SHERLOCK using the LightCycler 96 Systems (Roche) to detect SHERLOCK fluorescence, confirmed the use of an alternative amplification method performed before the SHERLOCK detection step, and positively detected four patient samples using the field-adapted SHERLOCK protocol (FIG. 14). The LightCycler 96 Systems (Roche) detected fluorescence output from Cas13a-based detection reactions performed on an assay-specific GBlock at a concentration of $10^9$ copies/μL (FIG. 14*a*), establishing the feasibility of using this machine in laboratories that do not have access to the plate reader used in published methods (Gootenberg et al., 2017).

Figure 14B:
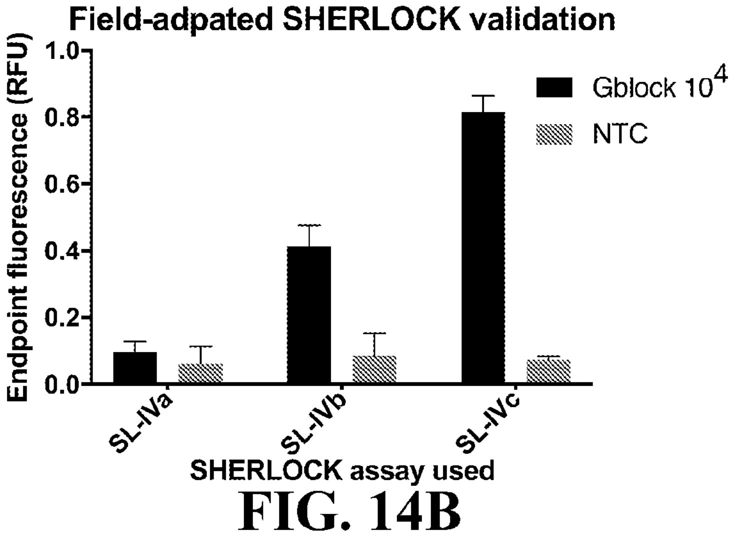

SHERLOCK detection reactions successfully detected GBlock templates amplified by the field-adapted RT-PCR amplification protocol (FIG. 14*b*). Assay-specific GBlock templates at a concentration of $10^4$ copies/∞ L were amplified using the RT-PCR and SPRI protocols described herein. SHERLOCK detection reactions were conducted with assays SL-IVa, SL-IVb, and SL-IVc using the amplified templates as input. Average endpoint fluorescence values were larger for GBlock templates than for no-input controls for all tested assays, supporting the use of this alternative amplification method. For SHERLOCK assay SL-IVc, GBlock template reactions had average endpoint fluorescence values that were 10-fold greater than the average endpoint fluorescence values of the no-input controls.

Future experiments can be conducted to further optimize the RT-PCR amplification step and the LightCycler 96 System fluorescent detection.

Adapting SHERLOCK Assays to Lateral Flow Readouts

To facilitate the use of SHERLOCKs in a resource-limited environment, the best SHERLOCK assay for each clade was adapted to a lateral flow visual detection format as described in the methods herein. Lateral flow assays were tested on a serial dilution of clade-specific GBlocks to assess their limit of detection and on a clade-specific patient sample to validate the assays' ability to detect clinical samples (FIG. 15).

Figure 15B:
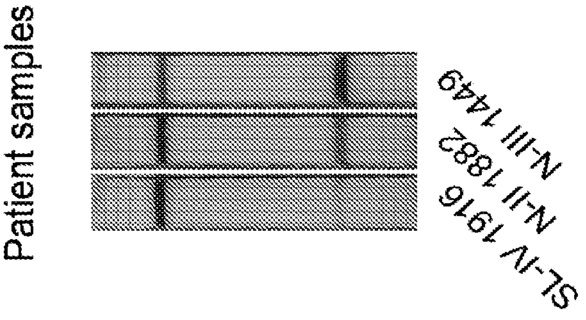
FIG. 15A-15B provides images of visual detection of serially diluted GBlocks and LASV clinical samples using lateral flow strips after 3 hours of Cas13a detection.
Figure 15A:
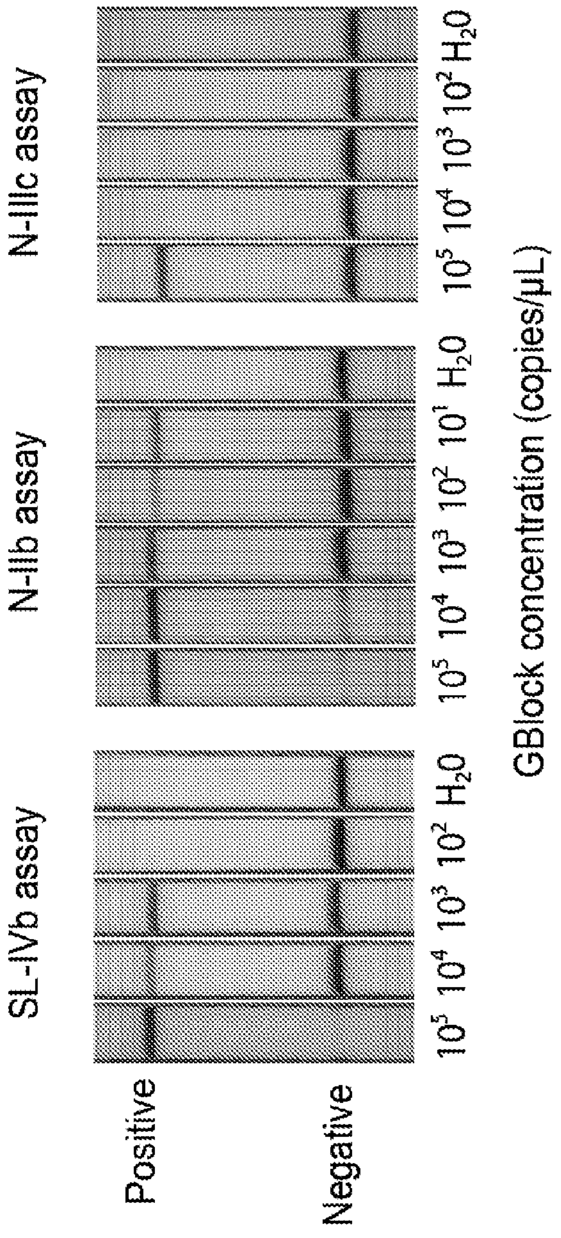

The SL-IVb lateral flow assay has a detection limit of 103, the N-IIb lateral flow assay has a detection limit of 101, and the N-IIIc lateral flow assay has a detection limit of 105 (FIG. 15*a*). All three lateral flow assays positively detected their respective clinical samples (FIG. 15*b*). These results indicate that the three LASV SHERLOCK lateral flow assays can be used to visually detect positive clinical samples.

DISCUSSION

Insights into LASV Detection Methods

In this work, limitations of current molecular LASV diagnostics were addressed in two ways: (1) improved quality of RT-qPCR methods and (2) development of a new modality that facilitates LASV diagnosis in the field. Each of these methods shows higher sensitivity to modern LASV strains than does the current gold standard LASV diagnostic, the Nikisins RT-qPCR assay. Preliminary field validation of these diagnostic methods confirmed the feasibility of their use in endemic regions.

The Broad RT-qPCR assay was developed using novel computational tools and a diverse set of current LASV strains, resulting in a higher sensitivity to LASV clades SL-IV and N-II than the Nikisins RT-qPCR.

The novel SHERLOCK detection platform was used to develop four clade-specific assays that will enable field diagnosis of current LASV strains in regions lacking the resources required to conduct RT-qPCR assays. Assays were designed using CATCH probe design software and a large number of SHERLOCK assays were tested before identifying the top assay for clades SL-IV, N-II, and N-III. The strongest SHERLOCKs for detection of clades SL-IV and N-III were the SL-IVb and N-IIIc assays, respectively. The N-IIa and N-IIb SHERLOCK assays detected different subsets of N-II viral samples and can thus be used together for diagnosis of the N-II clade. Each of the four chosen SHERLOCK assays shows superior detection of clade-specific LASV patient samples than does the Nikisins RT-qPCR assay.

Because SHERLOCK is a new technology, methods that standardize the quantification of positive samples are not readily available, so SHERLOCK results were calibrated to sequencing data, adjusting uncertainty cutoffs so that SHERLOCK assays yielded positive results for sequencing-positive but not sequencing-negative samples.

One limitation in designed LASV SHERLOCK assays is their off-target crRNA activity, which are in part due to the high divergence of the LASV genome. Each crRNA and RPA primer contained up to 10 degenerate base pairs in order to encompass viral diversity, and highly degenerate crRNA sequences can bind to and cut a large number of off-target sequences, which increases the reaction's background fluorescence and uncertainty. SHERLOCK assays target the least divergent regions of the LASV genome as identified by CATCH, suggesting that high uncertainty due to off-target crRNA activity is an intrinsic limitation of the application of SHERLOCK technology to LASV.

An additional limitation of both RT-qPCR and SHERLOCK detection methods lies in the issue of high LASV mutability, but SHERLOCK's rapid adaptability enables the assays to be quickly redesigned to detect viral mutations (Myhrvold et al., Science, in press).

The low sensitivity of the N-IIIc SHERLOCK to clade-specific patient samples demonstrates the challenges of developing SHERLOCK assays for minor or emerging viral clades with little available genetic information. In order to encompass known viral diversity within clade N-III, designed primers and crRNAs contained degenerate base pairs approximately every three nucleotides, many of which were based on three or more amino acids. Because of this diversity, limited success was achieved developing RPA primers with adequate binding efficiency to amplify the target region, as seen by the low RPA primer amplification (FIG. 9) and by the N-IIIc assay's poor limit of detection (FIG. 10). Currently, the Sabeti Lab is sequencing more viral genomes from the N-III clade. Additional genetic information about this rapidly emerging clade can be used to inform better primer and crRNA design for a more efficient and sensitive assay once available.

Future Directions of SHERLOCK Viral Diagnostics in Resource-Limited Contexts

In addition to the development of new LASV SHERLOCK assays, methods are disclosed herein for adapting SHERLOCK technology to relevant clinical settings. Adapting SHERLOCK technology to available resources at KGH and other West African laboratories, validating its use in the field. Rigorous optimization to improve the sensitivity and feasibility of field-adapted SHERLOCKs, as well as identify additional protocol adjustments will further facilitate the use of this technology in endemic regions.

LASV lateral flow assays were also tested on one patient sample as a proof of concept.

Example 3: Ebola Virus

One lesson of the 2014-2016 Ebola virus outbreak was the need for a point of care ebola virus diagnostic. The current standard diagnostic is RT-qPCR, which requires a trained staff—who need to perform multiple complex laboratory protocols, the process take from 2-6 hours, which is rather slow and costs around $100 USD. According to the WHO, we need a diagnostic that is simpler to use, faster and cheaper.

SHERLOCK involves selective isothermal amplification of nucleic acids, transcription of these amplified DNA fragments into RNAs, and when the RNA sequence of interest binds to the Cas13a-guideRNA complex, it catalyzes a collateral cleavage reaction, which results in cleavage of a reporter signal, allowing for rapid identification of low concentrations of specific nucleic acids.

Importantly, SHERLOCK can be developed into a paper test, that could cost as low as 61 cents per test, making it a great candidate for a point of care diagnostic, and has been shown to be highly sensitive and specific to multiple viruses (detects low copy number).

Figure 16:
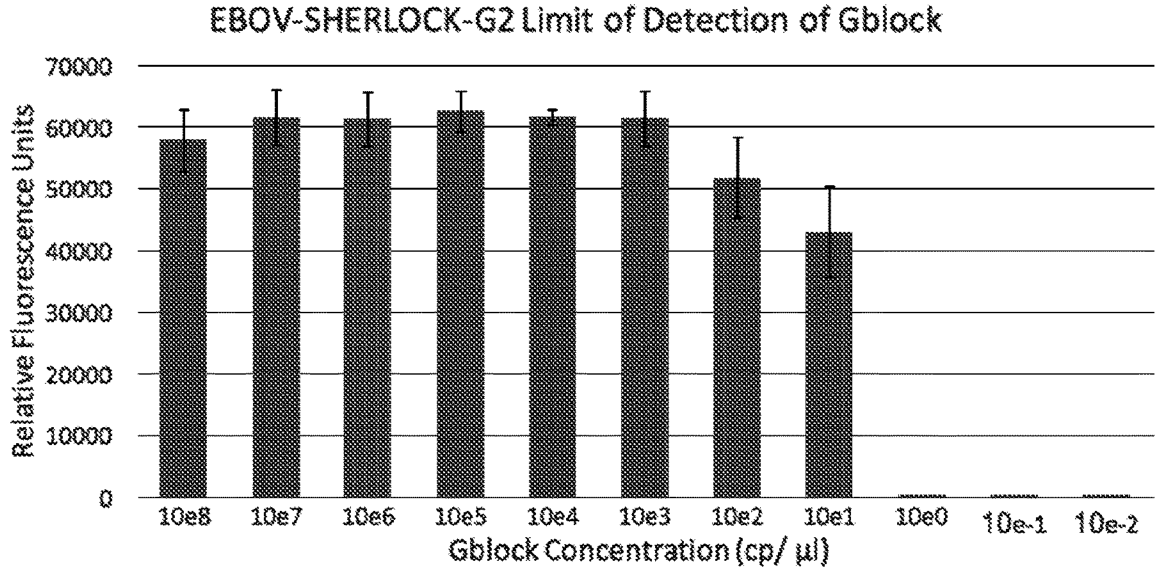
FIG. 16 provides a plot demonstrating the limit of detection of the EBOV-SHERLOCK-G2 against a serial dilution of Gblocks. On the X-axis is a serial dilution of gblock concentration, the y-axis is the RFU with the value of the water negative control subtracted. EBOV-SHERLOCK-G2 can consistently detect 10 copies per microliter of gblock.

The SHERLOCK development pipeline first involved designing a library of potential EBOV guides and primers. These guides and primers were designed to map conserved regions in the NP or Polymerase of a sequence alignment of EBOV genomes from before and during the outbreak. These guides were then tested against Ebola virus seedstock and then against custom gblocks. Selection for future testing was based on the guides limit of detection ability. As shown in FIG. 16, the EBOV-Sherlock-G2 can detect up to 10 copies per μL of gblock.

EBOV-SHERLOCK-G2 can detect EBOV in samples which are RT-qPCR negative.

Table 10A

TABLE 10A

| Name | Ebola Guide Sequences Full guide sequence | Spacer Sequence |
|---|---|---|
| EBOV_Guide_2 | TTT AAC CCA AAT AAC TTG CAC AGT TGA TGT TTT AGT CCC CTT CGT TTT GGT AGT CTA AAT CCC CTA TAG TGA GTC GTA TTA ATT TC (SEQ ID NO: 159) | ATCAACTGTGCAATGGGTTATTTGGGTTAA (SEQ ID NO: 166) |
| EBOV_Guide_9 | AGA ACA CTT GCT GCC ATG CCG GAA GAG GGT TTT AGT CCC CTT CGT TTT GGT AGT CTA AAT CCC CTA TAG TGA GTC GTA TTA ATT TC (SEQ ID NO: 161) | CCTCTTCCGGCATGGTGGCAGCAAGTGTTCT (SEQ ID NO: 164) |
| EBOV_Guide_10 | CTA TTC CTT CCG AAA TTG GTA GTA GGA GGT TTT AGT CCC CTT CGT TTT GGT AGT CTA AAT CCC CTA TAG TGA GTC GTA TTA ATT TC (SEQ ID NO: 163) | CTCCTACTACCTGGAATTTCGGAAGGAATAG (SEQ ID NO: 162) |
| EBOV_Guide_11 | CTT CCG AAA TTG GTA GTA GGA GAA AAG GGT TTT AGT CCC CTT CGT TTT GGT AGT CTA AAT CCC CTA TAG TGA GTC GTA TTA ATT TC (SEQ ID NO: 165) | CCTTTTCTCCTATGGCTACCAATTTCGGAAG (SEQ ID NO: 160) |
| EBOV_Guide_12 | CAC ACT CCC ATG TAT GAT TGA GCA ATT CGT TTT AGT CCC CTT CGT TTT GGT AGT CTA AAT CCC CTA TAG TGA GTC GTA TTA ATT TC (SEQ ID NO: 167) | GAATTGCTCAATCTGGATACATGGGAGTGTG (SEQ ID NO: 172) |
| EBOV_Guide_13 | ATT GGA GCC ACA CTC CCA TGT ATG ATT GGT TTT AGT CCC CTT CGT TTT GGT AGT CTA AAT CCC CTA TAG TGA GTC GTA TTA ATT TC (SEQ ID NO: 169) | CAATCATACATGTGGGGAGTGTGGCTCCAAT (SEQ ID NO: 170) |
| EBOV_Guide_14 | ACA GAT CCT GAG GGA ATA TTC ATG GGC AGT TTT AGT CCC CTT CGT TTT GGT AGT CTA AAT CCC CTA TAG TGA GTC GTA TTA ATT TC (SEQ ID NO: 171) | TGCCCATGAATATTTGGCCCTCAGGATCTGT (SEQ ID NO: 168) |

TABLE 10B

| Name | Ebola Primers Full RPA primer sequence | Primer w/o T7 promoter |
|---|---|---|
| EBOV_G2_F | gaaatTAATACGACTCACTATAgggGACAGACTGAGGAARATAACATTGCAAAG (SEQ ID NO: 173) | GACAGACTGAGGAARATAACATTGCAAAG (SEQ ID NO: 174) |
| EBOV_G2_R | CAATCATACATGGRAGTGTGGCTCCAATAA (SEQ ID NO: 175) | N/A |
| EBOV_G9_F | gaaatTAATACGACTCACTATAgggCAGTCAAGTAYTTGGAAGGGCACGGGTTC (SEQ ID NO: 176) | CAGTCAAGTAYTTGGAAGGGCACGGGTTC (SEQ ID NO: 177) |
| EBOV_G9_R | CTACTACCAATTTCGGAAGGAATAGACTTG (SEQ ID NO: 178) | N/A |
| EBOV_G11_G10_F | gaaatTAATACGACTCACTATAgggAAACATTAAGAGAACACTTGCTGCCATG (SEQ ID NO: 179) | AAACATTAAGAGAACACTTGCTGCCATG (SEQ ID NO: 180) |
| EBOV_G11_G10_R | ATCATGTGTCCTACTGATTGCCAAGCTGTT (SEQ ID NO: 181) | N/A |
| EBOV G12_G13_F | gaaatTAATACGACTCACTATAgggATTTAGCACAGATYCTGAGGGAATATTCAT (SEQ ID NO: 182) | ATTTAGCACAGATYCTGAGGGAATATTCAT (SEQ ID NO: 183) |
| EBOV_G12_G13_R | CTAACAATATGTTTCTTGACTGCYACTGAC (SEQ ID NO: 184) | N/A |
| EBOV_G14_F | gaaatTAATACGACTCACTATAgggTTATCTTGATCATTGTGATAATATCCTGGC (SEQ ID NO: 185) | TTATCTTGATCATTGTGATAATATCCTGGC (SEQ ID NO: 186) |

TABLE 10B-continued

| Name | Ebola Primers Full RPA primer sequence | Primer w/o T7 promoter |
|---|---|---|
| EBOV_G14_R | AACACTGCGGACATTGTTCGTAGGGTTTCA (SEQ ID NO: 187) | N/A |

TABLE 11A

| Name | Lassa Clade III RPA primers Primer sequence | Primer sequence w/o T7 sequence |
|---|---|---|
| NG_C3_ 1F | gaaatTAATACGACTCACTATAgggAGRTGGATGY TRATTGARGCYGARYTRAA (SEQ ID NO: 188) | AGRTGGATGYTRATTGAR GCYGARYTRAA (SEQ ID NO: 189) |
| NG_C3_ 2F | gaaatTAATACGACTCACTATAgggATTGARGCYG ARYTRAARTGTTTYGGRAA (SEQ ID NO: 190) | ATTGARGCYGARYTRAAR TGTTTYGGRAA (SEQ ID NO: 191) |
| NG_C3_ 3F | gaaatTAATACGACTCACTATAgggCARGTRGAYY TGAATGAHGCTGTYCARGC (SEQ ID NO: 192) | CARGTRGAYYTGAATGAH GCTGTYCARGC (SEQ ID NO: 193) |
| NG_C3_ 4F | gaaatTAATACGACTCACTATAgggTRAACATGAT TGAYACCAARAAGAGYTC (SEQ ID NO: 194) | TRAACATGATTGAYACCA ARAAGAGYTC (SEQ ID NO: 196) |
| NG_C3_ 5F | gaaatTAATACGACTCACTATAgggGCYTGYATGC TWGAYGGHGGYAAYATG (SEQ ID NO: 197) | GCYTGYATGCTWGAYGG HGGYAAYATG (SEQ ID NO: 198) |
| NG_C3_ 6F | gaaatTAATACGACTCACTATAgggGTYTCACCYC AAWCYATRGATGGSATYTT (SEQ ID NO: 199) | GTYTCACCYCAAWCYATR GATGGSATYTT (SEQ ID NO: 200) |
| NG_C3_ 1R | *TGRTTYTTCATDATMAGYTGRTCRTTWAT* (SEQ ID NO: 201) | N/A |
| NG_C3_ 2R | *TARTTRCARTATGGTATDCCCATRATRTC* (SEQ ID NO: 202) | N/A |
| NG_C3_ 3R | CATRTTRCCDCCRTCWAGCATRCARGCHCC (SEQ ID NO: 203) | N/A |
| NG_C3_ 4R | TATRTTYTCATAWGGRTTYCTYTCACCTGG (SEQ ID NO: 204) | N/A |
| NG_C3_ 5R | GAYGCAATGTAAGGCCAYCCRTCTCCTGA (SEQ ID NO: 205) | N/A |
| NG_C3_ 6R | ACYACAGTRTTTTCCCARGCYCTNCCM (SEQ ID NO: 206) | N/A |

TABLE 11B

| Name | Lassa Clade III crRNAs Spacer Sequence |
|---|---|
| G1_95 | TCATCRTGYTTYTCATTRCAYTTRGCHA (SEQ ID NO: 207) |
| G1_90 | TCATCATGYTTYTCATTRCAYTTRGCYA (SEQ ID NO: 208) |
| G2_95 | AYTCYTCATCRTGYTTYTCATTRCAYTT (SEQ ID NO: 209) |
| G2_90 | AYTCYTCATCATGYTTYTCATTRCAYTT (SEQ ID NO: 210) |
| G3_95 | WATRGCYTGYTTRTTRAARTCAAANAG (SEQ ID NO: 211) |
| G3_90 | WATRGCTTGYTTRTTRAARTCAAANAG (SEQ ID NO: 212) |
| G4_95 | GARCTYTTYTTRGTRTCAATCATRTTYA (SEQ ID NO: 213) |

TABLE 11B-continued

| Name | Lassa Clade III crRNAs Spacer Sequence |
|---|---|
| G4_90 | GARCTCTTYTTGGTRTCAATCATGTTYA (SEQ ID NO: 214) |
| G5_95 | RCTRAARTTGTARCCAGADAYRTTVA (SEQ ID NO: 215) |
| G5_90 | RCTRAARTTGTARCCAGADATGTTRA (SEQ ID NO: 216) |
| G6_95 | TACAAYTTYAGYYTRGGWGCYGCHGTVAA (SEQ ID NO: 217) |
| G6_90 | TACAAYTTYAGYYTRGGWGCYGCWGTVAA (SEQ ID NO: 218) |
| G6_85 | TTBACWGCRGCWCCYARRCTRAARTTGTA (SEQ ID NO: 219) |

TABLE 11B-continued

| Name | Lassa Clade III crRNAs Spacer Sequence |
|---|---|
| G7_95 | CATRTTRCCDCCRTCWAGCATRCARGCHCC (SEQ ID NO: 220) |
| G7_90 | CATRTTRCCDCCRTCWAGCATRCARGCYCC (SEQ ID NO: 221) |
| G8_95 | RGTYTCACCYCARWCYATRGATGGSAT (SEQ ID NO: 222) |
| G8_90 | RGTYTCACCYCAAWCYATRGATGGSAT (SEQ ID NO: 223) |
| G9_95 | AARATSCCATCYATRGWYTGRGGTGARAC (SEQ ID NO: 224) |
| G9_90 | AARATSCCATCYATRGWTTGRGGTGARAC (SEQ ID NO: 225) |
| G10_95 | ATRTTYTCATAWGGRTTYCTYTCACCTGG (SEQ ID NO: 226) |
| G11_95 | AYGCAAYGTARGGCCAYCCRTCYCCTGA (SEQ ID NO: 227) |
| G11_90 | AYGCAATGTAAGGCCAYCCRTCTCCTGA (SEQ ID NO: 228) |

TABLE 11C

| Name | Lassa Clade III Gblocks Sequence |
|---|---|
| NG_C3_GB1 (SEQ ID NO: 229) | GTTACTGCTTAACTAGATGGATGTTAATTGAAGCTGAACTGAAATGTTTTGGGAACACTGCAGTAGCTAAATGCAATGAGAAACATGATGAAGAATTTTGTGACATGCTGAGGCTTTTTGATTTCAACAAACAAGCCATTCAGAGGTTGAAGACTGAGGCCCAAATGAGCATTCAGCTTATCAACAAAGCAGTCAATGCCCTCATAAATGACCAGCTTATAATGAAAAATCATCTCAGAGACATCATGGGCATACCATACTGCAATTATAGCAAATATTGG |
| NG_C3_GB2 (SEQ ID NO: 230) | AAACAAGGACAGGTGGACTTGAATGATGCTGTTCAGGCCCTGACAGATTTGGGACTGATTTACACCGCAAAGTACCCAAATTCATCTGATTTAGATAGGCTTTCCCAGAGTCATCCCATATTAAACATGATTGACACCAAGAAGAGCTCCCTCAACATCTCTGGTTACAACTTTAGTCTGGGTGCTGCAGTAAAGGCAGGGGCTTGCATGCTTGATGGTGGCAACATGTTGGAGACAATCAAG |
| NG_C3_GB3 (SEQ ID NO: 231) | CATCCCATATTAAACATGATTGACACCAAGAAGAGCTCCCTCAACATCTCTGGTTACAACTTTAGTCTGGGTGCTGCAGTAAAGGCAGGGGCTTGCATGCTTGATGGTGGCAACATGTTGGAGACAATCAAGGTTTCACCCCAAACTATGGATGGGATCTTGAAATCAATCCTGAAGGTCAAAAGGAGCCTGGGGATGTTTGTGTCAGACACTCCAGGTGAGAGAAACCCTTATGAGAATATACTGTACAAAATCTGCCTATCAGGAGATGGATGGCCTTACATTGCATCAAGGACTTCA |
| NG_C3_GB4 (SEQ ID NO: 232) | TGCTGCAGTAAAGGCAGGGGCTTGCATGCTTGATGGTGGCAACATGTTGGAGACAATCAAGGTTTCACCCCAAACTATGGATGGGATCTTGAAATCAATCCTGAAGGTCAAAAGGAGCCTGGGGATGTTTGTGTCAGACACTCCAGGTGAGAGAAACCCTTATGAGAATATACTGTACAAAATCTGCCTATCAGGAGATGGATGGCCTTACATTGCATCAAGGACTTCAATCACTGGTAGAGCTTGGGAAAACACTGTAGTGGATTTAGAGT |

TABLE 12A

Lassa Nigeria Strain RPA primers

| Name | Primer sequence |
|---|---|
| LASV_NG_01_F | CARTAYGARGCVATGAGYTGYGAYTTYAATG (SEQ ID NO: 233) |
| LASV_NG_02_F | TTYAAYCARTAYGARGCVATGAGYTGYGA (SEQ ID NO: 234) |
| LASV_NG_03_F | CTYTAYRAYCAYDCBYTVATGAGYATYATYTC (SEQ ID NO: 235) |
| *LASV_NG_04_F* | *CTHAAYATGACNATGCCYYTRTCHTGYAC* (SEQ ID NO: 236) |
| LASV_NG_05_F | TGYCCYAARCCNCAYAGRMTHAAYCAHATGGG (SEQ ID NO: 237) |
| LASV_NG_06_F | AAYCTYTCYGAYGCVCAYARRARGRAYCT (SEQ ID NO: 238) |
| LASV_NG_07_F | *AACCACATGGGCATATGCTCATGTGGTCT* (SEQ ID NO: 239) |
| LASV_NG_00_R | AGGTTGTACTGAACACTTATCTTCCC (SEQ ID NO: 240) |
| LASV_NG_01_R | TGGGAAGATCACTGCCAGTTTTCTCGCCC (SEQ ID NO: 241) |
| LASV_NG_02_R | TATTGGTAGGAAGTCATTATACAATCCCA (SEQ ID NO: 242) |

TABLE 12A-continued

| Lassa Nigeria Strain RPA primers | |
|---|---|
| Name | Primer sequence |
| LASV_NG_03_R | GCTATGTAACTGCCACCCCAAGCCATCCTCAT (SEQ ID NO: 243) |
| LASV_NG_04_R | CCACCCCAAGCCATCCTCATAAAAGTCTG (SEQ ID NO: 244) |
| LASV_NG_05_R | TTTGAAAATGCTGTTTGGGATCAGTGCAA (SEQ ID NO: 245) |
| LASV_NG_06_R | TAATGGACTGCATAATGTATGATGCAGC (SEQ ID NO: 246) |
| LASV_NG_07_R | AGGAGATTTGAAAATGCTGTTTGGGATCA (SEQ ID NO: 247) |
| LASV_NG_08_R | ATGTATGATGCAGCTGTGTCAGGAGG (SEQ ID NO: 248) |

TABLE 12B

| Lassa Nigeria Strain crRNAs Name | Spacer Sequence |
|---|---|
| LASV_NG_01_0.95 | GTGCTATRTARCTGCCACCCCARGCCAT (SEQ ID NO: 249) |
| LASV_NG_01_0.9 | GTGCTATRTARCTGCCACCCCARGCCAT (SEQ ID NO: 250) |
| LASV_NG_01_0.85 | GTGCTATRTAACTGCCACCCCAAGCCAT (SEQ ID NO: 251) |
| LASV_NG_02_0.95 | TGCCACCCCARGCCATYCTCATRAARGT (SEQ ID NO: 252) |
| LASV_NG_02_0.9 | TGCCACCCCARGCCATYCTCATRAAAGT (SEQ ID NO: 253) |
| LASV_NG_02_0.85 | TGCCACCCCAAGCCATCCTCATRAAAGT (SEQ ID NO: 254) |
| LASV_NG_03_0.95 | ARTCACARCTCATYGCYTCATAYTGATT (SEQ ID NO: 255) |
| LASV_NG_03_0.9 | ARTCACARCTCATTGCYTCATACTGATT (SEQ ID NO: 256) |
| LASV_NG_03_0.85 | AGTCACARCTCATTGCTTCATACTGATT (SEQ ID NO: 257) |
| LASV_NG_04_0.95 | CACCCCARGCCATYCTCATRAARGTYTG (SEQ ID NO: 258) |
| LASV_NG_04_0.9 | CACCCCARGCCATYCTCATRAAAGTYTG (SEQ ID NO: 259) |
| LASV_NG_04_0.85 | CACCCCAAGCCATCCTCATRAAAGTYTG (SEQ ID NO: 260) |
| LASV_NG_05_0.95 | CACCCCARGCCATYCTCATRAARGTYTG (SEQ ID NO: 261) |
| LASV_NG_05_0.9 | CACCCCARGCCATYCTCATRAAAGTYTG (SEQ ID NO: 262) |
| LASV_NG_05_0.85 | CACCCCAAGCCATCCTCATRAAAGTYTG (SEQ ID NO: 263) |
| LASV_NG_06_0.95 | CARCTCATYGCYTCATAYTGATTRAART (SEQ ID NO: 264) |
| LASV_NG_06_0.9 | CARCTCATTGCYTCATACTGATTRAART (SEQ ID NO: 265) |
| LASV_NG_06_0.85 | CARCTCATTGCTTCATACTGATTRAAGT (SEQ ID NO: 266) |
| LASV_NG_07_0.95 | CATTRAARTCACARCTCATYGCYTCATA (SEQ ID NO: 267) |
| LASV_NG_07_0.9 | CATTGAARTCACARCTCATTGCYTCATA (SEQ ID NO: 268) |
| LASV_NG_07_0.85 | CATTGAAGTCACARCTCATTGCTTCATA (SEQ ID NO: 269) |
| LASV_NG_08_0.95 | TYTTYCCYCCATTRAARTCACARCTCAT (SEQ ID NO: 270) |
| LASV_NG_08_0.9 | TCTTYCCYCCATTGAARTCACARCTCAT (SEQ ID NO: 271) |
| LASV_NG_08_0.85 | TCTTYCCYCCATTGAAGTCACARCTCAT (SEQ ID NO: 272) |
| LASV_NG_09_0.95 | AGAACHTCAAGYCCCAARGTCGTCCTGTAA (SEQ ID NO: 273) |
| LASV_NG_09_0.9 | AGAACMTCAAGYCCCAARGTCGTCCTGTAA (SEQ ID NO: 274) |
| LASV_NG_09_0.85 | AGAACMTCAAGCCCCAARGTCGTCCTGTAA (SEQ ID NO: 275) |
| LASV_NG_10_0.95 | GCCHYTYGGCGGTGGGTCACGGGGGCCC (SEQ ID NO: 276) |

TABLE 12B-continued

| Lassa Nigeria Strain crRNAs Name | Spacer Sequence |
|---|---|
| LASV_NG_10_0.9 | GCCTTTYGGCGGTGGGTCACGGGGGCCC (SEQ ID NO: 277) |
| LASV_NG_10_0.85 | GCCTTTCGGCGGTGGGTCACGGGGGCCC (SEQ ID NO: 278) |
| LASV_NG_11_0.95 | GTCGTCCTGTAAAYGGACGCCCCCGTGA (SEQ ID NO: 279) |
| LASV_NG_11_0.9 | GTCGTCCTGTAAAYGGACGCCCCCGTGA (SEQ ID NO: 280) |
| LASV_NG_11_0.85 | GTCGTCCTGTAAATGGACGCCCCCGTGA (SEQ ID NO: 281) |

TABLE 12C

| Lassa Nigeria Strain gBlocks | |
|---|---|
| Name | Sequence |
| LASV_NG_ Gblock1 | ACCACAAGTTTTGTAACCTTTCTGATGCACATAAAAAGAATCTTTATGACCATG CTTTAATGAGTATCATCTCAACCTTCCACTTATCCATTCCTAACTTTAATCAGTA TGAAGCAATGAGTTGTGACTTCAATGGGGGGAAGATAAGTGTTCAGTACAACC TTAGCCACACTTATGCTGTAGATGCAGCCAACCACTGTGGGACCATTGCCAATG GCGTTCTTCAGACTTTTATGAGGATGGCTTGGGGTGGCAGTTACATAGCACTTG ATTCCG (SEQ ID NO: 282) |
| LASV_NG_ Gblock2 | TCCACTTATCCATTCCTAACTTTAATCAGTATGAAGCAATGAGTTGTGACTTCA ATGGGGGGAAGATAAGTGTTCAGTACAACCTTAGCCACACTTATGCTGTAGAT GCAGCCAACCACTGTGGGACCATTGCCAATGGCGTTCTTCAGACTTTTATGAGG ATGGCTTGGGGTGGCAGTTACATAGCACTTGATTCCGGAAAGGGGAGTTGGGA TTGTATAATGACTTCCTACCAATATTTGATAATCCAAAACACCACTTGGGAAGA TCACTGCCAGTTTTCTCGCCCATCCCCTATC (SEQ ID NO: 283) |
| LASV_NG_ Gblock3 | CATAGGGAAACCCTGCCCTAAACCACACAGACTCAACCACATGGGCATATGCT CATGTGGTCTGTACAAACATCCTGGTGTACCAGTCAAGTGGAAAAGATAGGAG ACAGACCCACCCATGGGCCCCCGTGACCCACCGCCGAAAGGCGGTGGGTCACG GGGGCGTCCATTTACAGGACGACCTTGGGGCTTGAGGTTCTAAACACCATGTCT CTGGGGAGAACTGCTCTTAAAACTGGTATATTGAGTCCTCCTGACACAGCTGCA TCATACATTATGCAGTCCATTAAAGCACAGTGC (SEQ ID NO: 284) |

TABLE 13A

| Lassa Sierra Leone Strain RPA primers | |
|---|---|
| Name | Primer sequence |
| LASV_HSL_01_F | CATYGMATCYTTGAGRGTCAT (SEQ ID NO: 285) |
| LASV_HSL_02_F | ARYTGRGARTADGTNARYCC (SEQ ID NO: 286) |
| LASV_HSL_03_F | CATCYTTGAGRGTCATNAGCTGAGAATA (SEQ ID NO: 287) |
| LASV_HSL_01_R | **AAYATMCTYTAYAARATHTG** (SEQ ID NO: 288) |
| LASV_HSL_02_R | **CCYGGYGARMGRAAYCCHTAYGA** (SEQ ID NO: 289) |
| LASV_HSL_03_R | AGGAATCCTTATGARAACATACTCTAYAA (SEQ ID NO: 290) |
| LASV_GPC_1_F | ACWTTYTTYCARGARGTRCCYCATGTNAT (SEQ ID NO: 291) |
| LASV_GPC_2_F | CATGTVATWGARGARGTSATRAAYATYGT (SEQ ID NO: 292) |
| LASV_GPC_3_F | AAYATGGARACHCTMAAYATGACYATGCC (SEQ ID NO: 293) |
| LASV_GPC_4_F | CCYAAYTTYAAYCARTWTGARGCAATGAG (SEQ ID NO: 294) |
| LASV_GPC_5_F | CARACYTTYATGAGRATGGCYTGGGGTGG (SEQ ID NO: 295) |

TABLE 13A-continued

| Lassa Sierra Leone Strain RPA primers | |
|---|---|
| Name | Primer sequence |
| LASV_GPC_6_F | TGGGAYTGYATHATGACBAGYTAYCARTA (SEQ ID NO: 296) |
| LASV_GPC_7_F | AGACCRTCHCCYATYGGBTAYCTYGGNCT (SEQ ID NO: 297) |
| LASV_GPC_8_F | CACCAGGRGGRTAYTGTYTRACYAGRTGGATG (SEQ ID NO: 298) |
| LASV_GPC_9_F | ACAGCTGTRGCMAARTGYAATGARAARCA (SEQ ID NO: 299) |
| LASV_GPC_10_F | GAYATYATGGGRATYCCRTACTGYAAYTA (SEQ ID NO: 300) |
| LASV_GPC_11_F | GCYGAYAAYATGATYACTGARATGYTRCA (SEQ ID NO: 301) |
| LASV_GPC_2_R | ACRATRTTYATSACYTCYTCWATBACATG (SEQ ID NO: 302) |
| LASV_GPC_3_R | GGCATRGTCATRTTKAGDGTYTCCATRTT (SEQ ID NO: 303) |
| LASV_GPC_4_R | CTCATTGCYTCAWAYTGRTTRAARTTRGG (SEQ ID NO: 304) |
| LASV_GPC_5_R | CCACCCCARGCCATYCTCATRAARGTYTG (SEQ ID NO: 305) |
| LASV_GPC_6_R | TAYTGRTARCTVGTCATDATRCARTCCCA (SEQ ID NO: 306) |
| LASV_GPC_7_R | AGNCCRAGRTAVCCRATRGGDGAYGGTCT (SEQ ID NO: 307) |
| LASV_GPC_8_R | CATCCAYCTRGTYARACARTAYCCYCCTGGTG (SEQ ID NO: 308) |
| LASV_GPC_9_R | TGYTTYTCATTRCAYTTKGCYACAGCTGT (SEQ ID NO: 309) |
| LASV_GPC_10_R | TARTTRCAGTAYGGRATYCCCATRATRTC (SEQ ID NO: 310) |
| LASV_GPC_11_R | TGYARCATYTCAGTRATCATRTTRTCRGC (SEQ ID NO: 311) |
| LASV_NP_12_F | TGRTCCCASACWGCRTTYTCAWAYTTYCT (SEQ ID NO: 312) |
| LASV_NP_13_F | ACATCWATYCCATGTGARTAYTTRGCATCYTG (SEQ ID NO: 313) |
| LASV_NP_14_F | TGTGARTAYTTRGCATCYTGYTTRAAYTGYTT (SEQ ID NO: 314) |
| LASV_NP_15_F | TCYTCRGGYCTYCCYTCRATRTCCATCCA (SEQ ID NO: 315) |
| LASV_NP_16_F | TCCCARGCYCTYCCTGTTATTGARGTYCTYGA (SEQ ID NO: 316) |
| LASV_NP_17_F | GTTATTGARGTYCTTGAYGCAATRTAYGGCCA (SEQ ID NO: 317) |
| LASV_NP_18_F | CTTGAYGCAATRTAYGGCCABCCRTCYCCYGA (SEQ ID NO: 318) |
| LASV_NP_19_F | CATRCARGCYCCYGCYTTHACAGCTGCRCCCA (SEQ ID NO: 319) |
| LASV_NP_12_R | AGRAARTWTGARAAYGCWGTSTGGGAYCA (SEQ ID NO: 320) |
| LASV_NP_13_R | CARGATGCYAARTAYTCACATGGRATWGATGT (SEQ ID NO: 321) |
| LASV_NP_14_R | AARCARTTYAARCARGATGCYAARTAYTCACA (SEQ ID NO: 322) |
| LASV_NP_15_R | TGGATGGAYATYGARGGRAGRCCYGARGA (SEQ ID NO: 323) |
| LASV_NP_16_R | TCRAGRACYTCAATAACAGGRAGRGCYTGGGA (SEQ ID NO: 324) |
| LASV_NP_17_R | TGGCCRTAYATTGCRTCAAGRACYTCAATAAC (SEQ ID NO: 325) |
| LASV_NP_18_R | TCRGGRGAYGGVTGGCCRTAYATTGCRTCAAG (SEQ ID NO: 326) |
| LASV_NP_19_R | TGGGYGCAGCTGTDAARGCRGGRGCYTGYATG (SEQ ID NO: 327) |
| LASV_HSL_01_F | CATYGMATCYTTGAGRGTCAT (SEQ ID NO: 328) |

TABLE 13B

| Lassa Sierra Leone Strain crRNAs | |
|---|---|
| Name | Spacer Sequence |
| LASV_1516_03_90 | TATTCTCAGCTNATGACYCTCAARGATG (SEQ ID NO: 329) |
| LASV_1516_05_90 | GARTCRGATGGGAAGCCACAGAARRCT (SEQ ID NO: 330) |
| LASV_1516_06_90 | ATYTRGARTCRGATGGGAAGCCACAGAA (SEQ ID NO: 331) |
| LASV_1516_07_90 | GTTGATYTRGARTCRGATGGGAAGCCAC (SEQ ID NO: 332) |
| LASV_1516_03_85_new | TATTCTCAGCTDATGACCCTCAARGATG (SEQ ID NO: 333) |
| LASV_1213_02_85 | agYaaYgaRatRaaactaattgaRattg (SEQ ID NO: 334) |
| LASV_1213_02_75 | agaaaagacatcaaactaattgaRattg (SEQ ID NO: 335) |
| LASV_1213_03_85 | gaatcacaaggWagYaaYgaRatRaaact (SEQ ID NO: 336) |
| LASV_1213_03_75 | gaatcacaaggWagaaaagacatcaaact (SEQ ID NO: 337) |
| LASV_1213_04_85 | ttgaatcacaaggWagYaaYgaRatRaa (SEQ ID NO: 338) |
| LASV_1213_04_75 | ttgaatcacaaggWagaaaagacatcaa (SEQ ID NO: 339) |
| LASV_1213_05_85 | ctcRttgaatcacaaggWagYaaYgaRa (SEQ ID NO: 340) |
| LASV_1213_05_75 | ctccttgaatcacaaggWagaaaagaca (SEQ ID NO: 341) |
| LASV_1213_06_85 | tggtRatRacctgRcagggYtcRgatgacat (SEQ ID NO: 342) |
| LASV_1213_06_75 | tggtcatRacctgRcaggggtcRgatgacat (SEQ ID NO: 343) |
| LASV_1213_07_75 | aaRatggtcatRacctgRcaggggtc (SEQ ID NO: 344) |
| LASV_1213_08_85 | acatWaggaaactcRttgaatcacaagg (SEQ ID NO: 345) |
| LASV_1213_08_75 | Acataaggaaactccttgaatcacaagg (SEQ ID NO: 346) |
| LASV_1213_9_85 | gaRatRaaactaattgaRattgccdca (SEQ ID NO: 347) |
| LASV_1213_9_75 | gacatcaaactaattgaRattgccdca (SEQ ID NO: 348) |
| LASV_1516_01_90 | aaYgatgcaatgRtgcaYcttgaRcc (SEQ ID NO: 349) |
| LASV_1516_01_85 | aaYgatgcaatgRtgcaacttgaRcc (SEQ ID NO: 350) |
| LASV_1516_02_90 | atgacRacaaYgatgcaatgRtgcaYc (SEQ ID NO: 351) |
| LASV_1516_02_85 | atgaccdcaaYgatgcaatgRtgcaac (SEQ ID NO: 352) |
| LASV_1516_04_85 | tRYcRgctgggctRacRtattacagct (SEQ ID NO: 353) |
| LASV_1516_04_75 | ttacRgctgggctRacctattacagct (SEQ ID NO: 354) |
| LASV_1516_05_90 | gaYtcYgatgggaagccacagaaYYct (SEQ ID NO: 355) |
| LASV_1516_05_85 | gaYtcYgatgggaagccacagaaaYct (SEQ ID NO: 356) |
| LASV_1516_05_75 | Gaatcagatgggaagccacagaaagct (SEQ ID NO: 357) |
| LASV_1516_06_90 | atRtYgaYtcYgatgggaagccacagaa (SEQ ID NO: 358) |
| LASV_1516_06_85 | atRtggaYtcYgatgggaagccacagaa (SEQ ID NO: 359) |
| LASV_1516_07_90 | gttgatRtYgaYtcYgatgggaagccac (SEQ ID NO: 360) |
| LASV_1516_07_85 | gttgatRtggaYtcYgatgggaagccac (SEQ ID NO: 361) |
| LASV_HSL_Guide_01_90 | GTGTTTTCCCARGCCCTTCCTGTTATTGA (SEQ ID NO: 362) |
| LASV_HSL_Guide_02_90 | CTTCCTGTTATTGARGTYCTTGATGCAAT (SEQ ID NO: 363) |
| LASV_HSL_Guide_02_85 | CTTCCTGTTATTGARGTTCTTGATGCAAT (SEQ ID NO: 364) |
| LASV_HSL_Guide_03_90 | CCTGTTATTGARGTYCTTGATGCAATRT (SEQ ID NO: 365) |
| LASV_HSL_Guide_03_85 | CCTGTTATTGARGTTCTTGATGCAATRT (SEQ ID NO: 366) |

TABLE 13C

| Lassa Sierra Leone Strain gBlocks | |
|---|---|
| Name | Sequence |
| gblock_ GPC_1 | ATAGTGACATTCTTCCAGGAAGTGCCTCATGTAATAGAAGAGGTGATGAACA TTGTTCTCATTGCACTGTCTATACTAGCAGTGCTGAAAGGTCTGTACAATTTTG CAACATGTGGCCTCGTTGGTTTGGTCACTTTCCTCCTGTTGTGTGGCAGGTCTT GCACAACCAGTCTTTACAAAGGGGTTTATGAGCTTCAGACTCTGGAACTAAAC ATGGAGA (SEQ ID NO: 367) |
| gblock_ GPC_2 | CTCTGGAACTAAACATGGAGACACTCAATATGACCATGCCTCTCTCCTGCACA AAGAACAACAGTCATCATTATATAATGGTGGGCAATGAGACAGGACTAGAAC TGACCTTGACCAACACGAGCATTATTAATCATAAATTTTGCAATCTGTCTGAT GCCCACAAAAAGAACCTCTATGACCACGCTCTTATGAGCATAATCTCAACTTT CCACTTGTCCATCCCCAACTTCAATCAGTA (SEQ ID NO: 368) |
| gblock_ NP_12F13R | TTCCACTGGATCTTCAGGTCTTCCTTCAATGTCCATCCAGGTCTTAGCATTTGG GTCAAGTTGCAGCATTGCATCCTTGAGGGTCATCAGCTGAGAATAGGTAAGCC CAGCGGTAAACCCTGCCGACTGCAGGGATTTATTGGAATTGTTGCTGCCAGCT TTCTGTGGCTTCCCATCTGATTCCAGATCAACGACAGTGTTTTCCCAGGCCCTT CCTGTTATTGAGGTTCTTGATGCAATATAT (SEQ ID NO: 369) |

TABLE 14A

| Marburg Primers | |
|---|---|
| Name | Primer sequence |
| MB_F1a | gaaatTAATACGACTCACTATAgggYCCTCATGTTCGTAATAAGAAGGTG ATATT (SEQ ID NO: 370) |
| MB_F1b | gaaatTAATACGACTCACTATAgggTTACATAGYTTGYTRGARTTRGGTAC AAAR (SEQ ID NO: 371) |
| MB_F3a | gaaatTAATACGACTCACTATAgggGGRGAAAAYGARAAYGATTGTGATG CAGAG (SEQ ID NO: 372) |
| MB_F3b | gaaatTAATACGACTCACTATAgggGTKCAGGAGGAYGAYYTGGCVGCAG GRCT (SEQ ID NO: 373) |
| MB_F4a | gaaatTAATACGACTCACTATAgggATTRAGACTWGTCAKTYTGTTAATAT TCTT (SEQ ID NO: 374) |
| MB_F5a | gaaatTAATACGACTCACTATAgggAATGAACAWGGDGTTGATCTYCCAC CWCCT (SEQ ID NO: 375) |
| MB_F5b | gaaatTAATACGACTCACTATAgggCCACCWCCTCCRTTRTAYRCTCAGG AAAA (SEQ ID NO: 376) |
| MB_F6a | gaaatTAATACGACTCACTATAgggCARGATCCYTTTGGCAGTATTGGWG ATGTA (SEQ ID NO: 377) |
| MB_F7a | gaaatTAATACGACTCACTATAgggGTCTYATYTTRATYCAARGKRYAAA AACTCT (SEQ ID NO: 378) |
| MB_F8b | gaaatTAATACGACTCACTATAgggAAAAACTCTYCCYRTTTTRGARATW GCYAG (SEQ ID NO: 379) |
| MB_F8a | gaaatTAATACGACTCACTATAgggACCYCAARATRTRGATTCRGTRTGCT CCGG (SEQ ID NO: 380) |
| MB_R1a | ATTCTTGATGACATCRAAYTCATARCCCGC (SEQ ID NO: 381) |

TABLE 14A-continued

| Marburg Primers | |
|---|---|
| Name | Primer sequence |
| MB_R1b | AATYAAAGGRCTGTAATGAGGTTCATTRGG (SEQ ID NO: 382) |
| MB_R3a | ATTAARGAAAATGTYCTYTCCTCRGTT (SEQ ID NO: 383) |
| MB_R3b | TCAATDGCATGYCTATTRATTAARGAAAAT (SEQ ID NO: 384) |
| MB_R4a | CTTCYARAAGATCTCCWARATCRATCCCTGA (SEQ ID NO: 385) |
| MB_R4b | GAATTRTARTARTGTTCAACACAYAAHGTC (SEQ ID NO: 386) |
| MB_R5a | TGYGGCCAATTCTGYTGATTRTCCTCATA (SEQ ID NO: 387) |
| MB_R6a | GAARGTYCTRCCYTTCTTTGTYACCACTCT (SEQ ID NO: 388) |
| MB_R6b | TCATTRGGATAAAGGAARGTYCTRCCYTTC (SEQ ID NO: 389) |
| MB_R7a | AACRTTCTTRGGAGGWACACCTGYCCTGAA (SEQ ID NO: 390) |
| MB_R8a | GTTACACTTATATTGTARCATGTTTTRGCT (SEQ ID NO: 391) |
| MB_R8b | GTTACACTTATATTGTARCATGTTTTRGCT (SEQ ID NO: 392) |

TABLE 14B

| Marburg Guides | |
|---|---|
| Name | Guide sequence |
| MB_G1a_95 | aYtaYaattcYgaYaaagataaattcaagttttagtccccttcgtttttggggtagtctaaatcccctatagtgagtcgtattaatttc (SEQ ID NO: 393) |
| MB_G1b_95 | agggatYgatYtWggagatcttYtRgaagttttagtccccttcgtttttggggtagtctaaatcccctatagtgagtcgtattaatttc (SEQ ID NO: 394) |
| MB_G1c_95 | Tgtaatcagataatagatgcaataaactgttttagtccccttcgtttttggggtagtctaaatcccctatagtgagtcgtattaatttc (SEQ ID NO: 395) |
| MB_G1c_90 | tgtaaYcagataatagatgcaataaactgttttagtccccttcgtttttggggtagtctaaatcccctatagtgagtcgtattaatttc (SEQ ID NO: 396) |
| MB_G3a_95 | atcaRactgcHaaatcYttRgaRctcttgttttagtccccttcgtttttggggtagtctaaatcccctatagtgagtcgtattaatttc (SEQ ID NO: 397) |
| MB_G3a_90 | atcaRactgcHaaatcYttggaRctcttgttttagtccccttcgtttttggggtagtctaaatcccctatagtgagtcgtattaatttc (SEQ ID NO: 398) |
| MB_G3b_95 | YacYgcYggtttaatYaaaaaYcaRaaYgttttagtccccttcgtttttggggtagtctaaatcccctatagtgagtcgtattaatttc (SEQ ID NO: 399) |
| MB_G3b_90 | tacYgcYggtttaatYaaaaaYcaRaaYgttttagtccccttcgtttttggggtagtctaaatcccctatagtgagtcgtattaatttc (SEQ ID NO: 400) |
| MB_G3c_95 | ttttttggccctggaatYgaaggactYtgttttagtccccttcgtttttggggtagtctaaatcccctatagtgagtcgtattaatttc (SEQ ID NO: 401) |
| MB_G3c_90 | tifittggccctggaatcgaaggactYtgttttagtccccttcgtttttggggtagtctaaatcccctatagtgagtcgtattaatttc (SEQ ID NO: 402) |
| MB_G4a_95 | cYcctcatgttcgtaataagaaggtgatgttttagtccccttcgtttttggggtagtctaaatcccctatagtgagtcgtattaatttc (SEQ ID NO: 403) |

TABLE 14B-continued

| Marburg Guides | |
|---|---|
| Name | Guide sequence |
| MB_G5b_95 | cYtttggcagtattggWgatgtaRatgggttttagtccccttcgtttttggggtagtctaaatcccctatagtgagtcgtattaatttc (SEQ ID NO: 404) |
| MB_G5b_90 | cctttggcagtattggtgatgtaRatgggttttagtccccttcgtttttggggtagtctaaatcccctatagtgagtcgtattaatttc (SEQ ID NO: 405) |
| MB_G5c_95 | tcaccRtctgctccYcaggaRgacacaagttttagtccccttcgtttttggggtagtctaaatcccctatagtgagtcgtattaatttc (SEQ ID NO: 406) |
| MB_G5d_95 | YtatgaggaYaatcaRcagaattggccRgttttagtccccttcgtttttggggtagtctaaatcccctatagtgagtcgtattaatttc (SEQ ID NO: 407) |
| MB_G5d_90 | YtatgaggataatcaRcagaattggccagttttagtccccttcgtttttggggtagtctaaatcccctatagtgagtcgtattaatttc (SEQ ID NO: 408) |
| MB_G6a_95 | atatYttRgaaccYataagRtcRccYtcgttttagtccccttcgtttttggggtagtctaaatcccctatagtgagtcgtattaatttc (SEQ ID NO: 409) |
| MB_G6d_95 | YttYacVaRYtatgaggaYaatcaRcaggttttagtccccttcgtttttggggtagtctaaatcccctatagtgagtcgtattaatttc (SEQ ID NO: 410) |
| MB_G6d_90 | YttYacRaRYtatgaggataatcaRcaggttttagtccccttcgtttttggggtagtctaaatcccctatagtgagtcgtattaatttc (SEQ ID NO: 411) |
| MB_G7a_95 | aaagttgctgattcccattRgaRgcatgttttagtccccttcgtttttggggtagtctaaatcccctatagtgagtcgtattaatttc (SEQ ID NO: 412) |
| MB_G7b_95 | acactgagYgggcaRaaagttgctgattgttttagtccccttcgtttttggggtagtctaaatcccctatagtgagtcgtattaatttc (SEQ ID NO: 413) |
| MB_G7d_95 | tRgattcRgtRtgctccggRacYctccagttttagtccccttcgtttttggggtagtctaaatcccctatagtgagtcgtattaatttc (SEQ ID NO: 414) |
| MB_G8c_95 | aRacagaagaYgtYcatctgatgggattgttttagtccccttcgtttttggggtagtctaaatcccctatagtgagtcgtattaatttc (SEQ ID NO: 415) |
| MB_G8d_95 | caggRcaggtgtWcctccYaagaaYgttgttttagtccccttcgtttttggggtagtctaaatcccctatagtgagtcgtattaatttc (SEQ ID NO: 416) |

TABLE 14C

| Marburg Gblocks | |
|---|---|
| Name | Sequence |
| MB GB4 | ATTAACATTGACATTGAGACTTGTCAGTCTGTTAATATTCTTGAAGAGATGGATTTACATAGTTTGTTAGAGTTGGGTACAAAACCTACTGCCCCTCATGTTCGTAATAAGAAGGTGATATTATTTGACACAAATCATCAGGTTAGTATTTGTAATCAGATAATAGATGCAATAAACTCAGGGATTGATCTTGGAGATCTTCTAGAAGGAGGTTTGCTGACTTTGTGTGTTGAACATTACTATAATTCTGATAAAGATAAATTCAACACAAGTCCTATC (SEQ ID NO: 417) |
| MB_GB1 | AGAGATGGATTTACATAGTTTGTTAGAGTTGGGTACAAAACCTACTGCCCCTCATGTTCGTAATAAGAAGGTGATATTATTTGACACAAATCATCAGGTTAGTATTTGTAATCAGATAATAGATGCAATAAACTCAGGGATTGATCTTGGAGATCTTCTAGAAGGAGGTTTGCTGACTTTGTGTGTTGAACATTACTATAATTCTGATAAAGATAAATTCAACACAAGTCCTATCGCGAAATATTTACGTGATGCGGGCTATGAATTCGATGTCATCAAGAATGCAGATGCAACCC (SEQ ID NO: 418) |
| MB_GB56 | AGGATCCGACAATGAACAAGGAGTTGATCTTCCACCTCCTCCGTTGTACGCTCAGGAAAAAAGACAGGACCCAATACAGCACCCGGCAGCAAGCTCTCAGGATCCCTTTGGCAGTATTGGTGATGTAAATGGTGATATCTTAGAACCCATAAGATCACCTTCTTCACCGTCTGCTCCTCAGGAAGACACAAGGGCAAGGGAAGCCTATGAATTATCGCCTGACTTTACAAATTATGAGGATAATCAGCAGAATTGGCCACAAAGAGTGGTGACAAAGAAGGGTAGGACTTTCCTTTATCCCAATGATCTTCTGCAG (SEQ ID NO: 419) |

TABLE 14C-continued

| Marburg Gblocks | |
|---|---|
| Name | Sequence |
| MB_GB78 | TTCTTTATCAGTCTCATCTTAATCCAAGGGATAAAAACTCTCCCTATT TTGGAGATAGCCAGTAACGATCAACCCCAAAATGTGGATTCGGTATG CTCCGGAACTCTCCAGAAAACAGAAGACGTCCATCTGATGGGATTTA CACTGAGCGGGCAAAAAGTTGCTGATTCCCCTTTGGAGGCATCCAAG CGATGGGCTTTCAGGACAGGTGTACCTCCCAAGAATGTTGAGTATAC GGAAGGGGAGGAAGCCAAAACATGCTACAATATAAGTGTAACGGAT CCCTCTGGAAAATCCTTGCTGTTAGATCCTCCCACCAACGTC (SEQ ID NO: 420) |
| MB_GB3 | ACTGCCTACTCTGGAGAAAATGAAAATGATTGTGATGCAGAGCTAAG AATTTGGAGTGTTCAGGAGGACGACCTGGCAGCAGGGCTCAGTTGGA TACCATTTTTTGGCCCTGGAATCGAAGGACTTTATACCGCTGGTTTAA TTAAAAATCAAAACAATTTGGTCTGCAGGTTGAGGCGTCTAGCCAAT CAAACTGCAAAATCCTTGGAACTCTTACTAAGGGTCACAACCGAGGA AAGAACATTTTCCTTAATCAATAGACATGCTATTGACTTTCTACTCA (SEQ ID NO: 195) |

Figure 14C:
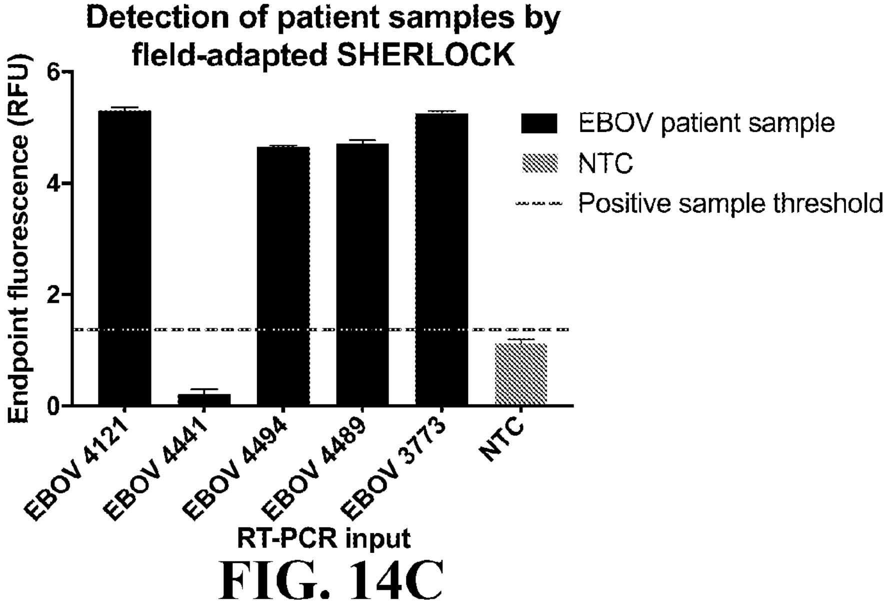
Figure 17:
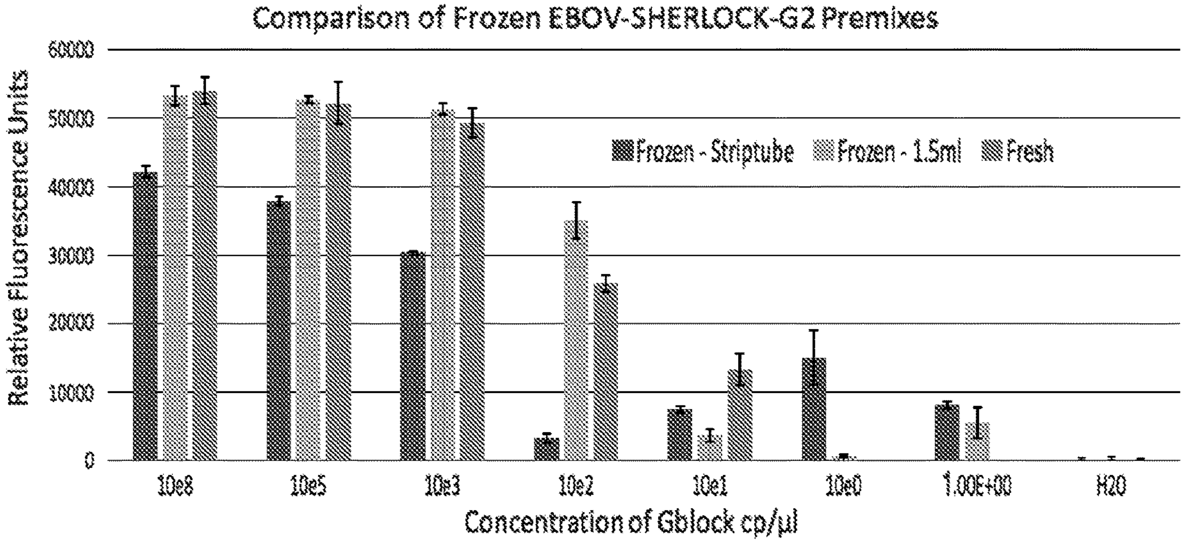
FIG. 17 charts a comparison of the use of EBOV-SHERLOCK-G2 premixes frozen and fresh samples, showing that EBOV-SHERLOCK-G2 can be frozen for a couple of weeks as a premix, allowing for rapid response lab kit development.

One advantage of the SHERLOCK method of detecting Ebola virus is that EBOV-SHERLOCK-G2 can be frozen for a couple of weeks as a premix, allowing for rapid response lab kit development. As shown in FIG. 17, the Cas13a protein is resilient, allowing reaction components were premeasured and separated into a few wells on a strip tube, the other were all of the components were mixed together in a 1.5 ml epi tube to provide premixes. These premixes were stored at −20 C and later compared to a fresh EBOV-SHERLOCK-G2 reaction. In a field test in Sierra Leone, which provided a good opportunity to test the EBOV-SHERLOCK in a resource limited setting. Currently, to set up a SHERLOCK reaction requires the mixing of 12 components, which when scaled up can increase the risk of human error. Before the field trip, Applicant tested two different premix combinations. One where the reaction components were premeasured and separated into a few wells on a strip tube, the other were all of the components were mixed together in a 1.5 ml epi tube. These premixes were stored at −20 C and later compared to a fresh EBOV-SHERLOCK-G2 reaction. Surprisingly, the premixed worked very well, and even seemed to out-perform the fresh at low levels of detection (FIG. 17). Some of these premixes were taken into to Sierra Leone and used in tests for Ebola utilizing a light cycler. The field-adapted SHERLOCK protocol described in the methods of Example 2 detected 4 of 5 tested EBOV clinical samples (FIG. 14*c*). Applicant defined positive samples as having endpoint fluorescence values that were greater than 3 SD above the no-input control. All samples were collected from individuals presenting fever and symptoms of Ebola, but other diagnostic information and sequencing date was not available.

Multiple novel diagnostics are provided herein for detection of LASV, EBOV, distinguishing between hemorrhagic viruses as well as distinguishing between strains of a hemorrhagic virus. RT-qPCR assays are well-established as a molecular viral detection method due to their sensitivity and rapid adaptability, and, as discussed herein, a novel RT-qPCR assay for LASV based on current viral strains that outperformed the gold standard LASV diagnostic, the Nikisins RT-qPCR assay, in detection of recent LASV patient samples is also presented. However, limitations in RT-qPCR technology prevent its adaptation to many resource-limited contexts, and an alternative diagnostic was also developed for such applications.

SHERLOCK technology presents an exciting new diagnostic alternative to existing RT-qPCR assays. SHERLOCK assays target nucleic acid and thus maintain the sensitivity and adaptability of RT-qPCR assays, and recent development in SHERLOCK technologies such as visual readouts enable SHERLOCK reactions to circumvent expensive equipment required by RT-qPCR assays (Gootenberg et al., 2017).

Four SHERLOCK assays for detection of clade-specific LASV were presented, with validation testing using sequencing-positive patient samples demonstrating that all four SHERLOCK assays are more sensitive than the Nikisins RT-qPCR. SHERLOCK assays are not cross-reactive with MARV or EBOV and thus can be used to diagnose individuals with symptomatic hemorrhagic fever. Field-applicability of the SHERLOCK pipeline by piloting its use at KGH in Sierra Leone is disclosed.

EBOV assays were also conducted, showing SHERLOCK methods were consistent in detecting EBOV in RT-qPCR positive samples and providing positive SHERLOCK results for some RT-qPCR negative samples, allowing for point of care diagnosis. Additionally, frozen premixes were shown to perform well as compared to fresh samples, and to outperform fresh samples at low levels of detection.

Further embodiments of the invention are described in the following numbered paragraphs.

Paragraph 1. A nucleic acid detection system for detecting the presence of hemorrhagic fever viruses in a sample comprising:

a CRISPR system comprising an effector protein and one or more guide molecules designed to bind to one or more corresponding target molecules of one or more hemorrhagic fever viruses; and an RNA-based masking construct.

Paragraph 2. The nucleic acid detection system of paragraph 1, wherein the one or more guide molecules are guide RNAs selected from the group consisting of SEQ ID NOs: 80, 87-92, 109-126, 139-156, 159-172, 207-228, 249-281, 329-366, and 393-416.

Paragraph 3. The nucleic acid detection system of paragraph 2, further comprising nucleic acid amplification reagents.

Paragraph 4. The nucleic acid detection system of paragraph 3, wherein the nucleic acid amplification reagents comprise recombinase polymerase amplification (RPA)

reagents, nucleic acid sequence-based amplification (NASBA) reagents, loop-mediated isothermal amplification (LAMP) reagents, strand displacement amplification (SDA) reagents, helicase-dependent amplification (HDA) reagents, nicking enzyme amplification reaction (NEAR) reagents, RT-PCR reagents, multiple displacement amplification (MDA) reagents, rolling circle amplification (RCA) reagents, ligase chain reaction (LCR) reagents, ramification amplification method (RAM) reagents, transposase based amplification reagents; or Programmable CRISPR Nicking Amplification (PCNA) reagents.

Paragraph 5. The nucleic acid detection system of paragraph 4, wherein the RPA reagents comprise one or more primer pairs selected from the group consisting of SEQ ID NOs: 78, 79, 81-86, 93-108, 127-138, 173-206, 233-248, 285-328, 370-392.

Paragraph 6. The nucleic acid detection system of paragraph 4, wherein the transposase-based amplification reagents comprise Tn5.

Paragraph 7. The nucleic acid detection system of paragraph 1, wherein the CRISPR system effector protein is an RNA-targeting effector protein.

Paragraph 8. The nucleic acid detection system of paragraph 7, wherein the RNA-targeting effector protein comprises one or more HEPN domains.

Paragraph 9. The nucleic acid detection system of paragraph 8, wherein the one or more HEPN domains comprise a RxxxxH motif sequence.

Paragraph 10. The nucleic acid detection system of paragraph 9, wherein the RxxxH motif comprises a R{N/H/K} $X_1X_2X_3$H sequence.

Paragraph 11. The nucleic acid detection system of paragraph 10, wherein $X_1$ is R, S, D, E, Q, N, G, or Y, and $X_2$ is independently I, S, T, V, or L, and $X_3$ is independently L, F, N, Y, V, I, S, D, E, or A.

Paragraph 12. The nucleic acid detection system of any one of paragraphs 1 to 11, wherein the CRISPR RNA-targeting effector protein is C2c2.

Paragraph 13. The nucleic acid detection system of paragraph 12, wherein the C2c2 is within 20 kb of a Cas 1 gene.

Paragraph 14. The nucleic acid detection system of paragraph 12, wherein the C2c2 effector protein is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira.*

Paragraph 15. The nucleic acid detection system of paragraph 14, wherein the C2c2 or Cas13b effector protein is from an organism selected from the group consisting of: *Leptotrichia* shahii; *Leptotrichia wadei* (Lw2); *Listeria seeligeri; Lachnospiraceae bacterium* MA2020*; Lachnospiraceae bacterium* NK4A179*;* [*Clostridium*]*aminophilum* DSM 10710*; Carnobacterium gallinarum* DSM 4847*; Carnobacterium gallinarum* DSM 4847 (second CRISPR Loci); *Paludibacter propionicigenes* WB4*; Listeria weihenstephanensis* FSL R9-0317*; Listeriaceae bacterium* FSL M6-0635*; Leptotrichia wadei* F0279*; Rhodobacter capsulatus* SB 1003*; Rhodobacter capsulatus* R121*; Rhodobacter capsulatus* DE442*; Leptotrichia buccalis* C-1013-b; *Herbinix hemicellulosilytica;* [*Eubacterium*] *rectale; Eubacteriaceae bacterium* CHKCI004*; Blautia* sp. Marseille-P2398*; Leptotrichia* sp. oral taxon 879 str. F0557*; Lachnospiraceae bacterium* NK4A144*; Chloroflexus aggregans; Demequina aurantiaca; Thalassospira* sp. TSL5-1*; Pseudobutyrivibrio* sp. OR37*; Butyrivibrio* sp. YAB3001*; Blautia* sp. Marseille-P2398*; Leptotrichia* sp. Marseille-P3007*; Bacteroides ihuae; Porphyromonadaceae bacterium* KH3CP3RA; *Listeria riparia*; and *Insolitispirillum peregrinum.*

Paragraph 16. The nucleic acid detection system of paragraph 15, wherein the C2c2 effector protein is a *L. wadei* F0279 or *L. wadei* F0279 (Lw2) C2c2 effector protein.

Paragraph 17. The nucleic acid detection system of any one of paragraphs 1 to 16, wherein the RNA-based masking construct suppresses generation of a detectable positive signal.

Paragraph 18. The nucleic acid detection system of paragraph 17, wherein the RNA-based masking construct suppresses generation of a detectable positive signal by masking the detectable positive signal, or generating a detectable negative signal instead.

Paragraph 19. The nucleic acid detection system of paragraph 17, wherein the RNA-based masking construct comprises a silencing RNA that suppresses generation of a gene product encoded by a reporting construct, wherein the gene product generates the detectable positive signal when expressed.

Paragraph 20. The nucleic acid detection system of paragraph 17, wherein the RNA-based masking construct is a ribozyme that generates the negative detectable signal, and wherein the positive detectable signal is generated when the ribozyme is deactivated.

Paragraph 21. The nucleic acid detection system of paragraph 20, wherein the ribozyme converts a substrate to a first color and wherein the substrate converts to a second color when the ribozyme is deactivated.

Paragraph 22. The nucleic acid detection system of paragraph 17, wherein the RNA-based masking agent is an RNA aptamer and/or comprises an RNA-tethered inhibitor.

Paragraph 23. The nucleic acid detection system of paragraph 22, wherein the aptamer or RNA-tethered inhibitor sequesters an enzyme, wherein the enzyme generates a detectable signal upon release from the aptamer or RNA tethered inhibitor by acting upon a substrate.

Paragraph 24. The nucleic acid detection system of paragraph 22, wherein the aptamer is an inhibitory aptamer that inhibits an enzyme and prevents the enzyme from catalyzing generation of a detectable signal from a substrate or wherein the RNA-tethered inhibitor inhibits an enzyme and prevents the enzyme from catalyzing generation of a detectable signal from a substrate.

Paragraph 25. The nucleic acid detection system of paragraph 24, wherein the enzyme is thrombin, protein C, neutrophil elastase, subtilisin, horseradish peroxidase, beta-galactosidase, or calf alkaline phosphatase.

Paragraph 26. The nucleic acid detection system of paragraph 25, wherein the enzyme is thrombin and the substrate is para-nitroanilide covalently linked to a peptide substrate for thrombin, or 7-amino-4-methylcoumarin covalently linked to a peptide substrate for thrombin.

Paragraph 27. The nucleic acid detection system of paragraph 22, wherein the aptamer sequesters a pair of agents that when released from the aptamers combine to generate a detectable signal.

Paragraph 28. The nucleic acid detection system of paragraph 17, wherein the RNA-based masking construct comprises an RNA oligonucleotide to which a detectable ligand and a masking component are attached.

Paragraph 29. The nucleic acid detection system of paragraph 17, wherein the RNA-based masking construct comprises a nanoparticle held in aggregate by bridge molecules, wherein at least a portion of the bridge molecules comprises RNA, and wherein the solution undergoes a color shift when the nanoparticle is disbursed in solution.

Paragraph 30. The nucleic acid detection system of paragraph 29, wherein the nanoparticle is a colloidal metal.

Paragraph 31. The nucleic acid detection system of paragraph 30, wherein the colloidal metal is colloidal gold.

Paragraph 32. The nucleic acid detection system of paragraph 17, wherein the RNA-based masking construct comprising a quantum dot linked to one or more quencher molecules by a linking molecule, wherein at least a portion of the linking molecule comprises RNA.

Paragraph 33. The nucleic acid detection system of paragraph 17, wherein the RNA-based masking construct comprises RNA in complex with an intercalating agent, wherein the intercalating agent changes absorbance upon cleavage of the RNA.

Paragraph 34. The nucleic acid detection system of paragraph 33, wherein the intercalating agent is pyronine-Y or methylene blue.

Paragraph 35. The nucleic acid detection system of paragraph 17, wherein the detectable ligand is a fluorophore and the masking component is a quencher molecule.

Paragraph 36. The nucleic acid detection system of anyone of paragraphs 1-35, comprising two or more CRISPR systems, each CRISPR system comprising an effector protein and one or more guide molecules designed to bind to one or more corresponding target molecules of one or more hemorrhagic fever viruses; and a set of RNA-based masking constructs; wherein each RNA-based masking construct comprises a cutting motif sequence that is preferentially cut by one of the CRISPR effector proteins after the CRISPR effector protein is activated.

Paragraph 37. A method for detecting viral nucleic acid in one or more samples, comprising:

contacting one or more samples with a nucleic acid detection system according to paragraph 1 or paragraph 36; and applying said contacted one or more samples sample to a lateral flow immunochromatographic assay.

Paragraph 38. A method for detecting viral nucleic acid in a sample comprising:

amplifying the sample nucleic acid;

combining the sample with an RNA effector protein, one or more guide molecules according to SEQ ID NOs: SEQ ID NOs: 80, 87-92, 109-126, 139-156, 159-172, 207-228, 249-281, 329-366, and 393-416, and an RNA-based masking construct, wherein the one or more guide molecules are designed to bind to corresponding virus specific target molecules;

activating the RNA effector protein via binding of the one or more guide molecules to the one or more virus-specific target molecules, wherein activating the RNA effector protein results in modification of the RNA-based masking construct such that a detectable positive signal is produced; and detecting the signal, wherein detection of the signal indicates the presence of a hemorrhagic fever virus; and wherein the method does not include the step of extracting nucleic acid from the sample.

Paragraph 39. The method of paragraph 38, wherein amplifying the sample nucleic acid comprises nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), RT-PCR, multiple displacement amplification (MDA), rolling circle amplification (RCA), ligase chain reaction (LCR), ramification amplification method (RAM), transposase based amplification, or Programmable CRISPR Nicking Amplification (PCNA).

Paragraph 40. The method of paragraph 39, wherein amplifying the sample nucleic acid comprises contacting the sample with one or more of the probes according to SEQ ID NOs: 78, 79, 81-86, 93-108, 127-138, 173-206, 233-248, 285-328, 370-392.

Paragraph 41. The method of paragraph 39, wherein the sample is a biological sample comprising blood, plasma, serum, urine, or saliva.

Paragraph 42. The method of paragraph 39, further comprising the step of applying the sample to one or more lateral flow strips.

Paragraph 43. The method of paragraph 42, wherein the lateral flow strip comprises an upstream first antibody directed against a first molecule, and a downstream second antibody directed against a second molecule, and wherein uncleaved RNA-based masking construct is bound by said first antibody if the target nucleic acid is not present in said sample, and wherein cleaved RNA-based masking construct is bound both by said first antibody and said second antibody if the target nucleic acid is present in said sample.

Paragraph 44. The system of any of paragraphs 1 to 37, wherein the masking construct comprises an RNA oligonucleotide designed to bind a G-quadruplex forming sequence, wherein a G-quadruplex structure is formed by the G-quadruplex forming sequence upon cleavage of the masking construct, and wherein the G-quadruplex structure generates a detectable positive signal.

Paragraph 45. The method of any of paragraphs 38 to 44, further comprising comparing the detectable positive signal with a (synthetic) standard signal.

Paragraph 46. The system or method according to any one of paragraphs 1 to 45, wherein the method distinguishes between two or more viruses or strains.

Paragraph 47. The system or method according to any one of paragraphs 1 to 46, wherein the hemorrhagic fever virus of interest is Lassa virus, Hantavirus, Crimean-Congo hemorrhagic fever virus, Lujo virus, Ebola virus, Marburg virus, or Rift Valley fever virus.

Paragraph 48. The system or method of paragraph 47, wherein the hemorrhagic fever virus of interest is Lassa virus.

Paragraph 49. The system or method according to paragraph 48, wherein the Lassa virus is SL-IV, N-II, or N-III.

Paragraph 50. The system or method of paragraph 46, wherein when the hemorrhagic fever virus of interest is Lassa virus, the one or more guide molecules are guide RNAs selected from the group consisting of SEQ ID NO: 87-92, 109-126, 139-156, 207-228, 249-281, 329-36;

when the hemorrhagic fever virus of interest is Ebola virus, the one or more guide molecules are guide RNAs selected from the group consisting of SEQ ID NO: 80, 159-172;

when the hemorrhagic fever virus of interest is Marburg virus, one or more guide molecules are guide RNAs selected from the group consisting of SEQ ID NO: 393-416.

Paragraph 51. A method of distinguishing between two or more hemorrhagic viruses, the method comprising: using the system of paragraph 1 or method of paragraph 38 wherein the one or more guide molecules comprise guide RNAs for the two or more hemorrhagic viruses.

Paragraph 52. A method of distinguishing between two or more strains of a hemorrhagic virus, comprising using system of paragraph 1 or method of paragraph 38 wherein the one or more guide molecules comprise guide RNAs for the two or more strains of a hemorrhagic virus.

Paragraph 53. A kit for detecting viral nucleic acids in a sample, comprising nucleic acid amplification reagents;

a CRISPR system comprising an effector protein and one or more of the guide RNAs according to SEQ ID NO: 80, 87-92, 109-126, 139-156, 159-172, 207-228, 249-281, 329-366, and 393-416, wherein the guide RNAs are designed to bind to corresponding target molecules;

an RNA-based masking construct; and one or more lateral flow strips.

Paragraph 54. The kit of paragraph 53, further comprising one or more of the probes according to SEQ ID NO: 78, 79, 81-86, 93-108, 127-138, 173-206, 233-248, 285-328, 370-392.

Paragraph 55. A diagnostic device comprising one or more individual discrete volumes, each individual discrete volume comprising a CRISPR system of any one of paragraph 1-36.

Paragraph 56. The device of paragraph 55, wherein each individual discrete volume further comprises one or more detection aptamers comprising a masked RNA polymerase promoter binding site or a masked primer binding site.

Paragraph 57. The device of paragraph 55, wherein each individual discrete volume further comprises nucleic acid amplification reagents.

Paragraph 58. The device of paragraph 55 wherein the target molecule is a target RNA and the individual discrete volumes further comprise a primer that binds the target RNA and comprises an RNA polymerase promoter.

Paragraph 59. The device of any one of paragraphs 55-58, wherein the individual discrete volumes are droplets.

Paragraph 60. The device of any one of paragraphs 55-59, wherein the individual discrete volumes are defined on a solid substrate.

Paragraph 61. The device of paragraph 60, wherein the individual discrete volumes are microwells.

Paragraph 62. The diagnostic device of any one of paragraphs 55-61, wherein the individual discrete volumes are spots defined on a substrate.

Paragraph 63. The device of paragraph 62, wherein the substrate is a flexible materials substrate.

Paragraph 64. The device of paragraph 63, wherein the flexible materials substrate is a paper substrate or a flexible polymer-based substrate.

Paragraph 65. The system of any one of paragraphs 1 to 36, further comprising an enrichment CRISPR system, wherein the enrichment CRISPR system is designed to bind the corresponding target molecules prior to detection by the detection CRISPR system.

Paragraph 66. The system of paragraph 65, wherein the enrichment CRISPR system comprises a catalytically inactive CRISPR effector protein.

Paragraph 67. The system of paragraph 65, wherein catalytically inactive CRISPR effector protein is a catalytically inactive C2c2.

Paragraph 68. The system of any one of paragraphs 65 to 67, wherein the enrichment CRISPR effector protein further comprises a tag, wherein the tag is used to pull down the enrichment CRISPR effector system, or to bind the enrichment CRISPR system to a solid substrate.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:

1. A nucleic acid detection system for detecting the presence of hemorrhagic fever viruses in a sample in a multiplex format comprising: a CRISPR system, comprising a Cas13 effector protein and multiple guide molecules each having a direct repeat and a guide sequence designed to bind to corresponding target molecules of hemorrhagic fever viruses comprising Lassa virus, Ebola virus, and Marburg virus, wherein the guide molecules targeting the Lassa virus are guide RNAs comprising a guide sequence having a nucleotide sequence selected from the group consisting of SEQ ID NOs: 87-92, 109-126, 139-156, 207-228, 249-281, and 329-36, wherein the guide molecules targeting the Ebola virus are guide RNAs comprising a guide sequence having a nucleotide sequence selected from the group consisting of SEQ ID NOs: 80, 162, 164, 166, 168, 170 and 172, wherein the guide molecules targeting the Marburg virus are guide RNAs comprising a guide sequence having a nucleotide sequence selected from the group consisting of SEQ ID NOs: 393-416, and an RNA-based masking construct.

2. The nucleic acid detection system of claim 1, further comprising nucleic acid amplification reagents, wherein the nucleic acid amplification reagents comprise recombinase polymerase amplification (RPA) reagents, nucleic acid sequence-based amplification (NASBA) reagents, loop-mediated isothermal amplification (LAMP) reagents, strand displacement amplification (SDA) reagents, helicase-dependent amplification (HDA) reagents, nicking enzyme amplification reaction (NEAR) reagents, RT-PCR reagents, multiple displacement amplification (MDA) reagents, rolling circle amplification (RCA) reagents, ligase chain reaction (LCR) reagents, ramification amplification method (RAM) reagents, transposase based amplification reagents, or Programmable CRISPR Nicking Amplification (PCNA) reagents.

3. The nucleic acid detection system of claim 2, wherein the RPA reagents comprise one or more primer pairs selected from the group consisting of SEQ ID NOs: 78, 79, 81-86, 93-108, 127-138, 173-206, 233-248, 285-328, 370-392, or wherein the transposase-based amplification reagents comprise a transposase of prokaryotic transposon 5 (Tn5).

4. The nucleic acid detection system of claim 1, wherein the CRISPR effector protein is an RNA-targeting effector protein, and wherein the RNA-targeting effector protein comprises one or more higher eukaryotes and prokaryotes nucleotide-binding (HEPN) domains, comprising a RxxxxH motif sequence, comprising a R{N/H/K]$X_1X_2X_3$H sequence, wherein $X_1$ is R, S, D, E, Q, N, G, or Y, and $X_2$ is independently I, S, T, V, or L, and $X_3$ is independently L, F, N, Y, V, I, S, D, E, or A.

5. The nucleic acid detection system of claim 1, wherein the Cas 13 effector protein is a C2c2 effector protein is within 20 kilobases (kb) of a Cas 1 gene, wherein the C2c2 effector protein is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*; or the C2c2 effector protein is a *L. wadei* F0279 or *L. wadei* F0279 (Lw2) C2c2 effector protein.

6. The nucleic acid detection system of claim 1, wherein the RNA-based masking construct suppresses generation of a detectable positive signal, and wherein:

- the RNA-based masking construct suppresses generation of a detectable positive signal by masking the detectable positive signal, or by generating a detectable negative signal instead;
- the RNA-based masking construct comprises a silencing RNA that suppresses generation of a gene product encoded by a reporting construct, wherein the gene product generates the detectable positive signal when expressed;
- the RNA-based masking construct is a ribozyme that generates the negative detectable signal, and wherein the positive detectable signal is generated when the ribozyme is deactivated, wherein the ribozyme converts a substrate to a first color and wherein the substrate converts to a second color when the ribozyme is deactivated;
- the RNA-based masking construct comprises an RNA oligonucleotide to which a detectable ligand and a masking component are attached;
- the RNA-based masking construct comprises a nanoparticle held in aggregate by bridge molecules, wherein at least a portion of the bridge molecules comprises RNA, and wherein the solution undergoes a color shift when the nanoparticle is disbursed in solution;
- the RNA-based masking construct comprising a quantum dot linked to one or more quencher molecules by a linking molecule, wherein at least a portion of the linking molecule comprises RNA;
- the RNA-based masking construct comprises RNA in complex with an intercalating agent, wherein the intercalating agent changes absorbance upon cleavage of the RNA; or
- the detectable ligand is a fluorophore and the masking component is a quencher molecule.

7. The nucleic acid detection system of claim 6, wherein the RNA-based masking agent is an RNA aptamer and/or comprises an RNA-tethered inhibitor, wherein the aptamer or RNA-tethered inhibitor sequesters an enzyme, wherein the enzyme generates a detectable signal upon release from the aptamer or RNA tethered inhibitor by acting upon a substrate; or wherein the aptamer is an inhibitory aptamer that inhibits an enzyme and prevents the enzyme from catalyzing generation of a detectable signal from a substrate or wherein the RNA-tethered inhibitor inhibits an enzyme and prevents the enzyme from catalyzing generation of a detectable signal from a substrate, and wherein, wherein the enzyme is thrombin, protein C, neutrophil elastase, subtilisin, horseradish peroxidase, beta-galactosidase, or calf alkaline phosphatase, and, wherein, the enzyme is thrombin and the substrate is para-nitroanilide covalently linked to a peptide substrate for thrombin, or 7-amino-4-methylcoumarin covalently linked to a peptide substrate for thrombin;

or wherein the aptamer sequesters a pair of agents that when released from the aptamers combine to generate a detectable signal.

8. The nucleic acid detection system of claim 6, wherein the RNA-based masking construct comprises a nanoparticle held in aggregate by bridge molecules, wherein at least a portion of the bridge molecules comprises RNA, and wherein the solution undergoes a color shift when the nanoparticle is disbursed in solution, wherein the nanoparticle is a colloidal metal, colloidal gold.

9. The nucleic acid detection system of claim 6, wherein the RNA-based masking construct comprises RNA in complex with an intercalating agent, wherein the intercalating agent changes absorbance upon cleavage of the RNA, wherein the intercalating agent is pyronine-Y or methylene blue.

10. The nucleic acid detection system of claim 1, further comprising two or more CRISPR systems, each CRISPR system comprising an Cas13 effector protein and guide molecules designed to bind to corresponding target molecules of hemorrhagic fever viruses; and a set of RNA-based masking constructs; wherein each RNA-based masking construct comprises a cutting motif sequence that is preferentially cut by one of the CRISPR effector proteins after the CRISPR effector protein is activated.

11. A method for detecting viral nucleic acid(s) in a sample in a multiplex format comprising: amplifying the sample nucleic acid; combining the sample with an Cas13 effector protein, multiple guide molecules designed to bind to corresponding virus specific target molecules comprising LASSA virus, Ebola virus and Marburg virus and an RNA-based masking construct, wherein the guide molecules targeting the Lassa virus are guide RNAs comprising a guide sequence having a nucleotide sequence selected from the group consisting of SEQ ID NOs: 87-92, 109-126, 139-156, 207-228, 249-281, and 329-36, wherein the guide molecules targeting the Ebola virus are guide RNAs comprising a guide sequence having a nucleotide sequence selected from the group consisting of SEQ ID NOs: 80, 162, 164, 166, 168, 170 and 172, wherein the guide molecules targeting the Marburg virus are guide RNAs comprising a guide sequence having a nucleotide sequence selected from the group consisting of SEQ ID NOs: 393-416, wherein each guide RNA further comprises a direct repeat sequence capable of binding to the Cas13 effector protein, activating the Cas13 effector protein via binding of the guide molecules to the virus-specific target molecules, wherein activating the Cas13 effector protein results in modification of the RNA-based masking construct such that a detectable positive signal is produced; and detecting the signal, wherein detection of the signal indicates the presence of Lassa virus, Ebola virus, or Marburg virus, or a combination thereof; wherein the method does not include a step of extracting nucleic acid from the sample, and wherein: the step of amplifying the sample nucleic acid comprises nucleic acid sequence-based amplification (NASBA), recombinase polymerase amplification (RPA), loop-mediated isothermal amplification (LAMP), strand displacement amplification (SDA), helicase-dependent amplification (HDA), nicking enzyme amplification reaction (NEAR), RT-PCR, multiple displacement amplification (MDA), rolling circle amplification (RCA), ligase chain reaction (LCR), ramification amplification method (RAM), transposase based amplification, or Programmable CRISPR Nicking Amplification (PCNA) wherein the sample is a biological sample comprising blood, plasma, serum, urine, or saliva.

12. The method of claim 11, wherein amplifying the sample nucleic acid comprises contacting the sample with one or more of the probes selected from the group consisting of SEQ ID NOs: 78, 79, 81-86, 93-108, 127-138, 173-206, 233-248, 285-328, 370-392.

13. The method of claim 11, further comprising the step of applying the sample to one or more lateral flow strips, wherein the lateral flow strip comprises an upstream first antibody directed against a first molecule, and a downstream second antibody directed against a second molecule, and wherein uncleaved RNA-based masking construct is bound by said first antibody if the target nucleic acid is not present in said sample, and wherein cleaved RNA-based masking construct is bound both by said first antibody and said second antibody if the target nucleic acid is present in said sample.

14. The system of claim 1, wherein the masking construct comprises an RNA oligonucleotide designed to bind a G-quadruplex forming sequence, wherein a G-quadruplex structure is formed by the G-quadruplex forming sequence upon cleavage of the masking construct, and wherein the G-quadruplex structure generates a detectable positive signal.

15. The method of claim 11, further comprising comparing the detectable positive signal with a (synthetic) standard signal.

16. The method of claim 11, wherein the Lassa virus is SL-IV, N-II, or N-III.

17. The method of claim 11, wherein the direct repeat has a nucleotide sequence of SEQ ID NO: 158.

18. A kit for detecting viral nucleic acids in a sample in a multiplex format, comprising nucleic acid amplification reagents; a CRISPR system comprising a Cas13 effector protein and multiple guide RNAs designed to bind to corresponding target molecules of hemorrhagic fever viruses comprising a Lassa virus, an Ebola virus and a Marburg virus, wherein the guide molecules targeting the Lassa virus are guide RNAs comprising a guide sequence having a nucleotide sequence selected from the group consisting of SEQ ID NOs: 87-92, 109-126, 139-156, 207-228, 249-281, and 329-36, wherein the guide molecules targeting the Ebola virus are guide RNAs comprising a guide sequence having a nucleotide sequence selected from the group consisting of SEQ ID NOs: 80, 162, 164, 166, 168, 170 and 172, wherein the guide molecules targeting the Marburg virus are guide RNAs comprising a guide sequence having a nucleotide sequence selected from the group consisting of SEQ ID NOs: 393-416, wherein each guide RNA further comprises a direct repeat sequence capable of binding to the Cas13 effector protein, an RNA-based masking construct; one or more lateral flow strips; and, one or more of the probes selected from the group consisting of SEQ ID NO: 78, 79, 81-86, 93-108, 127-138, 173-206, 233-248, 285-328, 370-392.

19. A diagnostic device comprising one or more individual discrete volumes, each individual discrete volume comprising a nucleic acid detection system of claim 1, wherein:

each individual discrete volume further comprises one or more detection aptamers comprising a masked RNA polymerase promoter binding site or a masked primer binding site;

each individual discrete volume further comprises nucleic acid amplification reagents;

the target molecule is a target RNA and the individual discrete volumes further comprise a primer that binds the target RNA and comprises an RNA polymerase promoter.

20. The device of claim 19, wherein the individual discrete volumes are droplets, or wherein the individual discrete volumes are defined on a solid substrate, wherein the individual discrete volumes are microwells, or are spots define on the substrate; wherein the solid substrate is a flexible materials substrate, and a paper or flexibly polymer-based substrate.

21. The nucleic acid detection system of claim 1, further comprising target molecule-specific enrichment CRISPR system, wherein the target molecule-specific enrichment CRISPR system is designed to bind and sequester the corresponding target molecules prior to detection by the CRISPR system, and wherein the target molecule-specific enrichment CRISPR system comprises a catalytically inactive CRISPR effector protein; wherein the catalytically inactive CRISPR effector protein is a catalytically inactive C2c2; or wherein the target molecule-specific enrichment CRISPR effector protein comprises a tag, wherein the tag is used to pull down the target molecule-specific enrichment CRISPR effector system, or to bind the target molecule-specific enrichment CRISPR system to a solid substrate.

22. The nucleic acid detection system of claim 1, wherein the Cas13 effector protein is a C2c2 effector protein or a Cas13b effector protein from an organism selected from the group consisting of: *Leptotrichia* shahii; *Leptotrichia wadei* (Lw2); *Listeria seeligeri; Lachnospiraceae bacterium* MA2020*; Lachnospiraceae bacterium* NK4A179*;* [*Clostridium*]*aminophilum* DSM 10710*; Carnobacterium gallinarum* DSM 4847*; Carnobacterium gallinarum* DSM 4847 (second CRISPR Loci); *Paludibacter propionicigenes* WB4*; Listeria weihenstephanensis* FSL R9-0317*; Listeriaceae bacterium* F SL M6-063 5*; Leptotrichia wadei* F0279*; Rhodobacter capsulatus* SB 1003*; Rhodobacter capsulatus* R121*; Rhodobacter capsulatus* DE442*; Leptotrichia buccalis* C-1013-b; *Herbinix hemicellulosilytica;* [*Eubacterium*] *rectale; Eubacteriaceae bacterium* CHKCI004*; Blautia* sp. Marseille-P2398*; Leptotrichia* sp. oral taxon 879 str. F0557*; Lachnospiraceae bacterium* NK4A144*; Chloroflexus aggregans; Demequina aurantiaca; Thalassospira* sp. TSL5-1*; Pseudobutyrivibrio* sp. OR37*; Butyrivibrio* sp. YAB3001*; Blautia* sp. Marseille-P2398*; Leptotrichia* sp. Marseille-P3007*; Bacteroides ihuae; Porphyromonadaceae bacterium* KH3CP3RA; *Listeria riparia*; and *Insolitispirillum peregrinum.*

23. The nucleic acid detection system of claim 1, wherein the direct repeat sequence has a nucleotide sequence of SEQ ID NO: 158.

* * * * *

SEQUENCE LISTING

```
<160> NUMBER OF SEQ ID NOS: 421

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = N, H, or K
<220> FEATURE:
<221> NAME/KEY: MISC_FEATURE
<222> LOCATION: (3)..(3)
<223> OTHER INFORMATION: Xaa = R, S, D, E, Q, N, G, or Y
<220> FEATURE:
<221> NAME/KEY: MISC_FEATURE
<222> LOCATION: (4)..(4)
<223> OTHER INFORMATION: Xaa = I, S, T, V, or L
<220> FEATURE:
<221> NAME/KEY: MISC_FEATURE
<222> LOCATION: (5)..(5)
<223> OTHER INFORMATION: Xaa = L, F, N, Y, V, I, S, D, E, or A

<400> SEQUENCE: 1
```

```
Arg Xaa Xaa Xaa Xaa His
1               5


<210> SEQ ID NO 2
<211> LENGTH: 191
<212> TYPE: DNA
<213> ORGANISM: Lassa virus

<400> SEQUENCE: 2

tgctggggat gcagccaacc attgtggcac tgttgcaaat ggtgtcttac agactttcat      60

gaggatggct tggggtggga gctacattgc tcttgactca ggccgtggca ggtgggactg     120

tattatgact agttatcaat atctgataat ccaaaataca acctgggaag atcactgcaa     180

ttctcaagac c                                                          191


<210> SEQ ID NO 3
<211> LENGTH: 192
<212> TYPE: DNA
<213> ORGANISM: Lassa virus

<400> SEQUENCE: 3

tgctggggat gcggccgaac actgtgggac agttgccaac ggagtgttgc aaacatttat      60

gagaatggcc tggggtggaa gatacattgc attagactca ggaaagggaa actgggactg     120

tataatgacc agctaccagt acctgataat tcaaaataca acatgggagg accactgcca     180

attctcaaga cc                                                         192


<210> SEQ ID NO 4
<211> LENGTH: 192
<212> TYPE: DNA
<213> ORGANISM: Lassa virus

<400> SEQUENCE: 4

tgctggggat gcagccagcc attgtgggac agttgcaaat ggtgttctgc aaactttcat      60

gagaatggct tggggtggga gctatattgc tcttgactct ggtcgtggca attgggactg     120

tatcatgact agttaccaat atctgataat tcagaataca acctgggagg atcattgcca     180

attctcaaga cc                                                         192


<210> SEQ ID NO 5
<211> LENGTH: 192
<212> TYPE: DNA
<213> ORGANISM: Lassa virus

<400> SEQUENCE: 5

tgctatagat gcggccaacc attgtggcac agttgcaaat ggtgttctac agactttcat      60

gaggatggct tggggtggga gttacattgc tcttgattca ggccgtggcg gatgggactg     120

tatcatgact agttatcaat atctgataat tcagaataca acctgggaag atcactgcca     180

gttctcaaga cc                                                         192


<210> SEQ ID NO 6
<211> LENGTH: 192
<212> TYPE: DNA
<213> ORGANISM: Lassa virus

<400> SEQUENCE: 6

tgctgtggat gcagccaacc attgtggcac agttgcaaat ggtgtcctac agactttcat      60

gaggatggct tggggtggga gctatattgc ccttgattca ggccgtggta attgggattg     120
```

tattatgact agttaccaat atctaataat tcaaaataca acctgggaag atcactgcca 180
gttctcaaga cc 192

<210> SEQ ID NO 7
<211> LENGTH: 192
<212> TYPE: DNA
<213> ORGANISM: Lassa virus

<400> SEQUENCE: 7
tgctgtggat gcagccaacc actgtggcac agttgcaaat ggtgtcctgc agactttcat 60
gaggatggcc tggggtggga gctatattgc ccttgattca ggccgtggta attgggattg 120
tatcatgact agttaccaat atctaataat tcagaatata acctgggaag atcactgcca 180
gttctcaaga cc 192

<210> SEQ ID NO 8
<211> LENGTH: 192
<212> TYPE: DNA
<213> ORGANISM: Lassa virus

<400> SEQUENCE: 8
tgctgtggat gcagccaacc attgtggcac agttgcaaat ggtgtcctac agactttcat 60
gaggatggcc tggggtggga gctatattgc ccttgattca ggccgtggaa attgggattg 120
tattatgacc agttaccaat atctaataat tcagaataca acctgggaag atcactgcca 180
gttctcaaga cc 192

<210> SEQ ID NO 9
<211> LENGTH: 192
<212> TYPE: DNA
<213> ORGANISM: Lassa virus

<400> SEQUENCE: 9
tgctgtggat gcagccaacc attgtggtac agttgcaaat ggtgtcctac agactttcat 60
gaggatggcc tggggtggga gctacattgc ccttgattca ggccgtggta attgggattg 120
tattatgacc agttaccaat atctaataat tcagaataca acctgggaag atcactgcca 180
gttctcaaga cc 192

<210> SEQ ID NO 10
<211> LENGTH: 192
<212> TYPE: DNA
<213> ORGANISM: Lassa virus

<400> SEQUENCE: 10
tgctgtggat gcagccaacc attgtggcac agttgcaaat ggtatcctac agactttcat 60
gaggatggcc tggggtggga gttatattgc ccttgattca ggccgtggca attgggattg 120
tattatgact agttaccaat atctaataat tcagaataca acctgggaag atcactgcca 180
gttctcaaga cc 192

<210> SEQ ID NO 11
<211> LENGTH: 192
<212> TYPE: DNA
<213> ORGANISM: Lassa virus

<400> SEQUENCE: 11
tgctgtggat gcagccaacc attgtggcac agttgcaaat ggtgtcctac agactttcat 60

```
gaggatggcc tggggtggga gctatattgc ccttgattca ggccgtggca attgggattg    120

cattatgact agttaccaat atctaataat tcagaataca acctgggaag atcactgcca    180

gttctcaaga cc                                                        192


<210> SEQ ID NO 12
<211> LENGTH: 192
<212> TYPE: DNA
<213> ORGANISM: Lassa virus

<400> SEQUENCE: 12

tgctggagat gcagccaagc attgtggcac agttgcgaat ggcgttttgc agaccttgat     60

gagaatggcc tggggtggga gttacattgc tcttgactca ggtcgcaatg gatgggattg    120

gtggatgact agttatcaat atctaataat tcaaaacaca acctgggaag atcactgcca    180

gttctcaaga cc                                                        192


<210> SEQ ID NO 13
<211> LENGTH: 192
<212> TYPE: DNA
<213> ORGANISM: Lassa virus

<400> SEQUENCE: 13

tgctgtagat gcagccaacc attgtggcac agtcgcaaat ggcgttttgc agactttcat     60

gaggatggcc tggggtggga gttacattgc tcttgattca ggccgcaatg ggtgggattg    120

tatcatgacc agttatcaat acctaattat tcagaacaca acttgggaag atcactgcca    180

attctcaaga cc                                                        192


<210> SEQ ID NO 14
<211> LENGTH: 192
<212> TYPE: DNA
<213> ORGANISM: Lassa virus

<400> SEQUENCE: 14

tgctggagat gcagccaacc attgtggcac agttgcaaat ggcgttttgc agaccttcat     60

gaggatggcc tggggtggga gctacattgc tcttgattca ggccgcaatg gatgggattg    120

cattatgact agttatcaat atctgataat tcagaataca acctgggacg atcactgcca    180

attctcaaga cc                                                        192


<210> SEQ ID NO 15
<211> LENGTH: 192
<212> TYPE: DNA
<213> ORGANISM: Lassa virus

<400> SEQUENCE: 15

tgctggagac gcagccaacc attgtggcac agttgcaaat ggcgttttgc agaccttcat     60

gaggatggcc tggggtggga gctacattgc tcttgattca ggccgtaatg ggtgggattg    120

cattatgacc agttatcaat atctgataat tcagaataca acctgggacg atcactgcca    180

attttcaaga cc                                                        192


<210> SEQ ID NO 16
<211> LENGTH: 192
<212> TYPE: DNA
<213> ORGANISM: Lassa virus

<400> SEQUENCE: 16

tgctggagat gcagctaacc attgtggcac agttgcaaat ggtgtccttc agactttcat     60
```

gaggatggct tggggtggaa gttatattgc tcttgattca ggccacggtg gatgggactg 120
tattatgacc agttatcagt atctaataat tcaaaatcaa acctgggaag atcactgcca 180
attcacaaga cc 192

<210> SEQ ID NO 17
<211> LENGTH: 192
<212> TYPE: DNA
<213> ORGANISM: Lassa virus

<400> SEQUENCE: 17
tgctggagat gcagccaacc attgtggtac agttgcaaat ggtgttttac aaaccttcat 60
gaggatggct tggggtggga gttacatcgc ccttgactca ggtcgtggca attgggactg 120
tattatgact agttatcaat acctaataat tcagaatacg acctgggatg atcattgcca 180
attctcaaga cc 192

<210> SEQ ID NO 18
<211> LENGTH: 192
<212> TYPE: DNA
<213> ORGANISM: Lassa virus

<400> SEQUENCE: 18
tgctgtggat gcagccaacc attgtggcac agttgcaaat ggtgtcttac agactttcat 60
gaggatggcc tggggtggag gatacattgc tcttgactca ggccgtggca attgggattg 120
cattatgacc agctatcaat atctgataat ccaaaacaca acctgggagg accactgcca 180
attctcaaga cc 192

<210> SEQ ID NO 19
<211> LENGTH: 189
<212> TYPE: DNA
<213> ORGANISM: Lassa virus

<400> SEQUENCE: 19
tgctggggat gcagccaacc attgtggcac agttgcaaat ggtgtcctgc agactttcat 60
gaggatggcc tggggtggaa gctacattgc tcttgactca ggccatgaat gggactgcat 120
tatgaccagc tatcaatacc tgataatcca aaatacaacc tgggacaatc attgccagtt 180
ctcaagacc 189

<210> SEQ ID NO 20
<211> LENGTH: 192
<212> TYPE: DNA
<213> ORGANISM: Lassa virus

<400> SEQUENCE: 20
tgctggggat gcagccaacc attgtggcac agttgcaaat ggtgtcctgc agactttcat 60
gaggatggcc tggggtggaa gctacattgc tcttgactca ggccatagca agtgggactg 120
cattatgacc agctatcaat acctgataat ccaaaacaca acctgggacg atcattgcca 180
gttctcaaga cc 192

<210> SEQ ID NO 21
<211> LENGTH: 192
<212> TYPE: DNA
<213> ORGANISM: Lassa virus

<400> SEQUENCE: 21
tgctggggat gcagccaacc attgtggcac agttgcaaat ggtgtcctgc agactttcat 60
gaggatggcc tggggtggaa gctacattgc tcttgactca ggccatagca agtgggactg 120
cattatgacc agctatcaat acctgataat ccaaaacaca acctgggacg atcattgcca 180
gttctcaaga cc 192

<210> SEQ ID NO 22
<211> LENGTH: 192
<212> TYPE: DNA
<213> ORGANISM: Lassa virus

<400> SEQUENCE: 22
tgctggggat gcagccaacc attgtggcac agttgcaaat ggtgtcctgc agactttcat 60
gaggatggcc tggggtggaa gctacattgc tcttgactca ggccatagca agtgggactg 120
cattatgacc agctatcaat acctgataat ccaaaacaca acctgggacg atcattgcca 180
gttctcaaga cc 192

<210> SEQ ID NO 23
<211> LENGTH: 187
<212> TYPE: DNA
<213> ORGANISM: Lassa virus

<400> SEQUENCE: 23
aaggtatttc caccattttg tgcatatgcc acataagtag ggttgagaga tagtccctcc 60
cttttatgtc agcttgcaag tcctttgaga ggaaaattaa attctgtaag acagtcaaga 120
ataaaaatgg acacatcatt gggccccact tactatgatc catgctataa gagacatgtg 180
ccaatga 187

<210> SEQ ID NO 24
<211> LENGTH: 189
<212> TYPE: DNA
<213> ORGANISM: Lassa virus

<400> SEQUENCE: 24
aaggtatttc caccatcttg tgcatgtgcc acataagcaa ggttgagaga taatctctct 60 ccctttatg tcagcttgta ggtcttttga aagaaagatt aaattttgta gaacagttaa 120
gaatagaaat ggacacatca ttgggcccca cttactgtga tccatgctgt aggaaacatg 180
tgccaggga 189

<210> SEQ ID NO 25
<211> LENGTH: 187
<212> TYPE: DNA
<213> ORGANISM: Lassa virus

<400> SEQUENCE: 25
aaggtatttc caccatttta tgcatgtgcc acataagtag ggttgagaga tagtccctcc 60
cttttatgtc agcttgcagg tcctttgaga gaaaaatcaa attctgtaag acagccaaga 120
ataaaaatgg acacatcatt gggccccatt tactgtgatc catgctataa gagacatgtg 180
ccaatga 187

<210> SEQ ID NO 26
<211> LENGTH: 187
<212> TYPE: DNA
<213> ORGANISM: Lassa virus

<400> SEQUENCE: 26
aaggtatttc caccatttta tgcatgtgcc acataagtag ggtcgaaaga tagtctctcc 60
cttttatatc agcttgcaaa tcctttgaga ggaaaattaa attctgtaag acagtcaaga 120
ataaaaatgg acacatcatt gggccccact tactatgatc catactatag gagacatgtg 180
ccaatga 187

<210> SEQ ID NO 27
<211> LENGTH: 187
<212> TYPE: DNA
<213> ORGANISM: Lassa virus

<400> SEQUENCE: 27
aaggtatctc caccatttta tgcatgtgcc acataagtag ggtcgagaga tagtccctcc 60
cttttatgtc agcttgcagg tcctttgaga ggaaaattaa gttctgcaag acagtcaaga 120
ataaaaatgg acacatcatt gggccccact tactatgatc catactatag gagacatgtg 180
ccagtga 187

<210> SEQ ID NO 28
<211> LENGTH: 187
<212> TYPE: DNA
<213> ORGANISM: Lassa virus

<400> SEQUENCE: 28
aaggtatctc caccatttta tgcatgtgcc acataagtaa ggtcgaaaga tagtccctcc 60
cttttatgtc agcctgcagg tcctttgaga ggaaaattaa attctgtaag acagtcaaga 120
ataaaaatgg acacatcatt gggccccact tactatgatc catactgtag gagacatgtg 180
ccaatga 187

<210> SEQ ID NO 29
<211> LENGTH: 187
<212> TYPE: DNA
<213> ORGANISM: Lassa virus

<400> SEQUENCE: 29
aaggtatttc caccatctta tgcatgtgcc acataagtaa agtcgaaaga tagtccctcc 60
cttttatgtc agcctgcaag tcctttgaga ggaaaattaa attctgtaag acagtcaaga 120
ataaaaatgg acacatcatt gggccccact tactatgatc catactgtag gagacatgtg 180
ccaatga 187

<210> SEQ ID NO 30
<211> LENGTH: 187
<212> TYPE: DNA
<213> ORGANISM: Lassa virus

<400> SEQUENCE: 30
agggtatttc caccatttta tgcatgtgcc acatgagtag ggttgagaga tagtccctcc 60
cttttatgtg accttgcaag tcctttgaga ggaaaattaa gttctgtaag acagtcaaga 120
ataaaaatgg acacatcatt gggccccatt tactatgatc catgctatag gagacatgtg 180
ctaatga 187

<210> SEQ ID NO 31
<211> LENGTH: 187
<212> TYPE: DNA
<213> ORGANISM: Lassa virus

<400> SEQUENCE: 31
agggtatttc caccatttta tgcatgtgcc acatgagtag ggttgagaga tagtccctcc 60
cctttatgtc agcatgcaag tcctttgaga ggaaaattaa attctgtaag acagttaaga 120
ataaaaatgg acacatcatt gggccccatt tactatgatc catactatag gagacatgtg 180
ctaatga 187

<210> SEQ ID NO 32
<211> LENGTH: 187
<212> TYPE: DNA
<213> ORGANISM: Lassa virus

<400> SEQUENCE: 32
agggtatttc caccatttta tgcatgtgcc acatgagtag ggttgagaga tagtccctcc 60
cctttatgtc agcatgcaag tcctttgaga ggaaaattaa attctgtaag acagttaaga 120
ataaaaatgg acacatcatt gggccccatt tactatgatc catactatag gagacatgtg 180
ctaatga 187

<210> SEQ ID NO 33
<211> LENGTH: 187
<212> TYPE: DNA
<213> ORGANISM: Lassa virus

<400> SEQUENCE: 33
agggtatttc caccatttta tgcatgtgcc acatgagtag ggttgagaga tagtccctcc 60
cctttatgtc agcatgcaag tcctttgaga ggaaaattaa attctgtaag acagttaaga 120
ataaaaatgg acacatcatt gggccccatt tactatgatc catactatag gagacatgtg 180
ctaatga 187

<210> SEQ ID NO 34
<211> LENGTH: 187
<212> TYPE: DNA
<213> ORGANISM: Lassa virus

<400> SEQUENCE: 34
agggtatttc caccatttta tgcatgtgcc acatgagtaa ggttgagaga tagtccctcc 60
cctttatgtc agcttgcaag tcctttgaga ggaaaattaa attttgtaag acagttaaga 120
ataaaaatgg acacatcatt gggccccatt tactatgatc catgctatag gagacatgtg 180
ctaatga 187

<210> SEQ ID NO 35
<211> LENGTH: 187
<212> TYPE: DNA
<213> ORGANISM: Lassa virus

<400> SEQUENCE: 35
agggtatttc caccatttta tgcatgtgcc acatgagtag ggttgagaga tagtccctcc 60
cctttatgtc agcttgcaag tcctttgaga ggaaaattaa attctgtaag acagttaaga 120
ataaaaatgg acacatcatt gggccccatt tactatgatc aatgctatag gagacatgtg 180
ctaatga 187

<210> SEQ ID NO 36
<211> LENGTH: 187
<212> TYPE: DNA
<213> ORGANISM: Lassa virus

<400> SEQUENCE: 36
aaggtatttc taccattttg tgcatgtgcc acataagtag ggttgaaaga tagtccctcc 60
cttttatgtc agcttgcaag tcctttgaga gaaaaattaa attctgtaag acagtcaaga 120
ataaaaatgg acacatcatt gggccccact tgctatgatc catgctataa gagacatgtg 180
ccaatga 187

<210> SEQ ID NO 37
<211> LENGTH: 186
<212> TYPE: DNA
<213> ORGANISM: Lassa virus

<400> SEQUENCE: 37
agggtatttc taccattttg tgcatatgcc acataagtaa ggttgaaaga tagtctctcc 60
cttttatgtc agcttgcaag tcctttgaga gaaaaattaa attctgtaag acagtcaaaa 120
taaaaatgga cacatcattg ggccccactt actatgatcc atactataag agacatgtgc 180
cagtga 186

<210> SEQ ID NO 38
<211> LENGTH: 187
<212> TYPE: DNA
<213> ORGANISM: Lassa virus

<400> SEQUENCE: 38
aaggtatttc taccattttg tgcatatgcc acataagtag ggttgaaaga tagtccctcc 60
cctttatgtc agcttgcaag tcttttgaga ggaaaattaa attctgtaag acagtcaaga 120
ataagaatgg acacatcata gggccccact tgctatgatc catgctataa gacacatgtg 180
ccaatga 187

<210> SEQ ID NO 39
<211> LENGTH: 187
<212> TYPE: DNA
<213> ORGANISM: Lassa virus

<400> SEQUENCE: 39
aaggtatttc caccattttg tgcatatgcc acatgagtag ggttgaaaga tagtccctcc 60
cttttatgtc agcttgcaag tcccttgaga ggaaaatcaa attctgtaag acagtcaaga 120
acaaaaatgg acacatcatt gggccccact tactatgatc catgctatag gacacatgcg 180
ctaatga 187

<210> SEQ ID NO 40
<211> LENGTH: 187
<212> TYPE: DNA
<213> ORGANISM: Lassa virus

<400> SEQUENCE: 40
aaggtatttc caccattttg tgcatatgcc acataagtag ggttgagagg tagtccctcc 60
cttttatgtc agcttgcaag tcctttgaga ggaaaattaa attctgcaaa acagtcaaga 120
ataaaaatgg acacatcatt gggccccact tactatgatc catgctataa gacacatgtg 180
ccaatga 187

<210> SEQ ID NO 41
<211> LENGTH: 187
<212> TYPE: DNA

<213> ORGANISM: Lassa virus

<400> SEQUENCE: 41
aaggtatttc caccatctta tgcatatgcc acataagtag ggttgagaga tagtccctcc 60
cttttatgtc agcttgcaag tccttcgaga ggaaaattaa attctgtaag acagtcaaaa 120
ataaaaacgg acacatcatt gggccccact tgctatgatc catgctataa gacacatgtg 180
ccaatga 187

<210> SEQ ID NO 42
<211> LENGTH: 186
<212> TYPE: DNA
<213> ORGANISM: Lassa virus

<400> SEQUENCE: 42
aaggtatttc caccatcttg tgcatatgcc acataagtag agttgagagg tagtccctcc 60
cttttatgtc agcctgcaag tcttcgagag gaaaattaaa ttctgtaaga cagtcaaaaa 120
taaaaatgga cacatcattg ggccccactt gctatgatcc atgctataag acacatgtgc 180
caatga 186

<210> SEQ ID NO 43
<211> LENGTH: 187
<212> TYPE: DNA
<213> ORGANISM: Lassa virus

<400> SEQUENCE: 43
aaggtatttc caccatcttg tgcatatgcc acataagtag agttgagagg tagtccctcc 60
cttttatgtc agcctgcaag tccttcgaga ggaaaatcaa attctgtaag acagtcaaaa 120
ataaaaatgg acacatcatt gggccccact tgctatgatc catgctataa gacacatgtg 180
ccaatga 187

<210> SEQ ID NO 44
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 44
gggaacaaag cugaaguacu uaccc 25

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
gggtagggcg ggttggga 18

<210> SEQ ID NO 46
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(25)
<223> OTHER INFORMATION: 3 prime thiol modifier

<400> SEQUENCE: 46
ttataactat tcctaaaaaa aaaaa 25

<210> SEQ ID NO 47
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime thiol modifier

<400> SEQUENCE: 47
aaaaaaaaaa ctcccctaat aacaat 26

<210> SEQ ID NO 48
<211> LENGTH: 45
<212> TYPE: RNA
<213> ORGANISM: Artificial Sequence
<220> FEATURE:
<223> OTHER INFORMATION: Synthetic Oligonucleotide

<400> SEQUENCE: 48
ggguaggaau aguuauaauu ucccuuuccc auuguuauua gggag 45

<210> SEQ ID NO 49
<211> LENGTH: 12
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime biotin modification
<220> FEATURE:
<221> NAME/KEY: misc_feature
<222> LOCATION: (12)..(12)
<223> OTHER INFORMATION: 3 prime Iowa Black modification

<400> SEQUENCE: 49
ucucguacgu uc 12

<210> SEQ ID NO 50
<211> LENGTH: 24
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime biotin modification
<220> FEATURE:
<221> NAME/KEY: misc_feature
<222> LOCATION: (24)..(24)
<223> OTHER INFORMATION: 3 primer Iowa Black modification

<400> SEQUENCE: 50
ucucguacgu ucucucguac guuc 24

<210> SEQ ID NO 51
<211> LENGTH: 6
<212> TYPE: PRT
<213> ORGANISM: Artificial Sequence
<220> FEATURE:

<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = N or H
<220> FEATURE:
<221> NAME/KEY: MISC_FEATURE
<222> LOCATION: (3)..(3)
<223> OTHER INFORMATION: Xaa = R, S, D, E, Q, N, G, Y, or H
<220> FEATURE:
<221> NAME/KEY: MISC_FEATURE
<222> LOCATION: (4)..(4)
<223> OTHER INFORMATION: Xaa = I, S, T, V, or L
<220> FEATURE:
<221> NAME/KEY: MISC_FEATURE
<222> LOCATION: (5)..(5)
<223> OTHER INFORMATION: Xaa = L, F, N, Y, V, I, S, D, E, or A

<400> SEQUENCE: 51

Arg Xaa Xaa Xaa Xaa His
1 5

<210> SEQ ID NO 52
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa = N or K
<220> FEATURE:
<221> NAME/KEY: MISC_FEATURE
<222> LOCATION: (3)..(3)
<223> OTHER INFORMATION: Xaa = R, S, D, E, Q, N, G, Y, or H
<220> FEATURE:
<221> NAME/KEY: MISC_FEATURE
<222> LOCATION: (4)..(4)
<223> OTHER INFORMATION: Xaa = I, S, T, V, or L
<220> FEATURE:
<221> NAME/KEY: MISC_FEATURE
<222> LOCATION: (5)..(5)
<223> OTHER INFORMATION: Xaa = L, F, N, Y, V, I, S, D, E, or A

<400> SEQUENCE: 52

Arg Xaa Xaa Xaa Xaa His
1 5

<210> SEQ ID NO 53
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 53
tgtggttggt gtggttggtt catggtcata ttggtttttt tttttttttc caaccacagt 60
ctctgt 66

<210> SEQ ID NO 54
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 54
ggttggtagt ctcgaattgc tctctttcac tggcc 35

<210> SEQ ID NO 55
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 55
gaaattaata cgactcacta taggggggttg gttcatggtc atattggt 48

<210> SEQ ID NO 56
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 56
gaaattaata cgactcacta taggggttg gtgtggttgg ttcatggtca tattggt 57

<210> SEQ ID NO 57
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 57
ggccagtgaa agagagcaat tcgagactac c 31

<210> SEQ ID NO 58
<211> LENGTH: 64
<212> TYPE: RNA
<213> ORGANISM: Artificial Sequence
<220> FEATURE:
<223> OTHER INFORMATION: Synthetic Oligonucleotide

<400> SEQUENCE: 58
gauuuagacu accccaaaaa cgaaggggac uaaaacccag ugaaagagag caauucgaga 60
cuac 64

<210> SEQ ID NO 59
<211> LENGTH: 64
<212> TYPE: RNA
<213> ORGANISM: Artificial Sequence
<220> FEATURE:
<223> OTHER INFORMATION: Synthetic Oligonucleotide

<400> SEQUENCE: 59
gauuuagacu accccaaaaa cgaaggggac uaaaacaaag agagcaauuc gagacuacca 60
acca 64

<210> SEQ ID NO 60
<211> LENGTH: 64
<212> TYPE: RNA
<213> ORGANISM: Artificial Sequence
<220> FEATURE:
<223> OTHER INFORMATION: Synthetic Oligonucleotide

<400> SEQUENCE: 60
gauuuagacu accccaaaaa cgaaggggac uaaaacagac uaccaaccac agagacugug 60
guug 64

<210> SEQ ID NO 61

<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 61
gttagatcgc aagcatatca ttgcgcttgc gatctaactg ctgcgccgcc gggaaaatac 60
tgtacggtta gatcgcatag tctcgaattg ctctctttca ctggcc 106

<210> SEQ ID NO 62
<211> LENGTH: 71
<212> TYPE: DNA
<213> ORGANISM: Artificial Sequence
<220> FEATURE:
<223> OTHER INFORMATION: Synthetic Oligonucleotide

<400> SEQUENCE: 62
gttagatcgc aagcatatca ttgcgcttgc gatctaactg ctgcgccgcc gggaaaatac 60
tgtacggtta g 71

<210> SEQ ID NO 63
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 63
atcgcatagt ctcgaattgc tctctttcac tggcc 35

<210> SEQ ID NO 64
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 64
gaaattaata cgactcacta tagggatcgc aagcatatca ttgcgcttgc 50

<210> SEQ ID NO 65
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 65
ggccagtgaa agagagcaat tcgagactat g 31

<210> SEQ ID NO 66
<211> LENGTH: 64
<212> TYPE: RNA
<213> ORGANISM: Artificial Sequence
<220> FEATURE:
<223> OTHER INFORMATION: Synthetic Oligonucleotide

<400> SEQUENCE: 66
gauuuagacu accccaaaaa cgaaggggac uaaaacccag ugaaagagag caauucgaga 60
cuau 64

<210> SEQ ID NO 67
<211> LENGTH: 64

<212> TYPE: RNA
<213> ORGANISM: Artificial Sequence
<220> FEATURE:
<223> OTHER INFORMATION: Synthetic Oligonucleotide

<400> SEQUENCE: 67
gauuuagacu accccaaaaa cgaaggggac uaaaacagag caauucgaga cuaugcgauc 60
uaac 64

<210> SEQ ID NO 68
<211> LENGTH: 64
<212> TYPE: RNA
<213> ORGANISM: Artificial Sequence
<220> FEATURE:
<223> OTHER INFORMATION: Synthetic Oligonucleotide

<400> SEQUENCE: 68
gauuuagacu accccaaaaa cgaaggggac uaaaacacua ugcgaucuaa ccguacagua 60
uuuu 64

<210> SEQ ID NO 69
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (10)..(10)
<223> OTHER INFORMATION: r = G or A
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: y = T/U or C

<400> SEQUENCE: 69
gatgcrgcyr aycaytgtg 19

<210> SEQ ID NO 70
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A

<400> SEQUENCE: 70
garaactggc agtgatcttc c 21

<210> SEQ ID NO 71
<211> LENGTH: 23
<212> TYPE: DNA
<213> ORGANISM: Artificial Sequence
<220> FEATURE:

<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime FAM tag
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (9)..(10)
<223> OTHER INFORMATION: Internal ZEN quencher
<220> FEATURE:
<221> NAME/KEY: misc_feature
<222> LOCATION: (23)..(23)
<223> OTHER INFORMATION: 3 prime Iowa Black modification

<400> SEQUENCE: 71
ttyatgagga tggcttgggg tgg 23

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 72
ggaatgagtg gtggtaatca agg 23

<210> SEQ ID NO 73
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 73
ttttcacatc ccaaactctc acc 23

<210> SEQ ID NO 74
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime FAM modification
<220> FEATURE:
<221> NAME/KEY: misc_feature
<222> LOCATION: (23)..(23)
<223> OTHER INFORMATION: 3 prime TAMRA modification

<400> SEQUENCE: 74
actccatctc tcccagcccg agc 23

<210> SEQ ID NO 75
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: y = T/U or C
<220> FEATURE:
<221> NAME/KEY: misc_feature
<222> LOCATION: (11)..(11)
<223> OTHER INFORMATION: r = G or A
<220> FEATURE:
<221> NAME/KEY: misc_feature
<222> LOCATION: (17)..(17)
<223> OTHER INFORMATION: r = G or A

<400> SEQUENCE: 75
ccaccatytt rtgcatrtgc ca 22

<210> SEQ ID NO 76
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (12)..(12)
<223> OTHER INFORMATION: h = A or C or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (24)..(24)
<223> OTHER INFORMATION: y = T/U or C

<400> SEQUENCE: 76
gcacatgtnt chtayagyat ggayca 26

<210> SEQ ID NO 77
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5 prime FAM modification
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: d = A or G or T/U
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: w = A or T/U
<220> FEATURE:
<221> NAME/KEY: misc_feature
<222> LOCATION: (26)..(26)
<223> OTHER INFORMATION: 3 prime Black Berry quencher

<400> SEQUENCE: 77
aartggggyc cdatgatgtg yccwtt 26

<210> SEQ ID NO 78
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: r = G or A

<400> SEQUENCE: 78
gacagactga ggaarataac attgcaaag 29

<210> SEQ ID NO 79
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (14)..(14)
<223> OTHER INFORMATION: r = G or A

<400> SEQUENCE: 79
caatcataca tggragtgtg gctccaataa 30

<210> SEQ ID NO 80
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 80
tttaacccaa ataacttgca cagttgat 28

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: y = T/U or C
<220> FEATURE:
<221> NAME/KEY: misc_feature
<222> LOCATION: (6)..(6)
<223> OTHER INFORMATION: m = A or C
<220> FEATURE:
<221> NAME/KEY: misc_feature
<222> LOCATION: (10)..(10)
<223> OTHER INFORMATION: y = T/U or C
<220> FEATURE:
<221> NAME/KEY: misc_feature
<222> LOCATION: (16)..(16)
<223> OTHER INFORMATION: r = G or A

<400> SEQUENCE: 81
catygmatcy ttgagrgtca t 21

<210> SEQ ID NO 82
<211> LENGTH: 20

<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: r = G or A
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: d = A or G or T/U
<220> FEATURE:
<221> NAME/KEY: misc_feature
<222> LOCATION: (15)..(15)
<223> OTHER INFORMATION: n = any nucleotide
<220> FEATURE:
<221> NAME/KEY: misc_feature
<222> LOCATION: (17)..(17)
<223> OTHER INFORMATION: r = G or A
<220> FEATURE:
<221> NAME/KEY: misc_feature
<222> LOCATION: (18)..(18)
<223> OTHER INFORMATION: y = T/U or C

<400> SEQUENCE: 82
arytgrgart adgtnarycc 20

<210> SEQ ID NO 83
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: y = T/U or C
<220> FEATURE:
<221> NAME/KEY: misc_feature
<222> LOCATION: (11)..(11)
<223> OTHER INFORMATION: r = G or A
<220> FEATURE:
<221> NAME/KEY: misc_feature
<222> LOCATION: (17)..(17)
<223> OTHER INFORMATION: n = any nucleotide

<400> SEQUENCE: 83
catcyttgag rgtcatnagc tgagaata 28

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)

<223> OTHER INFORMATION: m = A or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (18)..(18)
<223> OTHER INFORMATION: h = A or C or T/U

<400> SEQUENCE: 84
aayatmctyt ayaarathtg 20

<210> SEQ ID NO 85
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (10)..(10)
<223> OTHER INFORMATION: m = A or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: h = A or C or T/U
<220> FEATURE:
<221> NAME/KEY: misc_feature
<222> LOCATION: (21)..(21)
<223> OTHER INFORMATION: y = T/U or C

<400> SEQUENCE: 85
ccyggygarm graaycchta yga 23

<210> SEQ ID NO 86
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 86
aggaatcctt atgaraacat actctayaa 29

<210> SEQ ID NO 87
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: r = G or A

<400> SEQUENCE: 87
gtgttttccc argcccttcc tgttattga 29

<210> SEQ ID NO 88
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (18)..(18)
<223> OTHER INFORMATION: y = T/U or C

<400> SEQUENCE: 88
cttcctgtta ttgargtyct tgatgcaat 29

<210> SEQ ID NO 89
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: r = G or A

<400> SEQUENCE: 89
cttcctgtta ttgargttct tgatgcaat 29

<210> SEQ ID NO 90
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (27)..(27)
<223> OTHER INFORMATION: r = G or A

<400> SEQUENCE: 90
cctgttattg argtycttga tgcaatrt 28

<210> SEQ ID NO 91
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (27)..(27)
<223> OTHER INFORMATION: r = G or A

<400> SEQUENCE: 91
cctgttattg argttcttga tgcaatrt 28

<210> SEQ ID NO 92
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: r = G or A
<220> FEATURE:
<221> NAME/KEY: misc_feature
<222> LOCATION: (8)..(8)
<223> OTHER INFORMATION: y = T/U or C
<220> FEATURE:
<221> NAME/KEY: misc_feature
<222> LOCATION: (20)..(20)
<223> OTHER INFORMATION: r = G or A
<220> FEATURE:
<221> NAME/KEY: misc_feature
<222> LOCATION: (23)..(23)
<223> OTHER INFORMATION: y = T/U or C

<400> SEQUENCE: 92
ttgargtyct tgatgcaatr tayg 24

<210> SEQ ID NO 93
<211> LENGTH: 31
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(3)
<223> OTHER INFORMATION: y = T/U or C
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: v = A or G or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 93
cartaygarg cvatgagytg ygayttyaat g 31

<210> SEQ ID NO 94
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (18)..(18)
<223> OTHER INFORMATION: v = A or G or C
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 94
ttyaaycart aygargcvat gagytgyga 29

<210> SEQ ID NO 95
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (7)..(7)

```
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (13)..(13)
<223> OTHER INFORMATION: d = A or G or T/U
<220> FEATURE:
<221> NAME/KEY: misc_feature
<222> LOCATION: (15)..(15)
<223> OTHER INFORMATION: b = G or C or T/U
<220> FEATURE:
<221> NAME/KEY: misc_feature
<222> LOCATION: (16)..(16)
<223> OTHER INFORMATION: y = T/U or C
<220> FEATURE:
<221> NAME/KEY: misc_feature
<222> LOCATION: (18)..(18)
<223> OTHER INFORMATION: v = A or G or C
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: y = T/U or C
<220> FEATURE:
<221> NAME/KEY: misc_feature
<222> LOCATION: (30)..(30)
<223> OTHER INFORMATION: y = T/U or C

<400> SEQUENCE: 95

ctytayrayc aydcbytvat gagyatyaty tc                                32


<210> SEQ ID NO 96
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: h = A or C or T/U
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: n = any nucleotide
<220> FEATURE:
<221> NAME/KEY: misc_feature
<222> LOCATION: (18)..(19)
<223> OTHER INFORMATION: y = T/U or C
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: h = A or C or T/U
<220> FEATURE:
<221> NAME/KEY: misc_feature
<222> LOCATION: (27)..(27)
<223> OTHER INFORMATION: y = T/U or C

<400> SEQUENCE: 96
```

cthaayatga cnatgccyyt rtchtgyac 29

<210> SEQ ID NO 97
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: n = any nucleotide
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (19)..(19)
<223> OTHER INFORMATION: m= A or C
<220> FEATURE:
<221> NAME/KEY: misc_feature
<222> LOCATION: (21)..(21)
<223> OTHER INFORMATION: h = A or C or T/U
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: h = A or C or T/U

<400> SEQUENCE: 97
tgyccyaarc cncayagrmt haaycahatg gg 32

<210> SEQ ID NO 98
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:

<221> NAME/KEY: misc_feature
<222> LOCATION: (15)..(15)
<223> OTHER INFORMATION: v = A or G or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (20)..(21)
<223> OTHER INFORMATION: r = G or A
<220> FEATURE:
<221> NAME/KEY: misc_feature
<222> LOCATION: (23)..(23)
<223> OTHER INFORMATION: r = G or A
<220> FEATURE:
<221> NAME/KEY: misc_feature
<222> LOCATION: (25)..(25)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 98
aayctytcyg aygcvcayar rargrayct 29

<210> SEQ ID NO 99
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 99
aaccacatgg gcatatgctc atgtggtct 29

<210> SEQ ID NO 100
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 100
aggttgtact gaacacttat cttccc 26

<210> SEQ ID NO 101
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 101
tgggaagatc actgccagtt ttctcgccc 29

<210> SEQ ID NO 102
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 102
tattggtagg aagtcattat acaatccca 29

<210> SEQ ID NO 103
<211> LENGTH: 32

<212> TYPE: DNA
<213> ORGANISM: Artificial Sequence
<220> FEATURE:
<223> OTHER INFORMATION: Synthetic Oligonucleotide

<400> SEQUENCE: 103
gctatgtaac tgccacccca agccatcctc at 32

<210> SEQ ID NO 104
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 104
ccaccccaag ccatcctcat aaaagtctg 29

<210> SEQ ID NO 105
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 105
tttgaaaatg ctgtttggga tcagtgcaa 29

<210> SEQ ID NO 106
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 106
taatggactg cataatgtat gatgcagc 28

<210> SEQ ID NO 107
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 107
aggagatttg aaaatgctgt ttgggatca 29

<210> SEQ ID NO 108
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 108
atgtatgatg cagctgtgtc aggagg 26

<210> SEQ ID NO 109
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)

<223> OTHER INFORMATION: y = T/U or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: y = T/U or C

<400> SEQUENCE: 109
atggcytggg gtggcagyta yatagcac 28

<210> SEQ ID NO 110
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: y = T/U or C

<400> SEQUENCE: 110
atggcytggg gtggcagyta yatagcac 28

<210> SEQ ID NO 111
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (18)..(18)
<223> OTHER INFORMATION: y = T/U or C

<400> SEQUENCE: 111
acyttyatga gratggcytg gggtggca 28

<210> SEQ ID NO 112
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (18)..(18)
<223> OTHER INFORMATION: y = T/U or C

<400> SEQUENCE: 112
actttyatga gratggcytg gggtggca 28

<210> SEQ ID NO 113
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 113
aatcartatg argcratgag ytgtgayt 28

<210> SEQ ID NO 114
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 114
aatcagtatg argcaatgag ytgtgayt 28

<210> SEQ ID NO 115
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:

<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (21)..(21)
<223> OTHER INFORMATION: y = T/U or C

<400> SEQUENCE: 115
caracyttya tgagratggc ytggggtg 28

<210> SEQ ID NO 116
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (21)..(21)
<223> OTHER INFORMATION: y = T/U or C

<400> SEQUENCE: 116
caractttya tgagratggc ytggggtg 28

<210> SEQ ID NO 117
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (21)..(21)
<223> OTHER INFORMATION: y = T/U or C

<400> SEQUENCE: 117
caracyttya tgagratggc ytggggtg 28

<210> SEQ ID NO 118
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (21)..(21)
<223> OTHER INFORMATION: y = T/U or C

<400> SEQUENCE: 118
caractttya tgagratggc ytggggtg 28

<210> SEQ ID NO 119
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: y = T/U or C
<220> FEATURE:
<221> NAME/KEY: misc_feature
<222> LOCATION: (5)..(5)
<223> OTHER INFORMATION: y = T/U or C
<220> FEATURE:
<221> NAME/KEY: misc_feature
<222> LOCATION: (11)..(11)
<223> OTHER INFORMATION: r = G or A
<220> FEATURE:
<221> NAME/KEY: misc_feature
<222> LOCATION: (17)..(17)
<223> OTHER INFORMATION: r = G or A
<220> FEATURE:
<221> NAME/KEY: misc_feature
<222> LOCATION: (20)..(20)
<223> OTHER INFORMATION: r = G or A
<220> FEATURE:
<221> NAME/KEY: misc_feature
<222> LOCATION: (26)..(26)
<223> OTHER INFORMATION: y = T/U or C

<400> SEQUENCE: 119
ayttyaatca rtatgargcr atgagytg 28

<210> SEQ ID NO 120
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: y = T/U or C
<220> FEATURE:
<221> NAME/KEY: misc_feature
<222> LOCATION: (5)..(5)

<223> OTHER INFORMATION: y = T/U or C
<220> FEATURE:
<221> NAME/KEY: misc_feature
<222> LOCATION: (17)..(17)
<223> OTHER INFORMATION: r = G or A
<220> FEATURE:
<221> NAME/KEY: misc_feature
<222> LOCATION: (26)..(26)
<223> OTHER INFORMATION: y = T/U or C

<400> SEQUENCE: 120
ayttyaatca gtatgargca atgagytg 28

<210> SEQ ID NO 121
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: y = T/U or C

<400> SEQUENCE: 121
tatgargcra tgagytgtga yttyaatg 28

<210> SEQ ID NO 122
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (21)..(21)
<223> OTHER INFORMATION: y = T/U or C

<400> SEQUENCE: 122
tatgargcaa tgagytgtga yttcaatg 28

<210> SEQ ID NO 123
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: r = G or A

<400> SEQUENCE: 123
atgagytgtg ayttyaatgg rggraara 28

<210> SEQ ID NO 124
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: r = G or A

<400> SEQUENCE: 124
atgagytgtg ayttcaatgg rggraaga 28

<210> SEQ ID NO 125
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (13)..(13)
<223> OTHER INFORMATION: y = T/U or C
<220> FEATURE:
<221> NAME/KEY: misc_feature
<222> LOCATION: (19)..(19)
<223> OTHER INFORMATION: r = G or A
<220> FEATURE:
<221> NAME/KEY: misc_feature
<222> LOCATION: (25)..(25)
<223> OTHER INFORMATION: d = A or G or T/U

<400> SEQUENCE: 125
ttacaggacg acyttgggrc ttgadgttct 30

<210> SEQ ID NO 126
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (13)..(13)
<223> OTHER INFORMATION: y = T/U or C
<220> FEATURE:
<221> NAME/KEY: misc_feature
<222> LOCATION: (19)..(19)
<223> OTHER INFORMATION: r = G or A
<220> FEATURE:
<221> NAME/KEY: misc_feature
<222> LOCATION: (25)..(25)
<223> OTHER INFORMATION: k = G or T/U

<400> SEQUENCE: 126
ttacaggacg acyttgggrc ttgakgttct 30

<210> SEQ ID NO 127
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (10)..(10)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (25)..(25)
<223> OTHER INFORMATION: y = T/U or C
<220> FEATURE:
<221> NAME/KEY: misc_feature
<222> LOCATION: (27)..(27)
<223> OTHER INFORMATION: r = G or A

<400> SEQUENCE: 127
agrtggatgy trattgargc ygarytraa 29

<210> SEQ ID NO 128
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (13)..(13)
<223> OTHER INFORMATION: y = T/U or C
<220> FEATURE:
<221> NAME/KEY: misc_feature
<222> LOCATION: (15)..(15)
<223> OTHER INFORMATION: r = G or A
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: r = G or A

<400> SEQUENCE: 128
attgargcyg arytraartg tttyggraa 29

<210> SEQ ID NO 129
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(10)
<223> OTHER INFORMATION: y = T/U or C
<220> FEATURE:
<221> NAME/KEY: misc_feature
<222> LOCATION: (18)..(18)
<223> OTHER INFORMATION: h = A or C or T/U
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: r = G or A

<400> SEQUENCE: 129
cargtrgayy tgaatgahgc tgtycargc 29

<210> SEQ ID NO 130
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)

<223> OTHER INFORMATION: r = G or A
<220> FEATURE:
<221> NAME/KEY: misc_feature
<222> LOCATION: (14)..(14)
<223> OTHER INFORMATION: y = T/U or C
<220> FEATURE:
<221> NAME/KEY: misc_feature
<222> LOCATION: (20)..(20)
<223> OTHER INFORMATION: r = G or A
<220> FEATURE:
<221> NAME/KEY: misc_feature
<222> LOCATION: (26)..(26)
<223> OTHER INFORMATION: y = T/U or C

<400> SEQUENCE: 130
traacatgat tgayaccaar aagagytc 28

<210> SEQ ID NO 131
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: h = A or C or T/U
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: y = T/U or C

<400> SEQUENCE: 131
gcytgyatgc twgayggh gg yaayatg 27

<210> SEQ ID NO 132
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (13)..(13)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: s = G or C
<220> FEATURE:
<221> NAME/KEY: misc_feature
<222> LOCATION: (27)..(27)
<223> OTHER INFORMATION: y = T/U or C

<400> SEQUENCE: 132
gtytcaccyc aawcyatrga tggsatytt 29

<210> SEQ ID NO 133
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (12)..(12)
<223> OTHER INFORMATION: d = A or G or T/U
<220> FEATURE:
<221> NAME/KEY: misc_feature
<222> LOCATION: (15)..(15)
<223> OTHER INFORMATION: m = A or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: w = A or T/U

<400> SEQUENCE: 133
tgrttyttca tdatmagytg rtcrttwat 29

<210> SEQ ID NO 134
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(6)
<223> OTHER INFORMATION: r = G or A
<220> FEATURE:

<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (18)..(18)
<223> OTHER INFORMATION: d = A or G or T/U
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: r = G or A

<400> SEQUENCE: 134
tarttrcart atggtatdcc catratrtc 29

<210> SEQ ID NO 135
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: r = G or A
<220> FEATURE:
<221> NAME/KEY: misc_feature
<222> LOCATION: (7)..(7)
<223> OTHER INFORMATION: r = G or A
<220> FEATURE:
<221> NAME/KEY: misc_feature
<222> LOCATION: (10)..(10)
<223> OTHER INFORMATION: d = A or G or T/U
<220> FEATURE:
<221> NAME/KEY: misc_feature
<222> LOCATION: (13)..(13)
<223> OTHER INFORMATION: r = G or A
<220> FEATURE:
<221> NAME/KEY: misc_feature
<222> LOCATION: (16)..(16)
<223> OTHER INFORMATION: w = A or T/U
<220> FEATURE:
<221> NAME/KEY: misc_feature
<222> LOCATION: (22)..(22)
<223> OTHER INFORMATION: r = G or A
<220> FEATURE:
<221> NAME/KEY: misc_feature
<222> LOCATION: (25)..(25)
<223> OTHER INFORMATION: r = G or A
<220> FEATURE:
<221> NAME/KEY: misc_feature
<222> LOCATION: (28)..(28)
<223> OTHER INFORMATION: h = A or C or T/U

<400> SEQUENCE: 135
catrttrccd ccrtcwagca trcargchcc 30

<210> SEQ ID NO 136
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: r = G or A
<220> FEATURE:
<221> NAME/KEY: misc_feature
<222> LOCATION: (7)..(7)
<223> OTHER INFORMATION: y = T/U or C
<220> FEATURE:
<221> NAME/KEY: misc_feature
<222> LOCATION: (13)..(13)
<223> OTHER INFORMATION: w = A or T/U
<220> FEATURE:
<221> NAME/KEY: misc_feature
<222> LOCATION: (16)..(16)
<223> OTHER INFORMATION: r = G or A
<220> FEATURE:
<221> NAME/KEY: misc_feature
<222> LOCATION: (19)..(19)
<223> OTHER INFORMATION: y = T/U or C
<220> FEATURE:
<221> NAME/KEY: misc_feature
<222> LOCATION: (22)..(22)
<223> OTHER INFORMATION: y = T/U or C

<400> SEQUENCE: 136
tatrttytca tawggrttyc tytcacctg 29

<210> SEQ ID NO 137
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: r = G or A

<400> SEQUENCE: 137
gaygcaatgt aaggccaycc rtctcctga 29

<210> SEQ ID NO 138
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (21)..(21)
<223> OTHER INFORMATION: y = T/U or C
<220> FEATURE:
<221> NAME/KEY: misc_feature
<222> LOCATION: (24)..(24)
<223> OTHER INFORMATION: n = any nucleotide
<220> FEATURE:
<221> NAME/KEY: misc_feature
<222> LOCATION: (27)..(27)
<223> OTHER INFORMATION: m = A or C

<400> SEQUENCE: 138
acyacagtrt tttcccargc yctnccm 27

<210> SEQ ID NO 139
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: w = A or T/U

<400> SEQUENCE: 139
ctntttgayt tyaayaarca rgcyatw 27

<210> SEQ ID NO 140
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: y = T/U or C
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: w = A or T/U

<400> SEQUENCE: 140
ctntttgayt tyaayaarca agcyatw 27

<210> SEQ ID NO 141
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: r = G or A
<220> FEATURE:
<221> NAME/KEY: misc_feature
<222> LOCATION: (5)..(5)
<223> OTHER INFORMATION: y = T/U or C
<220> FEATURE:
<221> NAME/KEY: misc_feature
<222> LOCATION: (14)..(14)
<223> OTHER INFORMATION: y = T/U or C
<220> FEATURE:
<221> NAME/KEY: misc_feature
<222> LOCATION: (17)..(17)
<223> OTHER INFORMATION: y = T/U or C
<220> FEATURE:
<221> NAME/KEY: misc_feature
<222> LOCATION: (20)..(20)
<223> OTHER INFORMATION: r = G or A
<220> FEATURE:
<221> NAME/KEY: misc_feature
<222> LOCATION: (23)..(23)
<223> OTHER INFORMATION: r = G or A
<220> FEATURE:
<221> NAME/KEY: misc_feature
<222> LOCATION: (26)..(26)
<223> OTHER INFORMATION: y = T/U or C

<400> SEQUENCE: 141
traayatgat tgayacyaar aaragytc 28

<210> SEQ ID NO 142
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: r = G or A
<220> FEATURE:
<221> NAME/KEY: misc_feature
<222> LOCATION: (14)..(14)
<223> OTHER INFORMATION: y = T/U or C
<220> FEATURE:
<221> NAME/KEY: misc_feature
<222> LOCATION: (20)..(20)
<223> OTHER INFORMATION: r = G or A
<220> FEATURE:
<221> NAME/KEY: misc_feature
<222> LOCATION: (26)..(26)
<223> OTHER INFORMATION: y = T/U or C

<400> SEQUENCE: 142
traacatgat tgayaccaar aagagytc 28

<210> SEQ ID NO 143
<211> LENGTH: 26
<212> TYPE: DNA

<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: b = G or C or T/U
<220> FEATURE:
<221> NAME/KEY: misc_feature
<222> LOCATION: (5)..(5)
<223> OTHER INFORMATION: y = T/U or C
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (8)..(8)
<223> OTHER INFORMATION: h = A or C or T/U
<220> FEATURE:
<221> NAME/KEY: misc_feature
<222> LOCATION: (14)..(14)
<223> OTHER INFORMATION: y = T/U or C
<220> FEATURE:
<221> NAME/KEY: misc_feature
<222> LOCATION: (20)..(20)
<223> OTHER INFORMATION: y = T/U or C
<220> FEATURE:
<221> NAME/KEY: misc_feature
<222> LOCATION: (23)..(23)
<223> OTHER INFORMATION: y = T/U or C
<220> FEATURE:
<221> NAME/KEY: misc_feature
<222> LOCATION: (26)..(26)
<223> OTHER INFORMATION: y = T/U or C

<400> SEQUENCE: 143
tbaayrthtc tggytacaay ttyagy 26

<210> SEQ ID NO 144
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: y = T/U or C
<220> FEATURE:
<221> NAME/KEY: misc_feature
<222> LOCATION: (8)..(8)
<223> OTHER INFORMATION: h = A or C or T/U
<220> FEATURE:
<221> NAME/KEY: misc_feature
<222> LOCATION: (14)..(14)
<223> OTHER INFORMATION: y = T/U or C
<220> FEATURE:
<221> NAME/KEY: misc_feature
<222> LOCATION: (20)..(20)
<223> OTHER INFORMATION: y = T/U or C
<220> FEATURE:
<221> NAME/KEY: misc_feature
<222> LOCATION: (23)..(23)
<223> OTHER INFORMATION: y = T/U or C
<220> FEATURE:
<221> NAME/KEY: misc_feature
<222> LOCATION: (26)..(26)
<223> OTHER INFORMATION: y = T/U or C

<400> SEQUENCE: 144
tyaacathtc tggytacaay ttyagy 26

<210> SEQ ID NO 145
<211> LENGTH: 29

<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: b = G or C or T/U
<220> FEATURE:
<221> NAME/KEY: misc_feature
<222> LOCATION: (6)..(6)
<223> OTHER INFORMATION: d = A or G or T/U
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: w= A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (17)..(18)
<223> OTHER INFORMATION: r = G or A
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)
<223> OTHER INFORMATION: r = G or A

<400> SEQUENCE: 145
ttbacdgcrg cwccyarrct raarttgta 29

<210> SEQ ID NO 146
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: b = G or C or T/U
<220> FEATURE:
<221> NAME/KEY: misc_feature
<222> LOCATION: (6)..(6)
<223> OTHER INFORMATION: w = A or T/U
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (17)..(18)
<223> OTHER INFORMATION: r = G or A
<220> FEATURE:
<221> NAME/KEY: misc_feature
<222> LOCATION: (21)..(21)
<223> OTHER INFORMATION: r = G or A
<220> FEATURE:
<221> NAME/KEY: misc_feature
<222> LOCATION: (24)..(24)

<223> OTHER INFORMATION: r = G or A

<400> SEQUENCE: 146
ttbacwgcrg cwccyarrct raarttgta 29

<210> SEQ ID NO 147
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: d = A or G or T/U
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: w = A or T/U
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: h = A or C or T/U
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 147
ggdgcytgya tgctwgaygg hggyaayatg 30

<210> SEQ ID NO 148
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: r = G or A
<220> FEATURE:
<221> NAME/KEY: misc_feature
<222> LOCATION: (6)..(6)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (15)..(15)
<223> OTHER INFORMATION: w = A or T/U
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (21)..(21)
<223> OTHER INFORMATION: h = A or C or T/U
<220> FEATURE:
<221> NAME/KEY: misc_feature
<222> LOCATION: (24)..(24)
<223> OTHER INFORMATION: y = T/U or C
<220> FEATURE:
<221> NAME/KEY: misc_feature
<222> LOCATION: (27)..(27)
<223> OTHER INFORMATION: y = T/U or C

<400> SEQUENCE: 148
ggrgcytgya tgctwgaygg hggyaayatg 30

<210> SEQ ID NO 149
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: s = G or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (14)..(14)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 149
atsccatcya trgwytgrgg tgaracy 27

<210> SEQ ID NO 150
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: s = G or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:

<221> NAME/KEY: misc_feature
<222> LOCATION: (14)..(14)
<223> OTHER INFORMATION: w = A or T/U
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 150
atsccatcya trgwttgrgg tgaracy 27

<210> SEQ ID NO 151
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (13)..(13)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: s = G or C
<220> FEATURE:
<221> NAME/KEY: misc_feature
<222> LOCATION: (27)..(27)
<223> OTHER INFORMATION: y = T/U or C

<400> SEQUENCE: 151
gtytcaccyc arwcyatrga tggsatytt 29

<210> SEQ ID NO 152
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: y = T/U or C
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (13)..(13)
<223> OTHER INFORMATION: w = A or T/U
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: r = G or A
<220> FEATURE:
<221> NAME/KEY: misc_feature
<222> LOCATION: (24)..(24)
<223> OTHER INFORMATION: s = G or C
<220> FEATURE:
<221> NAME/KEY: misc_feature
<222> LOCATION: (27)..(27)
<223> OTHER INFORMATION: y = T/U or C

<400> SEQUENCE: 152
gtytcaccyc aawcyatrga tggsatytt 29

<210> SEQ ID NO 153
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (15)..(15)
<223> OTHER INFORMATION: y = T/U or C
<220> FEATURE:
<221> NAME/KEY: misc_feature
<222> LOCATION: (18)..(18)
<223> OTHER INFORMATION: w = A or T/U
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 153
ccaggtgara graayccwta tgaraayat 29

<210> SEQ ID NO 154
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: r = G or A
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (15)..(15)

<223> OTHER INFORMATION: y = T/U or C
<220> FEATURE:
<221> NAME/KEY: misc_feature
<222> LOCATION: (18)..(18)
<223> OTHER INFORMATION: w = A or T/U
<220> FEATURE:
<221> NAME/KEY: misc_feature
<222> LOCATION: (24)..(24)
<223> OTHER INFORMATION: r = G or A
<220> FEATURE:
<221> NAME/KEY: misc_feature
<222> LOCATION: (27)..(27)
<223> OTHER INFORMATION: y = T/U or C

<400> SEQUENCE: 154
ccaggtgara graayccwta tgaraayat 29

<210> SEQ ID NO 155
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: r = G or A
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (18)..(18)
<223> OTHER INFORMATION: y = T/U or C
<220> FEATURE:
<221> NAME/KEY: misc_feature
<222> LOCATION: (22)..(22)
<223> OTHER INFORMATION: r = G or A
<220> FEATURE:
<221> NAME/KEY: misc_feature
<222> LOCATION: (27)..(27)
<223> OTHER INFORMATION: r = G or A

<400> SEQUENCE: 155
tcaggrgayg grtggccyta crttgcrt 28

<210> SEQ ID NO 156
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: y = T/U or C
<220> FEATURE:
<221> NAME/KEY: misc_feature
<222> LOCATION: (12)..(12)
<223> OTHER INFORMATION: r = G or A
<220> FEATURE:
<221> NAME/KEY: misc_feature
<222> LOCATION: (27)..(27)
<223> OTHER INFORMATION: r = G or A

<400> SEQUENCE: 156
tcaggagayg grtggcctta cattgcrt 28

<210> SEQ ID NO 157
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 157
gaaattaata cgactcacta taggg 25

<210> SEQ ID NO 158
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 158
gatttagact accccaaaaa cgaaggggac taaaac 36

<210> SEQ ID NO 159
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 159
tttaacccaa ataacttgca cagttgatgt tttagtcccc ttcgtttttg ggtagtcta 60 aatcccctat agtgagtcgt attaatttc 89

<210> SEQ ID NO 160
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 160
ccttttctcc tactaccaat ttcggaag 28

<210> SEQ ID NO 161
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 161
agaacacttg ctgccatgcc ggaagagggt tttagtcccc ttcgtttttg ggtagtcta 60 aatcccctat agtgagtcgt attaatttc 89

<210> SEQ ID NO 162
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 162
ctcctactac caatttcgga aggaatag 28

<210> SEQ ID NO 163
<211> LENGTH: 89
<212> TYPE: DNA

<213> ORGANISM: Artificial Sequence
<220> FEATURE:
<223> OTHER INFORMATION: Synthetic Oligonucleotide

<400> SEQUENCE: 163
ctattccttc cgaaattggt agtaggaggt tttagtcccc ttcgtttttg gggtagtcta 60
aatcccctat agtgagtcgt attaatttc 89

<210> SEQ ID NO 164
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 164
cctcttccgg catggcagca agtgttct 28

<210> SEQ ID NO 165
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 165
cttccgaaat tggtagtagg agaaaagggt tttagtcccc ttcgtttttg gggtagtcta 60
aatcccctat agtgagtcgt attaatttc 89

<210> SEQ ID NO 166
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 166
atcaactgtg caagttattt gggttaaa 28

<210> SEQ ID NO 167
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 167
cacactccca tgtatgattg agcaattcgt tttagtcccc ttcgtttttg gggtagtcta 60
aatcccctat agtgagtcgt attaatttc 89

<210> SEQ ID NO 168
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 168
tgcccatgaa tattccctca ggatctgt 28

<210> SEQ ID NO 169
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 169
attggagcca cactcccatg tatgattggt tttagtcccc ttcgtttttg gggtagtcta 60
aatcccctat agtgagtcgt attaatttc 89

<210> SEQ ID NO 170
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 170
caatcataca tgggagtgtg gctccaat 28

<210> SEQ ID NO 171
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 171
acagatcctg agggaatatt catgggcagt tttagtcccc ttcgtttttg gggtagtcta 60
aatcccctat agtgagtcgt attaatttc 89

<210> SEQ ID NO 172
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 172
gaattgctca atcatacatg ggagtgtg 28

<210> SEQ ID NO 173
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 173
gaaattaata cgactcacta taggggacag actgaggaar ataacattgc aaag 54

<210> SEQ ID NO 174
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 174
gacagactga ggaarataac attgcaaag 29

<210> SEQ ID NO 175
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 175
caatcataca tggragtgtg gctccaataa 30

<210> SEQ ID NO 176
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 176
gaaattaata cgactcacta tagggcagtc aagtayttgg aagggcacgg gttc 54

<210> SEQ ID NO 177
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 177
cagtcaagta yttggaaggg cacgggttc 29

<210> SEQ ID NO 178
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 178
ctactaccaa tttcggaagg aatagacttg 30

<210> SEQ ID NO 179
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 179
gaaattaata cgactcacta tagggaaaca ttaagagaac acttgctgcc atg 53

<210> SEQ ID NO 180
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 180
aaacattaag agaacacttg ctgccatg 28

<210> SEQ ID NO 181
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 181
atcatgtgtc ctactgattg ccaagctgtt 30

<210> SEQ ID NO 182
<211> LENGTH: 55

<212> TYPE: DNA
<213> ORGANISM: Artificial Sequence
<220> FEATURE:
<223> OTHER INFORMATION: Synthetic Oligonucleotide

<400> SEQUENCE: 182
gaaattaata cgactcacta tagggattta gcacagatyc tgagggaata ttcat 55

<210> SEQ ID NO 183
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 183
atttagcaca gatyctgagg gaatattcat 30

<210> SEQ ID NO 184
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 184
ctaacaatat gtttcttgac tgcyactgac 30

<210> SEQ ID NO 185
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 185
gaaattaata cgactcacta tagggttatc ttgatcattg tgataatatc ctggc 55

<210> SEQ ID NO 186
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 186
ttatcttgat cattgtgata atatcctggc 30

<210> SEQ ID NO 187
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 187
aacactgcgg acattgttcg tagggtttca 30

<210> SEQ ID NO 188
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 188
gaaattaata cgactcacta tagggagrtg gatgytratt gargcygary traa 54

<210> SEQ ID NO 189
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 189
agrtggatgy trattgargc ygarytraa 29

<210> SEQ ID NO 190
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 190
gaaattaata cgactcacta tagggattga rgcygarytr aartgtttyg graa 54

<210> SEQ ID NO 191
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 191
attgargcyg arytraartg tttyggraa 29

<210> SEQ ID NO 192
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 192
gaaattaata cgactcacta tagggcargt rgayytgaat gahgctgtyc argc 54

<210> SEQ ID NO 193
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 193
cargtrgayy tgaatgahgc tgtycargc 29

<210> SEQ ID NO 194
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 194
gaaattaata cgactcacta tagggtraac atgattgaya ccaaraagag ytc 53

<210> SEQ ID NO 195
<211> LENGTH: 283
<212> TYPE: DNA
<213> ORGANISM: Marburg virus

<400> SEQUENCE: 195
actgcctact ctggagaaaa tgaaaatgat tgtgatgcag agctaagaat ttggagtgtt 60
caggaggacg acctggcagc agggctcagt tggataccat tttttggccc tggaatcgaa 120
ggactttata ccgctggttt aattaaaaat caaaacaatt tggtctgcag gttgaggcgt 180
ctagccaatc aaactgcaaa atccttggaa ctcttactaa gggtcacaac cgaggaaaga 240
acattttcct taatcaatag acatgctatt gactttctac tca 283

<210> SEQ ID NO 196
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 196
traacatgat tgayaccaar aagagytc 28

<210> SEQ ID NO 197
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 197
gaaattaata cgactcacta taggggcytg yatgctwgay gghggyaaya tg 52

<210> SEQ ID NO 198
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 198
gcytgyatgc twgayggvhgg yaayatg 27

<210> SEQ ID NO 199
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 199
gaaattaata cgactcacta taggggtytc accycaawcy atrgatggsa tytt 54

<210> SEQ ID NO 200
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 200
gtytcaccyc aawcyatrga tggsatytt 29

<210> SEQ ID NO 201
<211> LENGTH: 29
<212> TYPE: DNA
<213> ORGANISM: Artificial Sequence
<220> FEATURE:

<223> OTHER INFORMATION: Synthetic Oligonucleotide

<400> SEQUENCE: 201
tgrttyttca tdatmagytg rtcrttwat 29

<210> SEQ ID NO 202
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 202
tarttrcart atggtatdcc catratrtc 29

<210> SEQ ID NO 203
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 203
catrttrccd ccrtcwagca trcargchcc 30

<210> SEQ ID NO 204
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 204
tatrttytca tawggrttyc tytcacctgg 30

<210> SEQ ID NO 205
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 205
gaygcaatgt aaggccaycc rtctcctga 29

<210> SEQ ID NO 206
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(24)
<223> OTHER INFORMATION: n is a, c, g, or t

<400> SEQUENCE: 206
acyacagtrt tttcccargc yctnccm 27

<210> SEQ ID NO 207
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 207
tcatcrtgyt tytcattrca yttrgcha 28

<210> SEQ ID NO 208
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 208
tcatcatgyt tytcattrca yttrgcya 28

<210> SEQ ID NO 209
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 209
aytcytcatc rtgyttytca ttrcaytt 28

<210> SEQ ID NO 210
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 210
aytcytcatc atgyttytca ttrcaytt 28

<210> SEQ ID NO 211
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(25)
<223> OTHER INFORMATION: n is a, c, g, or t

<400> SEQUENCE: 211
watrgcytgy ttrttraart caaanag 27

<210> SEQ ID NO 212
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(25)
<223> OTHER INFORMATION: n is a, c, g, or t

<400> SEQUENCE: 212
watrgcttgy ttrttraart caaanag 27

<210> SEQ ID NO 213
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 213
garctyttyt trgtrtcaat catrttya 28

<210> SEQ ID NO 214
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 214
garctcttyt tggtrtcaat catgttya 28

<210> SEQ ID NO 215
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 215
rctraarttg tarccagada yrttva 26

<210> SEQ ID NO 216
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 216
rctraarttg tarccagada tgttra 26

<210> SEQ ID NO 217
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 217
tacaayttya gyytrggwgc ygchgtvaa 29

<210> SEQ ID NO 218
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 218
tacaayttya gyytrggwgc ygcwgtvaa 29

<210> SEQ ID NO 219
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 219
ttbacwgcrg cwccyarrct raarttgta 29

<210> SEQ ID NO 220
<211> LENGTH: 30

<212> TYPE: DNA
<213> ORGANISM: Artificial Sequence
<220> FEATURE:
<223> OTHER INFORMATION: Synthetic Oligonucleotide

<400> SEQUENCE: 220
catrttrccd ccrtcwagca trcargchcc 30

<210> SEQ ID NO 221
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 221
catrttrccd ccrtcwagca trcargcycc 30

<210> SEQ ID NO 222
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 222
rgtytcaccy carwcyatrg atggsat 27

<210> SEQ ID NO 223
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 223
rgtytcaccy caawcyatrg atggsat 27

<210> SEQ ID NO 224
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 224
aaratsccat cyatrgwytg rggtgarac 29

<210> SEQ ID NO 225
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 225
aaratsccat cyatrgwttg rggtgarac 29

<210> SEQ ID NO 226
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 226
atrttytcat awggrttyct ytcacctgg 29

<210> SEQ ID NO 227
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 227
aygcaaygta rggccayccr tcycctga 28

<210> SEQ ID NO 228
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 228
aygcaatgta aggccayccr tctcctga 28

<210> SEQ ID NO 229
<211> LENGTH: 281
<212> TYPE: DNA
<213> ORGANISM: Artificial Sequence
<220> FEATURE:
<223> OTHER INFORMATION: Synthetic Oligonucleotide

<400> SEQUENCE: 229
gttactgctt aactagatgg atgttaattg aagctgaact gaaatgtttt gggaacactg 60
cagtagctaa atgcaatgag aaacatgatg aagaattttg tgacatgctg aggctttttg 120
atttcaacaa acaagccatt cagaggttga agactgaggc ccaaatgagc attcagctta 180
tcaacaaagc agtcaatgcc ctcataaatg accagcttat aatgaaaaat catctcagag 240
acatcatggg cataccatac tgcaattata gcaaatattg g 281

<210> SEQ ID NO 230
<211> LENGTH: 243
<212> TYPE: DNA
<213> ORGANISM: Artificial Sequence
<220> FEATURE:
<223> OTHER INFORMATION: Synthetic Oligonucleotide

<400> SEQUENCE: 230
aaacaaggac aggtggactt gaatgatgct gttcaggccc tgacagattt gggactgatt 60
tacaccgcaa agtacccaaa ttcatctgat ttagataggc tttcccagag tcatcccata 120
ttaaacatga ttgacaccaa gaagagctcc ctcaacatct ctggttacaa ctttagtctg 180
ggtgctgcag taaaggcagg ggcttgcatg cttgatggtg gcaacatgtt ggagacaatc 240
aag 243

<210> SEQ ID NO 231
<211> LENGTH: 300
<212> TYPE: DNA
<213> ORGANISM: Artificial Sequence
<220> FEATURE:
<223> OTHER INFORMATION: Synthetic Oligonucleotide

<400> SEQUENCE: 231
catcccatat taaacatgat tgacaccaag aagagctccc tcaacatctc tggttacaac 60
tttagtctgg gtgctgcagt aaaggcaggg gcttgcatgc ttgatggtgg caacatgttg 120
gagacaatca aggtttcacc ccaaactatg gatgggatct tgaaatcaat cctgaaggtc 180
aaaaggagcc tggggatgtt tgtgtcagac actccaggtg agagaaaccc ttatgagaat 240
atactgtaca aaatctgcct atcaggagat ggatggcctt acattgcatc aaggacttca 300

<210> SEQ ID NO 232
<211> LENGTH: 272
<212> TYPE: DNA
<213> ORGANISM: Artificial Sequence
<220> FEATURE:
<223> OTHER INFORMATION: Synthetic Oligonucleotide

<400> SEQUENCE: 232
tgctgcagta aaggcagggg cttgcatgct tgatggtggc aacatgttgg agacaatcaa 60
ggtttcaccc caaactatgg atgggatctt gaaatcaatc ctgaaggtca aaaggagcct 120
ggggatgttt gtgtcagaca ctccaggtga gagaaaccct tatgagaata tactgtacaa 180
aatctgccta tcaggagatg gatggcctta cattgcatca aggacttcaa tcactggtag 240
agcttgggaa aacactgtag tggatttaga gt 272

<210> SEQ ID NO 233
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 233
cartaygarg cvatgagytg ygayttyaat g 31

<210> SEQ ID NO 234
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 234
ttyaaycart aygargcvat gagytgyga 29

<210> SEQ ID NO 235
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 235
ctytayrayc aydcbytvat gagyatyaty tc 32

<210> SEQ ID NO 236
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n is a, c, g, or t

<400> SEQUENCE: 236
cthaayatga cnatgccyyt rtchtgyac 29

<210> SEQ ID NO 237
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n is a, c, g, or t

<400> SEQUENCE: 237
tgyccyaarc cncayagrmt haaycahatg gg 32

<210> SEQ ID NO 238
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 238
aayctytcyg aygcvcayar rargrayct 29

<210> SEQ ID NO 239
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 239
aaccacatgg gcatatgctc atgtggtct 29

<210> SEQ ID NO 240
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 240
aggttgtact gaacacttat cttccc 26

<210> SEQ ID NO 241
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 241
tgggaagatc actgccagtt ttctcgccc 29

<210> SEQ ID NO 242
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 242
tattggtagg aagtcattat acaatccca 29

<210> SEQ ID NO 243
<211> LENGTH: 32

<212> TYPE: DNA
<213> ORGANISM: Artificial Sequence
<220> FEATURE:
<223> OTHER INFORMATION: Synthetic Oligonucleotide

<400> SEQUENCE: 243
gctatgtaac tgccacccca agccatcctc at 32

<210> SEQ ID NO 244
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 244
ccaccccaag ccatcctcat aaaagtctg 29

<210> SEQ ID NO 245
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 245
tttgaaaatg ctgtttggga tcagtgcaa 29

<210> SEQ ID NO 246
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 246
taatggactg cataatgtat gatgcagc 28

<210> SEQ ID NO 247
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 247
aggagatttg aaaatgctgt ttgggatca 29

<210> SEQ ID NO 248
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 248
atgtatgatg cagctgtgtc aggagg 26

<210> SEQ ID NO 249
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 249
gtgctatrta rctgccaccc cargccat 28

<210> SEQ ID NO 250
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 250
gtgctatrta rctgccaccc cargccat 28

<210> SEQ ID NO 251
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 251
gtgctatrta actgccaccc caagccat 28

<210> SEQ ID NO 252
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 252
tgccacccca rgccatyctc atraargt 28

<210> SEQ ID NO 253
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 253
tgccacccca rgccatyctc atraaagt 28

<210> SEQ ID NO 254
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 254
tgccacccca agccatcctc atraaagt 28

<210> SEQ ID NO 255
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 255
artcacarct catygcytca taytgatt 28

<210> SEQ ID NO 256
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 256
artcacarct cattgcytca tactgatt 28

<210> SEQ ID NO 257
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 257
agtcacarct cattgcttca tactgatt 28

<210> SEQ ID NO 258
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 258
caccccargc catyctcatr aargtytg 28

<210> SEQ ID NO 259
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 259
caccccargc catyctcatr aaagtytg 28

<210> SEQ ID NO 260
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 260
caccccaagc catcctcatr aaagtytg 28

<210> SEQ ID NO 261
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 261
caccccargc catyctcatr aargtytg 28

<210> SEQ ID NO 262
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 262
caccccargc catyctcatr aaagtytg 28

<210> SEQ ID NO 263
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 263
caccccaagc catcctcatr aaagtytg 28

<210> SEQ ID NO 264
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 264
carctcatyg cytcataytg attraart 28

<210> SEQ ID NO 265
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 265
carctcattg cytcatactg attraart 28

<210> SEQ ID NO 266
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 266
carctcattg cttcatactg attraagt 28

<210> SEQ ID NO 267
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 267
cattraartc acarctcaty gcytcata 28

<210> SEQ ID NO 268
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 268
cattgaartc acarctcatt gcytcata 28

<210> SEQ ID NO 269
<211> LENGTH: 28
<212> TYPE: DNA
<213> ORGANISM: Artificial Sequence
<220> FEATURE:
<223> OTHER INFORMATION: Synthetic Oligonucleotide

```
<400> SEQUENCE: 269

cattgaagtc acarctcatt gcttcata                                         28


<210> SEQ ID NO 270
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 270

tyttyccycc attraartca carctcat                                         28


<210> SEQ ID NO 271
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 271

tcttyccycc attgaartca carctcat                                         28


<210> SEQ ID NO 272
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 272

tcttyccycc attgaagtca carctcat                                         28


<210> SEQ ID NO 273
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 273

agaachtcaa gycccaargt cgtcctgtaa                                       30


<210> SEQ ID NO 274
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 274

agaacmtcaa gycccaargt cgtcctgtaa                                       30


<210> SEQ ID NO 275
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 275

agaacmtcaa gccccaargt cgtcctgtaa                                       30


<210> SEQ ID NO 276
```

<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 276
gcchytyggc ggtgggtcac gggggccc 28

<210> SEQ ID NO 277
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 277
gcctttyggc ggtgggtcac gggggccc 28

<210> SEQ ID NO 278
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 278
gcctttcggc ggtgggtcac gggggccc 28

<210> SEQ ID NO 279
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 279
gtcgtcctgt aaayggacgc ccccgtga 28

<210> SEQ ID NO 280
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 280
gtcgtcctgt aaayggacgc ccccgtga 28

<210> SEQ ID NO 281
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 281
gtcgtcctgt aaatggacgc ccccgtga 28

<210> SEQ ID NO 282
<211> LENGTH: 276
<212> TYPE: DNA
<213> ORGANISM: Artificial Sequence
<220> FEATURE:
<223> OTHER INFORMATION: Synthetic Oligonucleotide

<400> SEQUENCE: 282

```
accacaagtt ttgtaacctt tctgatgcac ataaaaagaa tctttatgac catgctttaa     60

tgagtatcat ctcaaccttc cacttatcca ttcctaactt taatcagtat gaagcaatga    120

gttgtgactt caatgggggg aagataagtg ttcagtacaa ccttagccac acttatgctg    180

tagatgcagc caaccactgt gggaccattg ccaatggcgt tcttcagact tttatgagga    240

tggcttgggg tggcagttac atagcacttg attccg                              276


<210> SEQ ID NO 283
<211> LENGTH: 299
<212> TYPE: DNA
<213> ORGANISM: Artificial Sequence
<220> FEATURE:
<223> OTHER INFORMATION: Synthetic Oligonucleotide

<400> SEQUENCE: 283

tccacttatc cattcctaac tttaatcagt atgaagcaat gagttgtgac ttcaatgggg     60

ggaagataag tgttcagtac aaccttagcc acacttatgc tgtagatgca gccaaccact    120

gtgggaccat tgccaatggc gttcttcaga cttttatgag gatggcttgg ggtggcagtt    180

acatagcact tgattccgga aaggggagtt gggattgtat aatgacttcc taccaatatt    240

tgataatcca aaacaccact tgggaagatc actgccagtt ttctcgccca tcccctatc     299


<210> SEQ ID NO 284
<211> LENGTH: 300
<212> TYPE: DNA
<213> ORGANISM: Artificial Sequence
<220> FEATURE:
<223> OTHER INFORMATION: Synthetic Oligonucleotide

<400> SEQUENCE: 284

catagggaaa ccctgcccta aaccacacag actcaaccac atgggcatat gctcatgtgg     60

tctgtacaaa catcctggtg taccagtcaa gtggaaaaga taggagacag acccacccat    120

gggcccccgt gacccaccgc cgaaaggcgg tgggtcacgg gggcgtccat ttacaggacg    180

accttggggc ttgaggttct aaacaccatg tctctgggga gaactgctct taaaactggt    240

atattgagtc ctcctgacac agctgcatca tacattatgc agtccattaa agcacagtgc    300


<210> SEQ ID NO 285
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 285

catygmatcy ttgagrgtca t                                               21


<210> SEQ ID NO 286
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (15)..(15)
<223> OTHER INFORMATION: n is a, c, g, or t

<400> SEQUENCE: 286

arytgrgart adgtnarycc                                                 20
```

<210> SEQ ID NO 287
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (17)..(17)
<223> OTHER INFORMATION: n is a, c, g, or t

<400> SEQUENCE: 287
catcyttgag rgtcatnagc tgagaata 28

<210> SEQ ID NO 288
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 288
aayatmctyt ayaarathtg 20

<210> SEQ ID NO 289
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 289
ccyggygarm graaycchta yga 23

<210> SEQ ID NO 290
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 290
aggaatcctt atgaraacat actctayaa 29

<210> SEQ ID NO 291
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: n is a, c, g, or t

<400> SEQUENCE: 291
acwttyttyc argargtrcc ycatgtnat 29

<210> SEQ ID NO 292
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 292
catgtvatwg argargtsat raayatygt 29

<210> SEQ ID NO 293
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 293
aayatggara chctmaayat gacyatgcc 29

<210> SEQ ID NO 294
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 294
ccyaayttya aycartwtga rgcaatgag 29

<210> SEQ ID NO 295
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 295
caracyttya tgagratggc ytggggtgg 29

<210> SEQ ID NO 296
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 296
tgggaytgya thatgacbag ytaycarta 29

<210> SEQ ID NO 297
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: n is a, c, g, or t

<400> SEQUENCE: 297
agaccrtchc cyatyggbta yctyggnct 29

<210> SEQ ID NO 298
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 298
caccaggrgg rtaytgtytr acyagrtgga tg 32

<210> SEQ ID NO 299

<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 299
acagctgtrg cmaartgyaa tgaraarca 29

<210> SEQ ID NO 300
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 300
gayatyatgg gratyccrta ctgyaayta 29

<210> SEQ ID NO 301
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 301
gcygayaaya tgatyactga ratgytrca 29

<210> SEQ ID NO 302
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 302
acratrttya tsacytcytc watbacatg 29

<210> SEQ ID NO 303
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 303
ggcatrgtca trttkagdgt ytccatrtt 29

<210> SEQ ID NO 304
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 304
ctcattgcyt cawaytgrtt raarttrgg 29

<210> SEQ ID NO 305
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 305
ccaccccarg ccatyctcat raargtytg 29

<210> SEQ ID NO 306
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 306
taytgrtarc tvgtcatdat rcartccca 29

<210> SEQ ID NO 307
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n is a, c, g, or t

<400> SEQUENCE: 307
agnccragrt avccratrgg dgayggtct 29

<210> SEQ ID NO 308
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 308
catccayctr gtyaracart ayccycctgg tg 32

<210> SEQ ID NO 309
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 309
tgyttytcat trcayttkgc yacagctgt 29

<210> SEQ ID NO 310
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 310
tarttrcagt ayggratycc catratrtc 29

<210> SEQ ID NO 311
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 311
tgyarcatyt cagtratcat rttrtcrgc 29

<210> SEQ ID NO 312
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 312
tgrtcccasa cwgcrttytc awayttyct 29

<210> SEQ ID NO 313
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 313
acatcwatyc catgtgarta yttrgcatcy tg 32

<210> SEQ ID NO 314
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 314
tgtgartayt trgcatcytg yttraaytgy tt 32

<210> SEQ ID NO 315
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 315
tcytcrggyc tyccytcrat rtccatcca 29

<210> SEQ ID NO 316
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 316
tcccargcyc tycctgttat tgargtycty ga 32

<210> SEQ ID NO 317
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 317
gttattgarg tycttgaygc aatrtayggc ca 32

<210> SEQ ID NO 318
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 318
cttgaygcaa trtayggcca bccrtcyccy ga 32

<210> SEQ ID NO 319
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 319
catrcargcy ccygcyttha cagctgcrcc ca 32

<210> SEQ ID NO 320
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 320
agraartwtg araaygcwgt stgggayca 29

<210> SEQ ID NO 321
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 321
cargatgcya artaytcaca tggratwgat gt 32

<210> SEQ ID NO 322
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 322
aarcarttya arcargatgc yaartaytca ca 32

<210> SEQ ID NO 323
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 323
tggatggaya tygarggrag rccygarga 29

<210> SEQ ID NO 324
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 324
tcragracyt caataacagg ragrgcytgg ga 32

<210> SEQ ID NO 325

<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 325
tggccrtaya ttgcrtcaag racytcaata ac 32

<210> SEQ ID NO 326
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 326
tcrggrgayg gvtggccrta yattgcrtca ag 32

<210> SEQ ID NO 327
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 327
tgggygcagc tgtdaargcr ggrgcytgya tg 32

<210> SEQ ID NO 328
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 328
catygmatcy ttgagrgtca t 21

<210> SEQ ID NO 329
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n is a, c, g, or t

<400> SEQUENCE: 329
tattctcagc tnatgacyct caargatg 28

<210> SEQ ID NO 330
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 330
gartcrgatg ggaagccaca gaarrct 27

<210> SEQ ID NO 331
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 331
atytrgartc rgatgggaag ccacagaa 28

<210> SEQ ID NO 332
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 332
gttgatytrg artcrgatgg gaagccac 28

<210> SEQ ID NO 333
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 333
tattctcagc tdatgaccct caargatg 28

<210> SEQ ID NO 334
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 334
agyaaygara traaactaat tgarattg 28

<210> SEQ ID NO 335
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 335
agaaaagaca tcaaactaat tgarattg 28

<210> SEQ ID NO 336
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 336
gaatcacaag gwagyaayga ratraaact 29

<210> SEQ ID NO 337
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 337
gaatcacaag gwagaaaaga catcaaact 29

<210> SEQ ID NO 338
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 338
ttgaatcaca aggwagyaay garatraa 28

<210> SEQ ID NO 339
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 339
ttgaatcaca aggwagaaaa gacatcaa 28

<210> SEQ ID NO 340
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 340
ctcrttgaat cacaaggwag yaaygara 28

<210> SEQ ID NO 341
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 341
ctccttgaat cacaaggwag aaaagaca 28

<210> SEQ ID NO 342
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 342
tggtratrac ctgrcagggy tcrgatgaca t 31

<210> SEQ ID NO 343
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 343
tggtcatrac ctgrcagggg tcrgatgaca t 31

<210> SEQ ID NO 344
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 344
aaratggtca tracctgrca ggggtc 26

<210> SEQ ID NO 345
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 345
acatwaggaa actcrttgaa tcacaagg 28

<210> SEQ ID NO 346
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 346
acataaggaa actccttgaa tcacaagg 28

<210> SEQ ID NO 347
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 347
garatraaac taattgarat tgccctca 28

<210> SEQ ID NO 348
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 348
gacatcaaac taattgarat tgccctca 28

<210> SEQ ID NO 349
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 349
aaygatgcaa tgrtgcayct tgarcc 26

<210> SEQ ID NO 350
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 350
aaygatgcaa tgrtgcaact tgarcc 26

<210> SEQ ID NO 351

<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 351
atgacrctca aygatgcaat grtgcayc 28

<210> SEQ ID NO 352
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 352
atgaccctca aygatgcaat grtgcaac 28

<210> SEQ ID NO 353
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 353
trycrgctgg gctracrtat tctcagct 28

<210> SEQ ID NO 354
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 354
ttacrgctgg gctracctat tctcagct 28

<210> SEQ ID NO 355
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 355
gaytcygatg ggaagccaca gaayyct 27

<210> SEQ ID NO 356
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 356
gaytcygatg ggaagccaca gaaayct 27

<210> SEQ ID NO 357
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 357
gaatcagatg ggaagccaca gaaagct 27

<210> SEQ ID NO 358
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 358
atrtygaytc ygatgggaag ccacagaa 28

<210> SEQ ID NO 359
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 359
atrtggaytc ygatgggaag ccacagaa 28

<210> SEQ ID NO 360
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 360
gttgatrtyg aytcygatgg gaagccac 28

<210> SEQ ID NO 361
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 361
gttgatrtgg aytcygatgg gaagccac 28

<210> SEQ ID NO 362
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 362
gtgttttccc argcccttcc tgttattga 29

<210> SEQ ID NO 363
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 363
cttcctgtta ttgargtyct tgatgcaat 29

<210> SEQ ID NO 364
<211> LENGTH: 29
<212> TYPE: DNA

<213> ORGANISM: Artificial Sequence
<220> FEATURE:
<223> OTHER INFORMATION: Synthetic Oligonucleotide

<400> SEQUENCE: 364
cttcctgtta ttgargttct tgatgcaat 29

<210> SEQ ID NO 365
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 365
cctgttattg argtycttga tgcaatrt 28

<210> SEQ ID NO 366
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 366
cctgttattg argttcttga tgcaatrt 28

<210> SEQ ID NO 367
<211> LENGTH: 220
<212> TYPE: DNA
<213> ORGANISM: Artificial Sequence
<220> FEATURE:
<223> OTHER INFORMATION: Synthetic Oligonucleotide

<400> SEQUENCE: 367
atagtgacat tcttccagga agtgcctcat gtaatagaag aggtgatgaa cattgttctc 60
attgcactgt ctatactagc agtgctgaaa ggtctgtaca attttgcaac atgtggcctc 120
gttggtttgg tcactttcct cctgttgtgt ggcaggtctt gcacaaccag tctttacaaa 180
ggggtttatg agcttcagac tctggaacta aacatggaga 220

<210> SEQ ID NO 368
<211> LENGTH: 241
<212> TYPE: DNA
<213> ORGANISM: Artificial Sequence
<220> FEATURE:
<223> OTHER INFORMATION: Synthetic Oligonucleotide

<400> SEQUENCE: 368
ctctggaact aaacatggag acactcaata tgaccatgcc tctctcctgc acaaagaaca 60
acagtcatca ttatataatg gtgggcaatg agacaggact agaactgacc ttgaccaaca 120
cgagcattat taatcataaa ttttgcaatc tgtctgatgc ccacaaaaag aacctctatg 180
accacgctct tatgagcata atctcaactt tccacttgtc catccccaac ttcaatcagt 240
a 241

<210> SEQ ID NO 369
<211> LENGTH: 244
<212> TYPE: DNA
<213> ORGANISM: Artificial Sequence
<220> FEATURE:
<223> OTHER INFORMATION: Synthetic Oligonucleotide

<400> SEQUENCE: 369
ttccactgga tcttcaggtc ttccttcaat gtccatccag gtcttagcat ttgggtcaag 60
ttgcagcatt gcatccttga gggtcatcag ctgagaatag gtaagcccag cggtaaaccc 120
tgccgactgc agggatttat tggaattgtt gctgccagct ttctgtggct tcccatctga 180
ttccagatca acgacagtgt tttcccaggc ccttcctgtt attgaggttc ttgatgcaat 240
atat 244

<210> SEQ ID NO 370
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 370
gaaattaata cgactcacta tagggycctc atgttcgtaa taagaaggtg atatt 55

<210> SEQ ID NO 371
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 371
gaaattaata cgactcacta tagggttaca tagyttgytr garttrggta caaar 55

<210> SEQ ID NO 372
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 372
gaaattaata cgactcacta tagggggrga aaaygaraay gattgtgatg cagag 55

<210> SEQ ID NO 373
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 373
gaaattaata cgactcacta taggggtkca ggaggaygay ytggcvgcag grct 54

<210> SEQ ID NO 374
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 374
gaaattaata cgactcacta tagggattra gactwgtcak tytgttaata ttctt 55

<210> SEQ ID NO 375
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 375
gaaattaata cgactcacta tagggaatga acawggdgtt gatctyccac cwcct 55

<210> SEQ ID NO 376
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 376
gaaattaata cgactcacta tagggccacc wcctccrttr tayrctcagg aaaa 54

<210> SEQ ID NO 377
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 377
gaaattaata cgactcacta tagggcarga tccytttggc agtattggwg atgta 55

<210> SEQ ID NO 378
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 378
gaaattaata cgactcacta taggggtcty atyttratyc aargkryaaa aactct 56

<210> SEQ ID NO 379
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 379
gaaattaata cgactcacta tagggaaaaa ctctyccyrt tttrgaratw gcyag 55

<210> SEQ ID NO 380
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 380
gaaattaata cgactcacta tagggaccyc aaratrtrga ttcrgtrtgc tccgg 55

<210> SEQ ID NO 381
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 381
attcttgatg acatcraayt catarcccgc 30

<210> SEQ ID NO 382
<211> LENGTH: 30

<212> TYPE: DNA
<213> ORGANISM: Artificial Sequence
<220> FEATURE:
<223> OTHER INFORMATION: Synthetic Oligonucleotide

<400> SEQUENCE: 382
aatyaaaggr ctgtaatgag gttcattrgg 30

<210> SEQ ID NO 383
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 383
attaargaaa atgtyctytc ctcrgtt 27

<210> SEQ ID NO 384
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 384
tcaatdgcat gyctattrat taargaaaat 30

<210> SEQ ID NO 385
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 385
cttcyaraag atctccwara tcratccctg a 31

<210> SEQ ID NO 386
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 386
gaattrtart artgttcaac acayaahgtc 30

<210> SEQ ID NO 387
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 387
tgyggccaat tctgytgatt rtcctcata 29

<210> SEQ ID NO 388
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 388
gaargtyctr ccyttctttg tyaccactct 30

<210> SEQ ID NO 389
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 389
tcattrggat aaaggaargt yctrccyttc 30

<210> SEQ ID NO 390
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 390
aacrttcttr ggaggwacac ctgycctgaa 30

<210> SEQ ID NO 391
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 391
gttacactta tattgtarca tgttttrgct 30

<210> SEQ ID NO 392
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 392
gttacactta tattgtarca tgttttrgct 30

<210> SEQ ID NO 393
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 393
aytayaattc ygayaaagat aaattcaagt tttagtcccc ttcgtttttg gggtagtcta 60
aatcccctat agtgagtcgt attaatttc 89

<210> SEQ ID NO 394
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 394
agggatygat ytwggagatc ttytrgaagt tttagtcccc ttcgtttttg gggtagtcta 60
aatcccctat agtgagtcgt attaatttc 89

<210> SEQ ID NO 395
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 395
tgtaatcaga taatagatgc aataaactgt tttagtcccc ttcgtttttg gggtagtcta 60
aatcccctat agtgagtcgt attaatttc 89

<210> SEQ ID NO 396
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 396
tgtaaycaga taatagatgc aataaactgt tttagtcccc ttcgtttttg gggtagtcta 60
aatcccctat agtgagtcgt attaatttc 89

<210> SEQ ID NO 397
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 397
atcaractgc haaatcyttr garctcttgt tttagtcccc ttcgtttttg gggtagtcta 60
aatcccctat agtgagtcgt attaatttc 89

<210> SEQ ID NO 398
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 398
atcaractgc haaatcyttg garctcttgt tttagtcccc ttcgtttttg gggtagtcta 60
aatcccctat agtgagtcgt attaatttc 89

<210> SEQ ID NO 399
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 399
yacygcyggt ttaatyaaaa aycaraaygt tttagtcccc ttcgtttttg gggtagtcta 60
aatcccctat agtgagtcgt attaatttc 89

<210> SEQ ID NO 400
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 400
tacygcyggt ttaatyaaaa aycaraaygt tttagtcccc ttcgtttttg gggtagtcta 60
aatcccctat agtgagtcgt attaatttc 89

<210> SEQ ID NO 401
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 401
ttttttggcc ctggaatyga aggactytgt tttagtcccc ttcgtttttg gggtagtcta 60
aatcccctat agtgagtcgt attaatttc 89

<210> SEQ ID NO 402
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 402
ttttttggcc ctggaatcga aggactytgt tttagtcccc ttcgtttttg gggtagtcta 60
aatcccctat agtgagtcgt attaatttc 89

<210> SEQ ID NO 403
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 403
cycctcatgt tcgtaataag aaggtgatgt tttagtcccc ttcgtttttg gggtagtcta 60
aatcccctat agtgagtcgt attaatttc 89

<210> SEQ ID NO 404
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 404
cytttggcag tattggwgat gtaratgggt tttagtcccc ttcgtttttg gggtagtcta 60
aatcccctat agtgagtcgt attaatttc 89

<210> SEQ ID NO 405
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 405
cctttggcag tattggtgat gtaratgggt tttagtcccc ttcgtttttg gggtagtcta 60
aatcccctat agtgagtcgt attaatttc 89

<210> SEQ ID NO 406
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 406
tcaccrtctg ctccycagga rgacacaagt tttagtcccc ttcgtttttg gggtagtcta 60
aatcccctat agtgagtcgt attaatttc 89

<210> SEQ ID NO 407
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 407
ytatgaggay aatcarcaga attggccrgt tttagtcccc ttcgtttttg gggtagtcta 60
aatcccctat agtgagtcgt attaatttc 89

<210> SEQ ID NO 408
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 408
ytatgaggat aatcarcaga attggccagt tttagtcccc ttcgtttttg gggtagtcta 60
aatcccctat agtgagtcgt attaatttc 89

<210> SEQ ID NO 409
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 409
atatyttrga accyataagr tcrccytcgt tttagtcccc ttcgtttttg gggtagtcta 60
aatcccctat agtgagtcgt attaatttc 89

<210> SEQ ID NO 410
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 410
yttyacvary tatgaggaya atcarcaggt tttagtcccc ttcgtttttg gggtagtcta 60
aatcccctat agtgagtcgt attaatttc 89

<210> SEQ ID NO 411
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 411
yttyacrary tatgaggata atcarcaggt tttagtcccc ttcgtttttg gggtagtcta 60
aatcccctat agtgagtcgt attaatttc 89

<210> SEQ ID NO 412
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 412
aaagttgctg attccccttt rgargcatgt tttagtcccc ttcgtttttg gggtagtcta 60
aatcccctat agtgagtcgt attaatttc 89

<210> SEQ ID NO 413
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 413
acactgagyg ggcaraaagt tgctgattgt tttagtcccc ttcgtttttg gggtagtcta 60
aatcccctat agtgagtcgt attaatttc 89

<210> SEQ ID NO 414
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 414
trgattcrgt rtgctccggr acyctccagt tttagtcccc ttcgtttttg gggtagtcta 60
aatcccctat agtgagtcgt attaatttc 89

<210> SEQ ID NO 415
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 415
aracagaaga ygtycatctg atgggattgt tttagtcccc ttcgtttttg gggtagtcta 60
aatcccctat agtgagtcgt attaatttc 89

<210> SEQ ID NO 416
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 416
caggrcaggt gtwcctccya agaaygttgt tttagtcccc ttcgtttttg gggtagtcta 60
aatcccctat agtgagtcgt attaatttc 89

<210> SEQ ID NO 417
<211> LENGTH: 279
<212> TYPE: DNA
<213> ORGANISM: Artificial Sequence
<220> FEATURE:
<223> OTHER INFORMATION: Synthetic Oligonucleotide

<400> SEQUENCE: 417
attaacattg acattgagac ttgtcagtct gttaatattc ttgaagagat ggatttacat 60
agtttgttag agttgggtac aaaacctact gcccctcatg ttcgtaataa gaaggtgata 120
ttatttgaca caaatcatca ggttagtatt tgtaatcaga taatagatgc aataaactca 180
gggattgatc ttggagatct tctagaagga ggtttgctga ctttgtgtgt tgaacattac 240
tataattctg ataaagataa attcaacaca agtcctatc 279

<210> SEQ ID NO 418
<211> LENGTH: 296
<212> TYPE: DNA
<213> ORGANISM: Artificial Sequence
<220> FEATURE:
<223> OTHER INFORMATION: Synthetic Oligonucleotide

<400> SEQUENCE: 418
agagatggat ttacatagtt tgttagagtt gggtacaaaa cctactgccc ctcatgttcg 60
taataagaag gtgatattat ttgacacaaa tcatcaggtt agtatttgta atcagataat 120
agatgcaata aactcaggga ttgatcttgg agatcttcta gaaggaggtt tgctgacttt 180
gtgtgttgaa cattactata attctgataa agataaattc aacacaagtc ctatcgcgaa 240
atatttacgt gatgcgggct atgaattcga tgtcatcaag aatgcagatg caaccc 296

<210> SEQ ID NO 419
<211> LENGTH: 316
<212> TYPE: DNA
<213> ORGANISM: Artificial Sequence
<220> FEATURE:
<223> OTHER INFORMATION: Synthetic Oligonucleotide

<400> SEQUENCE: 419
aggatccgac aatgaacaag gagttgatct tccacctcct ccgttgtacg ctcaggaaaa 60
aagacaggac ccaatacagc acccggcagc aagctctcag gatccctttg gcagtattgg 120
tgatgtaaat ggtgatatct tagaacccat aagatcacct tcttcaccgt ctgctcctca 180
ggaagacaca agggcaaggg aagcctatga attatcgcct gactttacaa attatgagga 240
taatcagcag aattggccac aaagagtggt gacaaagaag ggtaggactt tcctttatcc 300
caatgatctt ctgcag 316

<210> SEQ ID NO 420
<211> LENGTH: 324
<212> TYPE: DNA
<213> ORGANISM: Artificial Sequence
<220> FEATURE:
<223> OTHER INFORMATION: Synthetic Oligonucleotide

<400> SEQUENCE: 420
ttctttatca gtctcatctt aatccaaggg ataaaaactc tccctatttt ggagatagcc 60
agtaacgatc aaccccaaaa tgtggattcg gtatgctccg gaactctcca gaaaacagaa 120
gacgtccatc tgatgggatt tacactgagc gggcaaaaag ttgctgattc ccctttggag 180
gcatccaagc gatgggcttt caggacaggt gtacctccca agaatgttga gtatacggaa 240
ggggaggaag ccaaaacatg ctacaatata agtgtaacgg atccctctgg aaaatccttg 300
ctgttagatc ctcccaccaa cgtc 324

<210> SEQ ID NO 421
<211> LENGTH: 283
<212> TYPE: DNA

-continued

```
<213> ORGANISM: Artificial Sequence
<220> FEATURE:
<223> OTHER INFORMATION: Synthetic Oligonucleotide

<400> SEQUENCE: 421

actgcctact ctggagaaaa tgaaaatgat tgtgatgcag agctaagaat ttggagtgtt     60

caggaggacg acctggcagc agggctcagt tggataccat tttttggccc tggaatcgaa    120

ggactttata ccgctggttt aattaaaaat caaaacaatt tggtctgcag gttgaggcgt    180

ctagccaatc aaactgcaaa atccttggaa ctcttactaa gggtcacaac cgaggaaaga    240

acattttcct taatcaatag acatgctatt gactttctac tca                      283
```